United States Patent
Pinkerton et al.

(10) Patent No.: US 9,458,147 B2
(45) Date of Patent: Oct. 4, 2016

(54) SULFONAMIDE COMPOUNDS AND USES AS TNAP INHIBITORS

(71) Applicant: Sanford-Burnham Medical Research Institute, La Jolla, CA (US)

(72) Inventors: Anthony B. Pinkerton, La Jolla, CA (US); Russell Dahl, La Jolla, CA (US); Nicholas D. P. Cosford, La Jolla, CA (US); Jose Luis Millan, La Jolla, CA (US)

(73) Assignee: SANFORD-BURNHAM MEDICAL RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 14/379,475

(22) PCT Filed: Feb. 21, 2013

(86) PCT No.: PCT/US2013/027191
§ 371 (c)(1),
(2) Date: Aug. 18, 2014

(87) PCT Pub. No.: WO2013/126608
PCT Pub. Date: Aug. 29, 2013

(65) Prior Publication Data
US 2015/0011551 A1 Jan. 8, 2015

Related U.S. Application Data

(60) Provisional application No. 61/601,957, filed on Feb. 22, 2012.

(51) Int. Cl.
*C07D 213/76* (2006.01)
*C07D 215/38* (2006.01)
(Continued)

(52) U.S. Cl.
CPC ............ *C07D 417/04* (2013.01); *A61K 31/44* (2013.01); *A61K 31/50* (2013.01); *C07D 213/76* (2013.01);
(Continued)

(58) Field of Classification Search
CPC   C07D 213/76; C07D 215/38; C07D 409/04; C07D 405/04; C07D 409/12; C07D 417/04; C07D 405/12; C07D 401/12; C07D 401/04
USPC .................................... 514/235.2; 546/283.4
See application file for complete search history.

(56) References Cited

U.S. PATENT DOCUMENTS 5,607,954 A * 3/1997 Weidmann ........... C07D 213/81
 514/355
8,119,693 B2 * 2/2012 Millan ................. A61K 31/415
 514/604

(Continued)

FOREIGN PATENT DOCUMENTS

WO WO01/56607 8/2001
WO WO2007014008 * 2/2007

(Continued)

OTHER PUBLICATIONS

Chemical Abstracts; STN Registry Database Record for RN 878059-81-5, entered on Mar. 27, 2006.*

(Continued)

*Primary Examiner* — Noble Jarrell
*Assistant Examiner* — Daniel Carcanague
(74) *Attorney, Agent, or Firm* — Wilson, Sonsini, Goodrich & Rosati

(57) ABSTRACT

Described herein are compounds that modulate the activity of TNAP. In some embodiments, the compounds described herein inhibit TNAP. In certain embodiments, the compounds described herein are useful in the treatment of conditions associated with hyper-mineralization.

14 Claims, 2 Drawing Sheets

(51) Int. Cl.

| | | |
|---|---|---|
| C07D 409/04 | (2006.01) | |
| C07D 405/04 | (2006.01) | |
| C07D 409/12 | (2006.01) | |
| C07D 417/04 | (2006.01) | |
| C07D 405/12 | (2006.01) | |
| C07D 401/12 | (2006.01) | |
| C07D 401/04 | (2006.01) | |
| A61K 31/44 | (2006.01) | |
| A61K 31/50 | (2006.01) | |
| C07D 213/80 | (2006.01) | |
| C07D 213/82 | (2006.01) | |
| C07D 231/42 | (2006.01) | |
| C07D 333/36 | (2006.01) | |
| C07D 237/20 | (2006.01) | |
| C07D 239/69 | (2006.01) | |
| C07D 241/22 | (2006.01) | |
| C07D 261/16 | (2006.01) | |
| C07D 263/50 | (2006.01) | |
| C07D 271/113 | (2006.01) | |
| C07D 277/52 | (2006.01) | |
| C07D 285/135 | (2006.01) | |

(52) U.S. Cl.
CPC ........... *C07D 213/80* (2013.01); *C07D 213/82* (2013.01); *C07D 215/38* (2013.01); *C07D 231/42* (2013.01); *C07D 237/20* (2013.01); *C07D 239/69* (2013.01); *C07D 241/22* (2013.01); *C07D 261/16* (2013.01); *C07D 263/50* (2013.01); *C07D 271/113* (2013.01); *C07D 277/52* (2013.01); *C07D 285/135* (2013.01); *C07D 333/36* (2013.01); *C07D 401/04* (2013.01); *C07D 401/12* (2013.01); *C07D 405/04* (2013.01); *C07D 405/12* (2013.01); *C07D 409/04* (2013.01); *C07D 409/12* (2013.01)

(56) References Cited

U.S. PATENT DOCUMENTS

| | | | | |
|---|---|---|---|---|
| 8,686,003 B2* | 4/2014 | Millan | ................ | A61K 31/415 514/313 |
| 2006/0025455 A1* | 2/2006 | Amrein | ................ | C07D 213/76 514/352 |
| 2008/0132502 A1* | 6/2008 | Bengtsson | ........... | C07D 417/14 514/235.5 |
| 2008/0194584 A1* | 8/2008 | Birault | ................ | C07D 213/38 514/255.05 |
| 2008/0255109 A1* | 10/2008 | Roe | ..................... | C07D 217/02 514/230.5 |
| 2009/0053192 A1* | 2/2009 | Millan | ................ | A61K 31/519 424/94.6 |
| 2009/0069179 A1* | 3/2009 | Lohmann et al. | ............ | 504/100 |
| 2009/0076009 A1* | 3/2009 | Arnould | ............... | C07D 417/04 514/236.8 |
| 2009/0088459 A1* | 4/2009 | Dehmlow | ............. | C07C 311/03 514/357 |
| 2009/0118336 A1* | 5/2009 | David | ................ | C07D 417/14 514/341 |
| 2009/0156560 A1* | 6/2009 | Millan | ................ | A61K 31/415 514/107 |
| 2009/0239847 A1* | 9/2009 | Bruce | ................ | C07D 241/20 514/218 |
| 2010/0029609 A1* | 2/2010 | Berst | .................... | C07C 311/21 514/210.17 |
| 2010/0105711 A1* | 4/2010 | Fairhurst | .............. | C07D 417/14 514/275 |
| 2010/0137313 A1* | 6/2010 | Boriack-Sjodin | .... | C07D 239/48 514/236.5 |
| 2010/0292225 A1* | 11/2010 | Chamoin | ............ | C07D 213/76 514/226.5 |
| 2010/0311736 A1* | 12/2010 | Adams | ................ | C07D 213/76 514/230.5 |
| 2010/0331307 A1* | 12/2010 | Salituro | .............. | A61K 31/497 514/210.21 |
| 2012/0095044 A1* | 4/2012 | Millan | ................ | A61K 31/415 514/313 |

FOREIGN PATENT DOCUMENTS

| | | | |
|---|---|---|---|
| WO | WO-2007093599 A1 | | 8/2007 |
| WO | WO2008042867 | * | 4/2008 |
| WO | WO2009/017863 | | 2/2009 |
| WO | WO2010130638 | * | 11/2010 |
| WO | WO-2012101239 A1 | | 8/2012 |
| WO | WO2013/126608 | | 8/2013 |
| WO | WO2016054056 | * | 4/2016 |

OTHER PUBLICATIONS

Kim; J. Med. Chem. 2011, 54, 2455-2466.*
Kim; Bioorganic & Medicinal Chemistry Letters 21 (2011) 6977-6981.*
Chemical Abstracts STN Registry Database Record for 878062-17-0 entered on Mar. 27, 2006.*
PCT/US2013/027191 International Search Report and Written Opinion dated Jun. 28, 2013.
PCT/US2013/027191 International Preliminary Report on Patentability dated Sep. 4, 2014.
Dahl et al. Discovery and validation of a series of aryl sulfonamides as selective inhibitors of tissue-nonspecific alkaline phosphatase (TNAP). J Med Chem 52(21):6919-6925 (2009).
Thorarensen et al. Preparation of antibacterial benzoic acid derivatives. CAS No. 2004:182843 (2004).

* cited by examiner

SULFONAMIDE COMPOUNDS AND USES AS TNAP INHIBITORS

CROSS-REFERENCE TO RELATED APPLICATIONS

This application is the National Phase entry of International Application No. PCT/US2013/027191, filed Feb. 21, 2013, which claims the benefit of U.S. Provisional Application No. 61/601,957, filed Feb. 22, 2012, both of which are incorporated by reference herein in their entireties.

STATEMENT AS TO FEDERALLY SPONSORED RESEARCH

This invention was made with government support under RC1 HL101899 awarded by the National Institutes of Health. The government has certain rights in the invention.

BACKGROUND OF THE INVENTION

Among the human alkaline phosphatases, tissue-nonspecific alkaline phosphatase (TNAP) is essential for bone matrix mineralization. The biological function of TNAP is to hydrolyze extracellular inorganic pyrophosphate ($ePP_i$), which is an inhibitor of calcification. Low levels of $ePP_i$ have been associated with hyper-mineralization. There is a need for compounds that inhibit TNAP to prevent medical conditions associated with hyper-mineralization, for example, osteoarthritis, medial vascular calcification, and ankylosis.

SUMMARY OF THE INVENTION

Described herein are compounds that modulate the activity of TNAP. In some embodiments, the compounds described herein inhibit TNAP. In certain embodiments, the compounds described herein are useful in the treatment of conditions associated with hyper-mineralization.

In one aspect, provided herein are compounds of Formula I, or a pharmaceutically acceptable salts, polymorphs, solvates, tautomers, metabolites, or N-oxides thereof:

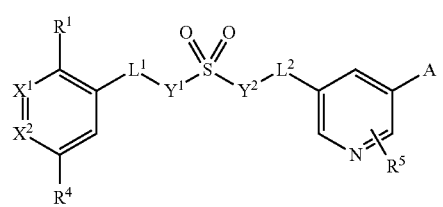

(Formula I)

wherein:
$Y^1$ and $Y^2$ are independently a bond or —N($R^6$)—, wherein at least one of $Y^1$ and $Y^2$ is —N($R^6$)—;
$L^1$ and $L^2$ are independently a bond or optionally substituted alkylene;
$X^1$ is =N— or =C($R^2$)—;
$X^2$ is =N— or =C($R^3$)—;
$R^1$ and $R^4$ are independently selected from the group consisting of hydrogen, —F, —Cl, —Br, —I, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^6$ is hydrogen, optionally substituted alkyl, optionally substituted alkenyl, or optionally substituted alkynyl;

$R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;

$R^9$ is selected from the group consisting of hydrogen, optionally substituted alkyl, haloalkyl, optionally substituted cycloalkyl, optionally substituted heterocycloalkyl, and optionally substituted phenyl; and A is selected from the group consisting of —C(O)—N($R^7$)—$R^8$, —C(O)—O—$R^9$, optionally substituted phenyl, and optionally substituted 5- or 6-membered heteroaryl.

In some embodiments described above or below, provided herein are compounds of Formula I, wherein $Y^1$ is a bond and $Y^2$ is —N($R^6$)—; $X^2$ is =C($R^3$)—; $L^1$ is a bond; $L^2$ is a bond; and $R^6$ is hydrogen as shown in Formula Ie:

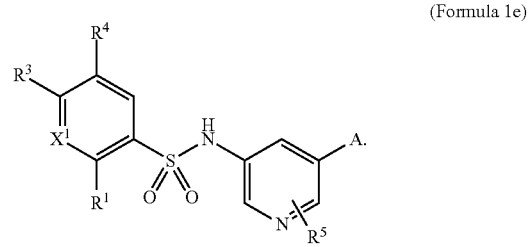

(Formula Ie)

In some embodiments described above or below, provided herein are compounds of Formula I, wherein A is optionally substituted phenyl or optionally substituted 5- or 6-membered heteroaryl. In some embodiments, A is selected from:

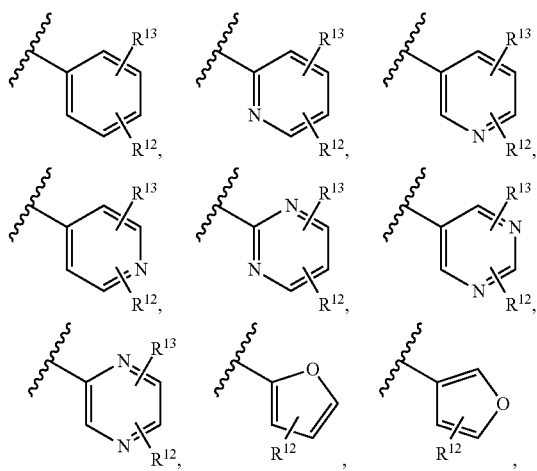

-continued

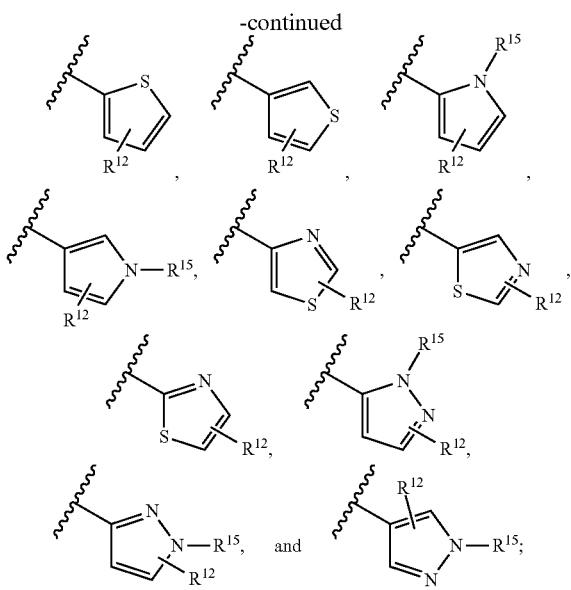

wherein:
R$^{12}$ and R$^{13}$ are independently selected from the group consisting of hydrogen, halogen, —CN, —OH, —C(O)—N(R$^{17}$)—R$^{18}$, —C(O)—O—R$^{19}$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl, wherein:
R$^{17}$ and R$^{18}$ are independently hydrogen, optionally substituted alkyl, haloalkyl, optionally substituted cycloalkyl, optionally substituted heterocycloalkyl, optionally substituted phenyl, or R$^{17}$ and R$^{18}$ together with the nitrogen atom to which they are attached form an optionally substituted heterocycloamino; and
R$^{19}$ is selected from the group consisting of hydrogen, optionally substituted alkyl, haloalkyl, optionally substituted cycloalkyl, optionally substituted heterocycloalkyl, and optionally substituted phenyl; and
R$^{15}$ is hydrogen or optionally substituted alkyl.

In another aspect, provided herein are compounds of Formula II, or pharmaceutically acceptable salts, polymorphs, solvates, tautomers, metabolites, or N-oxides thereof:

(Formula II)

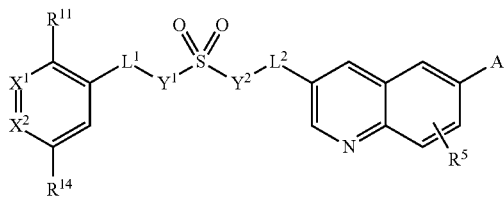

wherein:
Y$^1$ and Y$^2$ are independently a bond or —N(R$^6$)—, wherein at least one of Y$^1$ and Y$^2$ is —N(R$^6$)—;
L$^1$ and L$^2$ are independently a bond or optionally substituted alkylene;
X$^1$ is =N— or =C(R$^2$)—;
X$^2$ is =N— or =C(R$^3$)—;

R$^{11}$ is selected from the group consisting of Cl, —CN, —C(O)—N(R$^7$)—R$^8$, —C(O)—O—R$^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
R$^{14}$ is selected from the group consisting of hydrogen, Cl, Br, —CN, —C(O)—N(R$^7$)—R$^8$, —C(O)—O—R$^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
R$^2$, R$^3$, and R$^5$ are independently selected from the group consisting of hydrogen, halogen, —CN, —C(O)—N(R$^7$)—R$^8$, —C(O)—O—R$^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
R$^6$ is hydrogen, optionally substituted alkyl, optionally substituted alkenyl, or optionally substituted alkynyl;
R$^7$ and R$^8$ are independently hydrogen, optionally substituted alkyl, haloalkyl, optionally substituted cycloalkyl, optionally substituted heterocycloalkyl, optionally substituted phenyl, or R$^7$ and R$^8$ together with the nitrogen atom to which they are attached form an optionally substituted heterocycloamino;
R$^9$ is selected from the group consisting of optionally substituted alkyl, haloalkyl, optionally substituted cycloalkyl, optionally substituted heterocycloalkyl, and optionally substituted phenyl; and
A is selected from the group consisting of hydrogen, optionally substituted alkyl, —OH, optionally substituted alkoxy, optionally substituted haloalkoxy, —C(O)—N(R$^7$)—R$^8$, —C(O)—O—R$^9$, optionally substituted phenyl, and optionally substituted 5- or 6-membered heteroaryl,
wherein:
if A and R$^5$ are hydrogen and R$^1$ is methoxy, then R$^4$ is independently selected from the group consisting of hydrogen, —Cl, —CN, —C(O)—N(R$^7$)—R$^8$, —C(O)—O—R$^9$, optionally substituted C$_2$- to C$_6$-alkyl, optionally substituted cycloalkyl, optionally substituted heterocycloalkyl, optionally substituted C$_2$- to C$_6$-alkoxy, haloalkyl, haloalkoxy, optionally substituted phenyl, and optionally substituted 5- or 6-membered heteroaryl.

In some embodiments described above or below, provided herein are compounds of Formula II, wherein Y$^1$ is a bond and Y$^2$ is —N(R$^6$)—; X$^2$ is =C(R$^3$)—; L$^1$ is a bond; L$^2$ is a bond; and R$^6$ is hydrogen as shown in Formula IIe:

(Formula IIe)

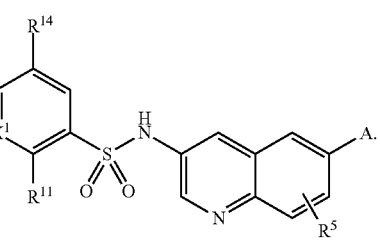

In a further aspect, provided herein are compounds Formula III, or pharmaceutically acceptable salts, polymorphs, solvates, tautomers, metabolites, or N-oxides thereof:

(Formula III)

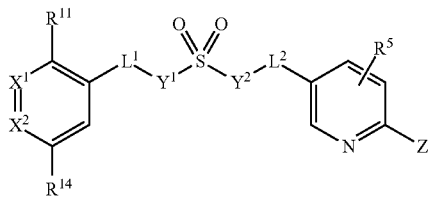

wherein:
- $Y^1$ and $Y^2$ are independently a bond or —N($R^6$)—;
- $L^1$ and $L^2$ are independently a bond or optionally substituted alkylene;
- $X^1$ is =N— or =C($R^2$)—;
- $X^2$ is =N— or =C($R^3$)—;
- $R^{11}$ is selected from the group consisting of Cl, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^{14}$ is selected from the group consisting of hydrogen, Cl, Br, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^6$ is hydrogen, optionally substituted alkyl, optionally substituted alkenyl, or optionally substituted alkynyl;
- $R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;
- $R^9$ is selected from the group consisting of optionally substituted alkyl, haloalkyl, optionally substituted cycloalkyl, optionally substituted heterocycloalkyl, and optionally substituted phenyl; and
- Z is hydrogen or —N($R^{17}$)—$R^{18}$, wherein:
  if Z and $R^5$ are hydrogen and $R^{11}$ is alkoxy, then $R^{14}$ is independently selected from the group consisting of hydrogen, Br, —CN, —C(O)—N($R^7$)—$R^8$, —C(O)—O—$R^9$, optionally substituted $C_2$- to $C_6$-alkyl, optionally substituted cycloalkyl, optionally substituted heterocycloalkyl, optionally substituted $C_2$- to $C_6$-alkoxy, haloalkyl, haloalkoxy, optionally substituted phenyl, and optionally substituted 5- or 6-membered heteroaryl; and $R^{17}$ and $R^{18}$ are independently hydrogen, optionally substituted alkyl, haloalkyl, optionally substituted cycloalkyl, optionally substituted heterocycloalkyl, optionally substituted phenyl, or $R^{17}$ and $R^{18}$ together with the nitrogen atom to which they are attached form an optionally substituted heterocycloamino.

In some embodiments described above or below, provided herein are compounds of Formula III, wherein $Y^1$ is a bond and $Y^2$ is —N($R^6$)—; $X^2$ is =C($R^3$)—; $L^1$ is a bond; $L^2$ is a bond; and $R^6$ is hydrogen as shown in Formula IIIe:

(Formula IIIe)

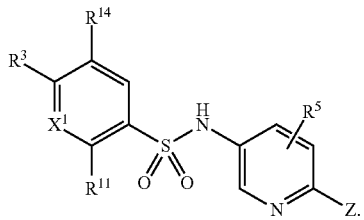

In another aspect, provided herein are compounds Formula IV, or pharmaceutically acceptable salts, polymorphs, solvates, tautomers, metabolites, or N-oxides thereof:

(Formula IV)

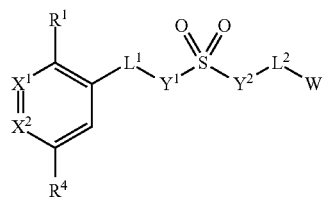

wherein:
- $Y^1$ and $Y^2$ are independently a bond or —N($R^6$)—;
- $L^1$ and $L^2$ are independently a bond or optionally substituted alkylene;
- $X^1$ is =N— or =C($R^2$)—;
- $X^2$ is =N— or =C($R^3$)—;
- $R^1$ and $R^4$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^6$ is hydrogen, optionally substituted alkyl, optionally substituted alkenyl, or optionally substituted alkynyl;
- $R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;

$R^9$ is selected from the group consisting of hydrogen, optionally substituted alkyl, haloalkyl, optionally substituted cycloalkyl, optionally substituted heterocycloalkyl, and optionally substituted phenyl; and W is selected from the group consisting of an optionally substituted 5-membered heteroaryl, an optionally substituted 6-membered heteroaryl other than pyridin-3-yl, an optionally substituted 9-membered heteroaryl, or an optionally substituted 10-membered heteroaryl other than quinolin-3-yl.

In some embodiments described above or below, provided herein are compounds of Formula IV, wherein $Y^1$ is a bond and $Y^2$ is —$N(R^6)$—; $X^2$ is =$C(R^3)$—; $L^1$ is a bond; $L^2$ is a bond; and $R^6$ is hydrogen as shown in Formula IVe:

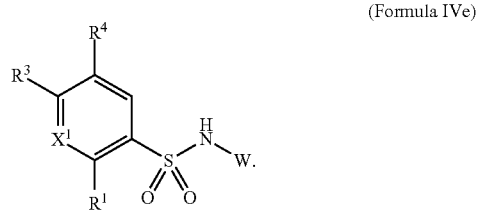

(Formula IVe)

In certain embodiments described above or below, provided herein are compounds of Formula IV, wherein W is selected from:

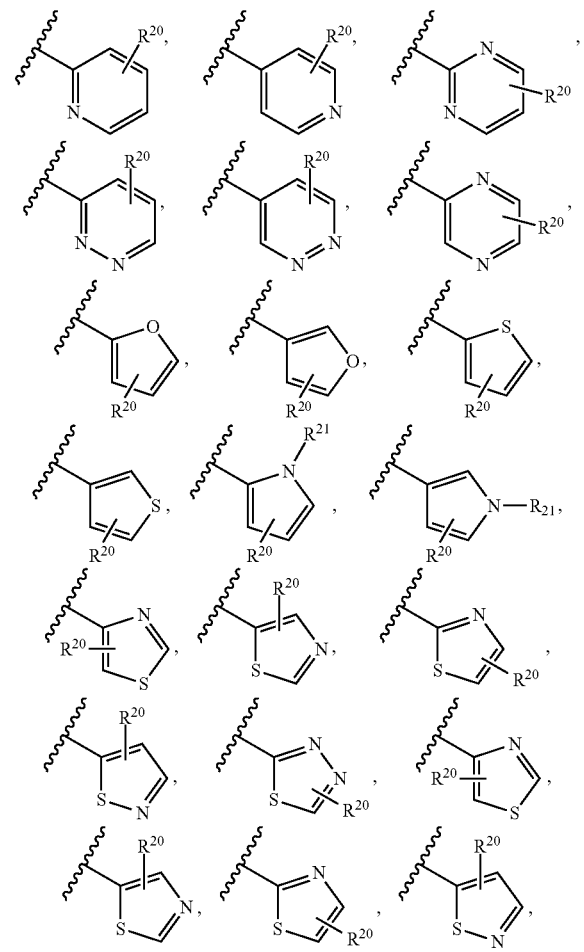

wherein:

$R^{20}$ is selected from the group consisting of hydrogen, halogen, —CN, —OH, —C(O)—N($R^{17}$)—$R^{18}$, —C(O)—O—$R^{19}$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl, wherein:

$R^{17}$ and $R^{18}$ are independently hydrogen, optionally substituted alkyl, haloalkyl, optionally substituted cycloalkyl, optionally substituted heterocycloalkyl, optionally substituted phenyl, or $R^{17}$ and $R^{18}$ together with the nitrogen atom to which they are attached form an optionally substituted heterocycloamino; and $R^{19}$ is selected from the group consisting of hydrogen, optionally substituted alkyl, haloalkyl, optionally substituted cycloalkyl, optionally substituted heterocycloalkyl, and optionally substituted phenyl; and $R^{21}$ is hydrogen or optionally substituted alkyl.

In a further aspect provided herein are pharmaceutical compositions comprising a compound of Formula I, Formula II, Formula III, or Formula IV, or a pharmaceutically acceptable salt thereof, and a pharmaceutically acceptable excipient.

In another aspect provided herein are methods of treating a disease in a subject mediated by tissue-nonspecific alkaline phosphatase (TNAP), which method comprises administering to the subject a pharmaceutical composition comprising a therapeutically effective amount of a compound of Formula I, Formula II, Formula III, or Formula IV, or a pharmaceutically acceptable salt thereof, and a pharmaceutically acceptable excipient. In some embodiments, the disease the disease is a vascular calcification, ectopic ossification in spinal ligaments, ankylosis, or osteoarthritis. In certain embodiments, the vascular calcification is an arterial calcification. In some embodiments, the vascular calcification is associated with diabetes mellitus I, diabetes mellitus II, idiopathic infantile arterial calcification (IIAC), Kawasaki disease, obesity, or increased age. In certain embodiments, the vascular calcification is associated with chronic renal disease (chronic renal insufficiency), end-stage renal disease, or pre- or post-dialysis or uremia. In other embodiments, the disease is a pathological calcification. In certain embodiments, the pathological calcification is ankylosing spondylitis, tumoral calcinosis, fibrodysplasia ossificans progressiva, progressive osseous heteroplasia, pseudoxanthoma elasticum, ankylosis, osteoarthritis, general arterial calcification in infancy (GACI), arterial calcification due to deficiency of CD73 (ACDC), Keutel syndrome, peritoneal calcification, heterotopic calcification in amputees, tibial artery calcification, bone metastasis, prosthetic calcification, or Paget's disease of bone

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
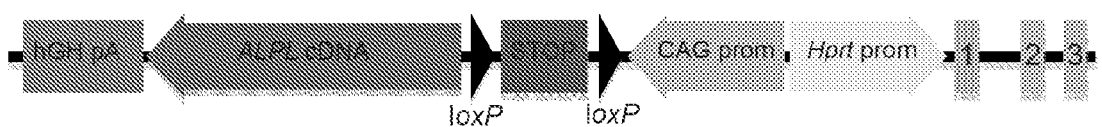
FIG. 1 is a schematic representation of the construct used to generate Hprt$^{ALPL}$ transgenic mice. The human ALPL cDNA is driven by the ubiquitous CAG promoter only when Cre-recombinase has excised the loxP-flanked STOP cassette. In recombined ES cells, Hprt is reconstituted by introduction of the human promoter and exons. The human growth hormone polyA signal was fused to the end of the ALPL cDNA. Diagram is not depicted to scale.

Alkaline phosphatases (APs) are dimeric enzymes present in most organisms (Millan J L 2006, Wiley-VCH Verlag GmbH & Co, Weinheim, Germany pp. 1-322). They catalyze the hydrolysis of phosphomonoesters with release of inorganic phosphate (Pi) and alcohol. In humans, three of the four isozymes are tissue-specific, i.e., the intestinal (IAP), placental (PLAP), and germ cell (GCAP) APs.

The fourth AP is tissue-nonspecific (TNAP or ALPL) and is expressed in bone, liver and kidney. Specifically, TNAP is expressed on the cell membranes of hypertrophic chrondrocytes, osteoblasts, and odontoblasts and is concentrated on the membranes of matrix vesicles budding from these cells. (Hoshi K, Amizuka N, Oda K, Ikehara Y, Ozawa H, Histochem Cell Biol 1997: 107:183-191; Miao D, Scutt A, H Histochem Cytochem 2002; 50: 333-340). TNAP has been found to hydrolyze extracellular pyrophosphate (ePPi) during the process of bone mineralization. (Johnson K A, Hessle L, Wennberg C, Mauro S, Narisawa S, Goding J, Sano K, Millan J L, Terkeltaub R 2000; Am J Phys Regulatory and Integrative Physiology 279: 81365-1377-17; Hessle L, Johnson K A, Anderson H C, Narisawa S, Sali A, Goding J W, Terkeltaub R, Millan J L 2002; Proc Natl Acad Sci USA 99:9445-9449; Johnson K, Goding J, Van Etten D, Sali A, Hu S I, Farley D, Krug H, Hessle L, Millan J L, Terkeltaub R 2003; J Bone Min Res 18:994-1004). This decreases the amount of ePPi, which is an inhibitor of hydroxyapatite formation, and provides phosphate (Pi) for the formation of hydroxyapatite. Thus, TNAP is an important player in bone generation, as the balance between ePPi and Pi is critical in mineralization. (Terkeltaub R A, Am J Physiol Cell Physiol 2001; 281: C1-C11).

Physiological calcification occurs in hard tissues, i.e., bone, growth-plate cartilage and dentin as part of normal development and maintenance of the skeletal system. Pathological calcification occurs in soft tissues, such as articular cartilage, cardiovascular tissues, the kidney, skin, muscles and tendon. (Kirsch T, Curr Opin Rhematol 2006: 18: 174-180). "Pathological calcification," as used herein, refers to any formation, growth or deposition of extracellular matrix hydroxyapatite (calcium phosphate) crystal deposits in any tissue other than bone, growth-plate cartilage and dentin, or to calcification in bone, growth-plate cartilage and dentin that is not part of normal development and maintenance of the skeletal system. Examples of disorders involving pathological calcification include ankylosing spondylitis, tumoral calcinosis, fibrodysplasia ossificans progressiva, progressive osseous heteroplasia, and pseudoxanthoma elasticum. Other conditions involving pathological calcification include ankylosis, osteoarthritis, general arterial calcification in infancy (GACI), arterial calcification due to deficiency of CD73 (ACDC), and Keutel syndrome. Pathological calcification has also been found to occur in peritoneal calcification, heterotopic calcification in amputees, tibial artery calcification, bone metastasis, prosthetic calcification, and Paget's disease of bone.

Vascular calcification is the most common form of pathological calcification. "Vascular calcification," as used herein, refers to formation, growth or deposition of extracellular matrix hydroxyapatite (calcium phosphate) crystal deposits in blood vessels. Vascular calcification encompasses coronary, valvular, aortic, and other blood vessel calcification. The term includes atherosclerotic and medial wall calcification.

TNAP has been found to play a role in pathological calcification of vascular tissues. Increased expression of TNAP has been found to accelerate calcification by bovine vascular smooth muscle cells (VSMCs) (Shioi A, Nishizawa Y, Jono S, Koyama H, Hosoi M, Morii H 1995, Arterioscler Thromb Vase Biot 15:2003-2009), and TNAP-rich vesicles are found at sites of mineralization in human arteries (Hsu H H, Camacho N P 1999, Atherosclerosis 143:353-362; Hui M, Li S Q, Holmyard D, Cheng P 1997, Calcified Tissue International 60:467-72; Hui M, Tenenbaum H C 1998, Anatomical Record 253:91-94. Tanimura A, McGregor D H, Anderson H C 1986, J Exp Pathol 2:261-273. Tanimura A, McGregor D H, Anderson H C 1986, J Exp Pathol 2:275-297). In addition, calcification of rat aorta and human valve interstitial cells in culture has been shown to be dependent on TNAP activity (Lomashvili K, Cobbs S, Hennigar R, Hardcastle K, O'Neill W C 2004, J Am. Soc. Nephrol. 15: 1392-1401; Mathieu P, Voisine P, Pepin A, Shetty R, Savard N, Dagenais F 2005, J Heart Valve Disease 14:353-357).

Vascular calcification is a well-recognized and common complication of chronic kidney disease (CKD) (Giachelli, C. J. Am. Soc. Nephrol. 15: 2959-64, 2004; Raggi, P. et al. J. Am. Coll. Cardiol. 39: 695-701, 2002). Studies show that abnormalities in calcium and phosphorus metabolism, resulting in increased HA deposition contribute to the development of arterial calcification, and to cardiovascular disease, in patients with end-stage renal disease (Goodman, W. et al. N. Engl. J. Med. 342: 1478-83, 2000; Guerin, A. et al.

Nephrol. Dial. Transplant 15:1014-21, 2000; Vattikuti, R. & Towler, D. Am. J. Physiol. Endocrinol. Metab. 286: E686-96, 2004). While the causes of vascular calcification in CKD remain to be elucidated, associated risk factors include age, gender, hypertension, time on dialysis, diabetes and glucose intolerance, obesity, and cigarette smoking (Zoccali C. Nephrol. Dial. Transplant 15: 454-7, 2000). These conventional risk factors, however, do not adequately explain the high mortality rates from cardiovascular causes in the patient population.

CKD is generally accompanied by secondary hyperparathyroidism (HPT). HPT is characterized by elevated parathyroid hormone (PTH) serum levels and disordered mineral metabolism. Elevations in serum calcium, phosphorus, and HA in patients with secondary HPT have been associated with an increased risk of vascular calcification (Chertow, G. et al. Kidney Int. 62: 245-52, 2002; Goodman, W. et al. N. Engl. J. Med. 342: 1478-83, 2000; Raggi, P. et al. J. Am. Coll. Cardiol. 39: 695-701, 2002). Commonly used therapeutic interventions for secondary HPT, such as calcium-based phosphate binders and doses of active vitamin D sterols can result in hypercalcemia and hyperphosphatemia (Chertow, G. et al. Kidney hit. 62: 245-52, 2002; Tan, A. et al. Kidney Int 51: 317-23, 1997; Gallieni, M. et al. Kidney Int 42: 1191-8, 1992), which are associated with the development or exacerbation of vascular calcification.

Some patients with end-stage renal disease develop a severe form of occlusive arterial disease called calciphylaxis or calcific uremic arteriolopathy. This syndrome is characterized by extensive calcium deposition in small arteries (Gipstein R. et al. Arch Intern Med 136: 1273-80, 1976; Richens G. et al. J Am Acad. Dermatol. 6: 537-9, 1982). In patients with this disease, arterial calcification and vascular occlusion lead to tissue ischemia and necrosis. Involvement of peripheral vessels can cause ulceration of the skin of the lower legs or gangrene of the digits of the feet or hands. Ischemia and necrosis of the skin and subcutaneous adipose tissue of the abdominal wall, thighs and/or buttocks are features of a proximal form of calcific uremic arteriolopathy (Budisavljevic M. et al. J Am Soc Nephrol. 7: 978-82, 1996; Ruggian J. et al. Am. J. Kidney Dis. 28: 409-14, 1996).

"Atherosclerotic calcification" refers vascular calcification occurring in atheromatous plaques along the intimal layer of arteries. Atherosclerotic calcification is associated with lipid-laden macrophages and intimal hyperplasia. "Medial calcification," "medial wall calcification," or "Monckeberg's sclerosis," as used herein, means calcification characterized by the presence of calcium in the medial wall of arteries. Medial calcification occurs in the media of a blood vessel in conjunction with a phenotypic transformation of smooth muscle cells into osteoblast-like cells.

Both forms of vascular calcification are associated with various diseases and disorders. For instance, both atherosclerotic and medial calcification has been found to be common in uremic patients (Proudfoot, D & Shanahan, C. Herz 26: 245-51, 2001; Chen, N. & Moe, S. Semin Nephrol 24: 61-8, 2004) and in patients with diabetes mellitus I and II. Conditions characterized by medial wall calcification include idiopathic infantile arterial calcification (IIAC), Kawasaki disease, end-stage renal disease, diabetes, and obesity. Medial wall calcification is also a general characteristic of increased age.

Atherosclerotic calcification is usually greatest in large, well-developed lesions, and such lesions have been found to increase with age (Wexler L. et al. Circulation 94: 1175-92, 1996; Rumberger J. et al. Mayo Clin Proc 1999; 74: 243-52). The extent of atherosclerotic calcification in patients with atherosclerosis generally corresponds to severity of disease. Unlike medial wall calcification, atherosclerotic vascular lesions, whether or not they contain calcium, impinge upon the arterial lumen and compromise blood flow. The localized deposition of calcium within atherosclerotic plaques likely occurs because of inflammation due to oxidized lipids and other oxidative stresses and infiltration by monocytes and macrophages (Berliner J. et al. Circulation 91: 2488-96, 1995).

Current therapies to normalize serum mineral levels or to decrease, inhibit, or prevent extraskeletal calcification are of limited efficacy and cause unacceptable side effects. Therefore, there exists a need for an effective method of inhibiting and preventing extraskeletal calcification.

Due to its role in hydrolyzing ePPi, inhibiting TNAP function reduces pathological calcification. In some embodiments, administration of a compound of Formula I-IV retards, reverses, or prevents the formation, growth or deposition of extracellular matrix hydroxyapatite crystal deposits. In certain embodiments, the invention provides a method of inhibiting, decreasing or preventing pathological calcification in an individual. In some embodiments, the invention provides a method of inhibiting, decreasing or preventing vascular calcification in an individual. In some embodiments, the present invention provides a method of treating or preventing atherosclerotic calcification, medial calcification, vascular calcification associated with diabetes mellitus I and II, idiopathic infantile arterial calcification (IIAC), Kawasaki disease, obesity, and/or increased age. In some embodiments, the invention provides a method of inhibiting, decreasing or preventing vascular calcification associated with chronic renal disease (chronic renal insufficiency) or end-stage renal disease.

DEFINITIONS

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —NH₂ radical.
"Cyano" or "nitrile" refers to the —CN radical.
"Hydroxy" or "hydroxyl" refers to the —OH radical.
"Nitro" refers to the —NO₂ radical.
"Oxo" refers to the =O substituent.
"Thioxo" refers to the =S substituent.

"Alkyl" refers to a straight or branched hydrocarbon chain radical, which is fully saturated or comprises unsaturations, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, vinyl, allyl, propynyl, and the like. Alkyl comprising unsaturations include alkenyl and alkynyl groups. Unless stated otherwise specifically in the specification, an alkyl group may be optionally substituted as described below.

"Alkylene" or "alkylene chain" refers to a straight or branched divalent hydrocarbon chain, as described for alkyl above. Unless stated otherwise specifically in the specification, an alkylene group may be optionally substituted as described below.

"Alkoxy" refers to a radical of the formula —OR$_a$ where R$_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloaklyls having from three to fifteen carbon atoms, from three to ten carbon atoms, from three to eight carbon atoms, from three to six carbon atoms, from three to five carbon atoms, or three to four carbon atoms. Monocyclic cyclcoalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted. Illustrative examples of cycloalkyl groups include, but are not limited to, the following moieties:

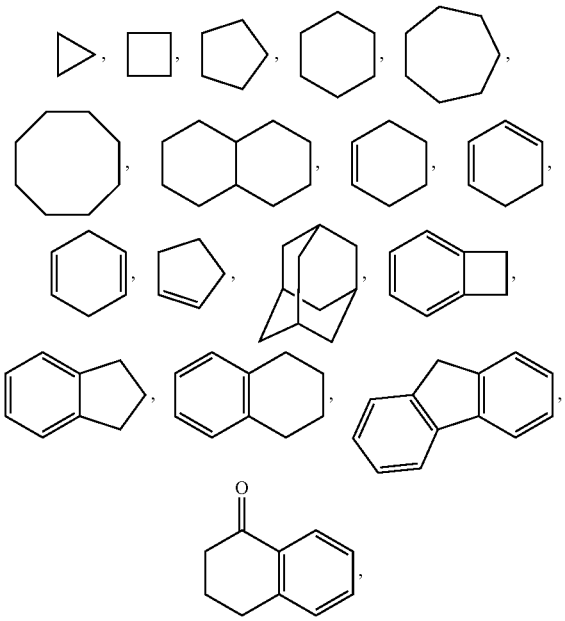

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —OR$_a$ where R$_a$ is a haloalkyl radical as defined. Unless stated otherwise specifically in the specification, a haloalkoxy group may be optionally substituted as described below.

"Heteroycycloalkyl" or "heterocyclyl" or "heterocyclic ring" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4,15-crown-5,18-crown-6,21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

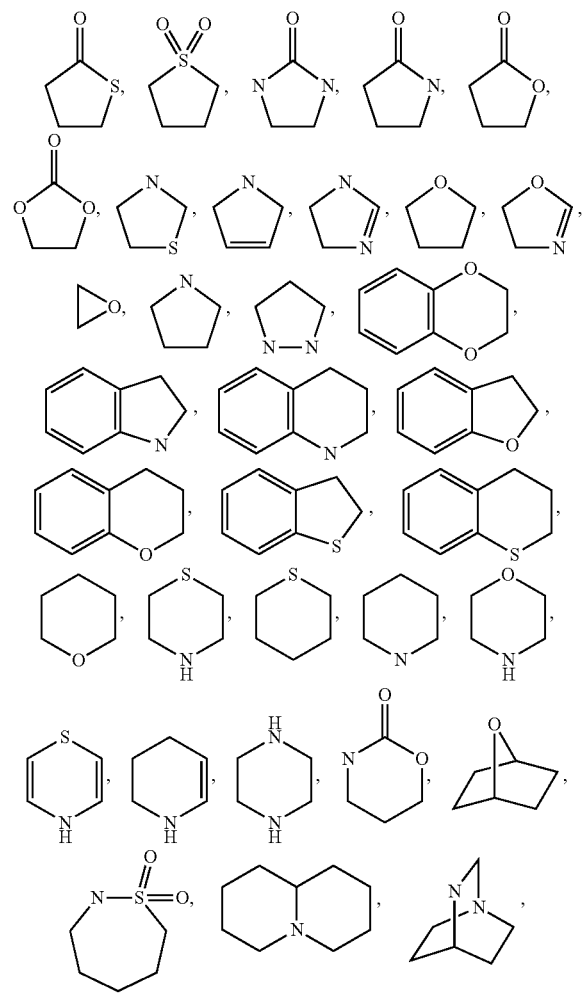

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzopyranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (e.g. alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, —CO$_2$H, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen, e.g., cancer does not metastasize and the like) or alleviation of the condition (e.g., reduction in tumor size, remission of cancer, absence of symptoms of autoimmune disease and the like). In other embodiments, treatment also includes prophylactic treatment (e.g., administration of a composition described herein when an individual is suspected to be suffering from a condition described herein).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

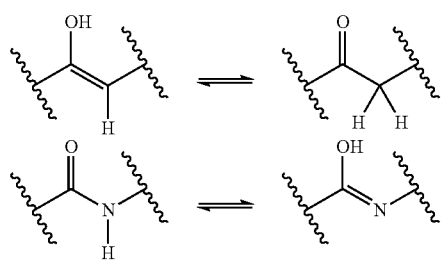

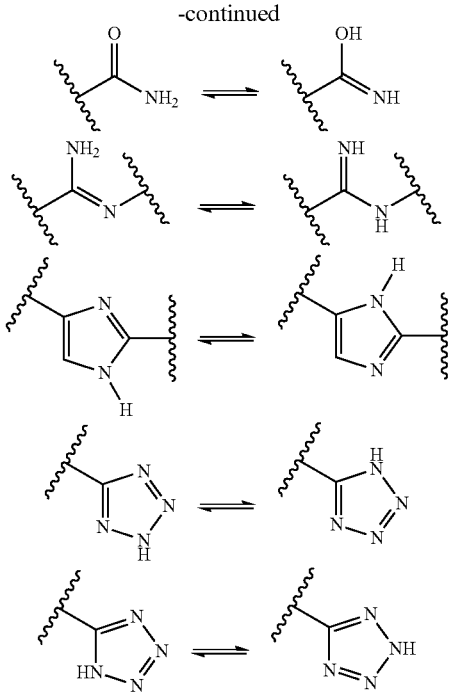

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

Compounds

Described herein are compounds that modulate the activity of TNAP. In some embodiments, the compounds described herein inhibit TNAP. In certain embodiments, the compounds described herein are useful in the treatment of conditions associated with hyper-mineralization.

In one aspect, provided herein are compounds of Formula I, or a pharmaceutically acceptable salts, polymorphs, solvates, tautomers, metabolites, or N-oxides thereof:

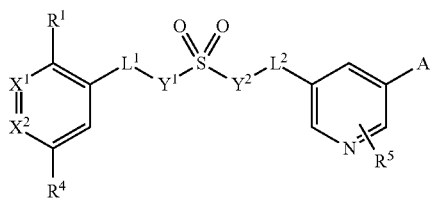

(Formula I)

wherein:
- $Y^1$ and $Y^2$ are independently a bond or —N($R^6$)—, wherein at least one of $Y^1$ and $Y^2$ is —N($R^6$)—;
- $L^1$ and $L^2$ are independently a bond or optionally substituted alkylene;
- $X^1$ is =N— or =C($R^2$)—;
- $X^2$ is =N— or =C($R^3$)—;
- $R^1$ and $R^4$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^6$ is hydrogen, optionally substituted alkyl, optionally substituted alkenyl, or optionally substituted alkynyl;
- $R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;
- $R^9$ is selected from the group consisting of hydrogen, optionally substituted alkyl, haloalkyl, optionally substituted cycloalkyl, optionally substituted heterocycloalkyl, and optionally substituted phenyl; and
- A is selected from the group consisting of —C(O)—N($R^7$)—$R^8$, —C(O)—O—$R^9$, optionally substituted phenyl, and optionally substituted 5- or 6-membered heteroaryl.

In some embodiments described above or below, provided herein are compounds of Formula I, wherein $Y^1$ is a bond and $Y^2$ is —N($R^6$)— as shown in Formula (Ia):

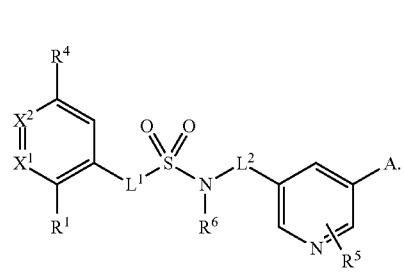

(Formula Ia)

In certain embodiments described above or below, provided herein are compounds of Formula I, wherein $Y^1$ is a bond and $Y^2$ is —N($R^6$)—; and $X^2$ is =C($R^3$)— as shown in Formula (Ib):

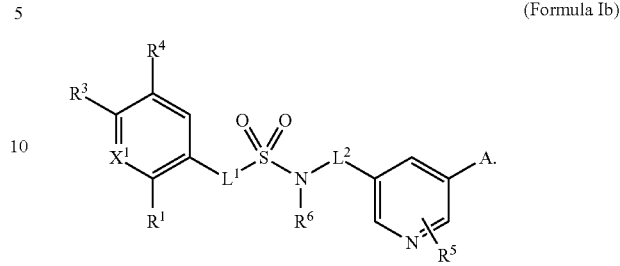

(Formula Ib)

In some embodiments described above or below, provided herein are compounds of Formula I, wherein $Y^1$ is a bond and $Y^2$ is —N($R^6$)—; $X^2$ is =C($R^3$)—; and $L^1$ is a bond as shown in Formula Ic:

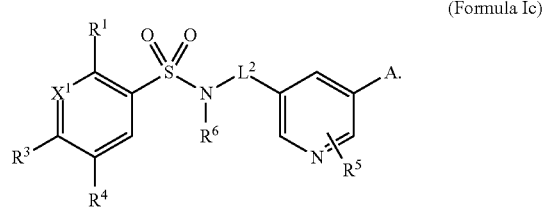

(Formula Ic)

In certain embodiments described above or below, provided herein are compounds of Formula I, wherein $Y^1$ is a bond and $Y^2$ is —N($R^6$)—; $X^2$ is =C($R^3$)—; $L^1$ is a bond; and $L^2$ is a bond as shown in Formula Id:

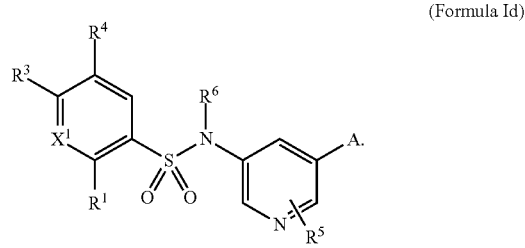

(Formula Id)

In some embodiments described above or below, provided herein are compounds of Formula I, wherein $Y^1$ is a bond and $Y^2$ is —N($R^6$)—; $X^2$ is =C($R^3$)—; $L^1$ is a bond; $L^2$ is a bond; and $R^6$ is hydrogen as shown in Formula Ie:

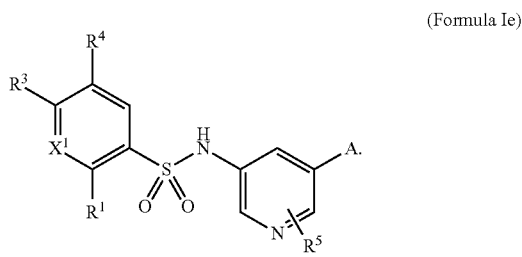

(Formula Ie)

For any embodiments described above or below, provided herein are compounds of Formula I, wherein $L^2$ is an optionally substituted alkylene.

For any embodiments described above or below, provided herein are compounds of Formula I, wherein $X^1$ is $=C(R^2)$—.

For any embodiments described above or below, provided herein are compounds of Formula I, wherein $R^2$, $R^3$, and $R^5$ are independently selected from the group consisting of hydrogen, —F, —Cl, —Br, —CN, —C(O)—OMe, methyl, —OMe, and —OCF$_3$. In some embodiments, $R^2$, $R^3$, and $R^5$ are independently selected from the group consisting of hydrogen, Cl, methyl, and —OMe. In certain embodiments, $R^2$ and $R^3$ are hydrogen.

For any embodiments described above or below, provided herein are compounds of Formula I, wherein W and $R^4$ are independently selected from the group consisting of hydrogen, —F, —Cl, —Br, —CN, —C(O)—N($R^7$)—$R^8$, —C(O)—O—$R^9$, methyl, —OMe, —OCF$_3$, optionally substituted phenyl, and optionally substituted 5- or 6-membered heteroaryl. In some embodiments, $R^4$ is optionally substituted phenyl or optionally substituted 5- or 6-membered heteroaryl. In certain embodiments, $R^4$ is —C(O)—N($R^7$)—$R^8$, —C(O)—O—$R^9$. In some embodiments, $R^1$ and $R^4$ are independently selected from the group consisting of —F, —Cl, —Br, —CN, —OMe, and —OCF$_3$. In certain embodiments, $R^1$ is —OMe or —OCF$_3$. In some embodiments, $R^1$ is —OMe and $R^4$ is —Cl.

In some embodiments described above or below, provided herein are compounds of Formula I, wherein A is optionally substituted phenyl or optionally substituted 5- or 6-membered heteroaryl. In some embodiments, A is selected from:

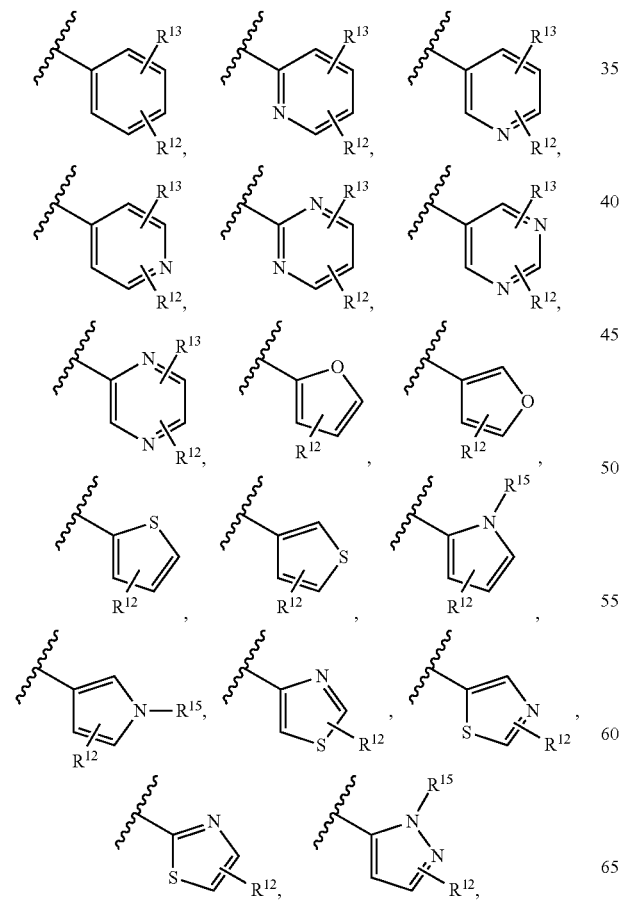

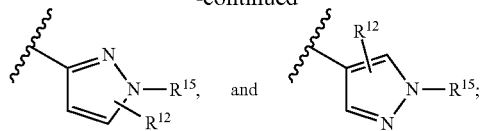

wherein:
$R^{12}$ and $R^{13}$ are independently selected from the group consisting of hydrogen, halogen, —CN, —OH, —C(O)—N($R^{17}$)—$R^{18}$, —C(O)—O—$R^{19}$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl, wherein:
$R^{17}$ and $R^{18}$ are independently hydrogen, optionally substituted alkyl, haloalkyl, optionally substituted cycloalkyl, optionally substituted heterocycloalkyl, optionally substituted phenyl, or $R^{17}$ and $R^{18}$ together with the nitrogen atom to which they are attached form an optionally substituted heterocycloamino; and $R^{19}$ is selected from the group consisting of hydrogen, optionally substituted alkyl, haloalkyl, optionally substituted cycloalkyl, optionally substituted heterocycloalkyl, and optionally substituted phenyl; and $R^{15}$ is hydrogen or optionally substituted alkyl.

In certain embodiments described above or below, provided herein are compounds of Formula I, wherein A is

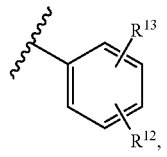

wherein $R^{12}$ and $R^{13}$ are independently selected from the group consisting of hydrogen, —F, —CN, —OH, —OMe, and —C(O)—O-Me.

In certain embodiments described above or below, provided herein are compounds of Formula I, wherein A is

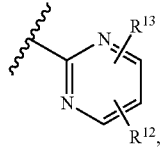

wherein $R^{12}$ and $R^{13}$ are independently selected from the group consisting of hydrogen, —F, —CN, —OH, —OMe, and —C(O)—O-Me.

In certain embodiments described above or below, provided herein are compounds of Formula I, wherein A is

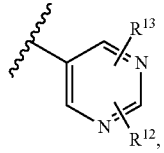

wherein $R^{12}$ and $R^{13}$ are independently selected from the group consisting of hydrogen, —F, —CN, —OH, —OMe, and —C(O)—O-Me.

In certain embodiments described above or below, provided herein are compounds of Formula I, wherein A is

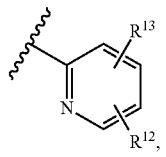

wherein $R^{12}$ and $R^{13}$ are independently selected from the group consisting of hydrogen, —F, —CN, —OH, —OMe, and —C(O)—O-Me.

In certain embodiments described above or below, provided herein are compounds of Formula I, wherein A is

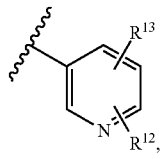

wherein $R^{12}$ and $R^{13}$ are independently selected from the group consisting of hydrogen, —F, —CN, —OH, —OMe, and —C(O)—O-Me.

In some embodiments described above or below, provided herein are compounds of Formula I, wherein A is —C(O)—O—$R^9$. In certain embodiments, $R^9$ is selected from hydrogen, optionally substituted alkyl, optionally substituted cycloalkyl, and optionally substituted phenyl. In some embodiments, $R^9$ is selected from hydrogen, methyl, ethyl, propyl, cyclohexyl, and phenyl.

In certain embodiments described above or below, provided herein are compounds of Formula I, wherein A is —C(O)—N($R^7$)—$R^8$. In some embodiments, $R^7$ and $R^8$ together with the nitrogen atom to which they are attached form an optionally substituted heterocycloamino. In certain embodiments, the optionally substituted heterocycloamino is an optionally substituted pyrrolidine, an optionally substituted piperidine, an optionally substituted morpholine, or an optionally substituted piperazine. In some embodiments, $R^7$ is hydrogen and $R^8$ is optionally substituted alkyl, optionally substituted cycloalkyl, or optionally substituted phenyl. In certain embodiments, $R^7$ is hydrogen and $R^8$ is selected from methyl, ethyl, propyl, 2-dimethylaminoethyl, 2-methoxyethyl, cyclohexyl, and phenyl. In some embodiments, $R^7$ and $R^8$ are hydrogen.

In another aspect, provided herein are compounds of Formula II, or pharmaceutically acceptable salts, polymorphs, solvates, tautomers, metabolites, or N-oxides thereof:

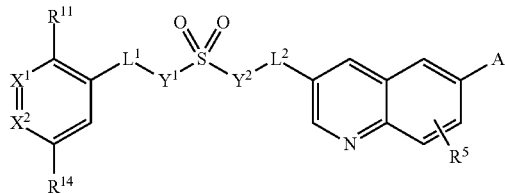

(Formula II)

wherein:

$Y^1$ and $Y^2$ are independently a bond or —N($R^6$)—, wherein at least one of $Y^1$ and $Y^2$ is —N($R^6$)—;

$L^1$ and $L^2$ are independently a bond or optionally substituted alkylene;

$X^1$ is =N— or =C($R^2$)—;

$X^2$ is =N— or =C($R^3$)—;

$R^{11}$ is selected from the group consisting of Cl, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^{14}$ is selected from the group consisting of hydrogen, Cl, Br, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^6$ is hydrogen, optionally substituted alkyl, optionally substituted alkenyl, or optionally substituted alkynyl;

$R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;

$R^9$ is selected from the group consisting of optionally substituted alkyl, haloalkyl, optionally substituted cycloalkyl, optionally substituted heterocycloalkyl, and optionally substituted phenyl; and A is selected from the group consisting of hydrogen, optionally substituted alkyl, —OH, optionally substituted alkoxy, optionally substituted haloalkoxy, —C(O)—N($R^7$)—$R^8$, —C(O)—O—$R^9$, optionally substituted phenyl, and optionally substituted 5- or 6-membered heteroaryl, wherein:

if A and $R^5$ are hydrogen and $R^1$ is methoxy, then $R^4$ is independently selected from the group consisting of hydrogen, —Cl, —CN, —C(O)—N($R^7$)—$R^8$, —C(O)—O—$R^9$, optionally substituted $C_2$- to $C_6$-alkyl, optionally substituted cycloalkyl, optionally substituted heterocycloalkyl, optionally substituted $C_2$- to $C_6$-alkoxy, haloalkyl, haloalkoxy, optionally substituted phenyl, and optionally substituted 5- or 6-membered heteroaryl.

In some embodiments described above or below, provided herein are compounds of Formula II, wherein $Y^1$ is a bond and $Y^2$ is —N($R^6$)— as shown in Formula IIa:

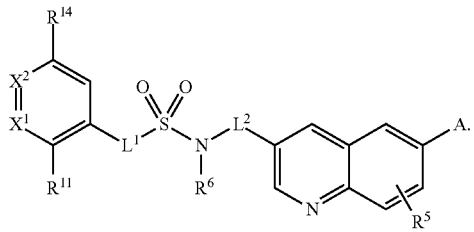
(Formula IIa)

In certain embodiments described above or below, provided herein are compounds of Formula II, wherein $Y^1$ is a bond and $Y^2$ is —N($R^6$)—; and $X^2$ is =C($R^3$)— as shown in Formula IIb:

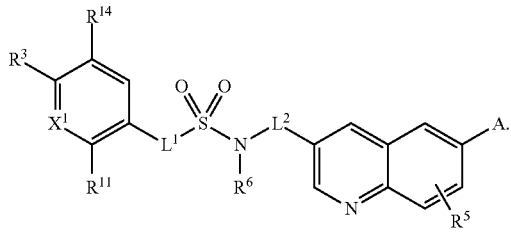
(Formula IIb)

In some embodiments described above or below, provided herein are compounds of Formula II, wherein $Y^1$ is a bond and $Y^2$ is —N($R^6$)—; $X^2$ is =C($R^3$)—; and $L^1$ is a bond as shown in Formula IIc.

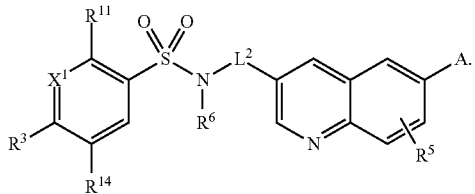
(Formula IIc)

In certain embodiments described above or below, provided herein are compounds of Formula II, wherein $Y^1$ is a bond and $Y^2$ is —N($R^6$)—; $X^2$ is =C($R^3$)—; $L^1$ is a bond; and $L^2$ is a bond as shown in Formula IId:

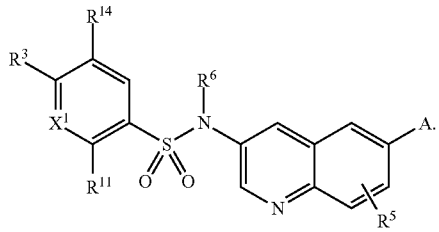
(Formula IId)

In some embodiments described above or below, provided herein are compounds of Formula II, wherein $Y^1$ is a bond and $Y^2$ is —N($R^6$)—; $X^2$ is =C($R^3$)—; $L^1$ is a bond; $L^2$ is a bond; and $R^6$ is hydrogen as shown in Formula IIe:

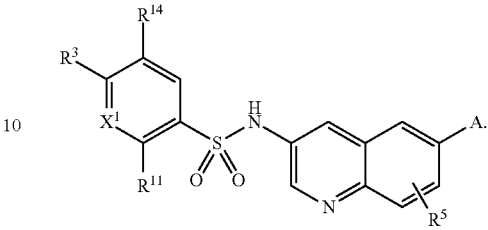
(Formula IIe)

For any embodiments described above or below, provided herein are compounds of Formula II, wherein $L^2$ is an optionally substituted alkylene.

For any embodiments described above or below, provided herein are compounds of Formula II, wherein $X^1$ is =C($R^2$)—.

For any embodiments described above or below, provided herein are compounds of Formula II, wherein $R^2$, $R^3$, and $R^5$ are independently selected from the group consisting of hydrogen, —Cl, —Br, —CN, —C(O)—OMe, methyl, —OMe, and —OCF$_3$. In some embodiments, $R^2$, $R^3$, and $R^5$ are independently selected from the group consisting of hydrogen, Cl, methyl, and —OMe. In certain embodiments, $R^2$ and $R^3$ are hydrogen.

In some embodiments described above or below, provided herein are compounds of Formula II, wherein $R^{11}$ is selected from the group consisting of —Cl, —CN, —C(O)—N($R^7$)—$R^8$, —C(O)—O—$R^9$, methyl, —OMe, —OCF$_3$, optionally substituted phenyl, and optionally substituted 5- or 6-membered heteroaryl; and $R^{14}$ is selected from the group consisting of hydrogen, —Cl, —Br, —CN, —C(O)—N($R^7$)—$R^8$, —C(O)—O—$R^9$, methyl, —OMe, —OCF$_3$, optionally substituted phenyl, and optionally substituted 5- or 6-membered heteroaryl. In certain embodiments, $R^{14}$ is optionally substituted phenyl or optionally substituted 5- or 6-membered heteroaryl. In some embodiments, $R^{14}$ is —C(O)—N($R^7$)—$R^8$ or —C(O)—O—$R^9$. In certain embodiments, $R^{11}$ and $R^{14}$ are independently selected from the group consisting of —Cl, —Br, —CN, —OMe, and —OCF$_3$. In some embodiments, $R^{11}$ is —OMe or —OCF$_3$.

In certain embodiments described above or below, provided herein are compounds of Formula II, wherein A is —C(O)—O—$R^9$. In some embodiments, $R^9$ is hydrogen or methyl.

In some embodiments described above or below, provided herein are compounds of Formula II, wherein A is —C(O)—N($R^7$)—$R^8$. In certain embodiments, $R^7$ is hydrogen and $R^8$ is optionally substituted alkyl, optionally substituted cycloalkyl, or optionally substituted phenyl. In some embodiments, $R^7$ is hydrogen and $R^8$ is selected from hydrogen, methyl, ethyl, propyl, cyclopropyl, and cyclohexyl.

In certain embodiments described above or below, provided herein are compounds of Formula II, wherein A is selected from optionally substituted alkyl, —OH, optionally substituted alkoxy, and optionally substituted haloalkoxy. In some embodiments, A is methyl, dimethylaminomethyl, —OH, —OMe, or —OCF$_3$.

In a further aspect, provided herein are compounds Formula III, or pharmaceutically acceptable salts, polymorphs, solvates, tautomers, metabolites, or N-oxides thereof:

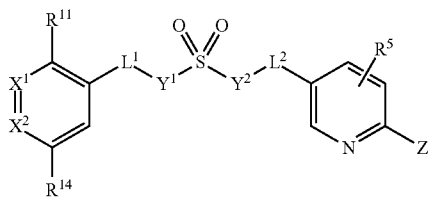

(Formula III)

wherein:
- $Y^1$ and $Y^2$ are independently a bond or —N($R^6$)—;
- $L^1$ and $L^2$ are independently a bond or optionally substituted alkylene;
- $X^1$ is =N— or =C($R^2$)—;
- $X^2$ is =N— or =C($R^3$)—;
- $R^{11}$ is selected from the group consisting of Cl, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^{14}$ is selected from the group consisting of hydrogen, Cl, Br, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^6$ is hydrogen, optionally substituted alkyl, optionally substituted alkenyl, or optionally substituted alkynyl;
- $R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;
- $R^9$ is selected from the group consisting of optionally substituted alkyl, haloalkyl, optionally substituted cycloalkyl, optionally substituted heterocycloalkyl, and optionally substituted phenyl; and
- Z is hydrogen or —N($R^{17}$)—$R^{18}$, wherein:
  - if Z and $R^5$ are hydrogen and $R^{11}$ is alkoxy, then $R^{14}$ is independently selected from the group consisting of hydrogen, Br, —CN, —C(O)—N($R^7$)—$R^8$, —C(O)—O—$R^9$, optionally substituted $C_2$- to $C_6$-alkyl, optionally substituted cycloalkyl, optionally substituted heterocycloalkyl, optionally substituted $C_2$- to $C_6$-alkoxy, haloalkyl, haloalkoxy, optionally substituted phenyl, and optionally substituted 5- or 6-membered heteroaryl; and
  - $R^{17}$ and $R^{18}$ are independently hydrogen, optionally substituted alkyl, haloalkyl, optionally substituted cycloalkyl, optionally substituted heterocycloalkyl, optionally substituted phenyl, or $R^{17}$ and $R^{18}$ together with the nitrogen atom to which they are attached form an optionally substituted heterocycloamino.

In some embodiments described above or below, provided herein are compounds of Formula III, wherein $Y^1$ is a bond and $Y^2$ is —N($R^6$)— as shown in Formula (IIIa):

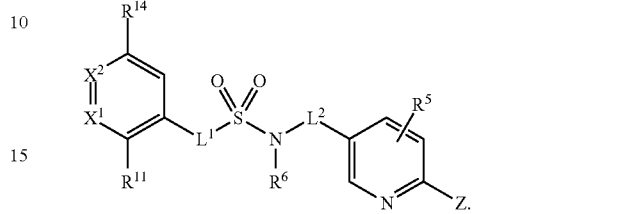

(Formula IIIa)

In certain embodiments described above or below, provided herein are compounds of Formula III, wherein $Y^1$ is a bond and $Y^2$ is —N($R^6$)—; and $X^2$ is =C($R^3$)— as shown in Formula IIIb:

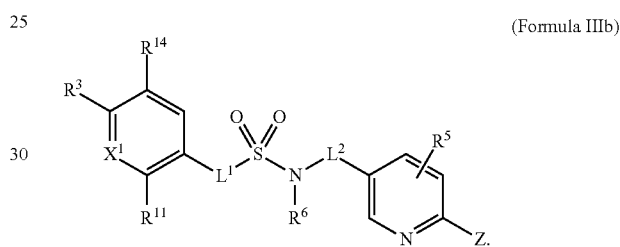

(Formula IIIb)

In some embodiments described above or below, provided herein are compounds of Formula III, wherein $Y^1$ is a bond and $Y^2$ is —N($R^6$)—; $X^2$ is =C($R^3$)—; and $L^1$ is a bond as shown in Formula IIIc:

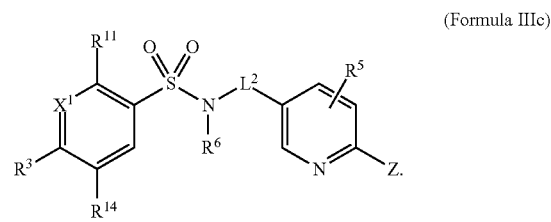

(Formula IIIc)

In certain embodiments described above or below, provided herein are compounds of Formula III, wherein $Y^1$ is a bond and $Y^2$ is —N($R^6$)—; $X^2$ is =C($R^3$)—; $L^1$ is a bond; and $L^2$ is a bond as shown in Formula IIId:

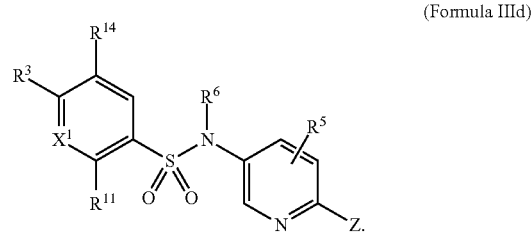

(Formula IIId)

In some embodiments described above or below, provided herein are compounds of Formula III, wherein $Y^1$ is a bond and $Y^2$ is —N($R^6$)—; $X^2$ is =C($R^3$)—; $L^1$ is a bond; $L^2$ is a bond; and $R^6$ is hydrogen as shown in Formula IIIe:

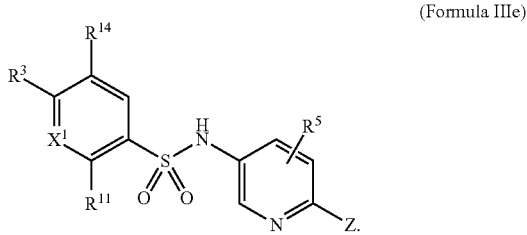

(Formula IIIe)

For any embodiments described above or below, provided herein are compounds of Formula III, wherein $L^2$ is an optionally substituted alkylene.

For any embodiments described above or below, provided herein are compounds of Formula III, wherein $X^1$ is =C($R^2$)—.

For any embodiments described above or below, provided herein are compounds of Formula III, wherein $R^2$, $R^3$, and $R^5$ are independently selected from the group consisting of hydrogen, —Cl, —Br, —CN, —C(O)—OMe, methyl, —OMe, and —OCF$_3$. In some embodiments, $R^2$, $R^3$, and $R^5$ are independently selected from the group consisting of hydrogen, Cl, methyl, and —OMe. In certain embodiments, $R^2$ and $R^3$ are hydrogen.

In some embodiments provided above or below, provided herein are compounds of Formula III, wherein $R^{11}$ is selected from the group consisting of Cl, —CN, —C(O)—N($R^7$)—$R^8$, —C(O)—O—$R^9$, methyl, —OMe, —OCF$_3$, optionally substituted phenyl, and optionally substituted 5- or 6-membered heteroaryl; and $R^{14}$ is selected from the group consisting of hydrogen, Cl, Br, —CN, —C(O)—N($R^7$)—$R^8$, —C(O)—O—$R^9$, methyl, —OMe, —OCF$_3$, optionally substituted phenyl, and optionally substituted 5- or 6-membered heteroaryl. In certain embodiments, $R^{14}$ is optionally substituted phenyl or optionally substituted 5- or 6-membered heteroaryl. In some embodiments, $R^{14}$ is —C(O)—N($R^7$)—$R^8$ or —C(O)—O—$R^9$. In certain embodiments, $R^{11}$ and $R^{14}$ are independently selected from the group consisting of —Cl, —Br, —CN, —OMe, and —OCF$_3$. In some embodiments, $R^{11}$ is —OMe or —OCF$_3$.

In certain embodiments provided above or below, provided herein are compounds of Formula III, wherein Z is —N($R^{17}$)—$R^{18}$. In some embodiments, Z is amino, methylamino, dimethylamino, diethylamino, 2-methoxyethylamino, dimethylamino, 2-(dimethylamino)ethylamino, morpholine, or 4-methylpiperazinyl.

In another aspect, provided herein are compounds Formula IV, or pharmaceutically acceptable salts, polymorphs, solvates, tautomers, metabolites, or N-oxides thereof:

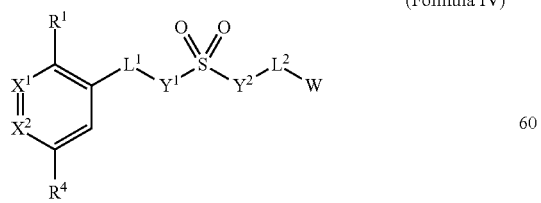

(Formula IV)

wherein:
$Y^1$ and $Y^2$ are independently a bond or —N($R^6$)—;
$L^1$ and $L^2$ are independently a bond or optionally substituted alkylene;

$X^1$ is =N— or =C($R^2$)—;
$X^2$ is =N— or =C($R^3$)—;
$R^1$ and $R^4$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
$R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
$R^6$ is hydrogen, optionally substituted alkyl, optionally substituted alkenyl, or optionally substituted alkynyl;
$R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;
$R^9$ is selected from the group consisting of hydrogen, optionally substituted alkyl, haloalkyl, optionally substituted cycloalkyl, optionally substituted heterocycloalkyl, and optionally substituted phenyl; and
W is selected from the group consisting of an optionally substituted 5-membered heteroaryl, an optionally substituted 6-membered heteroaryl other than pyridin-3-yl, an optionally substituted 9-membered heteroaryl, or an optionally substituted 10-membered heteroaryl other than quinolin-3-yl.

In some embodiments described above or below, provided herein are compounds of Formula IV, wherein $Y^1$ is a bond and $Y^2$ is —N($R^6$)— as shown in Formula IVa:

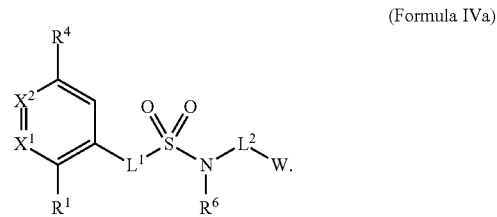

(Formula IVa)

In certain embodiments described above or below, provided herein are compounds of Formula IV, wherein $Y^1$ is a bond and $Y^2$ is —N($R^6$)—; and $X^2$ is =C($R^3$)— as shown in Formula IVb:

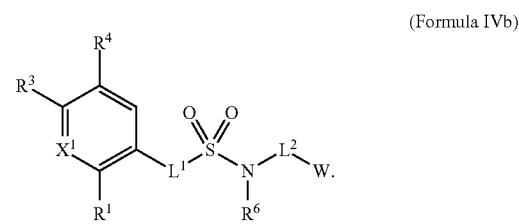

(Formula IVb)

In some embodiments described above or below, provided herein are compounds of Formula IV, wherein $Y^1$ is a bond and $Y^2$ is —N($R^6$)—; $X^2$ is =C($R^3$)—; and $L^1$ is a bond as shown in Formula IVc.

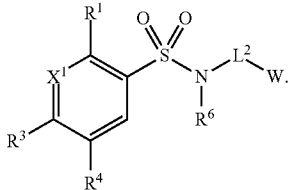

(Formula IVc)

In certain embodiments described above or below, provided herein are compounds of Formula IV, wherein $Y^1$ is a bond and $Y^2$ is —N($R^6$)—; $X^2$ is =C($R^3$)—; $L^1$ is a bond; and $L^2$ is a bond as shown in Formula IVd:

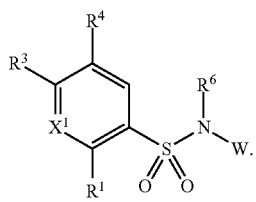

(Formula IVd)

In some embodiments described above or below, provided herein are compounds of Formula IV, wherein $Y^1$ is a bond and $Y^2$ is —N($R^6$)—; $X^2$ is =C($R^3$)—; $L^1$ is a bond; $L^2$ is a bond; and $R^6$ is hydrogen as shown in Formula IVe:

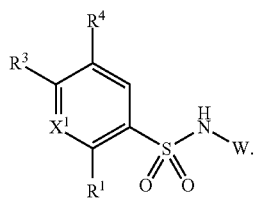

(Formula IVe)

For any embodiments described above or below, provided herein are compounds of Formula IV, wherein $L^2$ is an optionally substituted alkylene.

For any embodiments described above or below, provided herein are compounds of Formula IV, wherein $X^1$ is =C($R^2$)—.

For any embodiments described above or below, provided herein are compounds of Formula IV, wherein $R^2$, $R^3$, and $R^5$ are independently selected from the group consisting of hydrogen, —Cl, —Br, —CN, —C(O)—OMe, methyl, —OMe, and —OCF$_3$. In some embodiments, $R^2$, $R^3$, and $R^5$ are independently selected from the group consisting of hydrogen, Cl, methyl, and —OMe. In certain embodiments, $R^2$ and $R^3$ are hydrogen.

In some embodiments described above or below, provided herein are compounds of Formula IV, wherein W and $R^4$ are independently selected from the group consisting of hydrogen, —Cl, —Br, —CN, —C(O)—N($R^7$)—$R^8$, —C(O)—O—$R^9$, methyl, —OMe, —OCF$_3$, optionally substituted phenyl, and optionally substituted 5- or 6-membered heteroaryl. In embodiments, $R^4$ is optionally substituted phenyl or optionally substituted 5- or 6-membered heteroaryl. In some embodiments, $R^4$ is —C(O)—N($R^7$)—$R^8$ or —C(O)—O—$R^9$. In certain embodiments, $R^1$ and $R^4$ are independently selected from the group consisting of —Cl, —Br, —CN, —OMe, and —OCF$_3$. In some embodiments, $R^1$ is —OMe or —OCF$_3$.

In certain embodiments described above or below, provided herein are compounds of Formula IV, wherein W is selected from:

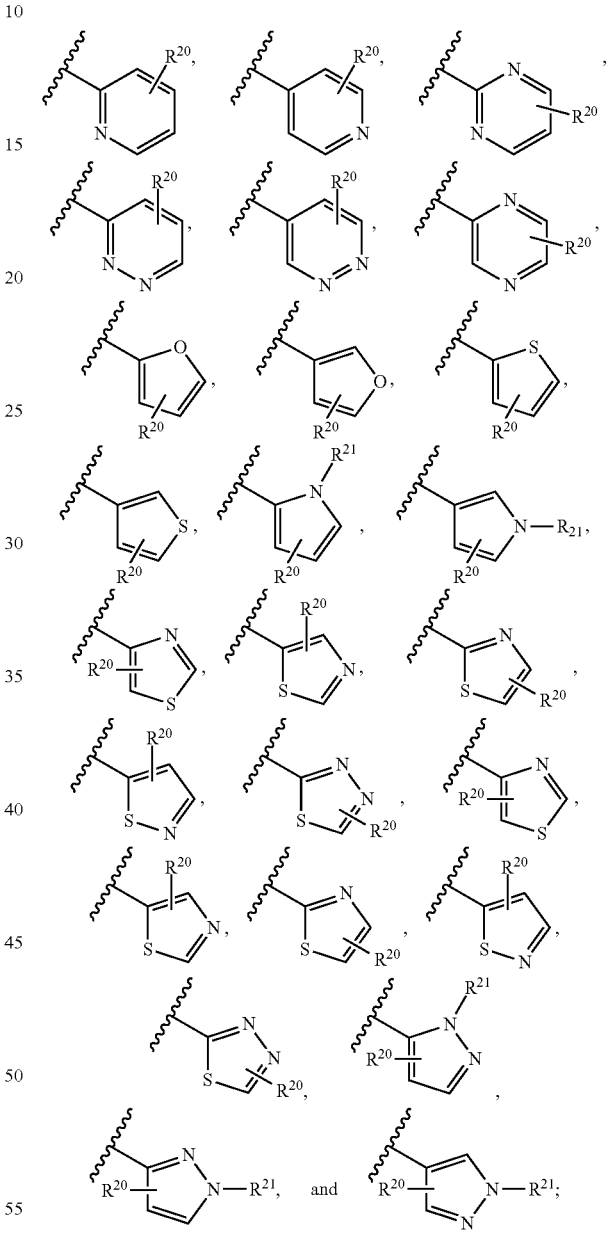

wherein:
$R^{20}$ is selected from the group consisting of hydrogen, halogen, —CN, —OH, —C(O)—N($R^{17}$)—$R^{18}$, —C(O)—O—$R^{19}$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl, wherein:
$R^{17}$ and $R^{18}$ are independently hydrogen, optionally substituted alkyl, haloalkyl, optionally substituted cycloalkyl, optionally substituted heterocycloalkyl, optionally substituted phenyl, or $R^{17}$ and $R^{18}$ together with the nitrogen atom to which they are attached form an optionally substituted heterocycloamino; and $R^{19}$ is selected from the group consisting of hydrogen, optionally substituted alkyl, haloalkyl, optionally substituted cycloalkyl, optionally substituted heterocycloalkyl, and optionally substituted phenyl; and $R^{21}$ is hydrogen or optionally substituted alkyl.

In some embodiments described above or below, provided herein is a compound of Formula IV, wherein $R^{20}$ is selected from hydrogen, optionally substituted alkyl, and haloalkyl. In certain embodiments, $R^{20}$ is methyl or trifluoromethyl. In some embodiments, $R^{21}$ is methyl.

Preparation of Compounds

Described herein are compounds of Formula I-IV that inhibit the activity of TNAP, and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions comprising at least one such compound or a pharmaceutically acceptable salt, pharmaceutically acceptable solvate, pharmaceutically active metabolite or pharmaceutically acceptable prodrug of such compound, and a pharmaceutically acceptable excipient are also provided.

Compounds of Formula I-IV may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001); Green and Wuts, PROTECTIVE GROUPS IN ORGANIC SYNTHESIS 3rd Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds Disclosed Herein

Isomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays.

Tritiated, i.e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The invention provides for methods of treating diseases by administering such polymorphs. The invention further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

Prodrugs are generally drug precursors that, following administration to an individual and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety. (See for example Bundgaard, "Design and Application of Prodrugs" in *A Textbook of Drug Design and Development*, Krosgaard-Larsen and Bundgaard, Ed., 1991, Chapter 5, 113-191, which is incorporated herein by reference).

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of compounds described herein can be prepared by methods described herein are otherwise known in the art (for further details see Saulnier et al., *Bioorganic and Medicinal Chemistry Letters*, 1994, 4, 1985). By way of example only, appropriate prodrugs can be prepared by reacting a non-derivatized compound with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for another derivative or active compound.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Compounds having free amino, amido, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

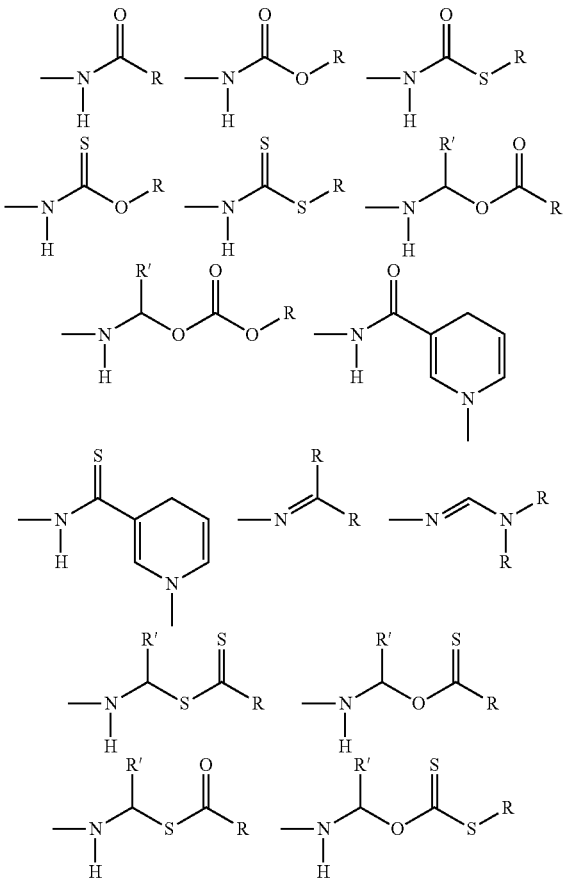

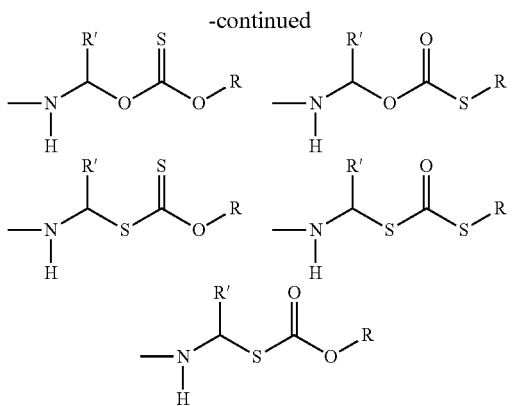

as well as sulfonamides and phosphonamides.

In certain instances, sites on any aromatic ring portions are susceptible to various metabolic reactions, therefore incorporation of appropriate substituents on the aromatic ring structures, can reduce, minimize or eliminate this metabolic pathway.

Metabolites

In some embodiments, compounds of Formula I-IV are susceptible to various metabolic reactions Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, the compounds of Formula I-IV described herein are metabolized upon administration to an organism in need to produce a metabolite that is then used to produce a desired effect, including a desired therapeutic effect.

Pharmaceutical Compositions/Formulations

In a further aspect provided herein are pharmaceutical compositions comprising a compound of Formula I, Formula II, Formula III, or Formula IV, or a pharmaceutically acceptable salt thereof, and a pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula I-IV and at least one pharmaceutically acceptable inactive ingredient. In some embodiments, the compounds described herein are administered as pharmaceutical compositions in which a compound of Formula I-IV is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula I-IV with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including a compound of Formula I-IV are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula I-IV as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Methods

In another aspect provided herein are methods of treating a disease in a subject mediated by tissue-nonspecific alkaline phosphatase (TNAP), which method comprises administering to the subject a pharmaceutical composition comprising a compound of Formula I, Formula II, Formula III, or Formula IV, or a pharmaceutically acceptable salt thereof, and a pharmaceutically acceptable excipient. In some embodiments, the disease is a medial vascular calcification, ectopic ossification in spinal ligaments, ankylosis, or osteoarthritis. In certain embodiments, the disease is arterial calcification.

In some embodiments, administration of a therapeutically effective amount of a compound of Formula I-IV retards or reverses the formation, growth or deposition of extracellular matrix hydroxyapatite crystal deposits. In certain embodiments, administration of a compound of Formula I-IV retards or reverses the formation, growth or deposition of extracellular matrix hydroxyapatite crystal deposits. In some embodiments, administration of the compound of the invention prevents the formation, growth or deposition of extracellular matrix hydroxyapatite crystal deposits.

In some embodiments, the invention provides a method of inhibiting, decreasing, treating, or preventing pathological calcification in an individual by administration of a therapeutically effective amount of a compound of Formula I-IV. In some embodiments, the present invention provides a method of treating or preventing a disorder characterized by pathological calcification, such as ankylosing spondylitis, tumoral calcinosis, fibrodysplasia ossificans progressiva, progressive osseous heteroplasia, pseudoxanthoma elasticum, ankylosis, osteoarthritis, general arterial calcification in infancy (GACI), arterial calcification due to deficiency of CD73 (ACDC), Keutel syndrome, peritoneal calcification, heterotopic calcification/ossification in amputees, tibial artery calcification, bone metastasis, prosthetic calcification, and/or Paget's disease of bone.

In certain embodiments, the invention provides a method of inhibiting, decreasing, treating, or preventing vascular calcification in an individual by administration of a compound of Formula I-IV. In some embodiments, the present invention provides a method of treating or preventing atherosclerotic calcification, medial calcification and other conditions characterized by vascular calcification. In some embodiments, the present invention provides a method of treating or preventing vascular calcification associated with diabetes mellitus I and II, idiopathic infantile arterial calcification (IIAC), Kawasaki disease, obesity, and/or increased age.

In some embodiments, the invention provides a method of inhibiting, decreasing, treating, or preventing vascular calcification associated with chronic renal disease (chronic renal insufficiency) or end-stage renal disease by administration of a therapeutically effective amount of a compound of Formula I-IV. In some embodiments, the invention provides a method of inhibiting, decreasing or preventing vascular calcification associated with pre- or post-dialysis uremia. In some embodiments, the invention provides a method of inhibiting, decreasing or preventing vascular calcification-associated chronic kidney disease, wherein the chronic kidney disease is associated with secondary hyperparathyroidism (HPT) characterized by elevated parathyroid hormone (PTH) levels. In some embodiments, the invention provides a method of inhibiting, decreasing or preventing symptoms associated with calciphylaxis, or calcific uremic arteriolopathy. In some embodiments, the invention provides a method of administering an effective amount of a TNAP inhibitor for reducing serum PTH without causing aortic calcification. In some embodiments, the invention provides a method of administering an effective amount of a TNAP inhibitor (e.g., a compound of Formula I-IV) for reducing serum creatinine level or preventing increase of serum creatinine level.

Assessment of Vascular Calcification

Methods of detecting and measuring vascular calcification are well known in the art. In some embodiments, methods of measuring calcification include direct methods of detecting and measuring extent of calcium-phosphorus depositions in blood vessels.

In some embodiments, direct methods of measuring vascular calcification comprise in vivo imaging methods such as plain film roentgenography, coronary arteriography; fluoroscopy, including digital subtraction fluoroscopy; cinefluorography; conventional, helical, and electron beam computed tomography; intravascular ultrasound (IVUS); magnetic resonance imaging; and transthoracic and transesophageal echocardiography. Persons skilled in the art most commonly use fluoroscopy and EBCT to detect calcification noninvasively. Coronary interventionalists use cinefluorography and IVUS to evaluate calcification in specific lesions before angioplasty.

In some embodiments, vascular calcification can be detected by plain film roentgenography. The advantage of this method is availability of the film and the low cost of the method, however, the disadvantage is its low sensitivity (Kelley M. & Newell J. Cardiol Clin. 1: 575-595, 1983). In some embodiments, fluoroscopy can be used to detect calcification in coronary arteries. Although fluoroscopy can detect moderate to large calcifications, its ability to identify small calcific deposits is low (Loecker et al. J. Am. Coll.

Cardiol. 19: 1167-1172, 1992). Fluoroscopy is widely available in both inpatient and outpatient settings and is relatively inexpensive. In some embodiments, vascular detection can be detected by conventional computed tomography (CT). Because calcium attenuates the x-ray beam, computed tomography (CT) is extremely sensitive in detecting vascular calcification. While conventional CT appears to have better capability than fluoroscopy to detect coronary artery calcification, its limitations are slow scan times resulting in motion artifacts, volume averaging, breathing misregistration, and inability to quantify amount of plaque (Wexler et al. Circulation 94: 1175-1192, 1996).

In some embodiments, calcification can be detected by helical or spiral computer tomography, which has considerably faster scan times than conventional CT. Overlapping sections also improve calcium detection. Coronary calcium imaging by helical CT has a sensitivity of 91% and a specificity of 52% when compared with angiographically significant coronary obstructive disease (Shemesh et al. Radiology 197: 779-783, 1995). Double-helix CT scanners appear to be more sensitive than single-helix scanners in detection of coronary calcification because of their higher resolution and thinner slice capabilities.

In some embodiments, Electron Beam Computed Tomography (EBCT) can be used for detection of vascular calcification. EBCT uses an electron gun and a stationary tungsten "target" rather than a standard x-ray tube to generate x-rays, permitting very rapid scanning times. Originally referred to as cine or ultrafast CT, the term EBCT is now used to distinguish it from standard CT scans because modern spiral scanners are also achieving subsecond scanning times. For purposes of detecting coronary calcium, EBCT images are obtained in 100 ms with a scan slice thickness of 3 mm. Thirty to 40 adjacent axial scans are obtained by table incrementation. The scans, which are usually acquired during one or two separate breath-holding sequences, are triggered by the electrocardiographic signal at 80% of the RR interval, near the end of diastole and before atrial contraction, to minimize the effect of cardiac motion. The rapid image acquisition time virtually eliminates motion artifact related to cardiac contraction. The unopacified coronary arteries are easily identified by EBCT because the lower CT density of periarterial fat produces marked contrast to blood in the coronary arteries, while the mural calcium is evident because of its high CT density relative to blood. Additionally, the scanner software allows quantification of calcium area and density. An arbitrary scoring system has been devised based on the x-ray attenuation coefficient, or CT number measured in Hounsfield units, and the area of calcified deposits (Agatston et al. J. Am. Coll. Cardiol. 15:827-832, 1990). A screening study for coronary calcium can be completed within 10 or 15 minutes, requiring only a few seconds of scanning time. Electron beam CT scanners are more expensive than conventional or spiral CT scanners and are available in relatively fewer sites.

In some embodiments, intravascular ultrasound (IVUS) can be used for detecting vascular calcification, in particular, coronary atherosclerosis (Waller et al. Circulation 85: 2305-2310, 1992). By using transducers with rotating reflectors mounted on the tips of catheters, it is possible to obtain cross-sectional images of the coronary arteries during cardiac catheterization. The sonograms provide information not only about the lumen of the artery but also about the thickness and tissue characteristics of the arterial wall. Calcification is seen as a hyperechoic area with shadowing: fibrotic noncalcified plaques are seen as hyperechoic areas without shadowing (Honye et al. Trends Cardiovasc Med. 1: 305-311, 1991). The disadvantages in use of IVUS, as opposed to other imaging modalities, are that it is invasive and currently performed only in conjunction with selective coronary angiography, and it visualizes only a limited portion of the coronary tree. Although invasive, the technique is clinically important because it can show atherosclerotic involvement in patients with normal findings on coronary arteriograms and helps define the morphological characteristics of stenotic lesions before balloon angioplasty and selection of atherectomy devices (Tuzcu et al. J. Am. Coll. Cardiol. 27: 832-838, 1996).

In some embodiments, vascular calcification can be measured by magnetic resonance imaging (MRI). In some embodiments, vascular calcification can be measured by transthoracic (surface) echocardiography, which is particularly sensitive to detection of mitral and aortic valvular calcification. In some embodiments, vascular calcification can be assessed ex vivo by Van Kossa method. This method relies upon the principle that silver ions can be displaced from solution by carbonate or phosphate ions due to their respective positions in the electrochemical series. The argentaffin reaction is photochemical in nature and the activation energy is supplied from strong visible or ultra-violet light. Since the demonstrable forms of tissue carbonate or phosphate ions are invariably associated with calcium ions the method can be considered as demonstrating sites of tissue calcium deposition.

Other methods of direct measuring calcification may include, but not limited to, immuno fluorescent staining and densitometry. In another aspect, methods of assessing vascular calcification include methods of measuring determinants and/or risk factors of vascular calcification. Such factors include, but are not limited to, serum levels of phosphorus, calcium, and calcium phosphorus product, parathyroid hormone (PTH), low-density lipoprotein cholesterol (LDL), high-density lipoprotein cholesterol (HDL), triglycerides, and creatinine Methods of measuring these factors are well known in the art. Other methods of assessing vascular calcification include assessing factors of bone formation. Such factors include bone formation markers such as bone-specific alkaline phosphatase (BSAP), osteocalcin (OC), carboxyterminal propeptide of type I collagen (PICP), and aminoterminal propeptide of type I collagen (PINP); serum bone resorption markers such as cross-linked C-telopeptide of type I collagen (ICTP), tartrate-resistant acid phosphatase, TRACP and TRAP5B, N-telopeptide of collagen cross-links (NTx), and C-telopeptide of collagen cross-links (CTx); and urine bone resorption markers, such as hydroxyproline, free and total pyridinolines (Pyd), free and total deoxypyridinolines (Dpd), N-telopeptide of collagen cross-links (NTx), and C-telopeptide of collagen crosslinks (CTx).

Administration of Pharmaceutical Composition

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In some embodiments, TNAP inhibitors (e.g., a compound of Formula I-IV) is administered alone or in combination with other drugs for treating vascular calcification, such as vitamin D sterols and/or RENAGEL®. Vitamin D sterols can include calcitriol, alfacalcidol, doxercalciferol, maxacalcitol or paricalcitol. In certain embodiments, the compounds of Formula I-IV are used with calcimimetics, vitamins and their analogs, antibiotics, lanthanum carbonate, lipid-lowering agents, such as LIPITOR®, anti-hypertensives, anti-inflammatory agents (steroidal and non-steroidal), inhibitors of pro-inflammatory cytokine (ENBREL®, KINERET®), and cardiovascular agents.

In some embodiments, the compositions disclosed herein are administered before, concurrently, or after administration of calcimimetics, vitamin D sterols and/or RENAGEL®. The dosage regimen for treating a disease condition with the combination therapy disclosed herein is selected in accordance with a variety of factors, including the type, age, weight, sex and medical condition of the patient, the severity of the disease, the route of administration, and the particular compound employed, and thus can vary widely.

In some embodiments, TNAP inhibitors (e.g., compound of Formula I-IV) are administered before or after administration of vitamin D sterols. In some embodiments, TNAP inhibitors are coadministered with vitamin D sterols. In certain embodiments, the methods disclosed herein are practiced to attenuate the mineralizing effect of calcitriol on vascular tissue. In some embodiments, the methods disclosed herein are used to reverse the effect of calcitriol of increasing the serum levels of calcium, phosphorus and calcium-phosphorus product thereby preventing or inhibiting vascular calcification. In some embodiments, the methods disclosed herein are used to stabilize or decrease serum creatinine levels. In some embodiments, in addition to creatinine level increase due to a disease, a further increase in creatinine level is due to treatment with vitamin D sterols such as calcitriol.

In additional embodiments, the compounds of Formula I-IV are administered in conjunction with surgical and non-surgical treatments. In one aspect, the methods disclosed herein can be practiced in injunction with dialysis.

In some embodiments, compounds of Formula I-IV and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like. In some embodiments, a compound of Formula I-IV is administered directly to the site of hyper-mineralization using a drug delivery device or formulation. In certain embodiments, the drug delivery device or formulation releases the compound for Formula I-IV over a period of time at the local target site.

It is further understood and herein contemplated that the disclosed inhibitors can be administered in conjunction with balloons tipped catheters and/or stents. It is contemplated herein that the stents, catheters, and/or balloons can be linked with the TNAP inhibitors (e.g., compounds of Formula I-IV) or administered concurrently with the use. By "linking" or "linked" is meant any method of placing a TNAP inhibitor onto the stent such as soaking, coating, infusing, or any known chemical methods. Also contemplated herein are time released methods of attaching a TNAP inhibitor to a balloon or stent. Thus, for example disclosed herein are stents used for treatment of a vascular condition, wherein the stent has been coated with a TNAP inhibitor. Also disclosed herein are methods of inhibiting, decreasing or preventing vascular calcification comprising administering to an individual a stent, balloon, and/or catheter that has been linked to a TNAP inhibitor. Thus, for example disclosed herein are methods of inhibiting, decreasing or preventing vascular calcification comprising administering to a subject a vascular stent coated with a TNAP inhibitor.

It is further understood and herein contemplated that the disclosed inhibitors can be administered in conjunction with prostheses, such as a prosthetic heart valve. It is contemplated herein that the prosthesis can be linked with the TNAP inhibitors or administered concurrently with the use. By "linking" or "linked" is meant any method of placing a TNAP inhibitor onto the prosthesis, such as soaking, coating, infusing, or any known chemical methods. Also contemplated herein are time released methods of attaching a TNAP inhibitor to a prosthesis. Thus, for example disclosed herein are prostheses used for treatment of a vascular condition, wherein the prosthesis has been coated with a TNAP inhibitor. Also disclosed herein are methods of inhibiting, decreasing or preventing prosthesis calcification, comprising administering to an individual a prosthesis that has been linked to a TNAP inhibitor.

It is further understood and herein contemplated that the disclosed inhibitors can be administered as a drug implant. It is contemplated herein that the TNAP inhibitors can be formulated into a sustained release particle for localized tissue insertion. Also contemplated herein are time released methods of localized administration of TNAP to a particular region of tissue. Thus, for example disclosed herein are TNAP inhibitor drug implants used for treatment of heterotopic ossification, wherein the sustained-release TNAP inhibitor drug implant is locally placed at a site of undesired hydroxyapatite deposition, such as subcutaneously at a site of amputation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

EXAMPLES

The following preparations of compound of Formula I-IV and intermediates are given to enable those of skill in the art to more clearly understand and to practice the present invention. They should not be considered as limiting the scope of the invention, but merely as illustrative and representative thereof.

SYNTHETIC EXAMPLES

Example I

Example I-1

5-Chloro-2-methoxy-N-pyridin-3-yl-benzenesulfonamide

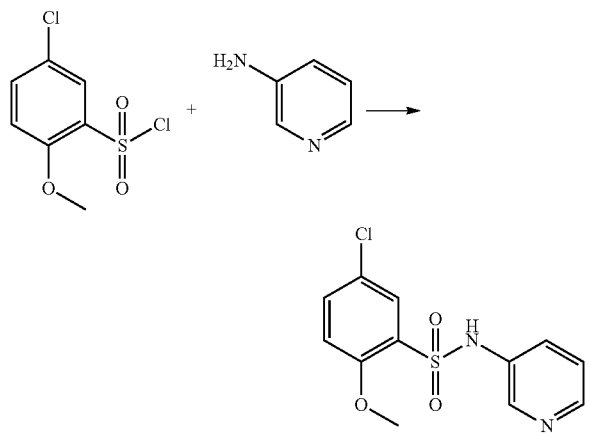

A mixture of 5-chloro-2-methoxy-benzenesulfonyl chloride (213 mg, 0.88 mmol), pyridine-3-ylamine (100 mg, 0.88 mmol), DMAP (10 mg, cat.) in pyridine (5 mL) was stirred at 50° C. for 2 h. LCMS indicated the reaction was complete. The solvent was evaporated in vacuum. The residue was treated with DCM (5 mL). The suspension was collected by filtration to give crude product, which was purified by prep-HPLC to afford 100 mg (yield: 38%) of 5-chloro-2-methoxy-N-pyridin-3-yl-benzenesulfonamide as pale yellow solid.

$^1$H NMR (DMSO-d6): δ=10.45 (1H, brs), 8.37 (1H, s), 8.32 (1H, d), 7.74 (1H, s), 7.69-7.64 (2H, m), 7.38 (1H, q), 7.25 (1H, d), 3.85 (3H, s). MS: m/z 398.9 (M+H$^+$).

Example I-2

2-Methoxy-N-pyridin-3-yl-5-trifluoromethyl-benzenesulfonamide

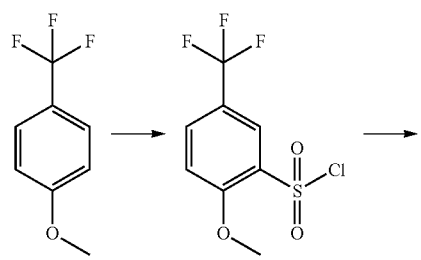

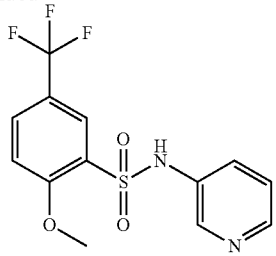

Step 1: To chlorosulfuric acid (15 mL) was added 1-methoxy-4-trifluoromethyl-benzene (3.0 g, 17 mmol) portionwise at 0° C. The mixture was stirred at room temperature overnight. The mixture was poured into ice. the aqueous layer was extracted with EtOAc (50 mL×3). The extracts were dried over Na$_2$SO$_4$ and the solution was filtered through a pad of silica gel, dried in vacuum to afford 500 mg (yield: 11%) of 2-methoxy-5-trifluoromethyl-benzenesulfonyl chloride as white solid.

$^1$H NMR (DMSO-d6): δ=7.90 (1H, d), 7.67 (1H, dd), 7.18 (1H, d), 3.84 (3H, s).

Step 2: The procedure is similar to Example I-1.

$^1$H NMR (DMSO-d6): δ=10.70 (1H, brs), 8.35 (1H, d), 8.28 (1H, dd), 8.03-7.98 (2H, m), 7.62-7.58 (1H, m), 7.43-7.34 (2H, m), 3.92 (3H, s). MS: m/z 332.9 (M+H$^+$).

Example I-3

5-Bromo-2-methoxy-N-pyridin-3-yl-benzenesulfonamide

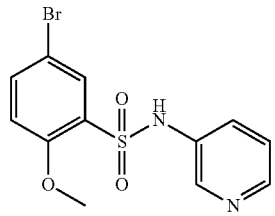 [SMILES: COc1ccc(Br)cc1S(=O)(=O)Nc1cccnc1]

This compound was prepared as described in Example I-1.

$^1$H NMR (DMSO-d6): δ=10.45 (1H, brs), 8.30 (1H, d), 8.23 (1H, d), 7.78-7.74 (2H, m), 7.49 (1H, d), 7.28 (1H, dd), 7.17 (1H, d), 3.85 (3H, s). MS: m/z 344.8 (M+H$^+$).

Example I-4

2-Methoxy-4-methyl-N-pyridin-3-yl-benzenesulfonamide

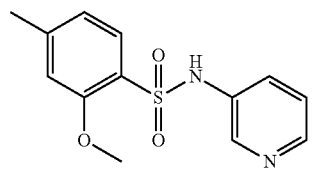 [SMILES: COc1cc(C)ccc1S(=O)(=O)Nc1cccnc1]

This compound was prepared as described in Example I-1.

1H NMR (DMSO-d6): δ=10.80 (1H, brs), 8.34 (1H, s), 8.26 (1H, d), 7.66 (1H, d), 7.63-7.60 (1H, m), 7.42-7.36 (1H, m), 7.01 (1H, s), 6.86 (1H, d), 3.82 (3H, s), 2.32 (3H, s). MS: m/z 279.0 (M+H$^+$).

Example I-5

2,4-Dimethoxy-N-pyridin-3-yl-benzenesulfonamide

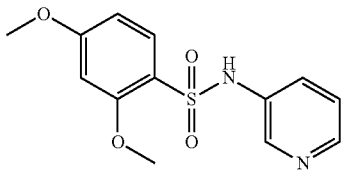 [SMILES: COc1ccc(S(=O)(=O)Nc2cccnc2)c(OC)c1]

This compound was prepared as described in Example I-1.

$^1$H NMR (DMSO-d6): δ=10.17 (1H, brs), 8.29 (1H, d), 8.18 (1H, d), 7.69 (1H, d), 7.51 (1H, dd), 7.30-7.23 (1H, m), 6.64 (1H, d), 6.58 (1H, d), 3.85 (3H, s), 3.79 (3H, s). MS: m/z 295.0 (M+H$^+$).

Example I-6

5-Cyano-2-methoxy-N-pyridin-3-yl-benzenesulfonamide

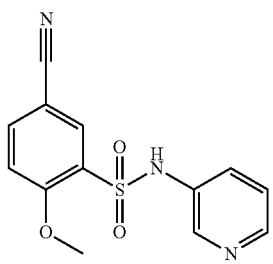 [SMILES: COc1ccc(C#N)cc1S(=O)(=O)Nc1cccnc1]

A mixture of 5-bromo-2-methoxy-N-(pyridin-3-yl)benzenesulfonamide (100 mg, 0.29 mmol), Zn(CN)$_2$ (136 mg, 1.16 mmol) and Pd(PPh$_3$)$_4$ (5% cat. amount) in DMF (3 mL) was bubbled with N$_2$ for 5 min and heated at 120° C. for 1 h under microwave irridation. After cooled to room temperature, the solvent was evaporated in vacuum. The residue was partitioned between DCM (5 mL) and H$_2$O (10 mL). The mixture was extracted with DCM (15 mL×3). The extracts were dried over Na$_2$SO$_4$ and concentrated in vacuum to give crude compound, which was purified by prep-HPLC to afford 30 mg (yield: 36%) of 5-cyano-2-methoxy-N-pyridin-3-yl-benzenesulfonamide as white solid.

$^1$H NMR (DMSO-d6): δ=10.57 (1H, brs), 8.30 (1H, s), 8.23 (1H, s), 8.17 (1H, s), 8.08 (1H, d), 7.49 (1H, d), 7.38 (1H, d), 7.28 (1H, d), 3.95 (s, 3H). MS: m/z 290.0 (M+H$^+$).

Example I-7

4-Methoxy-biphenyl-3-sulfonic acid pyridin-3-ylamide

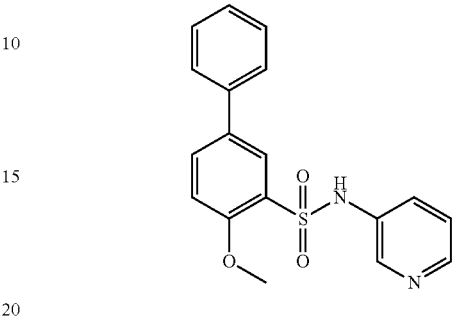

The mixture of 5-bromo-2-methoxy-N-pyridin-3-yl-benzenesulfonamide (50 mg, 0.15 mmol), phenylboronic acid (34 mg, 0.29 mmol), Pd(PPh$_3$)$_4$ (20 mg, cat.), K$_2$CO$_3$ (40 mg, 0.30 mmol) in DMF (2 mL) was stirred at 130° C. for 30 min under microwave irridation. After cooled to room temperature, the solvent was evaporated in vacuum. The residue was partitioned between DCM (5 mL) and H$_2$O (10 mL). The mixture was extracted with DCM (15 mL×3). The extracts were dried over Na$_2$SO$_4$ and concentrated in vacuum to give crude compound, which was purified by prep-TLC (EtOAc) to afford 22 mg (yield: 43%) of 4-methoxy-biphenyl-3-sulfonic acid pyridin-3-ylamide as yellow solid.

$^1$H NMR (CDCl3): δ=8.32 (1H, d), 8.24 (1H, d), 8.03 (1H, d), 7.73 (1H, dd), 7.66 (1H, d), 7.47 (2H, d), 7.42 (2H, t), 7.34 (1H, t), 7.19 (1H, t), 7.14 (1H, s), 7.08 (1H, s), 4.01 (3H, s). MS: m/z 341.0 (M+H$^+$).

Example I-8

2-Methoxy-N-pyridin-3-yl-5-thiophen-3-yl-benzenesulfonamide

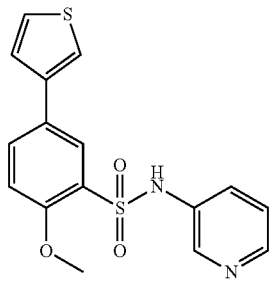 [SMILES: COc1ccc(-c2ccsc2)cc1S(=O)(=O)Nc1cccnc1]

$^1$H NMR (DMSO-d6): δ=10.81 (1H, brs), 8.28 (1H, s), 8.11 (1H, d), 8.03 (1H, d), 7.88 (1H, d), 7.83 (1H, s), 7.84 (1H, t), 7.48 (1H, d), 7.46 (1H, s), 7.21-7.17 (2H, m), 3.87 (3H, s). MS: m/z 347.0 (M+H$^+$).

Example I-9

5-Furan-3-yl-2-methoxy-N-pyridin-3-yl-benzenesulfonamide

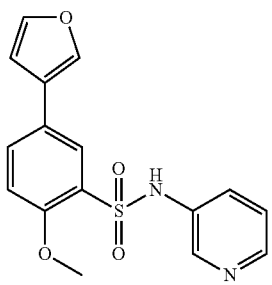 [SMILES: COc1ccc(-c2ccoc2)cc1S(=O)(=O)Nc1cccnc1]

$^1$H NMR (DMSO-d6): δ=10.44 (1H, brs), 8.35 (1H, s), 8.22-8.18 (2H, m), 7.94 (1H, s), 7.83 (1H, d), 7.74 (1H, s), 7.57 (1H, d), 7.32 (1H, d), 7.22 (1H, d), 6.94 (1H, s), 3.87 (3H, s). MS: m/z 331.0 (M+H$^+$).

Example I-10

2-Methoxy-5-pyridin-4-yl-N-pyridin-3-yl-benzenesulfonamide

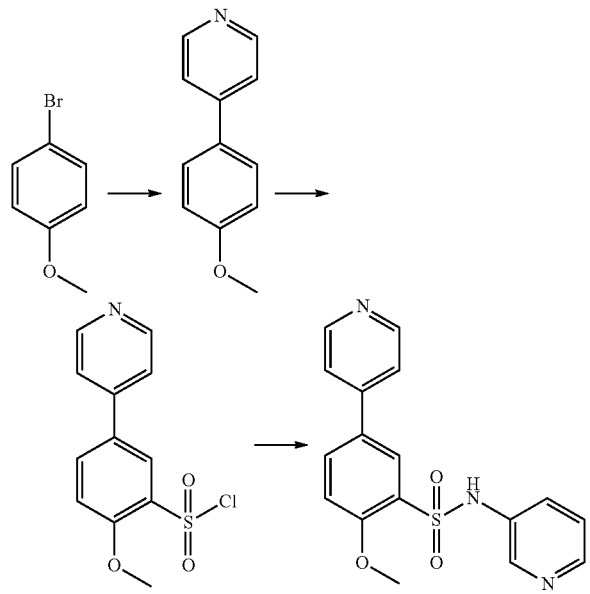

Step 1: The mixture of 1-bromo-4-methoxy-benzene (1.8 g, 10 mmol), pyridine-4-boronic acid (10 mmol), K$_2$CO$_3$ (2.7 g, 20 mmol), Pd(PPh$_3$)$_4$ (400 mg) in DMF (40 mL) was stirred at 120° C. for 4 h. TLC indicated the reaction was complete. The solvent was evaporated in vacuum. The residue was purified by silica gel column (PE/EtOAc, 20/1) to afford 1.28 g of 4-(4-methoxy-phenyl)-pyridine (yield: 69%) as white solid. MS: m/z 186.0 (M+H$^+$).

Step 2: To chlorosulfuric acid (10 mL) was added 4-(4-methoxy-phenyl)-pyridine (1.28 g, 6.91 mmol) portionwise at 0° C. and the mixture was stirred at room temperature for 4 h. The mixture was poured into ice-water, neutralized with saturated NaHCO$_3$ to pH=7-8 and extracted with EtOAc (25 mL×3). The extracts were dried over Na$_2$SO$_4$ and concentrated in vacuum to afford 600 mg (yield: 31%) of 2-methoxy-5-pyridin-4-yl-benzenesulfonyl chloride.

$^1$H NMR (DMSO-d6): δ=8.70 (1H, s), 8.29 (1H, s), 8.09 (1H, d), 7.77 (1H, d), 7.44-7.41 (2H, m), 7.36 (1H, d), 4.12 (3H, s).

Step 3: The procedure is similar to Example I-1.

$^1$H NMR (DMSO-d6): δ=10.45 (1H, brs), 8.61 (2H, d), 8.33 (1H, d), 8.19 (1H, d), 8.11 (1H, d), 8.07 (1H, dd), 7.67 (2H, d), 7.53 (1H, d), 7.34 (1H, d), 7.25 (1H, d), 3.93 (3H, s). MS: m/z 299.0 (M+H$^+$).

Example I-11

4-Chloro-2-methoxy-N-pyridin-3-yl-benzenesulfonamide

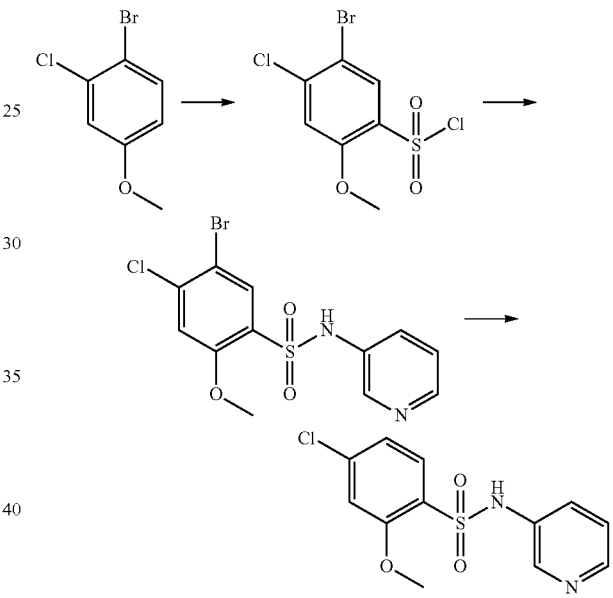

Step 1: To chlorosulfuric acid (20 mL) was added 1-bromo-2-chloro-4-methoxy-benzene (5.0 g, 23 mmol) dropwise at 0° C. The mixture was slowly warmed up to room temperature and was stirred at room temperature for 2 h. TLC indicated the reaction was complete. Then the mixture was poured into ice-water. The aqueous layer was extracted with EtOAc (20 mL×3). The extracts were dried over Na$_2$SO$_4$ and the solution was filtered through a pad of silica gel, dried in vacuum to afford 2.0 g (yield: 27%) of 5-bromo-4-chloro-2-methoxy-benzenesulfonyl chloride as white solid. $^1$H NMR (DMSO-d6): δ=7.90 (1H, s), 7.24 (1H, s), 3.79 (3H, s).

Step 2: The procedure is similar to Example I-1.

$^1$H NMR (DMSO-d6): δ=11.0 (1H, brs), 8.47-8.42 (2H, m), 8.04 (1H, t), 7.90-7.80 (1H, m), 7.58-7.56 (1H, m), 7.56 (1H, s), 3.84 (3H, s). MS: m/z 378.8 (M+H$^+$).

Step 3: The mixture of 5-bromo-4-chloro-2-methoxy-N-pyridin-3-yl-benzenesulfonamide (200 mg, 0.53 mmol), 10% Pd/C (40 mg) in EtOH/DMF (10 mL/10 mL) was stirred at room temperature under hydrogen balloon pressure for 2 days. The mixture was filtered and the filtrate was concentrated in vacuum to afford crude compound, which was purified by prep-HPLC to afford 40 mg of (25% yield) 4-chloro-2-methoxy-N-pyridin-3-yl-benzenesulfonamide as white solid.

$^1$H NMR (DMSO-d6): δ=10.62 (1H, brs), 8.35 (1H, s), 8.28 (1H, d), 7.79 (1H, d), 7.60 (1H, d), 7.41 (1H, t), 7.31 (1H, d), 7.13 (1H, dd), 3.88 (3H, s). MS: m/z 398.9 (M+H$^+$).

Example I-12

3-Chloro-4-methoxy-N-pyridin-3-yl-benzenesulfonamide

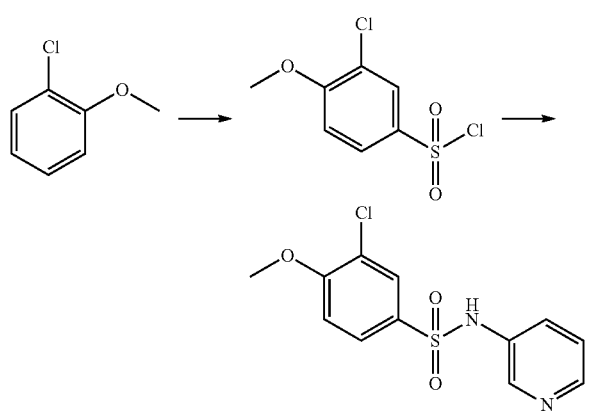

Step 1: The procedure is similar to step 1, Example I-10. $^1$H NMR (DMSO-d6): δ=8.01 (1H, s), 7.52 (1H, d), 6.98 (1H, d).

Step 2: The procedure is similar to Example I-1.

$^1$H NMR (DMSO-d6): δ=10.74 (1H, brs), 8.33-8.30 (2H, m), 7.79 (1H, d), 7.71 (1H, dd), 7.60-7.56 (1H, m), 7.38 (1H, dd), 7.31 (1H, d), 3.92 (3H, s). MS: m/z 299.0 (M+H$^+$).

Example I-13

3-Chloro-2-methoxy-N-pyridin-3-yl-benzenesulfonamide

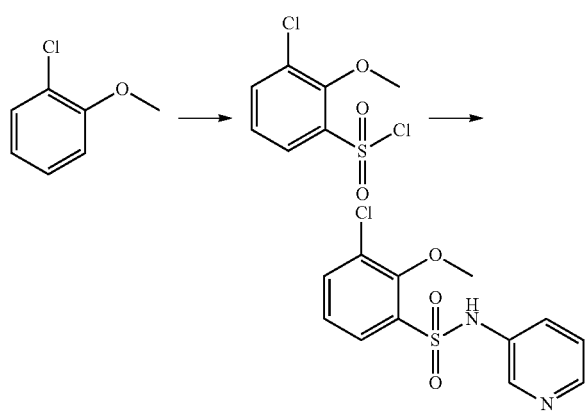

Step 1: To the mixture of 1-chloro-2-methoxy-benzene (1.75 g, 12.3 mmol) in THF (40 mL), was added s-BuLi (11.3 mL, 14.7 mmol) dropwise at −78° C. The mixture was stirred at −78° C. for 1 h. And then, SO$_2$ was injected with a balloon. The mixture was slowly warmed up to room temperature and stirred overnight. The reaction was diluted with anhydrous DCM (10 mL). NCS (4.9 g, 37 mmol) was added to the mixture portion-wise at 0° C. and the reaction was slowly warmed up to room temperature. The solvent was evaporated in vacuum. The residue was purified by silica gel column to afford 800 mg (yield: 27%) of 3-chloro-2-methoxy-benzenesulfonyl chloride. $^1$H NMR (DMSO-d6): δ=7.84-7.81 (2H, m), 7.10 (1H, d), 3.87 (3H, s).

Step 2: The procedure is similar to Example I-1.

$^1$H NMR (DMSO-d6): δ=10.90 (1H, brs), 8.32 (1H, d), 8.23 (1H, d), 7.65 (1H, dd), 7.44-7.40 (3H, m), 7.27 (1H, dd), 3.90 (3H, s). MS: m/z 349.0 (M+H$^+$).

Example I-14

4-Methoxy-3-(pyridin-3-ylsulfamoyl)-benzoic acid methyl ester

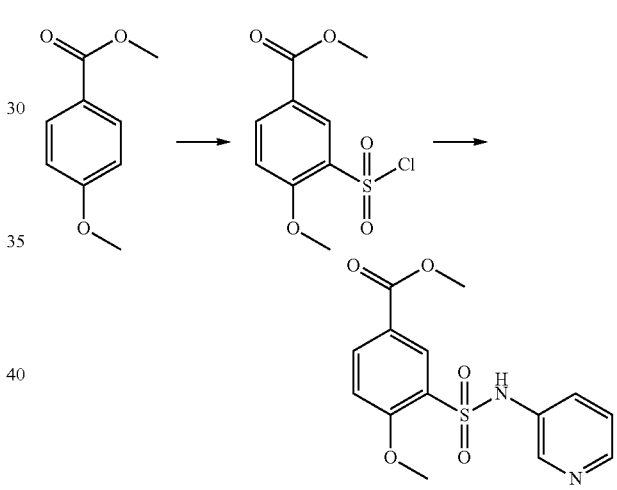

Step 1: To chlorosulfuric acid (40 mL) was added 4-methoxy-benzoic acid methyl ester (20 g, 0.12 mol) dropwise at 0° C. The mixture was then slowly warmed up to room temperature and was stirred at room temperature overnight. TLC indicated the reaction was complete. The mixture was poured into ice-water and extracted with EtOAc (200 mL×3). The extracts were dried over Na$_2$SO$_4$ and concentrated in vacuum to afford crude methyl 3-(chlorosulfonyl)-4-methoxybenzoate, which was purified by silica-gel chromatography (PE/EA, 100/1 to 10/1) to afford 1.6 g (5% yield) of methyl 3-(chlorosulfonyl)-4-methoxybenzoate as white solid. $^1$H NMR (CDCl$_3$): δ=8.65 (1H, s), 8.39 (1H, d), 7.18 (1H, d), 4.17 (3H, s), 3.94 (3H, s).

Step 2: This compound was prepared as described in Example I-1.

$^1$H NMR (DMSO-d6): δ=10.47 (1H, brs), 8.29 (1H, d), 8.21 (1H, dd), 8.13-8.08 (2H, m), 7.47 (1H, d), 7.32 (1H, dd), 7.25-7.22 (1H, m), 3.95 (3H, s), 3.83 (3H, s). MS: m/z 323.0 (M+H$^+$).

Example I-15

4-Methoxy-3-(pyridin-3-ylsulfamoyl)-benzamide

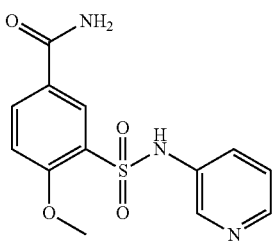 [SMILES: COc1ccc(C(N)=O)cc1S(=O)(=O)Nc1cccnc1]

Methyl 3-(chlorosulfonyl)-4-methoxybenzoate (100 mg, 0.31 mmol) and aqueous ammonia (2 mL) was heated in a sealed vessel at 120° C. for 18 hours. The reaction mixture was cooled to room temperature and concentrated to dryness. The residue was purified by prep-HPLC to afford 25 mg (yield: 26%) of 4-methoxy-3-(pyridin-3-ylsulfamoyl)-benzamide as white solid.

$^1$H NMR (DMSO-d6): δ=10.39 (1H, brs), 8.31 (2H, s), 8.19 (1H, d), 8.07 (2H, dd), 7.47 (1H, d), 7.42 (1H, s), 7.29-7.22 (2H, m), 3.92 (3H, s). MS: m/z 307.9 (M+H$^+$).

Example I-16

4-Methoxy-N-methyl-3-(pyridin-3-ylsulfamoyl)-benzamide

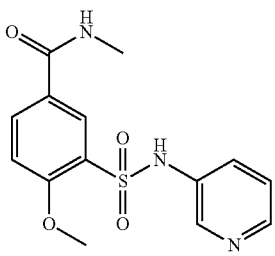 [SMILES: CNC(=O)c1ccc(OC)c(S(=O)(=O)Nc2cccnc2)c1]

Methyl 3-(chlorosulfonyl)-4-methoxybenzoate (100 mg, 0.31 mmol) and MeNH$_2$ alcohol solution (3 mL) was heated in a sealed vessel at 120° C. for 18 hours. The reaction mixture was cooled to room temperature and concentrated to dryness. The residue was purified by prep-HPLC to afford 32 mg (yield: 33%) of 4-methoxy-3-(pyridin-3-ylsulfamoyl)-benzamide as white solid.

$^1$H NMR (DMSO-d6): δ=10.60 (1H, brs), 8.58 (1H, d), 8.31-8.26 (3H, m), 8.07 (1H, d), 7.63 (1H, d), 7.49 (1H, dd), 7.26 (1H, d), 3.92 (3H, s), 2.76 (3H, d). MS: m/z 322.0 (M+H$^+$).

Example I-17

N-Ethyl-4-methoxy-3-(pyridin-3-ylsulfamoyl)-benzamide

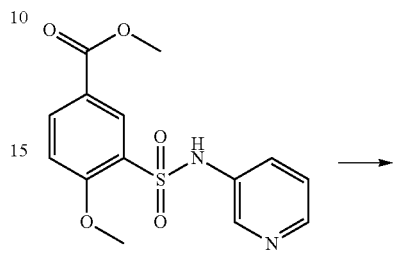

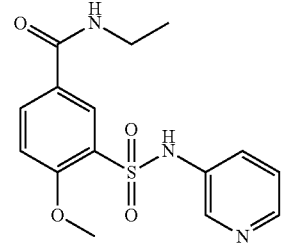

Step 1: The mixture of 4-methoxy-3-(pyridin-3-ylsulfamoyl)-benzoic acid methyl ester (1.5 g, 4.65 mmol), LiOH (0.45 g, 18.6 mmol) in THF/H$_2$O (10 mL/10 mL) was stirred at 50° C. for 2 h. THF was evaporated in vacuum. The aqueous layer was extracted with EtOAc (30 mL×3). The extracts were dried over Na$_2$SO$_4$ and concentrated in vacuum to afford 1.1 g of (yield: 77%) 4-methoxy-3-(N-(pyridin-3-yl)sulfamoyl)benzoic acid as yellow solid.

Step 2: The mixture of 4-methoxy-3-(N-(pyridin-3-yl)sulfamoyl)benzoic acid (100 mg, 0.32 mmol), HATU (127 mg, 0.34 mmol), DIPEA (124 mg, 0.96 mmol) and ethyl amine HCl salt (52 mg, 0.64 mmol) in DCM (3 mL) was stirred at room temperature overnight. The solvent was evaporated in vacuum. The residue was purified by prep-HPLC to afford 32 mg (yield: 30%) of N-ethyl-4-methoxy-3-(pyridin-3-ylsulfamoyl)-benzamide as yellow solid.

$^1$H NMR (DMSO-d6): δ=10.39 (1H, brs), 9.61 (1H, t), 8.30-8.26 (2H, m), 8.20 (1H, d), 8.07 (1H, dd), 7.48 (1H, d), 7.26-7.22 (2H, m), 3.92 (3H, s), 1.50 (2H, q), 1.10 (3H, t). MS: m/z 336.1 (M+H$^+$).

Example I-18

4-Methoxy-N-propyl-3-(pyridin-3-ylsulfamoyl)-benzamide

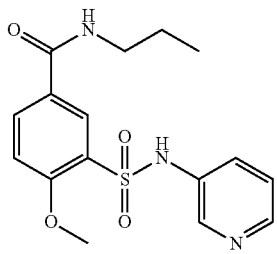 [SMILES: CCCNC(=O)c1ccc(OC)c(S(=O)(=O)Nc2cccnc2)c1]

This compound was prepared as described in Example I-17.

$^1$H NMR (DMSO-d6): δ=10.39 (1H, brs), 9.61 (1H, t), 8.30-8.26 (2H, m), 8.20 (1H, d), 8.07 (1H, dd), 7.48 (1H, d), 7.26-8.22 (2H, m), 3.94 (3H, s), 3.25-3.21 (2H, m), 1.53-1.50 (2H, m), 1.10 (3H, t). MS: m/z 350.1 (M+H$^+$).

Example I-19

4-Methoxy-N-phenyl-3-(pyridin-3-ylsulfamoyl)-benzamide

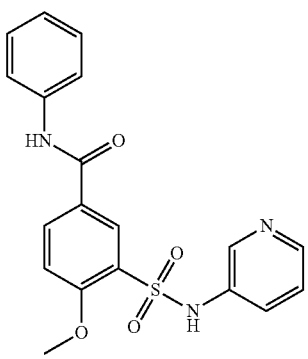 [SMILES: COc1ccc(C(=O)Nc2ccccc2)cc1S(=O)(=O)Nc1cccnc1]

This compound was prepared as described in Example I-17.

$^1$H NMR (DMSO-d6): δ=10.45 (1H, brs), 10.35 (1H, s), 8.42 (1H, d), 8.34 (1H, d), 8.22 (2H, d), 7.75 (2H, d), 7.52 (1H, dd), 7.37-7.34 (3H, m), 7.26 (1H, t), 7.12 (1H, t), 3.97 (3H, s). MS: m/z 384.1 (M+H$^+$).

Example I-20

N-Cyclohexyl-4-methoxy-3-(pyridin-3-ylsulfamoyl)-benzamide

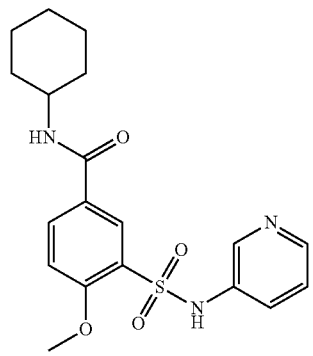 [SMILES: COc1ccc(C(=O)NC2CCCCC2)cc1S(=O)(=O)Nc1cccnc1]

This compound was prepared as described in Example I-17.

$^1$H NMR (DMSO-d6): δ=10.33 (1H, brs), 8.32 (1H, d), 8.29-8.25 (2H, m), 8.16 (1H, d), 8.05 (1H, dd), 7.45 (1H, d), 7.23-7.19 (2H, m), 3.88 (3H, s), 3.31-3.27 (1H, m), 1.75-1.25 (10H, m). MS: m/z 390.1 (M+H$^+$).

Example I-21

4-Methoxy-N-(2-methoxy-ethyl)-3-(pyridin-3-ylsulfamoyl)-benzamide

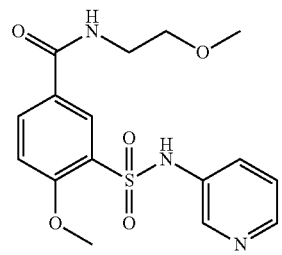 [SMILES: COCCNC(=O)c1ccc(OC)c(S(=O)(=O)Nc2cccnc2)c1]

This compound was prepared as described in Example I-17.

$^1$H NMR (DMSO-d6): δ=10.40 (1H, brs), 8.69 (1H, t), 8.34-8.30 (2H, m), 8.20 (1H, dd), 8.00 (1H, dd), 7.50 (1H, d), 7.29-7.25 (2H, m), 3.95 (3H, s), 3.45-3.39 (4H, m), 3.35 (3H, s). MS: m/z 366.1 (M+H$^+$).

Example I-22

2-Methoxy-5-(4-methyl-piperazine-1-carbonyl)-N-pyridin-3-yl-benzenesulfonamide

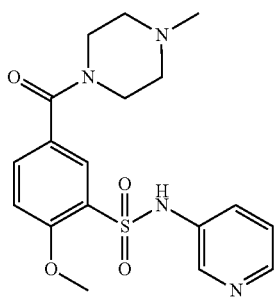 [SMILES: COc1ccc(C(=O)N2CCN(C)CC2)cc1S(=O)(=O)Nc1cccnc1]

This compound was prepared as described in Example I-17.

$^1$H NMR (DMSO-d6): δ=10.43 (1H, brs), 8.29 (1H, d), 8.21 (1H, dd), 8.13-8.10 (1H, m), 7.47 (1H, d), 7.32 (1H, dd), 7.25-7.21 (2H, m), 3.92 (3H, s), 3.57-3.17 (4H, m), 2.34-2.29 (4H, m), 2.20 (3H, s). MS: m/z 391.1 (M+H$^+$).

Example I-23

2-Methoxy-5-(morpholine-4-carbonyl)-N-pyridin-3-yl-benzenesulfonamide

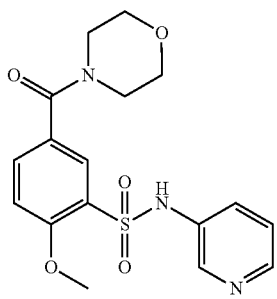 [SMILES: COc1ccc(C(=O)N2CCOCC2)cc1S(=O)(=O)Nc1cccnc1]

This compound was prepared as described in Example I-17.

$^1$H NMR (DMSO-d6): δ=10.40 (1H, brs), 8.29 (1H, d), 8.22 (1H, dd), 7.77-7.74 (1H, m), 7.64 (1H, dd), 7.48 (1H, d), 7.28-7.24 (2H, m), 3.91 (3H, s), 3.57-3.37 (8H, m). MS: m/z 378.1 (M+H$^+$).

Example II

Example II-1

5-Chloro-2-methoxy-N-quinolin-3-yl-benzenesulfonamide

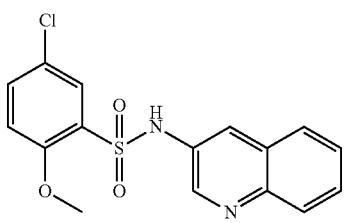 [SMILES: COc1ccc(Cl)cc1S(=O)(=O)Nc1cnc2ccccc2c1]

The mixture of 5-chloro-2-methoxy-benzenesulfonyl chloride (167 mg, 0.69 mmol), quinolin-3-ylamine (100 mg, 0.69 mmol), DMAP (10 mg, cat.) in pyridine (5 mL) was stirred at 50° C. for 2 h. LCMS indicated the reaction was complete. The solvent was evaporated in vacuum. The residue was triturated with DCM (5 mL). The suspension was collected by filtration to give crude product, which was purified by prep-HPLC to afford 100 mg (42% yield) of 5-chloro-2-methoxy-N-quinolin-3-yl-benzenesulfonamide as pale yellow solid.

$^1$H NMR (CDCl$_3$): δ=8.54 (1H, brs), 8.03 (1H, s), 7.97 (1H, d), 7.80-7.77 (2H, m), 7.65 (1H, t), 7.58 (1H, t), 7.41 (1H, d), 7.26 (1H, s), 6.96 (1H, d), 4.05 (3H, s). MS: m/z 295.0 (M+H$^+$).

Example II-2

2-Methoxy-N-quinolin-3-yl-5-trifluoromethyl-benzenesulfonamide

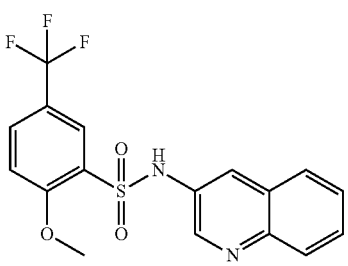 [SMILES: COc1ccc(C(F)(F)F)cc1S(=O)(=O)Nc1cnc2ccccc2c1]

$^1$H NMR (DMSO-d6): δ=10.63 (1H, brs), 8.70 (1H, d), 8.08 (1H, d), 7.91-7.85 (4H, m), 7.64 (1H, t), 7.55 (1H, t), 7.40 (1H, dd), 3.93 (3H, s). MS: m/z 382.9 (M+H$^+$).

Example II-3

2-Methoxy-4-methyl-N-quinolin-3-yl-benzenesulfonamide

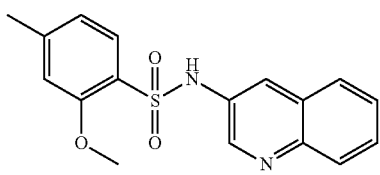 [SMILES: COc1cc(C)ccc1S(=O)(=O)Nc1cnc2ccccc2c1]

$^1$H NMR (CDCl$_3$): δ=8.52 (1H, brs), 8.03 (1H, s), 7.97 (1H, d), 7.75 (1H, d), 7.68 (1H, d), 7.62 (1H, t), 7.52 (1H, t), 7.29-7.25 (1H, m), 6.78 (1H, s), 6.74 (1H, d), 4.04 (3H, s), 2.32 (1H, s). MS: m/z 329.0 (M+H$^+$).

Example II-4

2,4-Dimethoxy-N-quinolin-3-yl-benzenesulfonamide

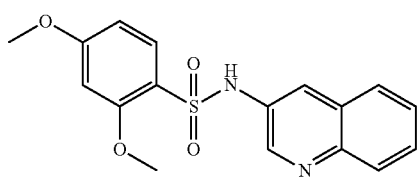 [SMILES: COc1ccc(S(=O)(=O)Nc2cnc3ccccc3c2)c(OC)c1]

$^1$H NMR (DMSO-d6): δ=10.45 (1H, brs), 8.66 (1H, d), 7.89-7.84 (3H, m), 7.75 (1H, d), 7.61 (1H, t), 7.53 (1H, t), 6.62 (1H, d), 6.55 (1H, dd), 3.85 (3H, s), 3.75 (1H, s). MS: m/z 345.0 (M+H$^+$).

Example II-5

5-Cyano-2-methoxy-N-quinolin-3-yl-benzenesulfonamide

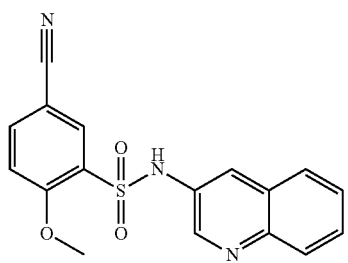 [SMILES: COc1ccc(C#N)cc1S(=O)(=O)Nc1cnc2ccccc2c1]

This compound was prepared as described in Example I-6.

$^1$H NMR (DMSO-d6): δ=10.86 (1H, brs), 8.70 (1H, s), 8.25 (1H, s), 8.05 (1H, d), 7.97-7.94 (3H, m), 7.62 (1H, t), 7.55 (1H, t), 7.36 (1H, dd), 3.95 (3H, s). MS: m/z 340.0 (M+H$^+$).

Example II-6

4-Methoxy-biphenyl-3-sulfonic acid quinolin-3-ylamide

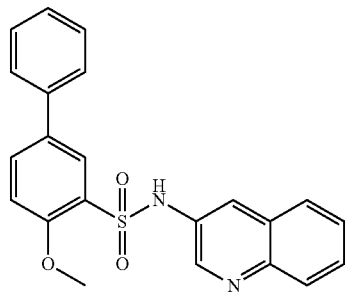 [SMILES: COc1ccc(-c2ccccc2)cc1S(=O)(=O)Nc1cnc2ccccc2c1]

This compound was prepared as described in Example I-7.

$^1$H NMR (DMSO-d6): δ=10.67 (1H, brs), 8.70 (1H, d), 8.05 (1H, d), 7.98 (1H, d), 7.90-7.84 (3H, m), 7.60-7.53 (3H, m), 7.48 (1H, t), 7.46 (2H, t), 7.37-7.33 (1H, m), 7.25 (1H, dd) 3.89 (3H, s). MS: m/z 391.0 (M+H$^+$).

Example II-7

5-Furan-3-yl-2-methoxy-N-quinolin-3-yl-benzenesulfonamide

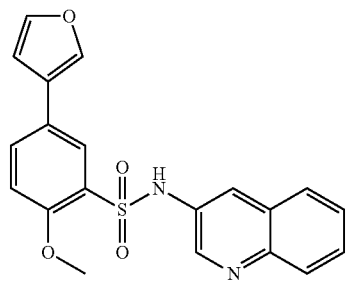 [SMILES: COc1ccc(-c2ccoc2)cc1S(=O)(=O)Nc1cnc2ccccc2c1]

$^1$H NMR (DMSO-d6): δ=10.64 (1H, brs), 8.70 (1H, d), 8.19 (1H, s), 7.98-7.94 (2H, m), 7.91-7.87 (2H, m), 7.76 (1H, dd), 7.73 (1H, s), 7.62 (1H, d), 7.52 (1H, d), 7.19 (1H, d), 6.93 (1H, s), 3.87 (3H, s). MS: m/z 381.0 (M+H$^+$).

Example II-8

2-Methoxy-N-quinolin-3-yl-5-thiophen-3-yl-benzenesulfonamide

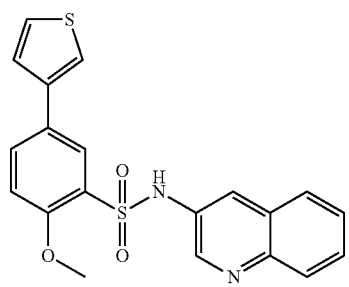 [SMILES: COc1ccc(-c2ccsc2)cc1S(=O)(=O)Nc1cnc2ccccc2c1]

$^1$H NMR (DMSO-d6): δ=10.67 (1H, brs), 8.70 (1H, d), 8.09 (1H, s), 8.02-7.98 (2H, m), 7.86-7.81 (4H, m), 7.63-

7.58 (2H, m), 7.50 (1H, d), 7.20 (1H, d), 3.89 (3H, s). MS: m/z 397.0 (M+H⁺).

Example II-9

2-Methoxy-5-pyridin-4-yl-N-quinolin-3-yl-benzenesulfonamide

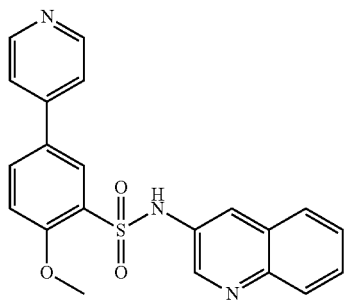 [SMILES: COc1ccc(-c2ccncc2)cc1S(=O)(=O)Nc1cnc2ccccc2c1]

This compound was prepared as described in Example I-10.

¹H NMR (DMSO-d6): δ=10.74 (1H, brs), 8.72 (1H, d), 8.62 (2H, d), 8.21 (1H, d), 8.04-8.00 (2H, m), 7.90-7.86 (2H, m), 7.71-7.68 (2H, m), 7.61 (1H, t), 7.51 (1H, t), 7.31 (1H, t), 3.93 (3H, s). MS: m/z 392.0 (M+H⁺).

Example II-10

4-Chloro-2-methoxy-N-quinolin-3-yl-benzenesulfonamide

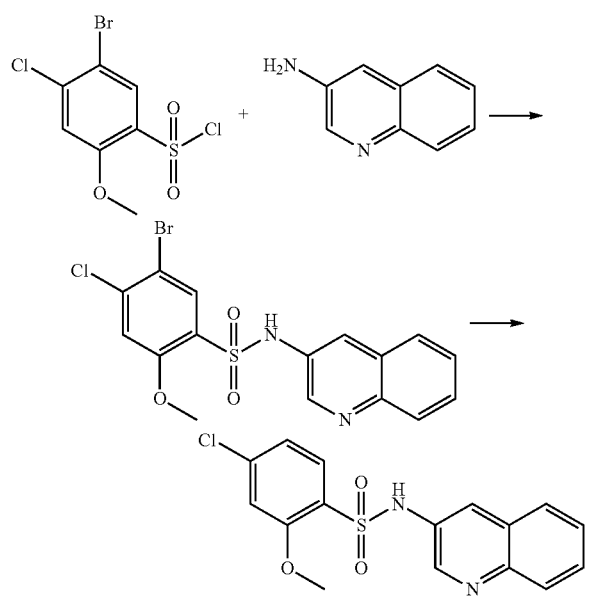

Step 1: The procedure to bromo-4-chloro-2-methoxy-N-quinolin-3-yl-benzenesulfonamide is similar to Example II-1.

¹H NMR (DMSO-d6): δ=10.82 (1H, brs), 8.88 (1H, d), 8.04 (1H, s), 7.98 (1H, s), 7.92-7.88 (2H, m), 7.83 (1H, t), 7.56 (1H, t), 7.51 (1H, s), 3.88 (3H, s). MS: m/z 428.8 (M+H⁺).

Step 2: To the mixture of 5-bromo-4-chloro-2-methoxy-N-quinolin-3-yl-benzenesulfonamide (100 mg, 0.23 mmol) in THF (3 mL) was added BuLi (0.3 mL, 2.5M in THF) dropwise at −78° C., and the mixture was stirred for another 3 h. The mixture was quenched with water and concentrated to give a crude product, which was purified by prep-HPLC to afford 40 mg (yield: 50%) of 4-chloro-2-methoxy-N-quinolin-3-yl-benzenesulfonamide as white solid.

¹H NMR (DMSO-d6): δ=10.69 (1H, brs), 8.88 (1H, s), 8.04-7.99 (3H, m), 7.81 (1H, d), 7.63 (1H, t), 7.55 (1H, t), 7.29 (1H, s), 7.10 (1H, d), 3.89 (3H, s). MS: m/z 349.0 (M+H⁺).

Example II-11

3-Chloro-4-methoxy-N-quinolin-3-yl-benzenesulfonamide

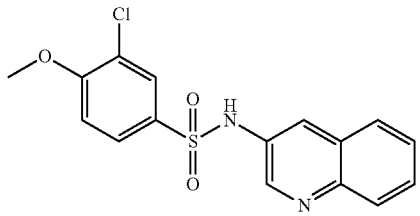 [SMILES: COc1ccc(S(=O)(=O)Nc2cnc3ccccc3c2)cc1Cl]

This compound was prepared as described in Example I-12.

¹H NMR (DMSO-d6): δ=10.74 (1H, brs), 8.62 (1H, d), 8.02 (1H, d), 7.97-7.94 (2H, m), 7.86 (1H, d), 7.73 (1H, dd), 7.65 (1H, t), 7.60 (1H, t), 7.26 (1H, d), 3.93 (3H, s). MS: m/z 349.0 (M+H⁺).

Example II-12

3-Chloro-2-methoxy-N-quinolin-3-yl-benzenesulfonamide

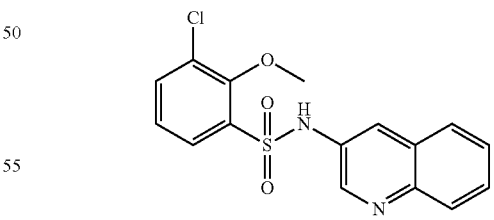

This compound was prepared as described in Example I-13.

¹H NMR (DMSO-d6): δ=11.22 (1H, brs), 8.77 (1H, d), 7.97-7.93 (3H, m), 7.77 (1H, d), 7.70 (1H, t), 7.62-7.59 (1H, m), 7.51 (1H, t), 7.45 (1H, t), 3.91 (3H, s). MS: m/z 349.0 (M+H⁺).

Example II-13

Methyl 4-methoxy-3-(N-(quinolin-3-yl)sulfamoyl)benzoate

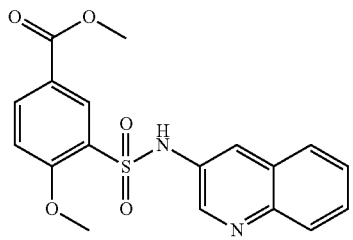 [SMILES: COC(=O)c1ccc(OC)c(S(=O)(=O)Nc2cnc3ccccc3c2)c1]

This compound was prepared as described in Example I-14.

$^1$H NMR (DMSO-d6): δ=10.74 (1H, brs), 8.67 (1H, d), 8.33 (1H, d), 8.11 (1H, dd), 7.95 (1H, d), 7.88 (2H, d), 7.63 (1H, m), 7.50-7.46 (1H, m), 7.31-7.28 (1H, m), 3.95 (3H, s), 3.81 (3H, s). MS: m/z 373.0 (M+H$^+$).

Example II-14

4-Methoxy-3-(quinolin-3-ylsulfamoyl)-benzamide

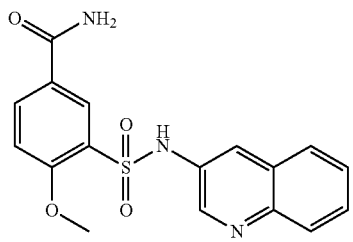 [SMILES: COc1ccc(C(N)=O)cc1S(=O)(=O)Nc1cnc2ccccc2c1]

This compound was prepared as described in Example I-15.

$^1$H NMR (DMSO-d6): δ=10.69 (1H, brs), 8.69 (1H, d), 8.37 (1H, d), 8.05-8.01 (2H, m), 7.96 (1H, d), 7.91-7.87 (2H, m), 7.63-7.60 (1H, m), 7.50-7.47 (1H, m), 7.29-7.26 (1H, m), 7.23 (1H, d), 3.9 (3H, s). MS: m/z 358.0 (M+H$^+$).

Example II-15

4-Methoxy-N-methyl-3-(quinolin-3-ylsulfamoyl)-benzamide

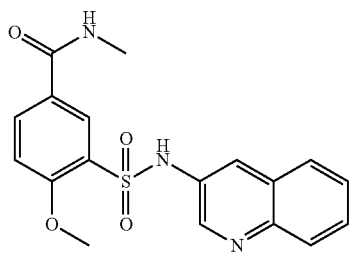 [SMILES: CNC(=O)c1ccc(OC)c(S(=O)(=O)Nc2cnc3ccccc3c2)c1]

This compound was prepared as described in Example I-16.

$^1$H NMR (DMSO-d6): δ=8.44-8.35 (3H, m), 7.84 (1H, dd), 7.71 (1H, t), 7.55-7.50 (2H, m), 7.33-7.29 (2H, m), 7.06 (1H, d), 7.00 (1H, brs), 3.76 (3H, s), 2.36 (3H, s). MS: m/z 372.0 (M+H$^+$).

Example II-16

N-Ethyl-4-methoxy-3-(quinolin-3-ylsulfamoyl)-benzamide

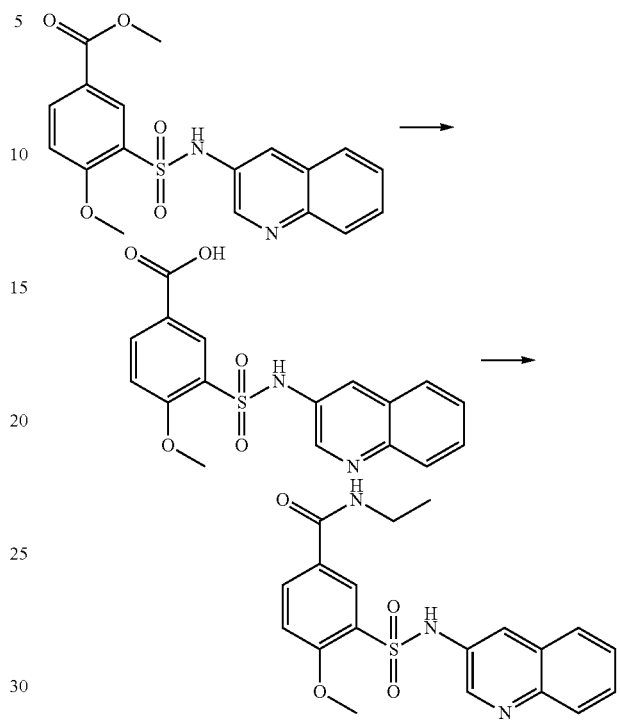

Step 1: The mixture of 4-methoxy-3-(quinolin-3-ylsulfamoyl)-benzoic acid methyl ester (2.6 g, 7.0 mmol), LiOH (1.5 g, 35 mmol) in THF/H$_2$O (10 mL/10 mL) was stirred at 50° C. for 2 h. LCMS indicated the reaction was complete. THF was evaporated in vacuum. The aqueous layer was extracted with EtOAc (30 mL×3). The extracts were dried over Na$_2$SO$_4$ and concentrated in vacuum to afford 1.8 g of (yield: 72%) 4-methoxy-3-(quinolin-3-ylsulfamoyl)-benzoic acid as yellow solid. MS: m/z 357.1 (M−H$^+$).

Step 2: The mixture of 4-methoxy-3-(quinolin-3-ylsulfamoyl)-benzoic acid (100 mg, 0.28 mmol), HATU (127 mg, 0.34 mmol), DIPEA (72 mg, 0.56 mmol) and ethyl amine HCl salt (46 mg, 0.56 mmol) in DCM (3 mL) was stirred at room temperature overnight. The solvent was evaporated in vacuum. The residue was purified by prep-HPLC to afford 30 mg (yield: 28%) of N-ethyl-4-methoxy-3-(quinolin-3-ylsulfamoyl)-benzamide as yellow solid. $^1$H NMR (DMSO-d6): δ=10.87 (1H, brs), 8.67 (1H, d), 8.56 (1H, t), 8.33 (1H, d), 8.04 (1H, dd), 7.95 (1H, d), 7.88-7.84 (2H, m), 7.61-7.58 (1H, m), 7.54-7.51 (1H, m), 7.25 (1H, d), 3.91 (3H, s), 3.24 (2H, q), 1.11 (3H, t). MS: m/z 386.1 (M+H$^+$).

Example II-17

4-Methoxy-N-propyl-3-(quinolin-3-ylsulfamoyl)-benzamide

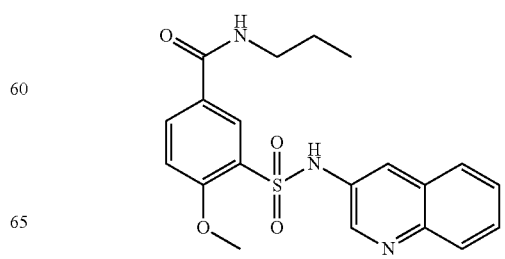

This compound was prepared as described in Example II-16.

¹H NMR (DMSO-d6): δ=10.68 (1H, brs), 8.69 (1H, d), 8.60-8.55 (1H, m), 8.35 (1H, d), 8.03 (1H, dd), 7.95 (1H, d), 7.88-7.84 (2H, m), 7.63 (1H, t), 7.54 (1H, t), 7.24 (1H, d), 3.91 (3H, s), 3.16 (2H, q), 1.50-1.46 (2H, m), 0.86 (3H, t). MS: m/z 400.1 (M+H⁺).

Example II-18

4-Methoxy-N-phenyl-3-(quinolin-3-ylsulfamoyl)-benzamide

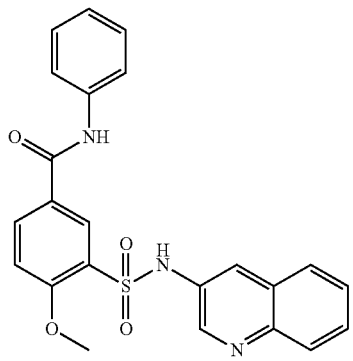 [SMILES: COc1ccc(C(=O)Nc2ccccc2)cc1S(=O)(=O)Nc1cnc2ccccc2c1]

This compound was prepared as described in Example II-16.

¹H NMR (DMSO-d6): δ=10.72 (1H, brs), 10.32 (1H, brs), 8.71 (1H, d), 8.46 (1H, d), 8.20 (1H, dd), 7.97-7.94 (1H, m), 7.88-7.84 (2H, m), 7.70-7.66 (2H, m), 7.62 (1H, m), 7.55-7.52 (1H, m), 7.32-7.28 (3H, m), 7.10-7.07 (1H, m), 3.95 (3H, s). MS: m/z 434.1 (M+H⁺).

Example II-19

N-Cyclohexyl-4-methoxy-3-(quinolin-3-ylsulfamoyl)-benzamide

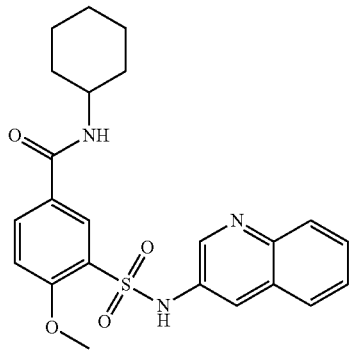 [SMILES: COc1ccc(C(=O)NC2CCCCC2)cc1S(=O)(=O)Nc1cnc2ccccc2c1]

This compound was prepared as described in Example II-16.

¹H NMR (DMSO-d6): δ=10.66 (1H, brs), 8.69 (1H, d), 8.34-8.30 (2H, m), 8.04 (1H, d), 7.95 (1H, d), 7.86-7.82 (2H, m), 7.63 (1H, t), 7.52 (1H, t), 7.21 (1H, d), 3.91 (3H, s), 3.72-3.68 (1H, m), 1.72-1.62 (4H, m), 1.57-1.53 (1H, m), 1.20-1.16 (4H, m), 1.10-1.07 (1H, m). MS: m/z 440.1 (M+H⁺).

Example II-20

4-Methoxy-N-(2-methoxy-ethyl)-3-(quinolin-3-yl-sulfamoyl)-benzamide

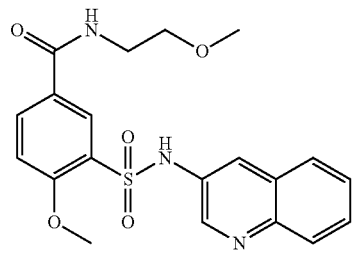 [SMILES: COCCNC(=O)c1ccc(OC)c(S(=O)(=O)Nc2cnc3ccccc3c2)c1]

This compound was prepared as described in Example II-16.

¹H NMR (DMSO-d6): δ=10.89 (1H, brs), 8.70-8.66 (2H, m), 8.36 (1H, d), 8.08 (1H, d), 7.97-7.93 (1H, m), 7.88-7.84 (2H, m), 7.65-7.62 (1H, m), 7.54-7.51 (1H, m), 7.26 (1H, d), 3.95 (3H, s), 3.40-3.32 (4H, m), 3.20 (3H, s). MS: m/z 416.1 (M+H⁺).

Example II-21

N-(2-Dimethylamino-ethyl)-4-methoxy-3-(quinolin-3-ylsulfamoyl)-benzamide

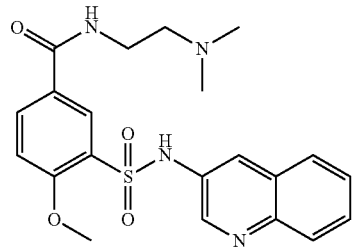 [SMILES: COc1ccc(C(=O)NCCN(C)C)cc1S(=O)(=O)Nc1cnc2ccccc2c1]

This compound was prepared as described in Example II-16.

¹H NMR (CD₃OD): δ=8.70 (1H, s), 8.43 (1H, d), 8.09-8.04 (2H, m), 7.93 (1H, d), 7.84 (1H, d), 7.70 (1H, t), 7.60 (1H, t), 7.30 (1H, d), 4.08 (3H, s), 3.72 (2H, t), 3.37 (2H, t), 2.96 (6H, s). MS: m/z 429.1 (M+H⁺).

Example II-22

2-Methoxy-5-(4-methyl-piperazine-1-carbonyl)-N-quinolin-3-yl-benzenesulfonamide

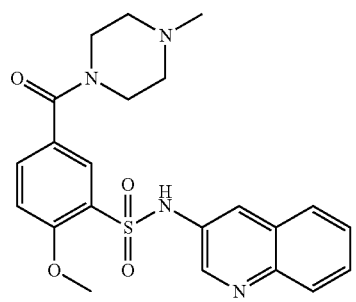 [SMILES: COc1ccc(C(=O)N2CCN(C)CC2)cc1S(=O)(=O)Nc1cnc2ccccc2c1]

This compound was prepared as described in Example II-16.

$^1$H NMR (CD$_3$OD): δ=8.77 (1H, d), 8.20 (1H, d), 8.05 (1H, d), 7.98 (1H, d), 7.91 (1H, d), 7.76-7.73 (1H, m), 7.65-7.62 (2H, m), 7.26 (1H, d), 4.00 (3H, s), 3.60-3.30 (8H, m), 2.94 (3H, s). MS: m/z 441.1 (M+H$^+$).

Example II-23

2-Methoxy-5-(morpholine-4-carbonyl)-N-quinolin-3-yl-benzenesulfonamide

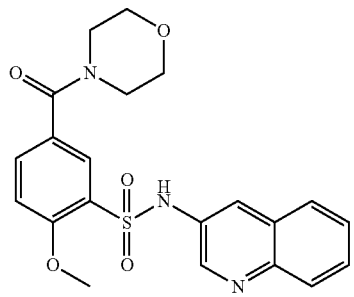 [SMILES: COc1ccc(C(=O)N2CCOCC2)cc1S(=O)(=O)Nc1cnc2ccccc2c1]

This compound was prepared as described in Example II-16.

$^1$H NMR (CD$_3$OD): δ=8.67 (1H, d), 8.13 (1H, d), 7.90-7.86 (3H, m), 7.70 (1H, t), 7.60 (2H, m), 7.22 (1H, d), 3.98 (3H, s), 3.50-2.50 (8H, m). MS: m/z 428.1 (M+H$^+$).

Example III

Example III-1

5-Bromo-2-methoxy-N-[5-(4-methoxy-phenyl)-pyridin-3-yl]-benzenesulfonamide

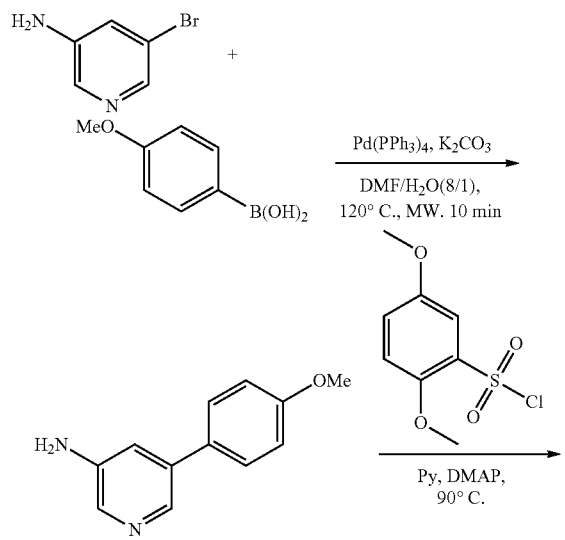

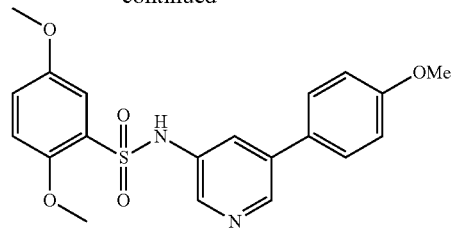

Step 1: A mixture of 5-bromopyridin-3-amine (300 mg, 1.74 mmol), 4-methoxyphenylboronic acid (395 mg, 2.60 mmol), K$_2$CO$_3$ (240 mg, 5.10 mmol) and Pd(PPh$_3$)$_4$ (197 mg, 0.17 mmol) in DMF/H$_2$O (5 ml/1 ml) was purged with N$_2$ for 20 min. Then the mixture was stirred at 120° C. under microwave irridation for 10 min. After cooled to room temperature, the solvent was removed in vacuum. The residue was diluted with EtOAc (30 mL). The mixture was washed with water, brine and dried over Na$_2$SO$_4$. The solution was evaporated to dryness and purified by silica gel column (DCM/MeOH, 1/0-40/1) to afford 264 mg (yield: 44%) of 5-(4-methoxyphenyl)pyridin-3-amine as white solid. MS: m/z 201.1 (M+H$^+$).

Step 2: A mixture of 5-(4-methoxyphenyl)pyridin-3-amine (70 mg, 0.35 mmol), 2,5-dimethoxybenzene-1-sulfonyl chloride (83 mg, 0.35 mmol) and DMAP (51 mg, 0.42 mmol) in pyridine (2 ml) was heated at 90° C. for 18 h. After cooled to room temperature, the solvent was removed in vacuum. The residue was diluted with EtOAc (20 mL). The mixture was washed with water, brine and dried over Na$_2$SO$_4$. The solution was evaporated to dryness and the residue was purified by prep-HPLC to afford 25 mg (yield: 18%) of 5-bromo-2-methoxy-N-[5-(4-methoxy-phenyl)-pyridin-3-yl]-benzenesulfonamide as off-white solid.

$^1$H NMR (DMSO-d6, 400 MHz): δ=10.42 (1H, brs), 8.48 (1H, s), 8.25 (1H, d), 7.65 (1H, s), 7.50 (2H, d), 7.32 (1H, d), 7.17-7.14 (2H, m), 7.05 (2H, d), 3.81 (3H, s), 3.80 (3H, s), 3.72 (3H, s). MS: m/z 401.1 (M+H$^+$).

Example III-2

5-Bromo-2-methoxy-N-[5-(4-methoxy-phenyl)-pyridin-3-yl]-benzenesulfonamide

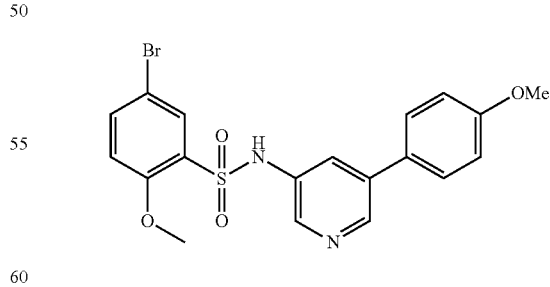

This compound was prepared as described in Example III-1.

$^1$H NMR (DMSO-d6, 400 MHz): δ=10.65 (1H, brs), 8.56 (1H, s), 8.29 (1H, d), 7.94 (1H, d), 8.35 (1H, dd), 7.69 (1H, s), 7.56 (2H, d), 7.22 (1H, d), 7.10 (2H, d), 3.91 (3H, s), 3.85 (3H, s). MS: m/z 448.9 (M+H$^+$).

Example III-3

5-Chloro-2-methoxy-N-[5-(4-methoxy-phenyl)-pyridin-3-yl]-benzenesulfonamide

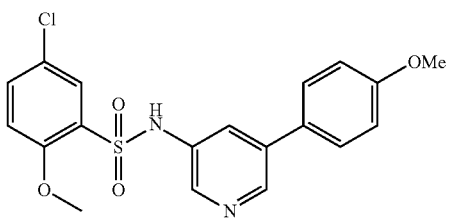 [SMILES: COc1ccc(-c2cncc(NS(=O)(=O)c3cc(Cl)ccc3OC)c2)cc1]

This compound was prepared as described in Example III-1.

$^1$H NMR (DMSO-d6, 400 MHz): δ=10.58 (1H, brs), 8.50 (1H, s), 8.24 (1H, s), 7.78 (1H, s), 7.66-7.54 (2H, m), 7.51 (2H, d), 7.23 (1H, d), 7.06 (2H, d), 3.86 (3H, s), 3.80 (3H, s). MS: m/z 404.9 (M+H$^+$).

Example III-4

N-(5-(4-(Benzyloxy)phenyl)pyridin-3-yl)-2,5-dimethoxybenzenesulfonamide

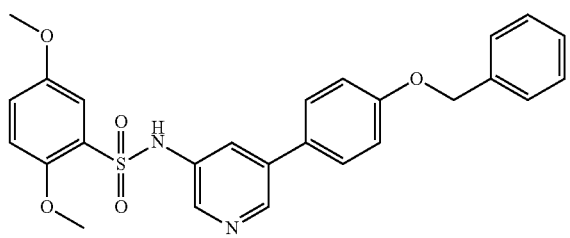 [SMILES: COc1ccc(OC)c(S(=O)(=O)Nc2cncc(-c3ccc(OCc4ccccc4)cc3)c2)c1]

This compound was prepared as described in Example III-1.

$^1$H NMR (DMSO, 400 HMz): δ=10.41 (1H, brs), 8.48 (1H, d), 8.24 (1H, d), 7.64 (1H, t), 7.51-7.31 (8H, m), 7.17-7.10 (4H, m), 5.16 (2H, s), 3.80 (3H, s), 3.72 (3H, s). MS: m/z 477.1 (M+H$^+$).

Example III-5

N-(5-(4-(Benzyloxy)phenyl)pyridin-3-yl)-5-bromo-2-methoxybenzenesulfonamide

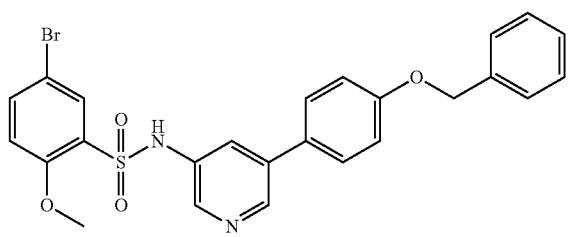 [SMILES: COc1ccc(Br)cc1S(=O)(=O)Nc1cncc(-c2ccc(OCc3ccccc3)cc2)c1]

This compound was prepared as described in Example III-1.

$^1$H NMR (DMSO-d6, 400 MHz): δ=10.58 (1H, brs), 8.52 (1H, d), 8.23 (1H, d), 7.88 (1H, d), 7.80-7.76 (1H, m), 7.64 (1H, d), 7.51 (2H, d), 7.47 (2H, d), 7.41 (2H, t), 7.35 (1H, d), 7.16 (1H, d), 7.13 (2H, d), 5.17 (2H, s) 3.85 (3H, s). MS: m/z 525.0 (M+H$^+$).

Example III-6

N-(5-(4-(benzyloxy)phenyl)pyridin-3-yl)-5-chloro-2-methoxybenzenesulfonamide

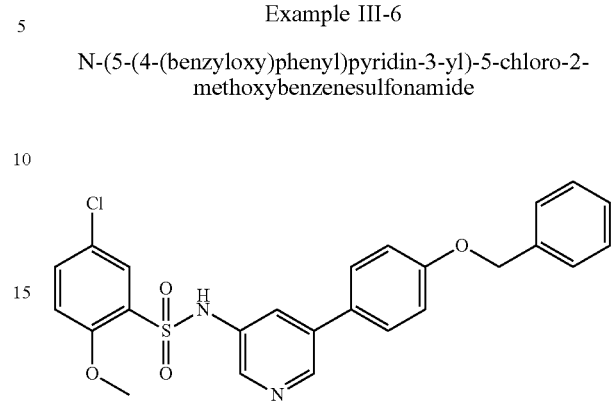

This compound was prepared as described in Example III-1.

$^1$H NMR (DMSO-d6, 400 HMz): δ=10.56 (1H, brs), 8.51 (1H, d), 8.24 (1H, d), 7.77 (1H, d), 7.64-7.53 (2H, m), 7.53-7.34 (7H, m), 7.24 (1H, d), 7.13 (2H, d), 5.17 (2H, s), 3.86 (3H, s). MS: m/z 481.1 (M+H$^+$).

Example III-7

N-[5-(4-Hydroxy-phenyl)-pyridin-3-yl]-2,5-dimethoxy-benzenesulfonamide

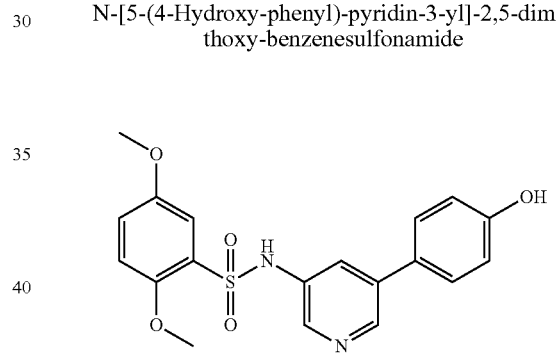

This compound was prepared as described in Example III-1.

$^1$H NMR (DMSO-d6, 400 HMz): δ=9.70 (1H, brs), 8.37 (1H, d), 8.17 (1H, d), 7.57 (1H, t), 7.37 (2H, d), 7.31 (1H, d), 7.13-7.09 (2H, m), 6.86 (2H, d), 3.78 (3H, s), 3.72 (3H, s). MS: m/z 387.0 (M+H$^+$).

Example III-8

5-Bromo-N-[5-(4-hydroxy-phenyl)-pyridin-3-yl]-2-methoxy-benzenesulfonamide

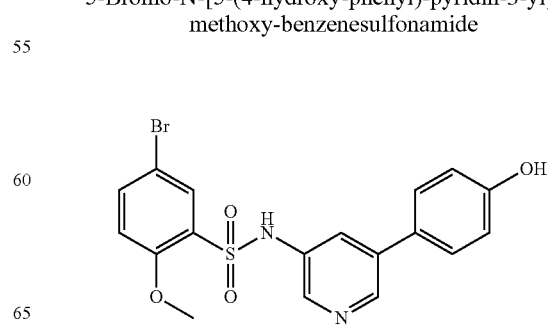

This compound was prepared as described in Example III-1.
¹H NMR (DMSO-d6, 400 HMz): δ=9.71 (1H, brs), 8.42 (1H, s), 8.16 (1H, d), 7.85 (1H, d), 7.74 (1H, dd), 7.55 (1H, t), 7.37-7.33 (2H, m), 7.15 (1H, d), 6.84 (2H, d), 3.82 (3H, s). MS: m/z 434.8 (M+H⁺).

Example III-9

5-Chloro-2-methoxy-N-(5-pyrimidin-2-yl-pyridin-3-yl)-benzenesulfonamide

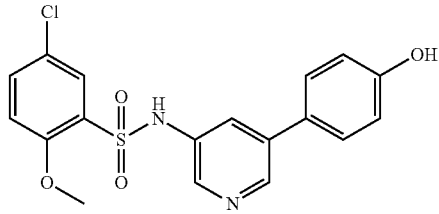 [SMILES: COc1ccc(Cl)cc1S(=O)(=O)Nc1cncc(-c2ccc(O)cc2)c1]

This compound was prepared as described in Example III-1.
¹H NMR (DMSO, 400 HMz): δ=9.70 (1H, brs), 8.37 (1H, d), 8.17 (1H, d), 7.57 (1H, t), 7.37 (2H, d), 7.31 (1H, d), 7.13-7.09 (2H, m), 6.86 (2H, d), 3.78 (3H, s), 3.72 (3H, s). MS: m/z 391.0 (M+H⁺).

Example III-10

2,5-Dimethoxy-N-(5-p-tolyl-pyridin-3-yl)-benzenesulfonamide

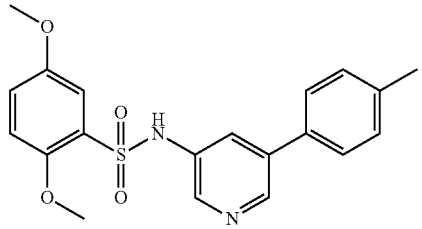 [SMILES: COc1ccc(OC)c(S(=O)(=O)Nc2cncc(-c3ccc(C)cc3)c2)c1]

This compound was prepared as described in Example III-1.
¹H NMR (DMSO-d6, 400 MHz): δ=10.44 (1H, brs), 8.49 (1H, s), 8.27 (1H, d), 7.66 (1H, d), 7.45 (2H, d), 7.33-7.28 (3H, m), 7.17-7.13 (2H, m), 3.80 (3H, s), 3.72 (3H, s), 2.35 (3H, s). MS: m/z 385.0 (M+H⁺).

Example III-11

5-Bromo-2-methoxy-N-(5-p-tolyl-pyridin-3-yl)-benzenesulfonamide

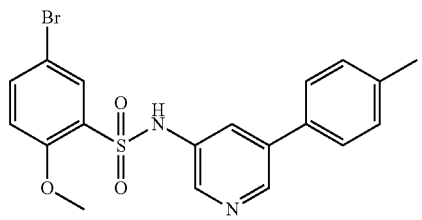

This compound was prepared as described in Example III-1.
¹H NMR (DMSO-d6, 400 MHz): δ=10.70 (1H, brs), 8.57 (1H, s), 8.30 (1H, s), 7.90 (1H, d), 7.80 (1H, dd), 7.72 (1H, d), 7.47 (2H, d), 7.32 (2H, d), 7.24 (1H, d), 3.84 (3H, s), 2.35 (3H, s). MS: m/z 432.9 (M+H⁺).

Example III-12

5-Chloro-2-methoxy-N-(5-p-tolyl-pyridin-3-yl)-benzenesulfonamide

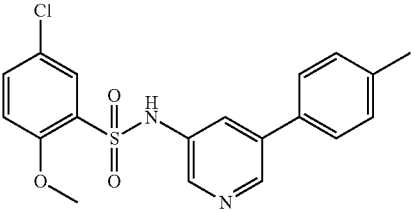 [SMILES: COc1ccc(Br)cc1S(=O)(=O)Nc1cncc(-c2ccc(C)cc2)c1]

This compound was prepared as described in Example III-1.
¹H NMR (DMSO-d6, 400 MHz): δ=10.67 (1H, brs), 8.56 (1H, s), 8.29 (1H, s), 7.79 (1H, s), 7.72 (1H, s), 7.67 (1H, dd), 7.47 (2H, d), 7.31 (2H, d), 7.24 (1H, d), 3.85 (3H, s), 2.35 (3H, s). MS: m/z 388.9 (M+H⁺).

Example III-13

2,5-Dimethoxy-N-(5-(4-(trifluoromethyl)phenyl)pyridin-3-yl)benzenesulfonamide

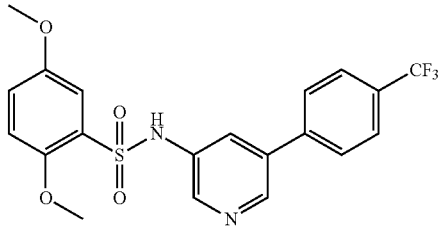 [SMILES: COc1ccc(OC)c(S(=O)(=O)Nc2cncc(-c3ccc(C(F)(F)F)cc3)c2)c1]

This compound was prepared as described in Example III-1.
¹H NMR (DMSO-d6, 400 MHz): δ=10.53 (1H, brs), 8.59 (1H, d), 8.36 (1H, d), 7.87 (2H, d), 7.82-7.75 (3H, m), 7.32 (1H, d), 7.18-7.13 (2H, m), 3.79 (3H, s), 3.72 (3H, s). MS: m/z 439.0 (M+H⁺).

Example III-14

5-Bromo-2-methoxy-N-(5-(4-(trifluoromethyl)phenyl)pyridin-3-yl)benzenesulfonamide

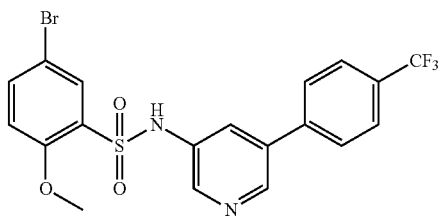

This compound was prepared as described in Example III-1.

¹H NMR (DMSO-d6, 400 MHz): δ=10.68 (1H, brs), 8.63 (1H, s), 8.36 (1H, s), 7.91-7.75 (7H, m), 7.18 (1H, d), 3.84 (3H, s). MS: m/z 486.8 (M+H⁺).

Example III-15

5-Chloro-2-methoxy-N-(5-(4-(trifluoromethyl)phenyl)pyridin-3-yl)benzenesulfonamide

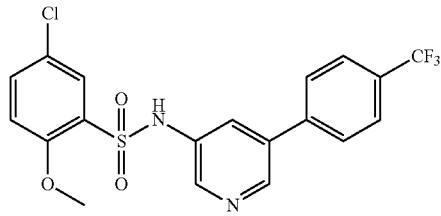 [SMILES: COc1ccc(Br)cc1S(=O)(=O)Nc1cncc(-c2ccc(C(F)(F)F)cc2)c1]

This compound was prepared as described in Example III-1.

¹H NMR (DMSO-d6, 400 MHz): δ=10.68 (1H, brs), 8.62 (1H, s), 8.36 (1H, d), 7.89-7.76 (6H, m), 7.67 (1H, dd), 7.24 (1H, d), 3.85 (3H, s). MS: m/z 442.9 (M+H⁺).

Example III-16

N-[5-(4-Fluoro-phenyl)-pyridin-3-yl]-2,5-dimethoxy-benzenesulfonamide

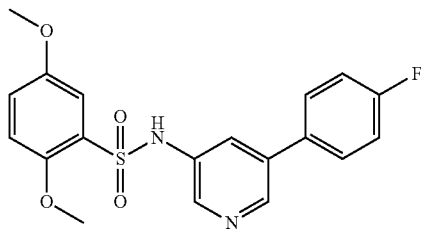 [SMILES: COc1ccc(OC)c(S(=O)(=O)Nc2cncc(-c3ccc(F)cc3)c2)c1]

This compound was prepared as described in Example III-1.

¹H NMR (DMSO-d6, 400 MHz): δ=10.47 (1H, brs), 8.50 (1H, s), 8.29 (1H, s), 7.68 (1H, s), 7.61 (2H, dd), 7.37-7.30 (3H, m), 7.17-7.13 (2H, m), 3.79 (3H, s), 3.72 (3H, s). MS: m/z 389.0 (M+H⁺).

Example III-17

5-Bromo-N-[5-(4-fluoro-phenyl)-pyridin-3-yl]-2-methoxy-benzenesulfonamide

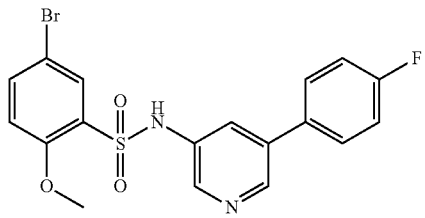 [SMILES: COc1ccc(Br)cc1S(=O)(=O)Nc1cncc(-c2ccc(F)cc2)c1]

This compound was prepared as described in Example III-1.

¹H NMR (DMSO-d6, 400 MHz): δ=10.62 (1H, brs), 8.53 (1H, s), 8.28 (1H, d), 7.89 (1H, d), 7.78 (1H, dd), 7.68-7.60 (3H, m), 7.34 (2H, t), 7.18 (1H, d), 3.84 (3H, s). MS: m/z 436.9 (M+H⁺).

Example III-18

5-Chloro-N-[5-(4-fluoro-phenyl)-pyridin-3-yl]-2-methoxy-benzenesulfonamide

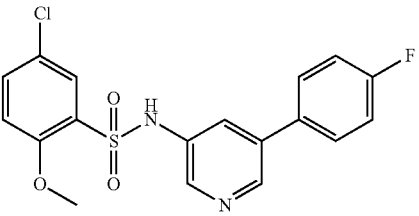 [SMILES: COc1ccc(Cl)cc1S(=O)(=O)Nc1cncc(-c2ccc(F)cc2)c1]

This compound was prepared as described in Example III-1.

¹H NMR (DMSO-d6, 400 MHz): δ=10.57 (1H, brs), 8.53 (1H, s), 8.29 (1H, s), 7.78 (1H, s), 7.68-7.60 (4H, m), 7.34 (2H, t), 7.23 (1H, d), 3.85 (3H, s). MS: m/z 392.9 (M+H⁺).

Example III-19

N-[5-(4-Chloro-phenyl)-pyridin-3-yl]-2,5-dimethoxy-benzenesulfonamide

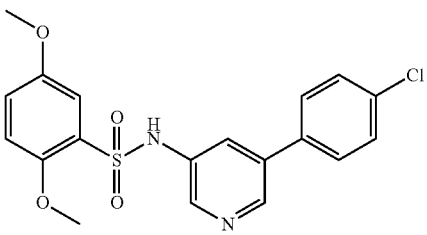 [SMILES: COc1ccc(OC)c(S(=O)(=O)Nc2cncc(-c3ccc(Cl)cc3)c2)c1]

This compound was prepared as described in Example III-1.

¹H NMR (DMSO-d6, 400 MHz): δ=10.49 (1H, brs), 8.53 (1H, s), 8.31 (1H, s), 7.70 (1H, s), 7.63-7.52 (4H, m), 7.32 (1H, d), 7.15-7.13 (2H, m), 3.79 (3H, s), 3.72 (3H, s). MS: m/z 404.9 (M+H⁺).

Example III-20

5-Bromo-N-[5-(4-chloro-phenyl)-pyridin-3-yl]-2-methoxy-benzenesulfonamide

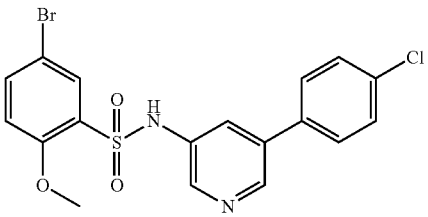 [SMILES: COc1ccc(Br)cc1S(=O)(=O)Nc1cncc(-c2ccc(Cl)cc2)c1]

This compound was prepared as described in Example III-1.

¹H NMR (DMSO-d6, 400 MHz): δ=10.65 (1H, brs), 8.55 (1H, s), 8.30 (1H, s), 7.89 (1H, s), 7.78 (1H, dd), 7.69 (1H, s), 7.63-7.54 (3H, m), 7.17 (2H, d), 3.84 (3H, s). MS: m/z 452.8 (M+H⁺).

Example III-21

5-Chloro-N-[5-(4-chloro-phenyl)-pyridin-3-yl]-2-methoxy-benzenesulfonamide

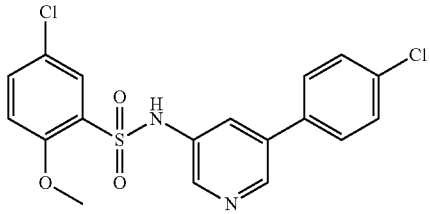 [SMILES: COc1ccc(Cl)cc1S(=O)(=O)Nc1cncc(-c2ccc(Cl)cc2)c1]

This compound was prepared as described in Example III-1.

¹H NMR (DMSO-d6, 400 MHz): δ=10.61 (1H, brs), 8.56 (1H, s), 8.30 (1H, s), 7.78 (1H, s), 7.77-7.54 (6H, m), 7.23 (1H, d), 3.85 (3H, s). MS: m/z 408.9 (M+H⁺).

Example III-22

N-[5-(4-Bromo-phenyl)-pyridin-3-yl]-2,5-dimethoxy-benzenesulfonamide

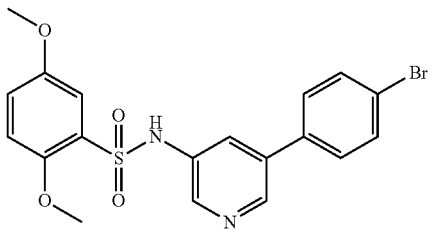 [SMILES: COc1ccc(OC)c(S(=O)(=O)Nc2cncc(-c3ccc(Br)cc3)c2)c1]

This compound was prepared as described in Example III-1.

¹H NMR (DMSO, 400 HMz): δ=10.46 (1H, s), 8.52 (1H, d), 8.32 (1H, d), 7.71-7.69 (3H, m), 7.53 (2H, dd), 7.31 (1H, d), 7.19-7.12 (2H, m), 3.79 (3H, s), 3.72 (3H, s). MS: m/z 448.7 (M+H⁺).

Example III-23

5-Bromo-N-[5-(4-bromo-phenyl)-pyridin-3-yl]-2-methoxy-benzenesulfonamide

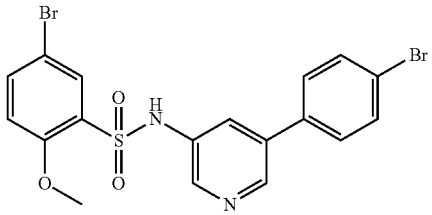 [SMILES: COc1ccc(Br)cc1S(=O)(=O)Nc1cncc(-c2ccc(Br)cc2)c1]

This compound was prepared as described in Example III-1.

1H NMR (DMSO, 400 HMz): δ=10.61 (1H, s), 8.56 (1H, d), 8.31 (1H, d), 7.88 (1H, d), 7.78 (1H, dd), 7.71-7.69 (3H, m), 7.54 (2H, dd), 7.18 (1H, d), 3.84 (3H, s). MS: m/z 496.7 (M+H⁺).

Example III-24

N-[5-(4-Bromo-phenyl)-pyridin-3-yl]-5-chloro-2-methoxy-benzenesulfonamide

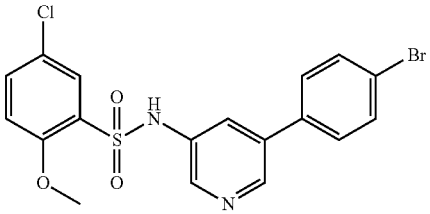 [SMILES: COc1ccc(Cl)cc1S(=O)(=O)Nc1cncc(-c2ccc(Br)cc2)c1]

This compound was prepared as described in Example III-1.

¹H NMR (DMSO, 400 HMz): δ=10.60 (1H, brs), 8.56 (1H, d), 8.31 (1H, d), 7.78 (1H, d), 7.68-7.71 (4H, m), 7.54 (2H, d), 7.24 (1H, d), 3.85 (3H, s). MS: m/z 452.8 (M+H⁺).

Example III-25

N-(5-Phenyl-pyridin-3-yl)-2,5-Dimethoxy-benzenesulfonamide

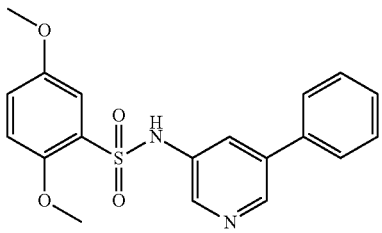 [SMILES: COc1ccc(OC)c(S(=O)(=O)Nc2cncc(-c3ccccc3)c2)c1]

This compound was prepared as described in Example III-1.

¹H NMR (DMSO-d6, 400 MHz): δ=10.48 (1H, brs), 8.52 (1H, s), 8.30 (1H, d), 7.70 (1H, s), 7.57-7.42 (6H, m), 7.32 (1H, d), 7.18-7.11 (1H, m), 3.80 (3H, s), 3.72 (3H, s). MS: m/z 371.0 (M+H⁺).

Example III-26

5-Bromo-2-methoxy-N-(5-phenyl-pyridin-3-yl)-benzenesulfonamide

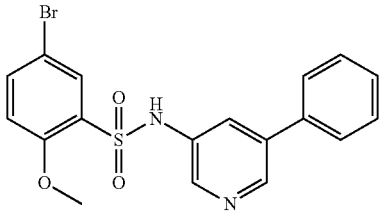 [SMILES: COc1ccc(Cl)cc1S(=O)(=O)Nc1cncc(-c2ccccc2)c1]

This compound was prepared as described in Example III-1.

¹H NMR (DMSO-d6, 400 MHz): δ=10.65 (1H, brs), 8.54 (1H, d), 8.29 (1H, d), 7.89 (1H, d), 7.79 (1H, dd), 7.69 (1H, t), 7.58-7.43 (5H, m), 7.18 (1H, d), 3.85 (3H, s). MS: m/z 418.9 (M+H⁺).

Example III-27

5-Chloro-2-methoxy-N-(5-phenyl-pyridin-3-yl)-benzenesulfonamide

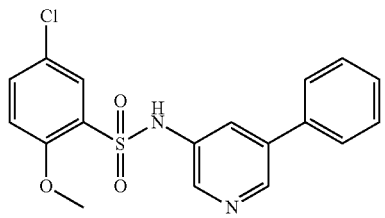

This compound was prepared as described in Example III-1.

¹H NMR (DMSO-d6, 400 MHz): δ=10.63 (1H, brs), 8.55 (1H, d), 8.30 (1H, d), 7.79 (1H, d), 7.71-7.65 (7H, m), 7.24 (1H, d), 3.86 (3H, s). MS: m/z 374.9 (M+H⁺).

Example III-28

4-[5-(2,5-Dimethoxy-benzenesulfonylamino)-pyridin-3-yl]-benzoic acid methyl ester

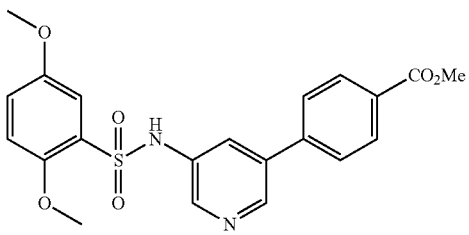 [SMILES: COC(=O)c1ccc(-c2cncc(NS(=O)(=O)c3cc(OC)ccc3OC)c2)cc1]

This compound was prepared as described in Example III-1.

¹H NMR (DMSO-d6, 400 MHz): δ=10.52 (1H, brs), 8.59 (1H, d), 8.34 (1H, d), 8.06 (2H, d), 7.78-7.71 (3H, d), 7.32 (1H, d), 7.20-7.11 (2H, m), 3.88 (3H, s), 3.79 (3H, s), 3.72 (3H, s). MS: m/z 429.0 (M+H⁺).

Example III-29

4-[5-(5-Bromo-2-methoxy-benzenesulfonylamino)-pyridin-3-yl]-benzoic acid methyl ester

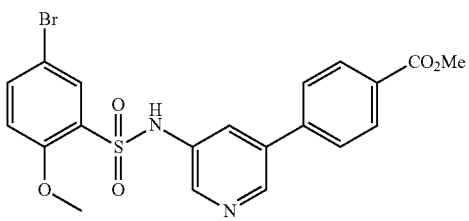

This compound was prepared as described in Example III-1.

¹H NMR (DMSO-d6, 400 MHz): δ=10.71 (1H, brs), 8.62 (1H, s), 8.35 (1H, s), 8.07 (2H, d), 7.91 (1H, d), 7.81-7.72 (4H, m), 7.18 (1H, d), 3.89 (3H, s), 3.84 (3H, s). MS: m/z 476.9 (M+H⁺).

Example III-30

4-[5-(5-Chloro-2-methoxy-benzenesulfonylamino)-pyridin-3-yl]-benzoic acid methyl ester

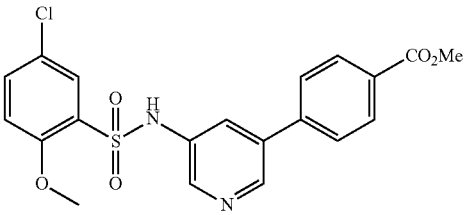 [SMILES: COC(=O)c1ccc(-c2cncc(NS(=O)(=O)c3cc(Br)ccc3OC)c2)cc1]

This compound was prepared as described in Example III-1.

¹H NMR (DMSO-d6, 400 MHz): δ=10.69 (1H, brs), 8.63 (1H, s), 8.35 (1H, s), 8.06 (2H, d), 7.81-7.72 (4H, m), 7.67 (1H, dd), 7.24 (1H, d), 3.89 (3H, s), 3.85 (3H, s). MS: m/z 432.9 (M+H⁺).

Example III-31

N-(5-(4-Cyanophenyl)pyridin-3-yl)-2,5-dimethoxy-benzenesulfonamide

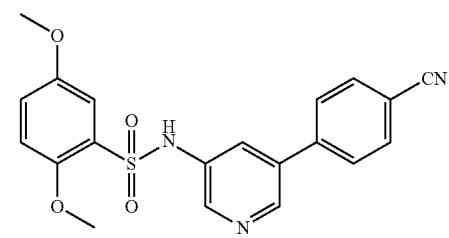 [SMILES: COc1ccc(OC)c(S(=O)(=O)Nc2cncc(-c3ccc(C#N)cc3)c2)c1]

This compound was prepared as described in Example III-1.

¹H NMR (DMSO-d6, 400 MHz): δ=10.56 (1H, brs), 8.60 (1H, s), 8.36 (1H, d), 7.97 (2H, d), 7.80-7.76 (3H, m), 7.32 (1H, d), 7.20-7.11 (2H, m), 3.79 (3H, s), 3.72 (3H, s). MS: m/z 396.0 (M+H⁺).

Example III-32

5-Bromo-N-(5-(4-cyanophenyl)pyridin-3-yl)-2-methoxybenzenesulfonamide

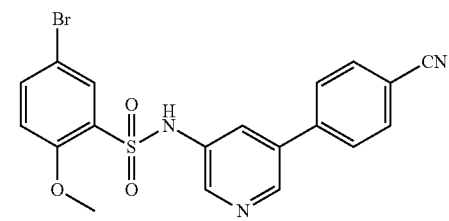

This compound was prepared as described in Example III-1.

¹H NMR (DMSO-d6, 400 MHz): δ=10.70 (1H, brs), 8.63 (1H, d), 8.35 (1H, d), 7.98 (2H, d), 7.89 (1H, d), 7.82-7.75 (4H, m), 7.18 (1H, d), 3.83 (3H, s). MS: m/z 443.9 (M+H⁺).

Example III-33

5-Chloro-N-(5-(4-cyanophenyl)pyridin-3-yl)-2-methoxybenzenesulfonamide

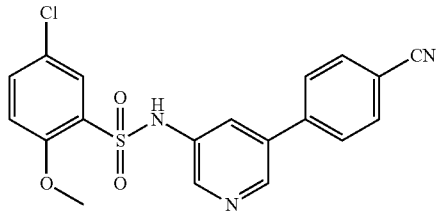 [SMILES: COc1ccc(Br)cc1S(=O)(=O)Nc1cncc(-c2ccc(C#N)cc2)c1]

This compound was prepared as described in Example III-1.

¹H NMR (DMSO-d6, 400 MHz): δ=10.68 (1H, brs), 8.64 (1H, s), 8.36 (1H, d), 7.97 (2H, d), 7.82-7.76 (4H, m), 7.67 (1H, dd), 7.24 (1H, d), 3.84 (3H, s). MS: m/z 399.9 (M+H⁺).

Example III-34

2,5-Dimethoxy-N-[5-(2-methoxy-phenyl)-pyridin-3-yl]-benzenesulfonamide

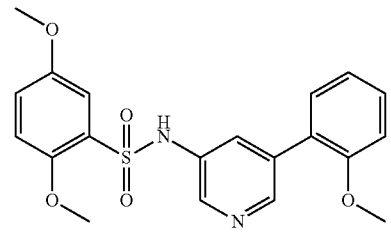 [SMILES: COc1ccc(OC)c(S(=O)(=O)Nc2cncc(-c3ccccc3OC)c2)c1]

This compound was prepared as described in Example III-1.

1H NMR (DMSO, 400 HMz): δ=10.39 (1H, brs), 8.29 (1H, d), 8.26 (1H, d), 7.61 (1H, t), 7.39 (1H, d), 7.29 (1H, d), 7.12-7.23 (4H, m), 7.04 (1H, t), 3.81 (3H, s), 3.72 (6H, d). MS: m/z 401.0 (M+H⁺).

Example III-35

5-Bromo-2-methoxy-N-[5-(2-methoxy-phenyl)-pyridin-3-yl]-benzenesulfonamide

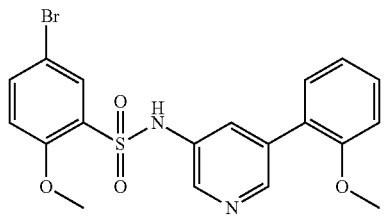

This compound was prepared as described in Example III-1.

¹H NMR (DMSO, 400 HMz): δ=10.54 (1H, brs), 8.31 (1H, s), 8.25 (1H, d), 7.86 (1H, d), 7.80 (1H, dd), 7.61 (1H, s), 7.39 (1H, t), 7.22 (2H, t), 7.14 (1H, d), 7.06 (1H, d), 3.87 (3H, s), 3.74 (3H, s). MS: m/z 448.9 (M+H⁺).

Example III-36

5-Chloro-2-methoxy-N-[5-(2-methoxy-phenyl)-pyridin-3-yl]-benzenesulfonamide

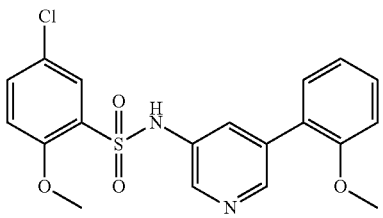 [SMILES: COc1ccccc1-c1cncc(NS(=O)(=O)c2cc(Br)ccc2OC)c1]

This compound was prepared as described in Example III-1.

¹H NMR (DMSO, 400 HMz): δ=10.54 (1H, brs), 8.32 (1H, d), 8.26 (1H, d), 7.75 (1H, d), 7.69 (1H, dd), 7.62 (1H, t), 7.42-7.38 (1H, m), 7.38-7.23 (2H, m), 7.13 (1H, d), 7.05 (1H, t), 3.87 (3H, s), 3.73 (3H, s). MS: m/z 448.9 (M+H⁺).

Example III-37

2,5-Dimethoxy-N-(5-(o-tolyl)pyridin-3-yl)benzenesulfonamide

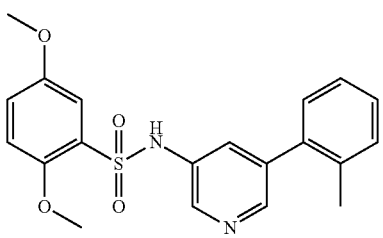 [SMILES: COc1ccc(OC)c(S(=O)(=O)Nc2cncc(-c3ccccc3C)c2)c1]

This compound was prepared as described in Example III-1.

¹H NMR (DMSO-d6, 400 MHz): δ=10.45 (1H, brs), 8.31 (1H, d), 8.18 (1H, d), 7.41 (1H, d), 7.33-7.26 (4H, m), 7.20-7.10 (3H, m), 3.81 (3H, s), 3.72 (3H, s), 2.04 (3H, s). MS: m/z 385.0 (M+H⁺).

Example III-38

5-Bromo-2-methoxy-N-(5-(o-tolyppyridin-3-yl)benzenesulfonamide

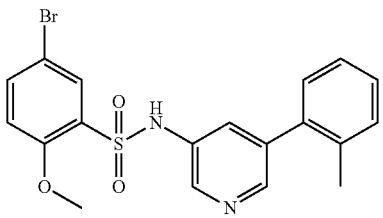

This compound was prepared as described in Example III-1.

¹H NMR (DMSO-d6, 400 MHz): δ=10.61 (1H, brs), 8.30 (1H, d), 8.20 (1H, d), 7.85-7.77 (2H, m), 7.41 (1H, t), 7.34-7.24 (3H, m), 7.19 (1H, d), 7.12 (1H, d), 3.87 (3H, s), 2.06 (3H, s). MS: m/z 432.9 (M+H⁺).

Example III-39

5-Chloro-2-methoxy-N-(5-o-tolyl-pyridin-3-yl)-benzenesulfonamide

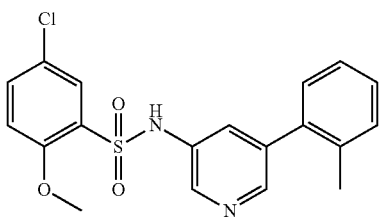

This compound was prepared as described in Example III-1.

¹H NMR (DMSO-d6, 400 MHz): δ=10.61 (1H, brs), 8.30 (1H, s), 8.19 (1H, s), 7.74 (1H, d), 7.71-7.65 (1H, m), 7.40 (1H, s), 7.32-7.22 (4H, m), 7.12 (1H, d), 3.87 (3H, s), 2.05 (3H, s). MS: m/z 389.0 (M+H⁺).

Example III-40

N-[5-(2-Chloro-phenyl)-pyridin-3-yl]-2,5-dimethoxy-benzenesulfonamide

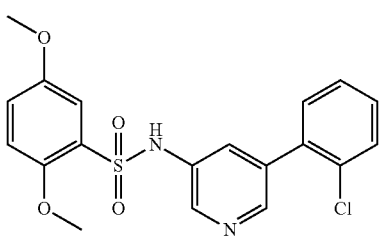

This compound was prepared as described in Example III-1.

¹H NMR (DMSO-d6, 400 MHz): δ=10.50 (1H, brs), 8.35 (1H, d), 8.24 (1H, d), 7.61-7.55 (2H, m), 7.47-7.33 (2H, m), 7.37 (1H, t), 7.29 (1H, d), 7.18-7.12 (2H, m), 3.80 (3H, s), 3.72 (3H, s). MS: m/z 404.9 (M+H⁺).

Example III-41

5-Bromo-N-[5-(2-chloro-phenyl)-pyridin-3-yl]-2-methoxy-benzenesulfonamide

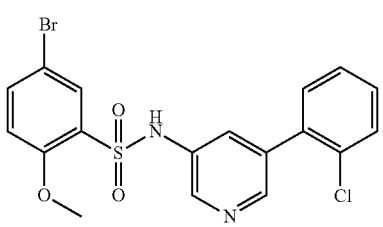 [SMILES: COc1ccc(Br)cc1S(=O)(=O)Nc1cncc(-c2ccccc2C)c1]

This compound was prepared as described in Example III-1.

¹H NMR (DMSO-d6, 400 MHz): δ=10.67 (1H, brs), 8.35 (1H, d), 8.27 (1H, d), 7.85 (1H, s), 7.79 (1H, dd), 7.61-7.36 (5H, m), 7.19 (1H, d), 3.87 (3H, s). MS: m/z 452.8 (M+H⁺).

Example III-42

5-Chloro-N-[5-(2-chloro-phenyl)-pyridin-3-yl]-2-methoxy-benzenesulfonamide

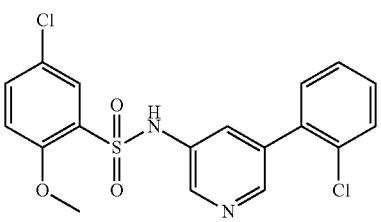 [SMILES: COc1ccc(Cl)cc1S(=O)(=O)Nc1cncc(-c2ccccc2C)c1]

This compound was prepared as described in Example III-1.

¹H NMR (DMSO-d6, 400 MHz): δ=10.67 (1H, brs), 8.34 (1H, d), 8.25 (1H, d), 7.74 (1H, d), 7.70-7.37 (6H, m), 7.24 (1H, d), 3.87 (3H, s). MS: m/z 408.9 (M+H⁺).

Example III-43

2,5-Dimethoxy-N-[5-(2-trifluoromethyl-phenyl)-pyridin-3-yl]-benzenesulfonamide

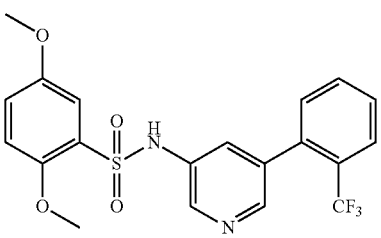 [SMILES: COc1ccc(OC)c(S(=O)(=O)Nc2cncc(-c3ccccc3Cl)c2)c1]

This compound was prepared as described in Example III-1.

¹H NMR (DMSO-d6, 400 MHz): δ=10.50 (1H, brs), 8.35 (1H, d), 8.13 (1H, s), 7.85 (1H, d), 7.75 (1H, t), 7.68 (1H, t), 7.44 (1H, s), 7.35 (1H, d), 7.25 (1H, d), 7.17 (1H, d), 7.13 (1H, d), 3.80 (3H, s), 3.70 (3H, s). MS: m/z 439.0 (M+H⁺).

Example III-44

5-Bromo-2-methoxy-N-[5-(2-trifluoromethyl-phenyl)-pyridin-3-yl]-benzenesulfonamide

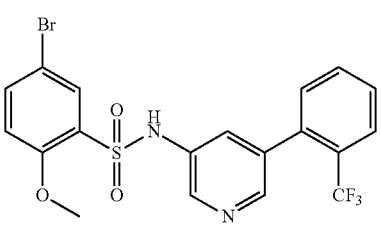

This compound was prepared as described in Example III-1.

¹H NMR (DMSO-d6, 400 MHz): δ=10.66 (1H, brs), 8.35 (1H, d), 8.17 (1H, s), 7.88-7.66 (5H, m), 7.44 (1H, s), 7.37 (1H, d), 7.18 (1H, d), 3.86 (3H, s). MS: m/z 486.9 (M+H⁺).

Example III-45

5-Bromo-2-methoxy-N-[5-(2-trifluoromethyl-phenyl)-pyridin-3-yl]-benzenesulfonamide

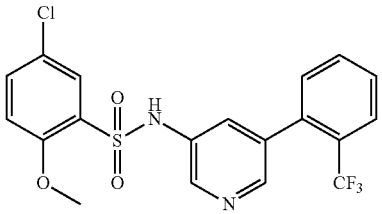 [SMILES: COc1ccc(Cl)cc1S(=O)(=O)Nc1cncc(-c2ccccc2C(F)(F)F)c1]

This compound was prepared as described in Example III-1.

¹H NMR (DMSO-d6, 400 MHz): δ=10.66 (1H, brs), 8.37 (1H, s), 8.18 (1H, s), 7.85 (1H, d), 7.78-7.64 (4H, m), 7.45 (1H, s), 7.37 (1H, d), 7.24 (1H, d), 3.870 (3H, s). MS: m/z 442.9 (M+H⁺).

Example III-46

2,5-Dimethoxy-N-[5-(3-methoxy-phenyl)-pyridin-3-yl]-benzenesulfonamide

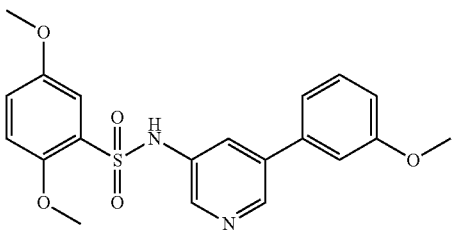 [SMILES: COc1cccc(-c2cncc(NS(=O)(=O)c3cc(OC)ccc3OC)c2)c1]

This compound was prepared as described in Example III-1.

¹H NMR (DMSO-d6, 400 HMz): δ=10.47 (1H, brs), 8.52 (1H, d), 8.30 (1H, d), 7.67 (1H, d), 7.41 (1H, t), 7.33 (1H, d), 7.06-7.20 (4H, m), 6.99 (1H, dd), 3.81 (6H, d), 3.72 (3H, s). MS: m/z 401.0 (M+H⁺).

Example III-47

5-Bromo-2-methoxy-N-[5-(3-methoxy-phenyl)-pyridin-3-yl]-benzenesulfonamide

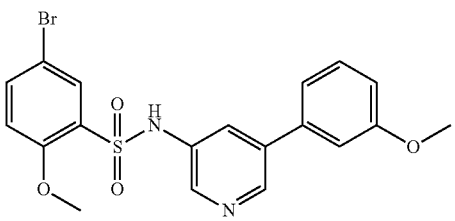 [SMILES: COc1cccc(-c2cncc(NS(=O)(=O)c3cc(Br)ccc3OC)c2)c1]

This compound was prepared as described in Example III-1.

¹H NMR (DMSO-d6, 400 HMz): δ=10.61 (1H, brs), 8.55 (1H, d), 8.30 (1H, d), 7.88 (1H, d), 7.79 (1H, dd), 7.67 (1H, t), 7.41 (1H, d), 7.19 (1H, d), 7.09 (2H, t), 7.00 (1H, dd), 3.85 (3H, s), 3.82 (3H, s). MS: m/z 448.9 (M+H⁺).

Example III-48

5-Chloro-2-methoxy-N-[5-(3-methoxy-phenyl)-pyridin-3-yl]-benzenesulfonamide

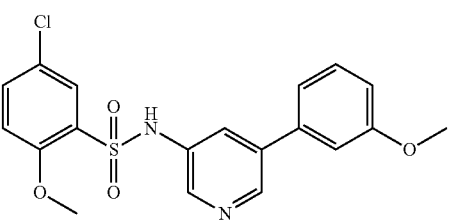 [SMILES: COc1cccc(-c2cncc(NS(=O)(=O)c3cc(Cl)ccc3OC)c2)c1]

This compound was prepared as described in Example III-1.

¹H NMR (DMSO-d6, 400 HMz): δ=10.60 (1H, brs), 8.56 (1H, d), 8.30 (1H, d), 7.78 (1H, d), 7.66-7.69 (2H, m), 7.42 (1H, t), 7.25 (1H, d), 7.12 (2H, t), 7.01 (1H, dd), 3.86 (3H, s), 3.82 (3H, s). MS: m/z 404.9 (M+H⁺).

Example III-49

2,5-Dimethoxy-N-(5-m-tolyl-pyridin-3-yl)-benzenesulfonamide

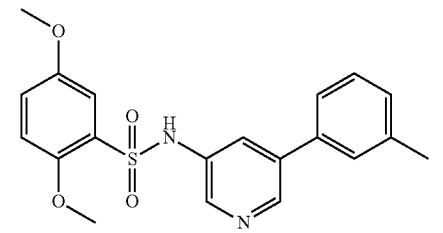 [SMILES: COc1ccc(OC)c(S(=O)(=O)Nc2cncc(-c3cccc(C)c3)c2)c1]

This compound was prepared as described in Example III-1.

¹H NMR (DMSO-d6, 400 MHz): δ=10.47 (1H, brs), 8.47 (1H, d), 8.28 (1H, d), 7.66 (1H, d), 7.39-7.32 (4H, m), 7.27-7.13 (3H, m), 3.80 (3H, s), 3.73 (3H, s), 2.37 (3H, s). MS: m/z 385.0 (M+H⁺).

Example III-50

5-Bromo-2-methoxy-N-(5-m-tolyl-pyridin-3-yl)-benzenesulfonamide

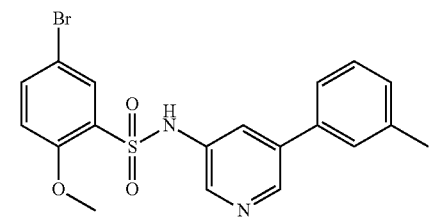

This compound was prepared as described in Example III-1.

$^1$H NMR (DMSO-d6, 400 MHz): δ=10.63 (1H, brs), 8.52 (1H, d), 8.29 (1H, d), 7.91 (1H, d), 7.79 (1H, dd), 7.66 (1H, t), 7.40-7.34 (3H, m), 7.26-7.16 (2H, m), 3.85 (3H, s), 2.38 (3H, s). MS: m/z 432.9 (M+H$^+$).

Example III-51

5-Chloro-2-methoxy-N-(5-m-tolyl-pyridin-3-yl)-benzenesulfonamide

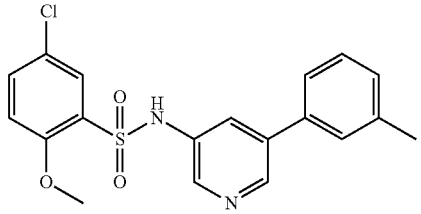 [SMILES: COc1ccc(Cl)cc1S(=O)(=O)Nc1cncc(-c2cccc(C)c2)c1]

This compound was prepared as described in Example III-1.

$^1$H NMR (DMSO-d6, 400 MHz): δ=10.62 (1H, brs), 8.52 (1H, d), 8.28 (1H, d), 7.80 (1H, d), 7.71-7.65 (2H, m), 7.39-7.34 (3H, m), 7.26-7.23 (2H, m), 3.86 (3H, s), 2.38 (3H, s). MS: m/z 389.0 (M+H$^+$).

Example III-52

N-[5-(3-Chloro-phenyl)-pyridin-3-yl]-2,5-dimethoxy-benzenesulfonamide

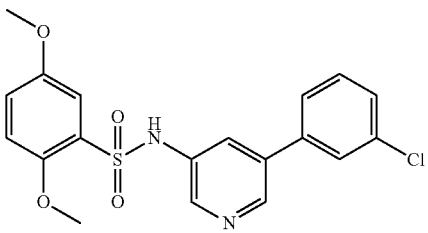 [SMILES: COc1ccc(OC)c(S(=O)(=O)Nc2cncc(-c3cccc(Cl)c3)c2)c1]

This compound was prepared as described in Example III-1.

$^1$H NMR (DMSO-d6, 400 MHz): δ=10.53 (1H, brs), 8.56 (1H, s), 8.33 (1H, d), 7.72 (1H, s), 7.62 (1H, s), 7.53-7.51 (3H, m), 7.33 (1H, d), 7.19-7.12 (2H, m), 3.79 (3H, s), 3.73 (3H, s). MS: m/z 405.0 (M+H$^+$).

Example III-53

5-Bromo-N-[5-(3-chloro-phenyl)-pyridin-3-yl]-2-methoxy-benzenesulfonamide

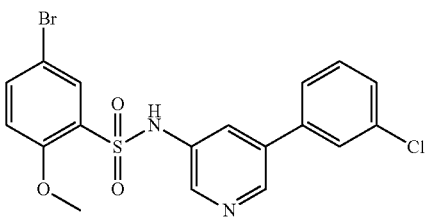 [SMILES: COc1ccc(Br)cc1S(=O)(=O)Nc1cncc(-c2cccc(Cl)c2)c1]

This compound was prepared as described in Example III-1.

$^1$H NMR (DMSO-d6, 400 MHz): δ=10.64 (1H, brs), 8.58 (1H, d), 8.32 (1H, d), 7.90 (1H, d), 7.79 (1H, dd), 7.70 (1H, t), 7.65 (1H, s), 7.56-7.50 (3H, m), 7.18 (1H, d), 3.84 (3H, s). MS: m/z 452.8 (M+H$^+$).

Example III-54

5-Chloro-N-[5-(3-chloro-phenyl)-pyridin-3-yl]-2-methoxy-benzenesulfonamide

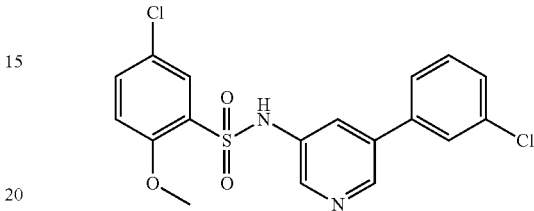

This compound was prepared as described in Example III-1.

$^1$H NMR (DMSO-d6, 400 MHz): δ=10.64 (1H, brs), 8.58 (1H, d), 8.32 (1H, d), 7.79 (1H, d), 7.72-7.63 (3H, m), 7.55-7.50 (3H, m), 7.24 (1H, d), 3.85 (3H, s). MS: m/z 408.9 (M+H$^+$).

Example III-55

N-(5-(2,4-Dimethoxyphenyl)pyridin-3-yl)-2,5-dimethoxybenzenesulfonamide

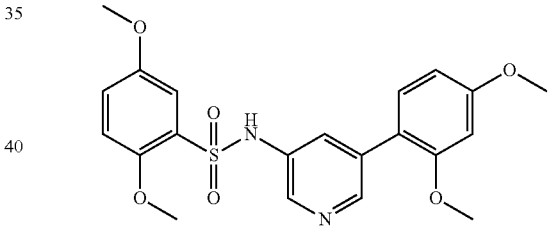

This compound was prepared as described in Example III-1.

$^1$H NMR (DMSO, 400 HMz): δ=10.33 (1H, brs), 8.25 (1H, d), 8.21 (1H, d), 7.58 (1H, d), 7.28 (1H, d), 7.14-7.18 (3H, m), 6.66 (1H, d), 6.62 (1H, dd), 3.81 (3H, s), 3.80 (3H, s), 3.72 (6H, d). MS: m/z 431.0 (M+H$^+$).

Example III-56

5-Bromo-N-(5-(2,4-dimethoxyphenyl)pyridin-3-yl)-2-methoxybenzenesulfonamide

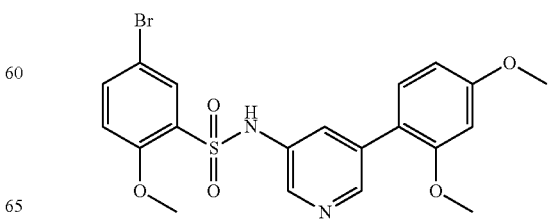

This compound was prepared as described in Example III-1.

¹H NMR (DMSO-d6, 400 MHz): δ=10.50 (1H, brs), 8.28 (1H, d), 8.20 (1H, d), 7.84 (1H, d), 7.79 (1H, dd), 7.58 (1H, s), 7.22-7.15 (2H, m), 6.67 (1H, d), 6.65-6.60 (1H, m), 3.87 (3H, s), 3.81 (3H, s), 3.76 (3H, s). MS: m/z 478.9 (M+H⁺).

Example III-57

5-Chloro-N-(5-(2,4-dimethoxyphenyl)pyridin-3-yl)-2-methoxybenzenesulfonamide

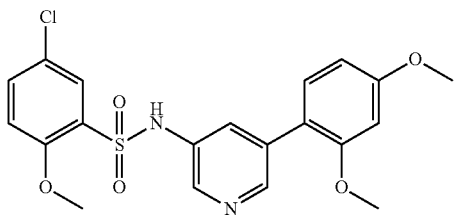 [SMILES: COc1ccc(-c2cncc(NS(=O)(=O)c3cc(Br)ccc3OC)c2)c(OC)c1]

This compound was prepared as described in Example III-1.

¹H NMR (DMSO, 400 HMz): δ=10.51 (1H, brs), 8.27 (1H, d), 8.21 (1H, d), 7.74 (1H, d), 7.68 (1H, dd), 7.58 (1H, t), 7.26 (1H, d), 7.17 (1H, d), 6.67 (1H, d), 6.63 (1H, dd), 3.87 (3H, s), 3.80 (3H, s), 3.73 (3H, s). MS: m/z 434.9 (M+H⁺).

Example III-58

N-([2,3'-Bipyridin]-5'-yl)-2,5-dimethoxybenzenesulfonamide

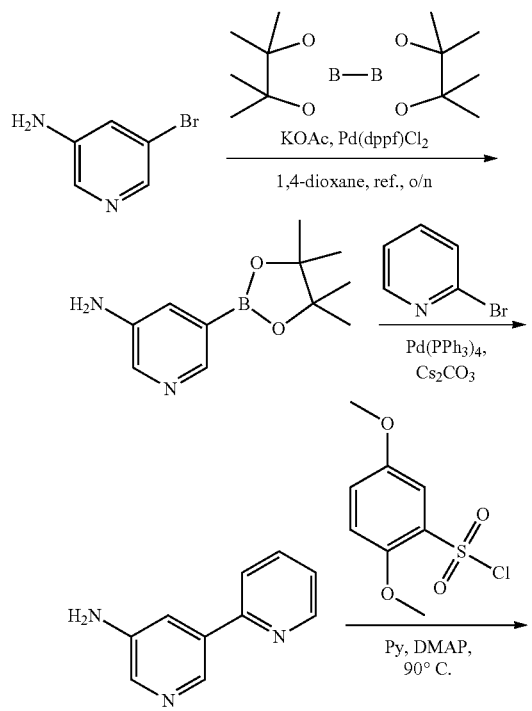

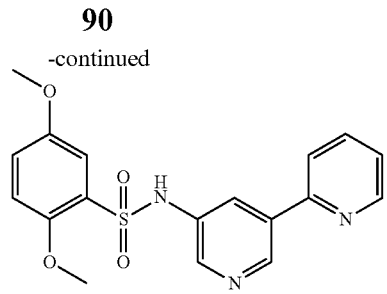

Step 1, 2: 5-Bromo-pyridin-3-ylamine (1.0 g, 5.8 mmol), bis(pinacolato)diboron (1.46 g, 5.7 mmol), Pd(dppf)Cl₂ (200 mg), AcOK (1.1 g, 11.4 mmol) were stirred in 1,4-dioxane (15 mL) at 100° C. under N₂ for 4 h. After cooled to room temperature, to the mixture was added 2-bromo-pyridine (0.91 g, 5.7 mmol), Cs₂CO₃ (7.4 g, 22.8 mmol), Pd(PPh₃)₄ (200 mg), water (3 mL). The mixture was then heated to 100° C. under N₂ for 2 h. The solvent was concentrated under reduced pressure. The residue was dissolved in water and the aqueous phase was extracted with EtOAc (30 mL×3). The organic layer was washed with brine, dried over anhydrous Na₂SO₄ and concentrated to dryness under reduced pressure. The crude was purified via silic gel column (DCM/MeOH, 20/1) to afford 300 mg (2-step yield: 30%) of [2,3']Bipyridinyl-5'-ylamine. MS: m/z 172.0 (M+H⁺).

Step 3: This compound was prepared as described in Example III-1.

¹H NMR (DMSO-d₆, 400 HMz): δ=10.48 (1H, brs), 8.87 (1H, s), 8.69 (1H, d), 8.36 (1H, s), 8.22 (1H, s), 7.91-7.95 (2H, m), 7.32-7.43 (2H, m), 7.13-7.14 (2H, m), 3.80 (3H, s), 3.72 (3H, s). MS: m/z 372.1 (M+H⁺).

Example III-59

N-([2,3'-Bipyridin]-5'-yl)-5-bromo-2-methoxybenzenesulfonamide

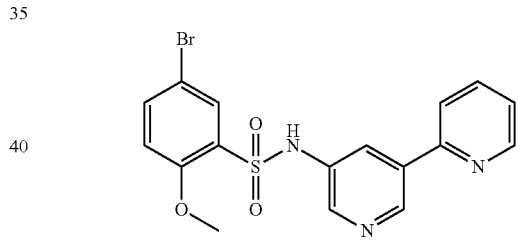

This compound was prepared as described in Example III-1.

¹H NMR (DMSO-d₆, 400 HMz): δ=10.63 (1H, brs), 8.91 (1H, s), 8.71 (1H, d), 8.37 (1H, s), 8.22 (1H, s), 7.98-7.75 (4H, m), 7.41-7.44 (1H, m), 7.17 (1H, d), 3.85 (3H, s). MS: m/z 420.1 (M+H⁺).

Example III-60

N-([2,3'-Bipyridin]-5'-yl)-5-chloro-2-methoxybenzenesulfonamide

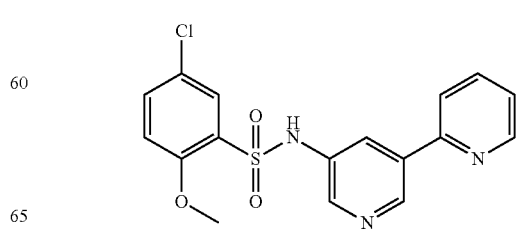

This compound was prepared as described in Example III-1.

$^1$H NMR (DMSO-d$_6$, 400 HMz): δ=10.62 (1H, brs), 8.90 (1H, s), 8.70 (1H, d), 8.36 (1H, s), 8.21 (1H, s), 7.98-7.89 (2H, m), 7.76 (1H, d), 7.66-7.64 (1H, m), 7.40-7.44 (1H, m), 7.22-7.24 (1H, m), 3.85 (3H, s). MS: m/z 376.0 (M+H$^+$).

Example III-61

N-([3,3'-Bipyridin]-5-yl)-2,5-dimethoxybenzenesulfonamide

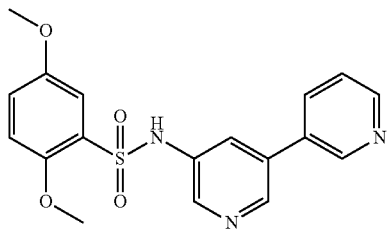 [SMILES: COc1ccc(OC)c(S(=O)(=O)Nc2cncc(-c3cccnc3)c2)c1]

This compound was prepared as described in Example III-1.

$^1$H NMR (DMSO-d6, 400 MHz): δ=10.54 (1H, brs), 8.77 (1H, d), 8.63 (1H, dd), 8.58 (1H, d), 8.35 (1H, d), 8.00 (1H, dt), 7.74 (1H, t), 7.53 (1H, dd), 7.33 (1H, d), 7.20-7.12 (2H, m), 3.80 (3H, s), 3.72 (3H, s). MS: m/z 372.0 (M+H$^+$).

Example III-62

N-([3,3'-Bipyridin]-5-yl)-5-bromo-2-methoxybenzenesulfonamide

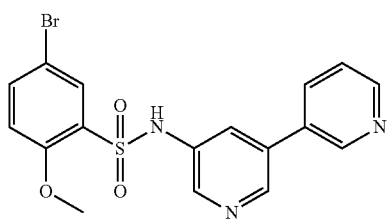 [SMILES: COc1ccc(Br)cc1S(=O)(=O)Nc1cncc(-c2cccnc2)c1]

This compound was prepared as described in Example III-1.

$^1$H NMR (DMSO-d6, 400 MHz): δ=10.68 (1H, brs), 8.80 (1H, s), 8.64 (1H, d), 8.62 (1H, s), 8.35 (1H, d), 8.01 (1H, d), 7.90 (1H, d), 7.79 (1H, dd), 7.74 (1H, s), 7.56-7.50 (1H, m), 7.18 (1H, d), 3.85 (3H, s). MS: m/z 419.9 (M+H$^+$).

Example III-63

N-([3,3'-Bipyridin]-5-yl)-5-chloro-2-methoxybenzenesulfonamide

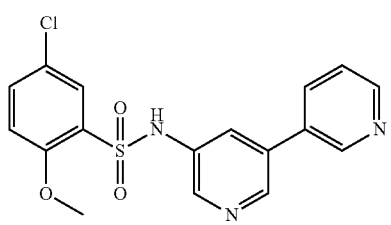 [SMILES: COc1ccc(Cl)cc1S(=O)(=O)Nc1cncc(-c2cccnc2)c1]

This compound was prepared as described in Example III-1.

$^1$H NMR (DMSO-d6, 400 MHz): δ=10.68 (1H, brs), 8.80 (1H, d), 8.62 (1H, dd), 8.60 (1H, dd), 8.34 (1H, d), 8.01 (1H, dt), 7.75 (2H, dd), 7.67 (1H, dd), 7.55-7.50 (1H, m), 7.24 (1H, d), 3.85 (3H, s). MS: m/z 375.9 (M+H$^+$).

Example III-64

N-([3,4'-Bipyridin]-5-yl)-2,5-dimethoxybenzenesulfonamide

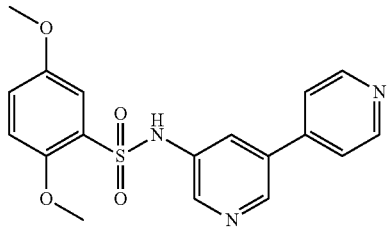 [SMILES: COc1ccc(OC)c(S(=O)(=O)Nc2cncc(-c3ccncc3)c2)c1]

This compound was prepared as described in Example III-1.

$^1$H NMR (DMSO-d6, 400 MHz): δ=10.58 (1H, brs), 8.69-8.64 (3H, m), 8.38 (1H, s), 7.81 (1H, s), 7.63-7.60 (2H, m), 7.33 (1H, s), 7.20-7.12 (2H, m), 3.79 (3H, s), 3.72 (3H, s). MS: m/z 372.0 (M+H$^+$).

Example III-65

N-([3,4'-Bipyridin]-5-yl)-5-bromo-2-methoxybenzenesulfonamide

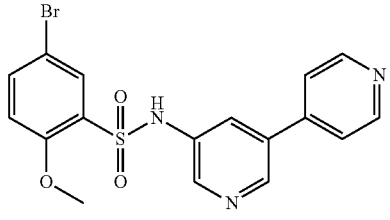 [SMILES: COc1ccc(Cl)cc1S(=O)(=O)Nc1cncc(-c2ccncc2)c1]

This compound was prepared as described in Example III-1.

$^1$H NMR (DMSO, 400 HMz): δ=10.72 (1H, brs), 8.72-8.65 (3H, m), 8.38 (1H, d), 7.91 (1H, d), 7.81-7.77 (2H, m), 7.63 (2H, dd), 7.18 (1H, d), 3.84 (3H, s). MS: m/z 419.9 (M+H$^+$).

Example III-66

N-([3,4'-Bipyridin]-5-yl)-5-chloro-2-methoxybenzenesulfonamide

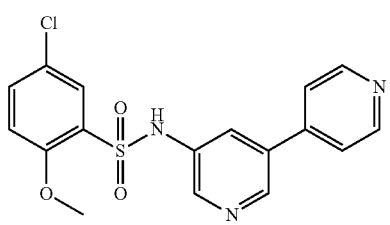

This compound was prepared as described in Example III-1.

¹H NMR (DMSO-d6, 400 MHz): δ=10.76 (1H, brs), 8.82 (2H, d), 8.76 (1H, d), 8.42 (1H, d), 7.92-7.88 (3H, m), 7.80 (1H, d), 7.68 (1H, dd), 7.24 (1H, d), 3.84 (3H, s). MS: m/z 375.9 (M+H⁺).

Example III-67

N-(5-(Furan-2-yl)pyridin-3-yl)-2,5-dimethoxybenzenesulfonamide

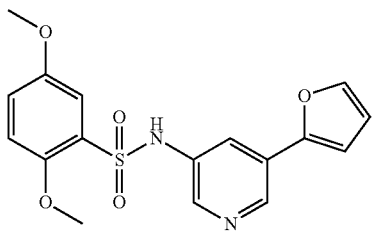

This compound was prepared as described in Example III-1.

¹H NMR (DMSO-d6, 400 HMz): δ=10.49 (1H, brs), 8.59 (1H, d), 8.20 (1H, d), 7.84 (1H, d), 7.74 (1H, t), 7.31 (1H, d), 7.16-7.04 (3H, m), 6.63 (1H, dd), 3.80 (3H, s), 3.72 (3H, s). MS: m/z 360.9 (M+H⁺).

Example III-68

5-Bromo-N-(5-(furan-2-yl)pyridin-3-yl)-2-methoxybenzenesulfonamide

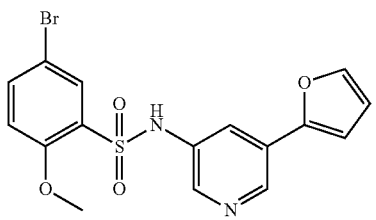 [SMILES: COc1ccc(Br)cc1S(=O)(=O)Nc1cncc(-c2ccco2)c1]

This compound was prepared as described in Example III-1.

¹H NMR (DMSO-d6, 400 HMz): δ=10.63 (1H, brs), 8.63 (1H, d), 8.19 (1H, d), 7.72-7.87 (4H, m), 7.18 (1H, d), 7.17 (1H, d), 6.64 (1H, dd), 3.85 (3H, s). MS: m/z 408.8 (M+H⁺).

Example III-69

5-Chloro-N-(5-(furan-2-yl)pyridin-3-yl)-2-methoxybenzenesulfonamide

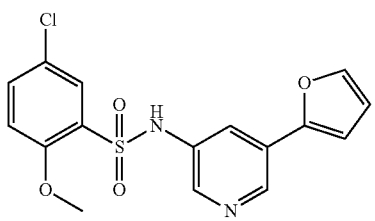

This compound was prepared as described in Example III-1.

¹H NMR (DMSO-d6, 400 HMz): δ=10.63 (1H, brs), 8.63 (1H, d), 8.19 (1H, d), 7.84 (1H, d), 7.76-7.65 (3H, m), 7.24 (1H, d), 7.07 (1H, d), 6.64 (1H, dd), 3.85 (3H, s). MS: m/z 364.9 (M+H⁺).

Example III-70

N-(5-(Furan-3-yl)pyridin-3-yl)-2,5-dimethoxybenzenesulfonamide

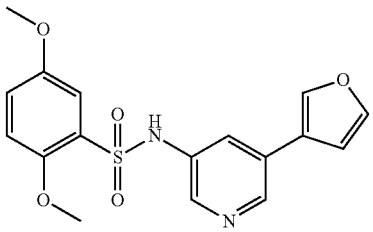 [SMILES: COc1ccc(OC)c(S(=O)(=O)Nc2cncc(-c3ccoc3)c2)c1]

This compound was prepared as described in Example III-1.

¹H NMR (DMSO-d6, 400 MHz): δ=10.36 (1H, brs), 8.51 (1H, d), 8.22 (1H, s), 8.16 (1H, d), 7.80 (1H, s), 7.62 (1H, t), 7.31 (1H, d), 7.19-7.10 (2H, m), 6.88 (1H, s), 3.80 (3H, s), 3.72 (3H, s). MS: m/z 361.0 (M+H⁺).

Example III-71

5-Bromo-N-(5-(furan-3-yl)pyridin-3-yl)-2-methoxybenzenesulfonamide

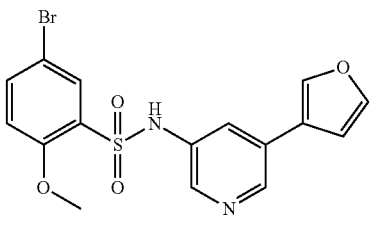 [SMILES: COc1ccc(Br)cc1S(=O)(=O)Nc1cncc(-c2ccoc2)c1]

This compound was prepared as described in Example III-1.

¹H NMR (DMSO-d6, 400 MHz): δ=10.51 (1H, brs), 8.54 (1H, s), 8.24 (1H, s), 8.15 (1H, d), 7.87 (1H, d), 7.81-7.60 (2H, m), 7.61 (1H, s), 7.18 (1H, d), 6.90 (1H, s), 3.85 (3H, s). MS: m/z 408.9 (M+H⁺).

Example III-72

5-Chloro-N-(5-(furan-3-yl)pyridin-3-yl)-2-methoxybenzenesulfonamide

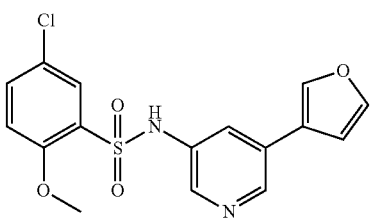

This compound was prepared as described in Example III-1.

¹H NMR (DMSO-d6, 400 MHz): δ=10.51 (1H, brs), 8.54 (1H, d), 8.24 (1H, s), 8.16 (1H, d), 7.81-7.75 (2H, m), 7.68-7.61 (2H, m), 7.24 (1H, d), 6.90 (1H, d), 3.86 (3H, s). MS: m/z 364.9 (M+H⁺).

Example III-73

2,5-Dimethoxy-N-(5-(thiophen-2-yl)pyridin-3-yl)benzenesulfonamide

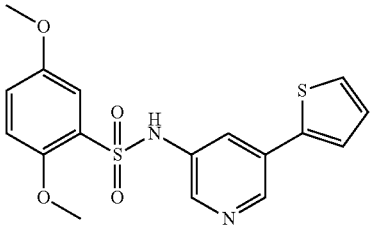 [SMILES: COc1ccc(OC)c(S(=O)(=O)Nc2cncc(-c3cccs3)c2)c1]

This compound was prepared as described in Example III-1.

¹H NMR (DMSO-d6, 400 MHz): δ=10.51 (1H, brs), 8.54 (1H, d), 8.24 (1H, s), 8.16 (1H, d), 7.81-7.75 (2H, m), 7.68-7.61 (2H, m), 7.24 (1H, d), 6.90 (1H, d), 3.86 (3H, s). MS: m/z 364.9 (M+H⁺).

Example III-74

5-Bromo-2-methoxy-N-(5-(thiophen-2-yl)pyridin-3-yl)benzenesulfonamide

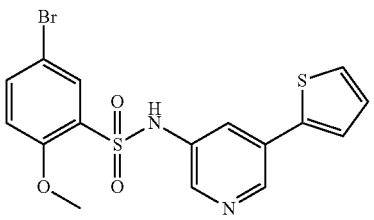 [SMILES: COc1ccc(Br)cc1S(=O)(=O)Nc1cncc(-c2cccs2)c1]

This compound was prepared as described in Example III-1.

¹H NMR (DMSO-d6, 400 MHz): δ=10.64 (1H, brs), 8.60 (1H, d), 8.22 (1H, d), 7.89 (1H, d), 7.79 (1H, dd), 7.68-7.62 (2H, m), 7.56 (1H, dd), 7.20-7.17 (2H, m), 3.86 (3H, s). MS: m/z 424.8 (M+H⁺).

Example III-75

5-Chloro-2-methoxy-N-(5-(thiophen-2-yl)pyridin-3-yl)benzenesulfonamide

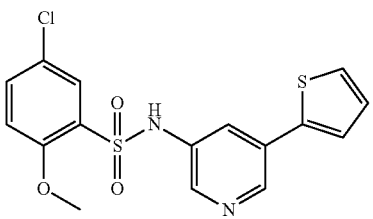 [SMILES: COc1ccc(Cl)cc1S(=O)(=O)Nc1cncc(-c2cccs2)c1]

This compound was prepared as described in Example III-1.

¹H NMR (DMSO-d6, 400 MHz): δ=10.63 (1H, brs), 8.60 (1H, d), 8.22 (1H, d), 7.78 (1H, d), 7.69-7.64 (3H, m), 7.55 (1H, dd), 7.24 (1H, d), 7.18 (1H, dd), 3.86 (3H, s). MS: m/z 380.9 (M+H⁺).

Example III-76

2,5-Dimethoxy-N-(5-(thiophen-3-yl)pyridin-3-yl)benzenesulfonamide

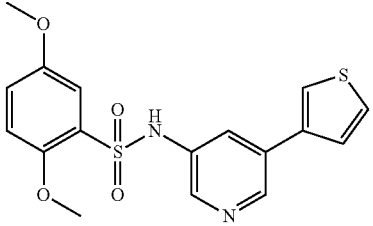

This compound was prepared as described in Example III-1.

¹H NMR (DMSO-d6, 400 MHz): δ=10.39 (1H, brs), 8.60 (1H, s), 8.21 (1H, s), 7.91 (1H, s), 7.73-7.68 (2H, m), 7.45 (1H, d), 7.31 (1H, d), 7.16-7.13 (2H, m), 3.80 (3H, s), 3.71 (3H, s). MS: m/z 377.0 (M+H⁺).

Example III-77

5-Bromo-2-methoxy-N-(5-(thiophen-3-yl)pyridin-3-yl)benzenesulfonamide

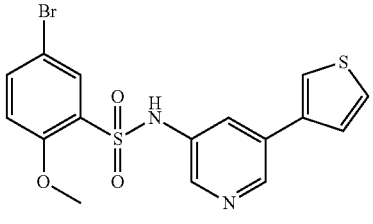

This compound was prepared as described in Example III-1.

¹H NMR (DMSO-d6, 400 MHz): δ=10.54 (1H, brs), 8.63 (1H, s), 8.21 (1H, s), 7.93 (1H, s), 7.87 (1H, d), 7.80-7.72 (3H, m), 7.47 (1H, d), 7.18 (1H, d), 3.86 (3H, s). MS: m/z 424.9 (M+H⁺).

Example III-78

5-Chloro-2-methoxy-N-(5-(thiophen-3-yl)pyridin-3-yl)benzenesulfonamide

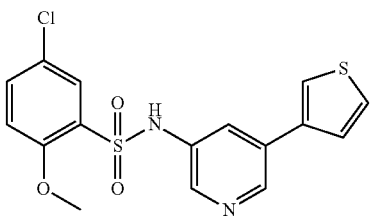 [SMILES: COc1ccc(Cl)cc1S(=O)(=O)Nc1cncc(-c2ccsc2)c1]

This compound was prepared as described in Example III-1.

¹H NMR (DMSO-d6, 400 MHz): δ=10.55 (1H, brs), 8.63 (1H, s), 8.21 (1H, s), 7.93 (1H, d), 7.78-7.63 (4H, m), 7.47 (1H, d), 7.23 (1H, d), 3.87 (3H, s). MS: m/z 380.9 (M+H⁺).

Example III-79

2,5-Dimethoxy-N-(5-(thiazol-2-yl)pyridin-3-yl)benzenesulfonamide

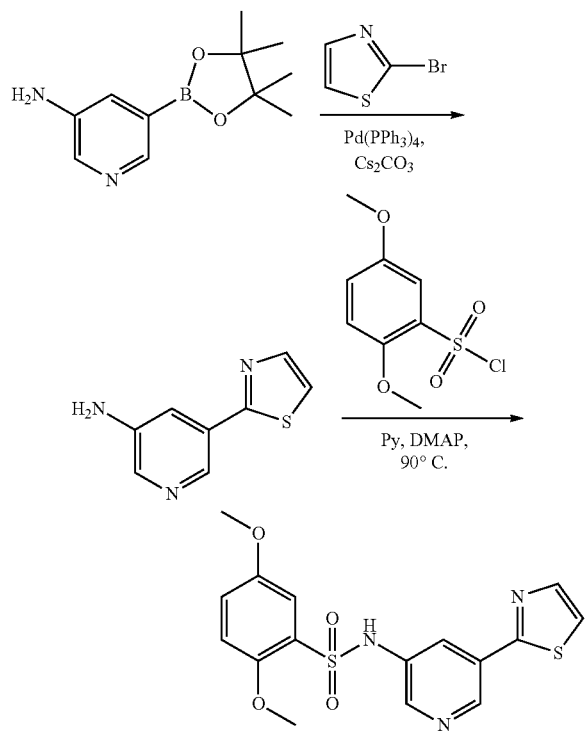

Step 1: 5-(4,4,5,5-Tetramethyl-[1,3,2]dioxaborolan-2-yl)-pyridin-3-ylamine (1.25 g, 5.7 mmol), 2-bromo-thiazole (923 mg, 5.7 mmol), Cs₂CO₃ (7.4 g, 22.8 mmol), Pd(PPh₃)₄ (200 mg) were stirred in 1,4-dioxane (15 mL) and water (3 mL) at 100° C. under N₂ for 4 h. Then the solvent was concentrated under reduced-pressure. The residue was dissolved in water and the aqueous phase was extracted with EtOAc (30 mL×3). The organic layer was washed with brine, dried over anhydrous Na₂SO₄ and concentrated to dryness under reduced pressure. The crude was purified via silica gel column (DCM/MeOH, 20/1) to afford 350 mg (yield: 35%) of 5-thiazol-2-yl-pyridin-3-ylamine. MS: m/z 177.9 (M+H⁺).

Step 2: This compound was prepared as described in Example III-1.

¹H NMR (DMSO-d₆, 400 HMz): δ=10.65 (1H, brs), 8.87 (1H, d), 8.39 (1H, d), 8.06 (1H, t), 7.99 (1H, d), 7.89 (1H, d), 7.34 (1H, d), 7.17-7.11 (2H, m), 3.79 (3H, s), 3.78 (3H, s). MS: m/z 378.0 (M+H⁺).

Example III-80

5-Bromo-2-methoxy-N-(5-(thiazol-2-yl)pyridin-3-yl)benzenesulfonamide

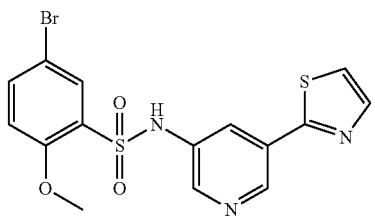 [SMILES: COc1ccc(Br)cc1S(=O)(=O)Nc1cncc(-c2nccs2)c1]

This compound was prepared as described in Example III-1.

¹H NMR (DMSO-d₆, 400 HMz): δ=10.76 (1H, brs), 8.78 (1H, s), 8.40 (1H, s), 8.05-8.00 (2H, m), 7.91-7.87 (2H, m), 7.79-7.77 (1H, m), 7.18 (1H, d), 3.84 (3H, s). MS: m/z 425.9 (M+H⁺).

Example III-81

5-Chloro-2-methoxy-N-(5-(thiazol-2-yl)pyridin-3-yl)benzenesulfonamide

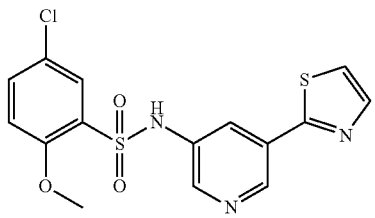

This compound was prepared as described in Example III-1.

¹H NMR (DMSO-d₆, 400 HMz): δ=10.78 (1H, brs), 8.79 (1H, s), 8.41 (1H, s), 8.07-8.01 (2H, m), 7.92 (1H, s), 7.80 (1H, s), 7.69-7.67 (1H, m), 7.25 (1H, d), 3.86 (3H, s). MS: m/z 382.0 (M+H⁺).

Example III-82

2,5-Dimethoxy-N-(5-(thiazol-5-yl)pyridin-3-yl)benzenesulfonamide

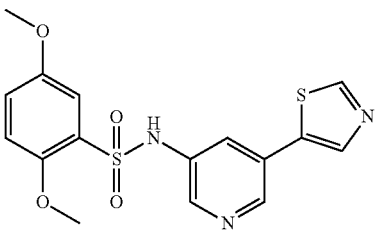 [SMILES: COc1ccc(OC)c(S(=O)(=O)Nc2cncc(-c3cncs3)c2)c1]

This compound was prepared as described in Example III-79.

¹H NMR (DMSO-d₆, 400 HMz): δ=10.45 (1H, brs), 9.24 (1H, d), 8.81 (1H, d), 8.29-8.27 (2H, m), 8.11 (1H, t), 7.31 (1H, d), 7.17-7.12 (2H, m), 3.80 (3H, s), 3.72 (3H, s). MS: m/z 378.0 (M+H⁺).

Example III-83

5-Bromo-2-methoxy-N-(5-(thiazol-5-yl)pyridin-3-yl)benzenesulfonamide

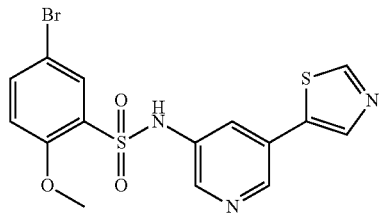

This compound was prepared as described in Example III-79.
¹H NMR (DMSO-d₆, 400 HMz): δ=10.58 (1H, brs), 9.25 (1H, d), 8.85 (1H, s), 8.31 (1H, s), 8.27 (1H, d), 8.10 (1H, s), 7.85 (1H, d), 7.78-7.75 (1H, m), 7.17 (1H, d), 3.85 (3H, s). MS: m/z 425.9 (M+H⁺).

Example III-84

5-Chloro-2-methoxy-N-(5-(thiazol-5-yl)pyridin-3-yl)benzenesulfonamide

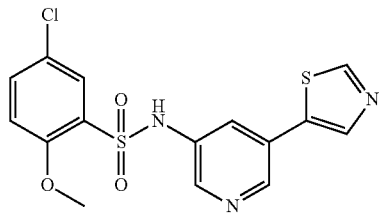 [SMILES: COc1ccc(Cl)cc1S(=O)(=O)Nc1cncc(-c2cncs2)c1]

This compound was prepared as described in Example III-79.
¹H NMR (DMSO-d₆, 400 HMz): δ=10.59 (1H, brs), 9.25 (1H, d), 8.85 (1H, d), 8.31 (1H, d), 8.27 (1H, d), 8.11 (1H, t), 7.75 (1H, d), 7.65 (1H, dd), 7.23 (1H, d), 3.86 (3H, s). MS: m/z 382.0 (M+H⁺).

Example III-85

2,5-Dimethoxy-N-(5-(thiazol-4-yl)pyridin-3-yl)benzenesulfonamide

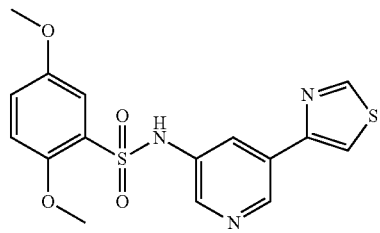 [SMILES: COc1ccc(OC)c(S(=O)(=O)Nc2cncc(-c3cscn3)c2)c1]

This compound was prepared as described in Example III-79.
¹H NMR (DMSO-d₆, 400 HMz): δ=10.53 (1H, brs), 9.17 (1H, s), 8.60 (1H, s), 8.33 (1H, s), 8.27 (1H, d), 7.66 (1H, s), 7.33 (1H, d), 7.18-7.10 (2H, m), 3.79 (3H, s), 3.73 (3H, s). MS: m/z 378.0 (M+H⁺).

Example III-86

5-Bromo-2-methoxy-N-(5-(thiazol-4-yl)pyridin-3-yl)benzenesulfonamide

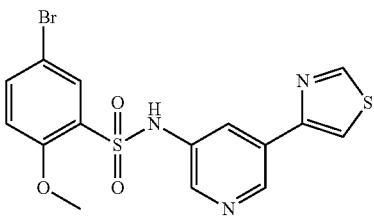

This compound was prepared as described in Example III-79.
¹H NMR (DMSO-d₆, 400 HMz): δ=10.67 (1H, brs), 9.19 (1H, s), 8.64 (1H, d), 8.35 (1H, s), 8.27 (1H, d), 7.89 (1H, d), 7.80 (1H, dd), 7.66 (1H, t), 7.18 (1H, d), 3.85 (3H, s). MS: m/z 425.9 (M+H⁺).

Example III-87

5-Chloro-2-methoxy-N-(5-(thiazol-4-yl)pyridin-3-yl)benzenesulfonamide

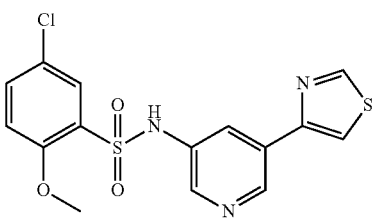 [SMILES: COc1ccc(Cl)cc1S(=O)(=O)Nc1cncc(-c2cscn2)c1]

This compound was prepared as described in Example III-79.
¹H NMR (DMSO-d₆, 400 HMz): δ=10.67 (1H, brs), 9.18 (1H, s), 8.63 (1H, s), 8.34 (1H, d), 8.27 (1H, d), 7.79 (1H, d), 7.69-7.65 (2H, m), 7.23 (1H, d), 3.85 (3H, s). MS: m/z 382.0 (M+H⁺).

Example III-88

2,5-Dimethoxy-N-(5-(1-methyl-1H-pyrazol-4-yl)pyridin-3-yl)benzenesulfonamide

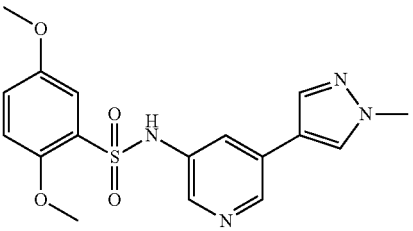 [SMILES: COc1ccc(OC)c(S(=O)(=O)Nc2cncc(-c3cnn(C)c3)c2)c1]

This compound was prepared as described in Example III-1.
¹H NMR (DMSO, 400 MHz): δ=10.30 (1H, brs), 8.45 (1H, d), 8.16 (1H, s), 8.10 (1H, d), 7.80 (1H, s), 7.58 (1H, t), 7.30 (1H, d), 7.15-7.11 (2H, m), 3.86 (3H, s), 3.80 (3H, s), 3.71 (3H, s). MS: m/z 375.1 (M+H⁺).

Example III-89

5-Bromo-2-methoxy-N-(5-(1-methyl-1H-pyrazol-4-yl)pyridin-3-yl)benzenesulfonamide

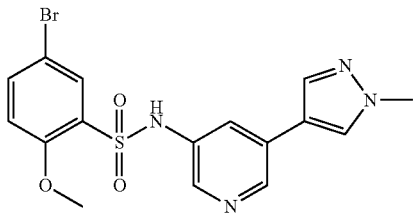 [SMILES: COc1ccc(Br)cc1S(=O)(=O)Nc1cncc(-c2cnn(C)c2)c1]

This compound was prepared as described in Example III-1.
¹H NMR (DMSO, 400 MHz): δ=10.45 (1H, brs), 8.49 (1H, d), 8.17 (1H, s), 8.09 (1H, d), 7.87-7.76 (3H, m), 7.57 (1H, t), 7.18 (1H, d), 3.87 (3H, s), 3.86 (3H, s). MS: m/z 423.0 (M+H⁺).

Example III-90

5-Chloro-2-methoxy-N-(5-(1-methyl-1H-pyrazol-4-yl)pyridin-3-yl)benzenesulfonamide

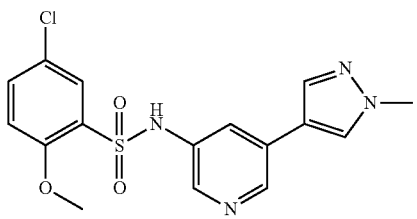 [SMILES: COc1ccc(Cl)cc1S(=O)(=O)Nc1cncc(-c2cnn(C)c2)c1]

This compound was prepared as described in Example III-1.
¹H NMR (DMSO, 400 MHz): δ=10.45 (1H, brs), 8.49 (1H, d), 8.17 (1H, s), 8.09 (1H, d), 7.82 (1H, s), 7.66 (1H, d), 7.65 (1H, dd), 7.57 (1H, t), 7.23 (1H, d), 3.87 (3H, s). MS: m/z 379.0 (M+H⁺).

Example III-91

2,5-Dimethoxy-N-(5-(pyrimidin-2-yl)pyridin-3-yl)benzenesulfonamide

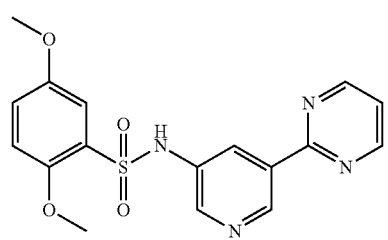 [SMILES: COc1ccc(OC)c(S(=O)(=O)Nc2cncc(-c3ncccn3)c2)c1]

This compound was prepared as described in Example III-79.
¹H NMR (DMSO-d6, 400 MHz): δ=10.60 (1H, brs), 9.14 (1H, s), 8.93 (2H, d), 8.50-8.43 (2H, m), 7.52 (1H, t), 7.33 (1H, d), 7.16-7.12 (2H, m), 3.79 (3H, s), 3.73 (3H, s). MS: m/z 373.0 (M+H⁺).

Example III-92

5-Bromo-2-methoxy-N-(5-(pyrimidin-2-yl)pyridin-3-yl)benzenesulfonamide

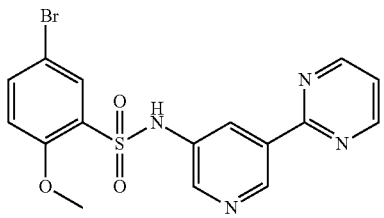 [SMILES: COc1ccc(Br)cc1S(=O)(=O)Nc1cncc(-c2ncccn2)c1]

This compound was prepared as described in Example III-79.
¹H NMR (DMSO-d6, 400 MHz): δ=10.71 (1H, brs), 9.17 (1H, d), 8.95 (2H, d), 8.48 (1H, t), 8.44 (1H, d), 7.87 (1H, d), 7.78-7.75 (1H, m), 7.53 (1H, t), 7.17 (1H, d), 3.84 (3H, s). MS: m/z 421.0 (M+H⁺).

Example III-93

5-Chloro-2-methoxy-N-(5-(pyrimidin-2-yl)pyridin-3-yl)benzenesulfonamide

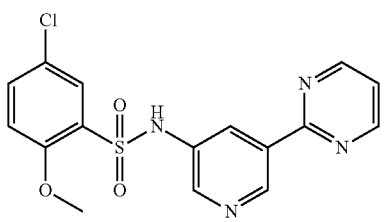

This compound was prepared as described in Example III-79.
¹H NMR (DMSO-d6, 400 MHz): δ=10.72 (1H, brs), 9.17 (1H, d), 8.95 (2H, d), 8.48 (1H, t), 8.45 (1H, d), 7.76 (1H, d), 7.65 (1H, dd), 7.53 (1H, t), 7.23 (1H, d), 3.85 (3H, s). MS: m/z 377.0 (M+H⁺).

Example III-94

2,5-Dimethoxy-N-(5-(pyrazin-2-yl)pyridin-3-yl)benzenesulfonamide

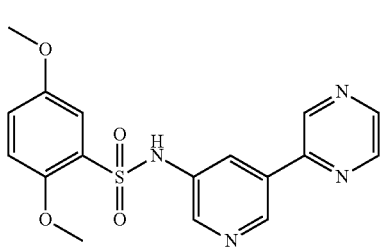 [SMILES: COc1ccc(OC)c(S(=O)(=O)Nc2cncc(-c3cnccn3)c2)c1]

This compound was prepared as described in Example III-79.

<sup>1</sup>H NMR (DMSO-d6, 400 MHz): δ=10.59 (1H, brs), 9.26 (1H, s), 8.97 (1H, s), 8.77 (1H, s), 8.69 (1H, s), 8.43 (1H, s), 8.25 (1H, s), 7.34 (1H, s), 7.12-7.18 (2H, m), 3.80 (3H, s), 3.73 (3H, s). MS: m/z 373.0 (M+H⁺).

Example III-95

5-Bromo-2-methoxy-N-(5-(pyrazin-2-yl)pyridin-3-yl)benzenesulfonamide

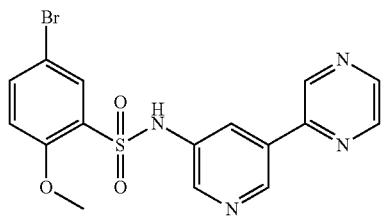 [SMILES: COc1ccc(Br)cc1S(=O)(=O)Nc1cncc(-c2cnccn2)c1]

This compound was prepared as described in Example III-79.

¹H NMR (DMSO-d6, 400 MHz): δ=10.73 (1H, s), 9.28 (1H, s), 9.02 (1H, s), 8.79-8.78 (1H, m), 8.70 (1H, s), 8.43 (1H, s), 8.24 (1H, s), 7.89 (1H, s), 7.77-7.80 (1H, m), 7.17 (1H, d), 3.85 (3H, s). MS: m/z 421.0 (M+H⁺).

Example III-96

5-Chloro-2-methoxy-N-(5-(pyrazin-2-yl)pyridin-3-yl)benzenesulfonamide

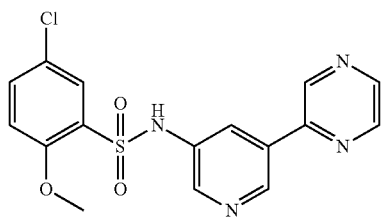 [SMILES: COc1ccc(Cl)cc1S(=O)(=O)Nc1cncc(-c2cnccn2)c1]

This compound was prepared as described in Example III-79.

¹H NMR (DMSO-d6, 400 MHz): δ=10.74 (1H, brs), 9.29 (1H, s), 9.02 (1H, s), 8.79-8.70 (2H, m), 8.45 (1H, s), 8.26 (1H, s), 7.66-7.80 (2H, m), 7.24-7.26 (1H, m), 3.87 (3H, s). MS: m/z 377.0 (M+H⁺).

Example IV

Example IV-1

Methyl 5-(5-bromo-2-methoxyphenylsulfonamido)nicotinate

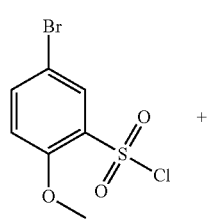 +

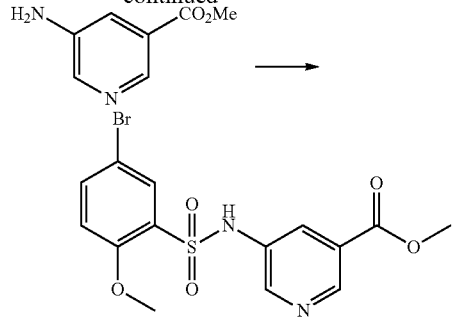

To a solution of methyl 5-aminonicotinate (100 mg, 0.66 mmol) in pyridine (5 mL) was added 5-bromo-2-methoxy-benzene-1-sulfonyl chloride (186 mg, 0.66 mmol) and DMAP (10 mg, 0.08 mmol), and the mixture was then heated at 60° C. overnight. LC-MS showed the reaction was complete. The resultant mixture was concentrated in vacuum and the residue was triturated with methanol by ultrasonic-wave to give 87 mg (yield: 33%) of methyl 5-(5-bromo-2-methoxyphenylsulfonamido) nicotinate as a white solid.

¹H NMR (DMSO-d6): δ=10.82 (1H, brs), 8.74 (1H, d), 8.52 (1H, d), 8.00 (1H, d), 7.87 (1H, d), 7.80 (1H, d), 7.18 (1H, d), 3.86 (3H, s), 3.80 (3H, s). MS: m/z 401.0 (M+H⁺).

Example IV-2

Ethyl 5-(5-bromo-2-methoxyphenylsulfonamido)nicotinate

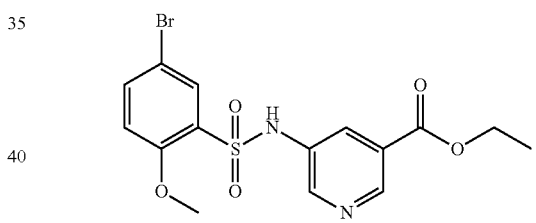

¹H NMR (DMSO-d6): δ=10.82 (1H, brs), 8.73 (1H, s), 8.53 (1H, s), 7.98 (1H, s), 7.87 (1H, s), 7.80 (1H, d), 7.18 (1H, d), 4.32 (2H, q), 3.81 (3H, s), 1.31 (3H, t). MS: m/z 414.9 (M+H⁺).

Example IV-3

Propyl 5-(5-bromo-2-methoxyphenylsulfonamido)nicotinate

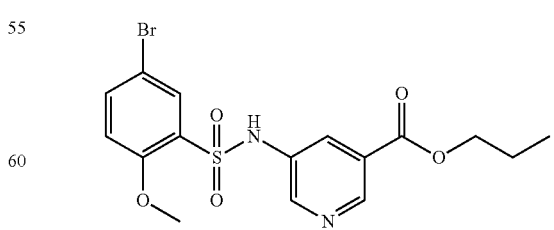

¹H NMR (DMSO-d6): δ=10.83 (1H, brs), 8.73 (1H, d), 8.54 (1H, d), 7.99 (1H, s), 7.87 (1H, d), 7.79 (1H, dd), 7.18 (1H, d), 4.25-4.21 (2H, m), 3.82 (3H, s), 1.74-1.68 (2H, m), 0.96 (2H, t). MS: m/z 429.0 (M+H⁺).

Example IV-4

Cyclohexyl 5-(5-bromo-2-methoxyphenylsulfonamido)nicotinate

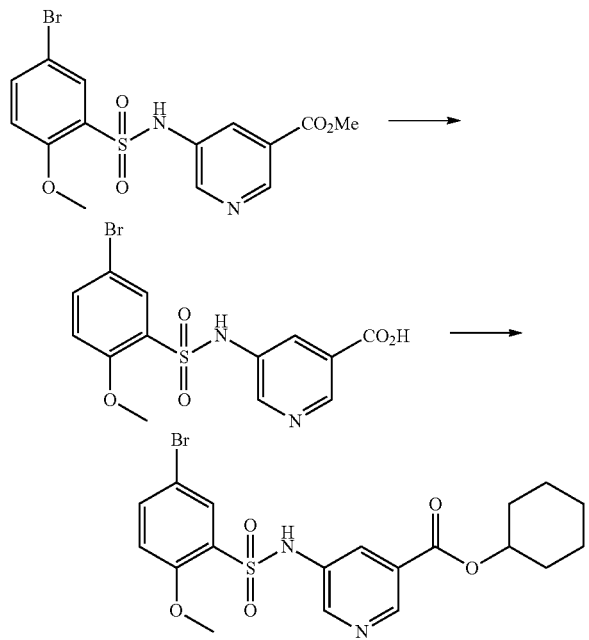

Step 1: To a solution of methyl 5-(5-bromo-2-methoxyphenylsulfonamido)nicotinate (1 g, 2.5 mmol) in THF (20 mL) was added aq. NaOH (2M, 10 mL), it was then heated at 60° C. for 3 h. TLC showed that the reaction was complete. The solution was concentrated in vacuum to remove THF. The remaining aqueous phase was adjusted pidified to pH=2 with 2N HCl. The resulting solid was filtered to give 0.95 g (yield: 98%) of 5-(5-bromo-2-methoxyphenylsulfonamido)nicotinic acid as a white solid.

Step 2: To a solution of 5-(5-bromo-2-methoxyphenylsulfonamido)nicotinic acid (80 mg, 0.21 mmol) in cyclohexanol (5 mL) was added SOCl$_2$ (0.2 mL), it was then refluxed overnight. LC-MS showed the reaction was complete. The resultant was concentrated in vacuum to remove cyclohexanol. The residue was re-crystallized from methanol to give 54 mg (yield: 55%) of cyclohexyl 5-(5-bromo-2-methoxyphenylsulfonamido) nicotinate as a white solid.

$^1$H NMR (DMSO-d6): δ=10.84 (1H, brs), 8.73 (1H, d), 8.54 (1H, d), 7.98 (1H, t), 7.87 (1H, d), 7.81 (1H, dd), 7.18 (1H, d), 4.96-4.92 (1H, m), 3.83 (3H, s), 1.84-1.62 (4H, m), 1.58-1.34 (6H, m). MS: m/z 469.0 (M+H$^+$)

Example IV-5

Phenyl 5-(5-bromo-2-methoxyphenylsulfonamido)nicotinate

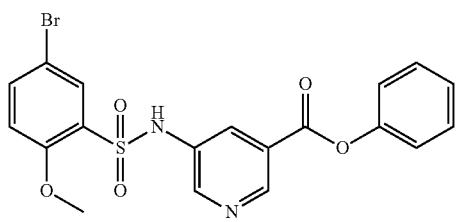

$^1$H NMR (DMSO-d6): δ=10.90 (1H, brs), 8.93 (1H, s), 8.61 (1H, d), 8.13 (1H, s), 7.89 (1H, d), 7.82 (1H, d), 7.48 (2H, t), 7.36-7.30 (3H, m), 7.20 (1H, d), 3.84 (3H, s). MS: m/z 463.0 (M+H$^+$)

Example IV-6

Methyl 5-(5-chloro-2-methoxyphenylsulfonamido)nicotinate

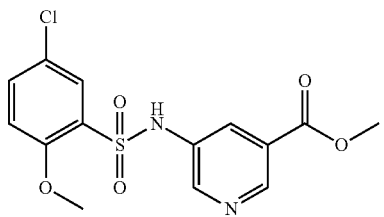

1H NMR (DMSO-d6): δ=10.82 (1H, brs), 8.73 (1H, s), 8.54 (1H, d), 7.99 (1H, s), 7.77 (1H, d), 7.68 (1H, dd), 7.23 (1H, d), 3.86 (3H, s), 3.82 (3H, s). MS: m/z 356.1 (M+H$^+$).

Example IV-7

Ethyl 5-(5-chloro-2-methoxyphenylsulfonamido)nicotinate

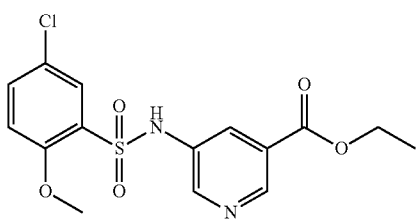 [SMILES: CCOC(=O)c1cncc(NS(=O)(=O)c2cc(Br)ccc2OC)c1]

$^1$H NMR (DMSO-d6): δ=10.83 (1H, brs), 8.74 (1H, d), 8.52 (1H, d), 7.98 (1H, s), 7.77 (1H, d), 7.68 (1H, dd), 7.23 (1H, d), 4.33-4.29 (2H, m), 3.82 (3H, s), 1.31 (2H, t). MS: m/z 371.0 (M+H$^+$).

Example IV-8

Propyl 5-(5-chloro-2-methoxyphenylsulfonamido)nicotinate

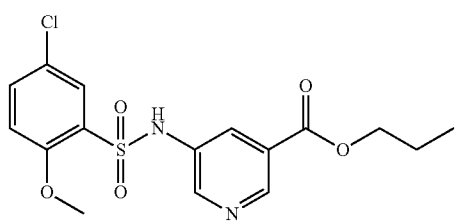 [SMILES: CCCOC(=O)c1cncc(NS(=O)(=O)c2cc(Br)ccc2OC)c1]

$^1$H NMR (DMSO-d6): δ=10.84 (1H, brs), 8.74 (1H, d), 8.54 (1H, d), 7.99 (1H, t), 7.77 (1H, d), 7.69 (1H, dd), 7.23 (1H, d), 4.23 (2H, t), 3.82 (3H, s), 1.75-1.67 (2H, m), 0.96 (2H, t). MS: m/z 385.0 (M+H$^+$).

Example IV-9

Cyclohexyl 5-(5-chloro-2-methoxyphenylsulfonamido)nicotinate

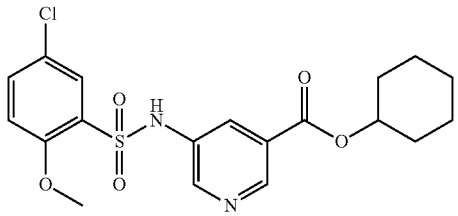 [SMILES: COc1ccc(Cl)cc1S(=O)(=O)Nc1cncc(C(=O)OC2CCCCC2)c1]

$^1$H NMR (DMSO-d6): δ=10.84 (1H, brs), 8.74-8.73 (1H, d), 8.55-8.54 (1H, d), 7.99 (1H, s), 7.78-7.77 (1H, d), 7.71 (1H, dd), 7.26-7.24 (1H, d), 4.97-4.93 (1H, m), 3.84 (3H, s), 1.86-1.83 (2H, m), 1.73-1.67 (2H, m), 1.58-1.35 (6H, m). MS: m/z 425.1 (M+H$^+$).

Example IV-10

Phenyl 5-(5-chloro-2-methoxyphenylsulfonamido)nicotinate

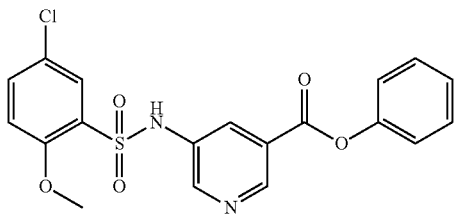 [SMILES: COc1ccc(Cl)cc1S(=O)(=O)Nc1cncc(C(=O)Oc2ccccc2)c1]

$^1$H NMR (DMSO-d6): δ=10.90 (1H, brs), 8.92 (1H, s), 8.62 (1H, d), 8.13 (1H, s), 7.80 (1H, d), 7.71 (1H, dd), 7.52-7.45 (2H, m), 7.35-7.25 (4H, m), 3.85 (3H, s). MS: m/z 419.0 (M+H$^+$).

Example IV-11

Methyl 5-(2,5-dimethoxyphenylsulfonamido)nicotinate

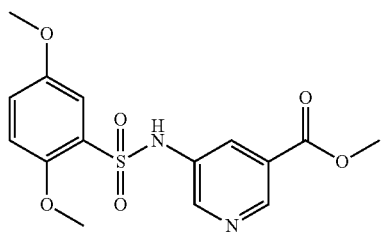 [SMILES: COC(=O)c1cncc(NS(=O)(=O)c2cc(OC)ccc2OC)c1]

$^1$H NMR (DMSO-d6): δ=10.70 (1H, brs), 8.71 (1H, d), 8.53 (1H, d), 8.01 (1H, t), 7.32 (1H, d), 7.22-7.12 (2H, m), 3.86 (3H, s), 3.76 (3H, s), 3.74 (3H, s). MS: m/z 353.1 (M+H$^+$).

Example IV-12

Ethyl 5-(2,5-dimethoxyphenylsulfonamido)nicotinate

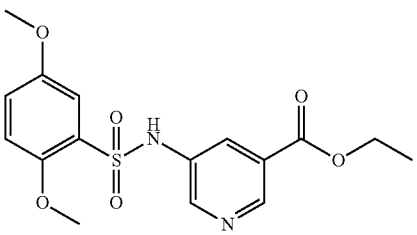 [SMILES: CCOC(=O)c1cncc(NS(=O)(=O)c2cc(OC)ccc2OC)c1]

$^1$H NMR (DMSO-d6): δ=10.70 (1H, brs), 8.71 (1H, d), 8.54 (1H, d), 7.99 (1H, t), 7.32 (1H, d), 7.19-7.12 (2H, m), 4.32 (2H, q), 3.77 (3H, s), 3.74 (3H, s), 1.31 (3H, t). MS: m/z 367.1 (M+H$^+$).

Example IV-13

Propyl 5-(2,5-dimethoxyphenylsulfonamido)nicotinate

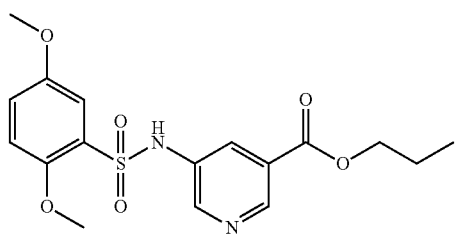 [SMILES: CCCOC(=O)c1cncc(NS(=O)(=O)c2cc(OC)ccc2OC)c1]

$^1$H NMR (DMSO-d6): δ=10.69 (1H, s), 8.70 (1H, s), 8.53-8.52 (1H, d), 7.99 (1H, s), 7.31-7.30 (1H, d), 7.20-7.12 (2H, m), 4.24-4.21 (2H, t), 3.76 (3H, s), 3.73 (3H, s), 1.72-1.67 (2H, m), 0.96-0.92 (3H, t) ppm MS: m/z 381 (M+H$^+$)

Example IV-14

Cyclohexyl 5-(2,5-dimethoxyphenylsulfonamido)nicotinate

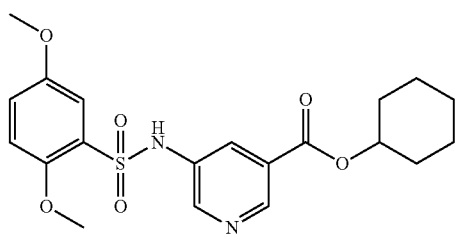 [SMILES: COc1ccc(OC)c(S(=O)(=O)Nc2cncc(C(=O)OC3CCCCC3)c2)c1]

$^1$H NMR (DMSO-d6): δ=10.69 (1H, brs), 8.70 (1H, s), 8.54 (1H, d), 7.99 (1H, s), 7.33 (1H, d), 7.19-7.15 (2H, m), 4.97-4.92 (1H, m), 3.78 (3H, s), 3.74 (3H, s), 1.88-1.82 (2H, m), 1.72-1.64 (2H, m), 1.55-1.36 (6H, m). MS: m/z 421.2 (M+H$^+$).

Example IV-15

Phenyl 5-(2,5-dimethoxyphenylsulfonamido)nicotinate

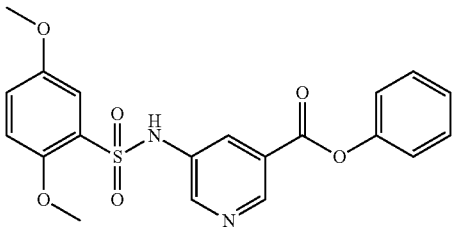 [SMILES: COc1ccc(OC)c(S(=O)(=O)Nc2cncc(C(=O)Oc3ccccc3)c2)c1]

$^{1}$H NMR (DMSO-d6): δ=10.78 (1H, brs), 8.89 (1H, d), 8.61 (1H, d), 8.13 (1H, d), 7.48 (2H, t), 7.35-7.27 (4H, m), 7.22-7.15 (2H, m), 3.79 (3H, s), 3.73 (3H, s). MS: m/z 415.1 (M+H$^{+}$).

Example IV-16

5-(5-Bromo-2-methoxyphenylsulfonamido)-N-methylnicotinamide

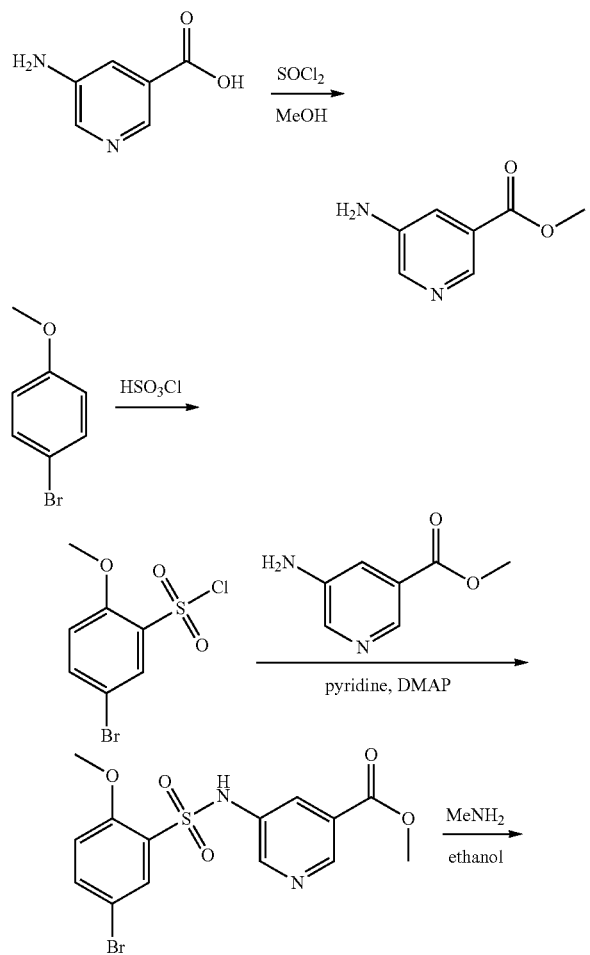

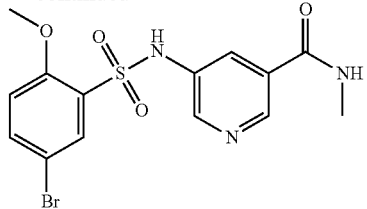

Step 1: To a stirred solution of 5-amino-nicotinic acid (10.0 g, 72.5 mmol) in methanol (100 mL) was added SOCl$_2$ (10.4 g, 86.9 mmol) dropwise at 0° C. The mixture was allowed warm to room temperature and then refluxed for 16 hours. The mixture was cooled, concentrated in vacuum and the residue was diluted with water (200 mL). The mixture was neutralized with aqueous NaHCO$_3$ solution to pH=7. The aqueous mixture was extracted with DCM (100 mL×2). The combined organic layers were washed with brine (100 mL×2), dried over anhydrous Na$_2$SO$_4$, filtered and the filtrate was concentrated in vacuum to dryness to give 9.5 g (yield: 86%) of 5-amino-nicotinic acid methyl ester as white solid.

$^{1}$H NMR (DMSO-d$_6$, 400 MHz): δ=8.24 (1H, d), 8.12 (1H, d), 7.42 (1H, dd), 5.65 (2H, brs), 3.84 (3H, s).

Step 2: To a stirred HSO$_3$Cl (100 g) was added 1-bromo-4-methoxy-benzene (15.0 g, 80.6 mmol) dropwise at 25° C. The mixture was stirred at this temperature for 16 hours. The mixture was poured into ice water (1 L) dropwise and the resulting solid was filtered. The solid was evaporated in vacuum to dryness to give 17.3 g (yield: 75%) of 5-bromo-2-methoxy-benzenesulfonyl chloride as white solid.

$^{1}$H NMR (DMSO-d$_6$, 400 MHz): δ=7.77 (1H, d), 7.47 (1H, dd), 6.96 (1H, d), 3.76 (3H, s).

Step 3: To a stirred mixture of 5-amino-nicotinic acid methyl ester (6.5 g, 42.8 mmol) and 5-bromo-2-methoxy-benzenesulfonyl chloride (15.8 g, 55.6 mmol) in pyridine (60 mL) was added DMAP (260 mg, 2.14 mmol). The mixture was stirred at 80° C. for 17 hours. The mixture was cooled, concentrated in vacuum to dryness. The residue was diluted with MeOH (100 mL) and stirred for 30 minutes. The suspended solid was filtered and washed with methanol (50 mL), evaporated in vacuum to dryness to give 12.1 g (yield: 70%) of 5-(5-bromo-2-methoxy-benzenesulfonylamino)-nicotinic acid methyl ester as white solid.

$^{1}$H NMR (DMSO-d$_6$, 400 MHz): δ=10.86 (1H, brs), 8.80 (1H, s), 8.59 (1H, d), 8.06 (1H, s), 7.93 (1H, d), 7.85 (1H, dd), 7.24 (1H, d), 3.92 (3H, s), 3.86 (3H, s).

Step 4: To a solution of methylamine ethanol solution (30-33%, 30 mL) was added 5-(5-bromo-2-methoxy-benzenesulfonylamino)-nicotinic acid methyl ester (2.0 g, 5 mmol). The mixture was stirred at 80° C. for 17 hours, cooled, and concentrated in vacuum to dryness. The residue was purified by silica gel chromatography (from DCM to DCM/MeOH=20/1) to give white solid. The solid was washed with methanol (10 mL) and evaporated in vacuum to dryness to give 1.2 g (yield: 60%) of 5-(5-bromo-2-methoxy-benzenesulfonylamino)-N-methylnicotinamide as white solid.

$^{1}$H NMR (DMSO-d$_6$, 400 MHz): δ=10.62 (1H, brs), 8.61-8.65 (2H, m), 8.40 (1H, d), 7.89 (1H, dd), 7.83 (1H, d), 7.77 (1H, dd), 7.17 (1H, d), 3.82 (3H, s), 2.77 (3H, d). MS: m/z 400.0 (M+H$^{+}$).

Example IV-17

5-(5-Bromo-2-methoxy-benzenesulfonylamino)-nicotinamide

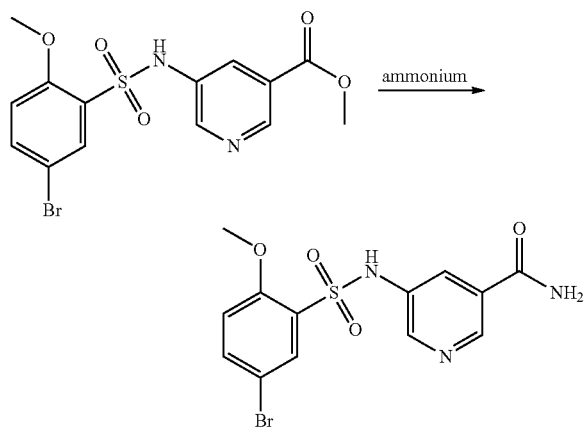

To a solution of ammonium hydroxide (28-29%, 60 mL) was added 5-(5-bromo-2-methoxy-benzenesulfonylamino)-nicotinic acid methyl ester (10.0 g, 25 mmol). The mixture was stirred at 80° C. for 16 hours, cooled, and concentrated to give white solid. The solid was washed with methanol (20 mL×2) and evaporated in vacuum to dryness to give 8.2 g (yield: 85%) of 5-(5-bromo-2-methoxy-benzenesulfonylamino)-nicotinamide as white solid.

$^1$H NMR (DMSO-$d_6$, 400 MHz): δ=10.62 (1H, brs), 8.70 (1H, d), 8.41 (1H, d), 8.13 (1H, brs), 7.91 (1H, s), 7.83 (1H, d), 7.77 (1H, dd), 7.61 (1H, brs), 7.17 (1H, d), 3.82 (3H, s). MS: m/z 385.9 (M+H$^+$).

Example IV-18

5-(5-Bromo-2-methoxyphenylsulfonamido)-N-ethyl-nicotinamide

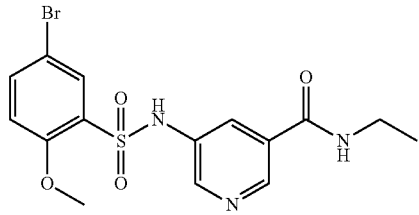 [SMILES: CCNC(=O)c1cncc(NS(=O)(=O)c2cc(Br)ccc2OC)c1]

$^1$H NMR (DMSO-d6): δ=10.65 (1H, brs), 8.68-8.64 (2H, m), 8.40 (1H, d), 7.88 (1H, s), 7.84 (1H, s), 7.78 (1H, d), 7.18 (1H, d), 3.82 (3H, s), 3.27-3.24 (2H, m), 1.12-1.08 (3H, t). MS: m/z 414.1 (M+H$^+$).

Example IV-19

5-(5-Bromo-2-methoxyphenylsulfonamido)-N-propylnicotinamide

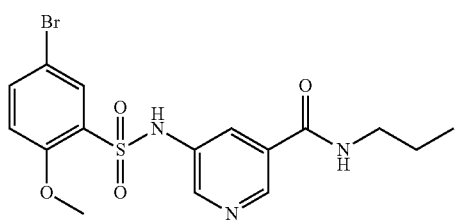

$^1$H NMR (DMSO-d6): δ=10.64 (1H, brs), 8.66-8.63 (2H, m), 8.47 (1H, s), 7.87-7.83 (3H, m), 7.18 (1H, s), 3.81 (3H, s), 3.21-3.17 (2H, m), 1.53-1.49 (2H, m), 0.89-0.82 (3H, m). MS: m/z 427.1 (M+H$^+$).

Example IV-20

5-(5-Bromo-2-methoxyphenylsulfonamido)-N-cyclohexylnicotinamide

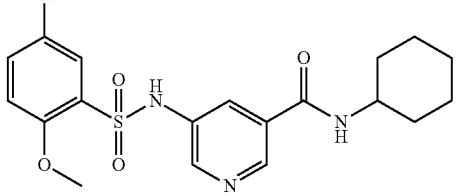

To a solution of 5-(5-bromo-2-methoxyphenylsulfonamido)nicotinic acid (80 mg, 0.21 mmol) in DMF (5 mL) was added DIEA (21 mg, 0.21 mmol), cyclohexylamine (20 mg, 0.21 mmol) and HATU (80 mg, 0.21 mmol), it was then stirred at room temperature for 4 h. LC-MS showed the reaction was complete. The resultant was concentrated in vacuum to remove most of DMF and the residue was re-crystallized from methanol to give 50 mg (yield: 51%) of 5-(5-bromo-2-methoxyphenylsulfonamido)-N-cyclohexylnicotinamide as a white solid.

$^1$H NMR (DMSO-d6): δ=10.62 (1H, brs), 8.66 (1H, s), 8.44-8.38 (2H, m), 7.86 (1H, s), 7.83 (1H, d), 7.78 (1H, dd), 7.18 (1H, d), 3.82 (3H, s), 3.70-3.81 (1H, m) 1.80-1.57 (5H, m), 1.32-1.10 (5H, m). MS: m/z 468.1 (M+H$^+$)

Example IV-21

5-(5-Bromo-2-methoxyphenylsulfonamido)-N-(2-methoxyethyl)nicotinamide

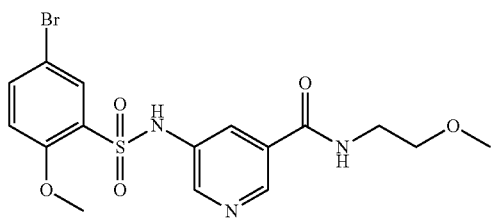

$^1$H NMR (DMSO-d6): δ=10.65 (1H, brs), 8.75 (1H, s), 8.67 (1H, s), 8.40 (1H, d), 7.89 (1H, s), 7.84 (1H, d), 7.79 (1H, dd), 7.17 (1H, d), 3.81 (3H, s), 3.39-3.44 (4H, m), 3.22 (3H, s). MS: m/z 444.0 (M+H$^+$)

Example IV-22

5-(5-Bromo-2-methoxyphenylsulfonamido)-N-(2-(dimethylamino)ethyl)nicotinamide

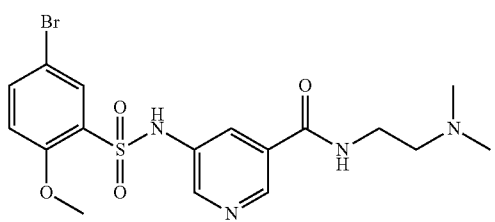

¹H NMR (DMSO-d6): δ=10.72 (1H, brs), 9.42 (1H, brs, TFA salt), 8.91 (1H, t), 8.72 (1H, s), 8.43 (1H, d), 7.94 (1H, s), 7.84 (1H, d), 7.79 (1H, dd), 7.19 (1H, d), 3.84 (3H, s), 3.61-3.58 (2H, m), 3.27-3.23 (2H, m), 2.84 (3H, s), 2.83 (3H, s). MS: m/z 457.1 (M+H⁺).

Example IV-23

5-(5-Bromo-2-methoxyphenylsulfonamido)-N-phenylnicotinamide

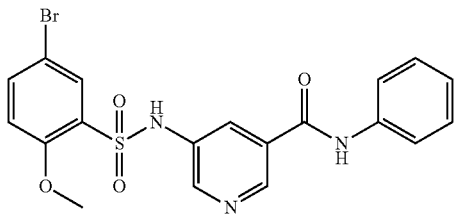

¹H NMR (DMSO-d6): δ=10.73 (1H, brs), 10.45 (1H, brs), 8.81 (1H, s), 8.48 (1H, d), 7.95 (1H, s), 7.86 (1H, d), 7.79 (1H, dd), 7.72 (2H, d), 7.36 (2H, t), 7.16 (1H, d), 7.13 (1H, t), 3.84 (3H, s). MS: m/z 462.0 (M+H⁺).

Example IV-24

5-Bromo-2-methoxy-N-(5-(morpholine-4-carbonyl)pyridin-3-yl)benzenesulfonamide

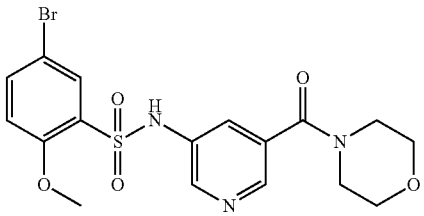

¹H NMR (DMSO-d6): δ=10.70 (1H, brs), 8.36 (1H, d), 8.28 (1H, s), 7.86 (1H, d), 7.79 (1H, dd), 7.48 (1H, s), 7.17 (1H, d), 3.84 (3H, s), 3.70-3.50 (6H, m), 3.17-3.12 (2H, m). MS: m/z 456.0 (M+H⁺)

Example IV-25

5-Bromo-2-methoxy-N-(5-(4-methylpiperazine-1-carbonyl)pyridin-3-yl)benzenesulfonamide

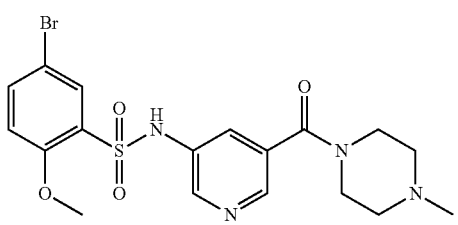 [SMILES: COc1ccc(Br)cc1S(=O)(=O)Nc1cncc(C(=O)N2CCN(C)CC2)c1]

¹H NMR (DMSO-d6): δ=10.71 (1H, brs), 8.35 (1H, s), 8.24 (1H, s), 7.84 (1H, d), 7.79 (1H, dd), 7.44 (1H, s), 7.17 (1H, d), 3.84 (3H, s), 3.60-3.56 (2H, m), 3.16-3.10 (2H, m), 2.37-2.34 (2H, m), 2.33-2.18 (5H, s). MS: m/z 469.0 (M+H⁺)

Example IV-26

5-(5-Chloro-2-methoxyphenylsulfonamido)nicotinamide

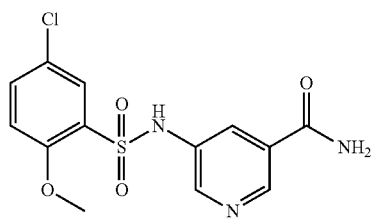 [SMILES: COc1ccc(Cl)cc1S(=O)(=O)Nc1cncc(C(N)=O)c1]

¹H NMR (DMSO-d6): δ=10.65 (1H, brs), 8.70 (1H, d), 8.42 (1H, d), 8.15 (1H, s), 7.91 (1H, t), 7.74 (1H, d), 7.68-7.63 (2H, m), 7.23 (1H, d), 3.83 (3H, s). MS: m/z 342.0 (M+H⁺).

Example IV-27

5-(5-Chloro-2-methoxyphenylsulfonamido)-N-methylnicotinamide

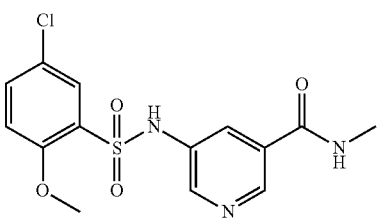 [SMILES: CNC(=O)c1cncc(NS(=O)(=O)c2cc(Cl)ccc2OC)c1]

¹H NMR (DMSO-d6): δ=10.65 (1H, brs), 8.67-8.62 (2H, m), 8.41 (1H, s), 7.89 (1H, s), 7.73 (1H, s), 7.74-7.66 (1H, m), 7.24-7.22 (1H, m), 3.83 (3H, s), 2.77 (3H, s). MS: m/z 356.0 (M+H⁺)

Example IV-28

5-(5-Chloro-2-methoxyphenylsulfonamido)-N-ethylnicotinamide

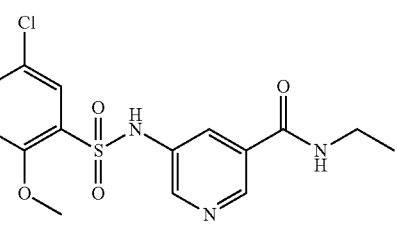

¹H NMR (DMSO-d6): δ=10.64 (1H, brs), 8.67-8.65 (2H, m), 8.41 (1H, d), 7.88 (1H, s), 7.74 (1H, d), 7.69 (1H, dd), 7.23 (1H, d), 3.83 (3H, s), 3.28-3.25 (2H, m), 1.10 (3H, t). MS: m/z 370.1 (M+H⁺)

Example IV-29

5-(5-Chloro-2-methoxyphenylsulfonamido)-N-propylnicotinamide

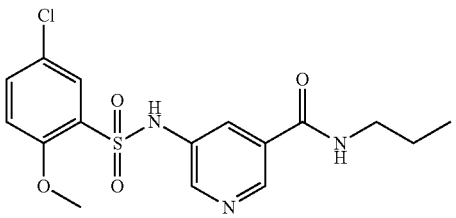 [SMILES: CCCNC(=O)c1cncc(NS(=O)(=O)c2cc(Cl)ccc2OC)c1]

¹H NMR (DMSO-d6): δ=10.66 (1H, brs), 8.66-8.63 (2H, m), 8.39 (1H, d), 7.87 (1H, t), 7.73 (1H, d), 7.66 (1H, d), 7.23 (1H, d), 3.83 (3H, s), 3.20 (2H, q), 1.52-1.50 (2H, m), 0.875 (3H, t). MS: m/z 384.1 (M+H⁺).

Example IV-30

5-(5-Chloro-2-methoxyphenylsulfonamido)-N-cyclohexylnicotinamide

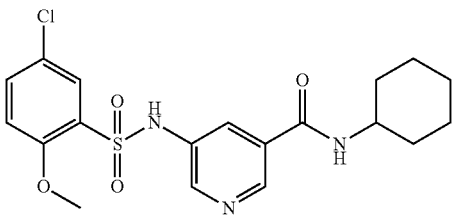 [SMILES: COc1ccc(Cl)cc1S(=O)(=O)Nc1cncc(C(=O)NC2CCCCC2)c1]

¹H NMR (DMSO-d6): δ=10.63 (1H, brs), 8.65 (1H, s), 8.42-8.38 (2H, m), 7.85 (1H, d), 7.72 (1H, d), 7.68 (1H, dd), 7.23 (1H, d), 3.83 (3H, s), 3.74-3.71 (1H, m) 1.80-1.71 (5H, m), 1.30-1.10 (5H, m). MS: m/z 424.1 (M+H⁺)

Example IV-31

5-(5-Chloro-2-methoxyphenylsulfonamido)-N-phenylnicotinamide

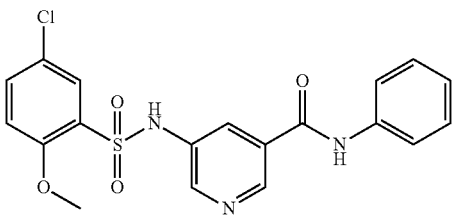 [SMILES: COc1ccc(Cl)cc1S(=O)(=O)Nc1cncc(C(=O)Nc2ccccc2)c1]

¹H NMR (DMSO-d6): δ=10.73 (1H, brs), 10.45 (1H, s), 8.81 (1H, s), 8.49 (1H, s), 7.96 (1H, s), 7.77-7.68 (4H, m), 7.39-7.35 (2H, t), 7.27-7.24 (1H, d), 7.15-7.11 (1H, m), 3.86 (3H, s). MS: m/z 418.1 (M+H⁺)

Example IV-32

5-(5-Chloro-2-methyoxyphenylsulfonamido)-N-(2-methoxyethyl)nicotinamide

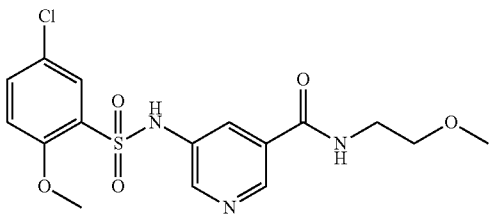 [SMILES: COCCNC(=O)c1cncc(NS(=O)(=O)c2cc(Cl)ccc2OC)c1]

¹H NMR (DMSO-d6): δ=10.66 (1H, brs), 8.75-8.73 (1H, m), 8.67 (1H, d), 8.41 (1H, d), 7.90 (1H, t), 7.74 (1H, d), 7.68 (1H, dd), 7.23 (1H, d), 3.83 (3H, s), 3.44-3.40 (4H, m), 3.26 (3H, s). MS: m/z 400.1 (M+H⁺).

Example IV-33

5-(5-Chloro-2-methoxyphenylsulfonamido)-N-(2-(dimethylamino)ethyl)nicotinamide

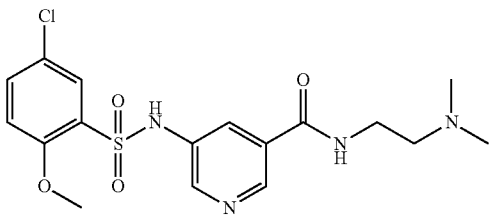 [SMILES: COc1ccc(Cl)cc1S(=O)(=O)Nc1cncc(C(=O)NCCN(C)C)c1]

¹H NMR (DMSO-d6): δ=10.73 (1H, brs), 9.56 (1H, brs, TFA salt), 8.93-8.91 (1H, m), 8.72 (1H, s), 8.45 (1H, d), 7.95 (1H, s), 7.75 (1H, d), 7.69 (1H, dd), 7.25 (1H, d), 3.85 (3H, s), 3.62-3.58 (2H, m), 3.27-3.25 (2H, m), 2.85 (3H, s), 2.84 (3H, s). MS: m/z 413.1 (M+H⁺)

Example IV-34

5-Chloro-2-methoxy-N-(5-(morpholine-4-carbonyl)pyridin-3-yl)benzenesulfonamide

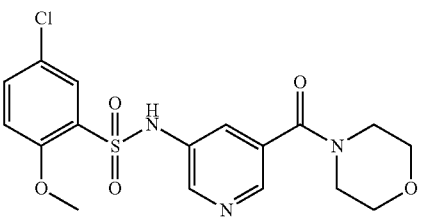 [SMILES: COc1ccc(Cl)cc1S(=O)(=O)Nc1cncc(C(=O)N2CCOCC2)c1]

¹H NMR (DMSO-d6): δ=10.70 (1H, brs), 8.37 (1H, d), 8.28 (1H, d), 7.76 (1H, d), 7.69 (1H, dd), 7.48 (1H, t), 7.23 (1H, d), 3.84 (3H, s), 3.75-3.47 (6H, m), 3.18-3.12 (2H, m). MS: m/z 412.1 (M+H⁺).

Example IV-35

5-Chloro-2-methoxy-N-(5-(4-methylpiperazine-1-carbonyl)pyridin-3-yl)benzenesulfonamide

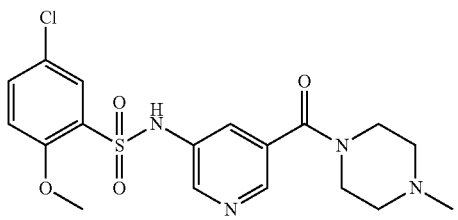 [SMILES: COc1ccc(Cl)cc1S(=O)(=O)Nc1cncc(C(=O)N2CCN(C)CC2)c1]

$^1$H NMR (DMSO-d6): δ=10.77 (1H, brs), 10.18 (1H, brs, TFA salt), 8.38 (1H, s), 8.25 (1H, s), 7.76 (1H, d), 7.69 (1H, dd), 7.61 (1H, d), 7.24 (1H, d), 3.83 (3H, s), 3.81-3.00 (8H, m), 2.82 (3H, s). MS: m/z 425.1 (M+H$^+$).

Example IV-36

5-(2,5-Dimethoxyphenylsulfonamido)nicotinamide

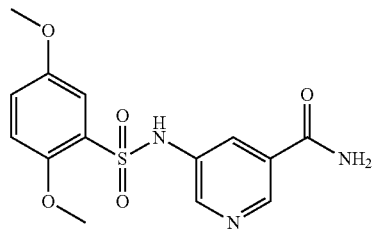 [SMILES: COc1ccc(OC)c(S(=O)(=O)Nc2cncc(C(N)=O)c2)c1]

$^1$H NMR (DMSO-d6): δ=10.51 (1H, brs), 8.66 (1H, s), 8.40 (1H, d), 8.13 (1H, s), 7.91 (1H, s), 7.61 (1H, s), 7.28 (1H, d), 7.16-7.11 (2H, m), 3.77 (3H, s), 3.73 (3H, s). MS: m/z 338.1 (M+H$^+$).

Example IV-37

5-(2,5-Dimethoxyphenylsulfonamido)-N-methylnicotinamide

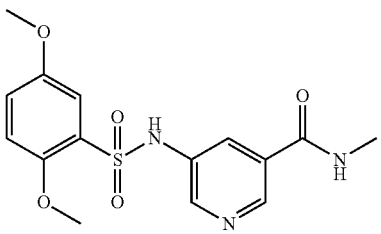 [SMILES: CNC(=O)c1cncc(NS(=O)(=O)c2cc(OC)ccc2OC)c1]

$^1$H NMR (DMSO-d6): δ=10.51 (1H, brs), 8.63-8.59 (2H, m), 8.40 (1H, d), 7.89 (1H, s), 7.28 (1H, d), 7.17-7.12 (2H, m), 3.77 (3H, s), 3.72 (3H, s), 2.75 (3H, d). MS: m/z 352.1 (M+H$^+$)

Example IV-38

5-(2,5-Dimethoxyphenylsulfonamido)-N-propylnicotinamide

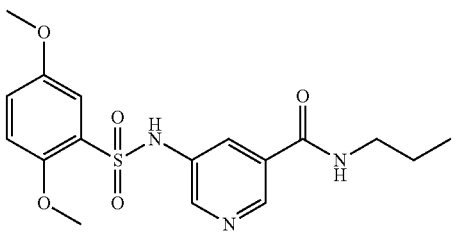 [SMILES: CCCNC(=O)c1cncc(NS(=O)(=O)c2cc(OC)ccc2OC)c1]

$^1$H NMR (DMSO-d6): δ=10.53 (1H, brs), 8.64-8.61 (2H, m), 8.40 (1H, d), 7.88 (1H, s), 7.28 (1H, d), 7.19-7.10 (2H, m), 3.77 (3H, s), 3.73 (3H, s), 3.18 (2H, q), 1.55-1.46 (2H, m), 0.87 (3H, t). MS: m/z 380.1 (M+H$^+$)

Example IV-39

5-(2,5-Dimethoxyphenylsulfonamido)-N-cyclohexylnicotinamide

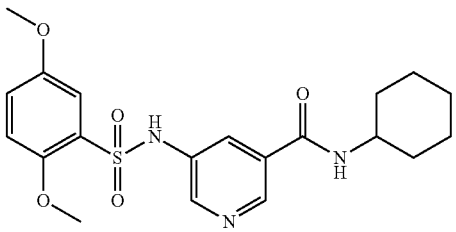 [SMILES: COc1ccc(OC)c(S(=O)(=O)Nc2cncc(C(=O)NC3CCCCC3)c2)c1]

$^1$H NMR (DMSO-d6): δ=10.49 (1H, brs), 8.62 (1H, s), 8.41-8.36 (2H, m), 7.86 (1H, d), 7.28 (1H, d), 7.17-7.12 (2H, m), 3.77 (3H, s), 3.76-3.72 (4H, m), 1.75-1.52 (5H, m), 1.29-1.00 (5H, m). MS: m/z 420.2 (M+H$^+$).

Example IV-40

5-(2,5-Dimethoxyphenylsulfonamido)-N-phenylnicotinamide

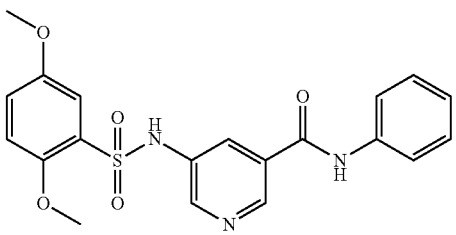 [SMILES: COc1ccc(OC)c(S(=O)(=O)Nc2cncc(C(=O)Nc3ccccc3)c2)c1]

$^1$H NMR (DMSO-d6): δ=10.60 (1H, brs), 10.43 (1H, brs), 8.77 (1H, s), 8.48 (1H, d), 7.96 (1H, d), 7.72 (2H, m), 7.38-7.30 (3H, m), 7.19-7.11 (3H, m), 3.79 (3H, s), 3.73 (3H, s). MS: m/z 414.1 (M+H$^+$)

Example IV-41

5-(2,5-Dimethoxyphenylsulfonamido)-N-(2-methoxyethyl)nicotinamide

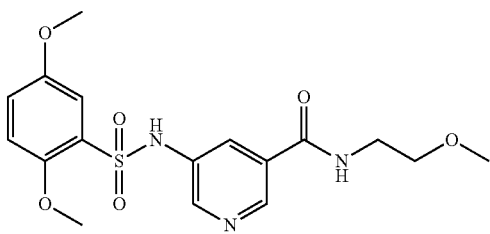 [SMILES: COCCNC(=O)c1cncc(NS(=O)(=O)c2cc(OC)ccc2OC)c1]

¹H NMR (DMSO-d6): δ=10.51 (1H, brs), 8.72 (1H, s), 8.63 (1H, s), 8.40 (1H, s), 7.89 (1H, s), 7.29 (1H, s), 7.13 (2H, m), 3.77 (3H, s), 3.72 (3H, s), 3.43-3.39 (4H, m), 3.24 (3H, s). MS: m/z 396.2 (M+H⁺).

Example IV-42

5-(2,5-Dimethoxyphenylsulfonamido)-N-(2-(dimethylamino)ethyl)nicotinamide

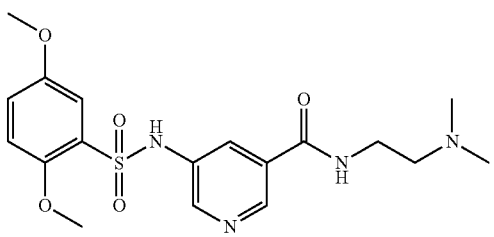 [SMILES: COc1ccc(OC)c(S(=O)(=O)Nc2cncc(C(=O)NCCN(C)C)c2)c1]

¹H NMR (DMSO-d6): δ=10.59 (1H, brs), 9.35 (1H, brs, TFA salt), 8.86 (1H, s), 8.67 (1H, s), 8.43 (1H, d), 7.94 (1H, s), 7.29 (1H, d), 7.19-7.13 (2H, m), 3.78 (3H, s), 3.73 (3H, s), 3.59-3.56 (2H, m), 3.26-3.22 (2H, m), 2.84 (3H, s), 2.83 (3H, s). MS: m/z 409.2 (M+H⁺)

Example IV-43

2,5-Dimethoxy-N-(5-(morpholine-4-carbonyl)pyridin-3-yl)benzenesulfonamide

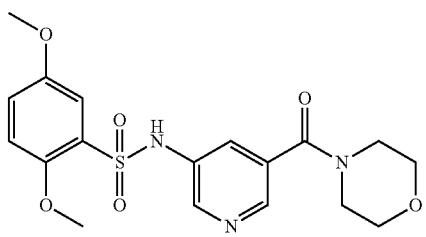 [SMILES: COc1ccc(OC)c(S(=O)(=O)Nc2cncc(C(=O)N3CCOCC3)c2)c1]

¹H NMR (DMSO-d6): δ=10.56 (1H, brs), 8.37 (1H, d), 8.24 (1H, d), 7.47 (1H, t), 7.29 (1H, d), 7.18-7.10 (2H, m), 3.78 (3H, s), 3.73 (3H, s), 3.72-3.48 (6H, m), 3.45-3.10 (2H, m). MS: m/z 408.1 (M+H⁺).

Example IV-44

2,5-Dimethoxy-N-(5-(4-methylpiperazine-1-carbonyl)pyridin-3-yl)benzenesulfonamide

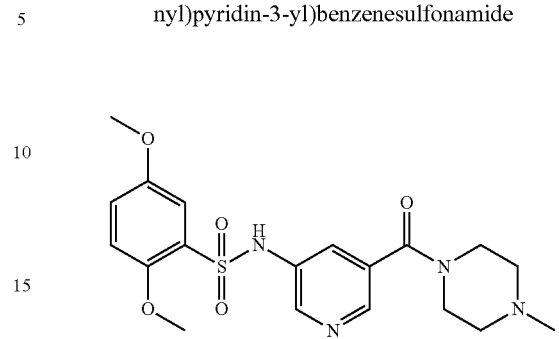

¹H NMR (DMSO-d6): δ=10.63 (1H, brs), 10.17 (1H, brs, TFA salt), 8.37 (1H, d), 8.29 (1H, d), 7.60 (1H, t), 7.30 (1H, d), 7.20-7.13 (2H, m), 3.77 (3H, s), 3.74 (3H, s), 3.61-3.00 (8H, m), 2.81 (3H, s). MS: m/z 421.2 (M+H⁺).

Example V

Example V-1

5-Bromo-2-methoxy-N-(thiophen-3-yl)benzenesulfonamide

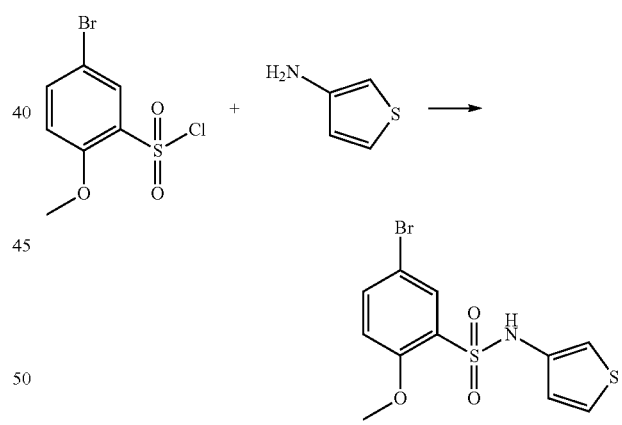

The mixture of 5-bromo-2-methoxy-benzenesulfonyl chloride (145 mg, 0.51 mmol), Thiophen-3-ylamine (50 mg, 0.51 mmol), DMAP (75 mg, 0.61 mmol) in pyridine (2 mL) was stirred at 60° C. for 4 h. And then, water (10 mL) was added and the reaction mixture was extracted with DCM (10 mL×3). The extracts were dried over Na₂SO₄ and concentrated to dryness. The residue was purified by prep-HPLC to afford 60 mg (yield: 36%) of 5-bromo-2-methoxy-N-(thiophen-3-yl)benzenesulfonamide.

¹H NMR (DMSO-d6): δ=10.28 (1H, brs), 7.78-7.75 (2H, m), 7.38 (1H, dd), 7.18 (1H, d), 6.86-6.83 (2H, m), 3.90 (3H, s). MS: m/z 348.0 (M+H⁺).

Example V-2

2,5-Dimethoxy-N-(thiophen-3-yl)benzenesulfonamide

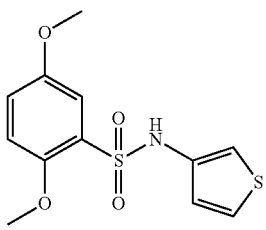 [SMILES: COc1ccc(OC)c(S(=O)(=O)Nc2ccsc2)c1]

¹H NMR (DMSO-d6): δ=10.15 (1H, s), 7.37-7.36 (1H, d), 7.25-7.24 (1H, d), 7.15-7.13 (2H, m), 6.84-6.81 (2H, m), 3.84 (3H, s), 3.73 (3H, s). MS: m/z 300 (M+H⁺).

Example V-3

5-Bromo-2-methoxy-N-oxazol-2-yl-benzenesulfonamide

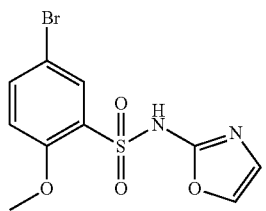 [SMILES: COc1ccc(Br)cc1S(=O)(=O)Nc1ncco1]

This compound was prepared as described in Example V-1.

¹H NMR (DMSO-d6, 400 MHz): δ=11.90 (1H, s), 7.89 (1H, d), 7.74 (1H, dd), 7.66 (1H, d), 7.29 (1H, d), 7.16 (1H, d), 3.73 (3H, s). MS: m/z 334.9 (M+H⁺).

Example V-4

2,5-Dimethoxy-N-oxazol-2-yl-benzenesulfonamide

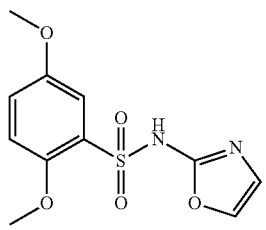 [SMILES: COc1ccc(OC)c(S(=O)(=O)Nc2ncco2)c1]

This compound was prepared as described in Example V-1.

¹H NMR (DMSO-d6, 400 MHz): δ=11.76 (1H, s), 7.64 (1H, s), 7.35 (1H, d), 7.27 (1H, s), 7.14-7.10 (2H, m), 3.77 (3H, s), 3.67 (3H, s). MS: m/z 285.1 (M+H⁺).

Example V-5

5-Bromo-2-methoxy-N-(3-methyl-isoxazol-5-yl)-benzenesulfonamide

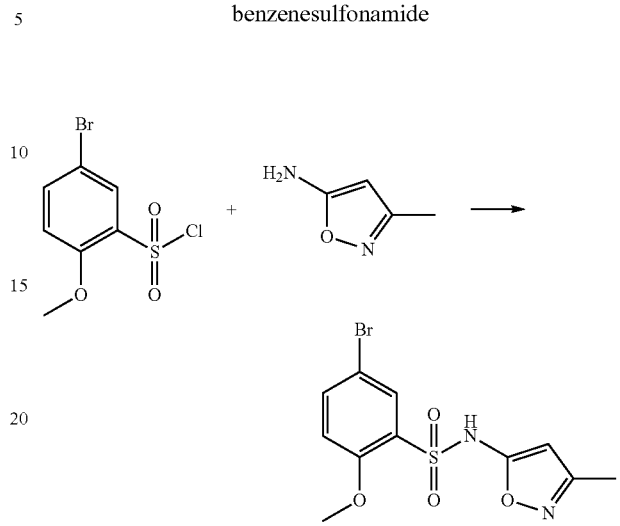

The mixture of 5-bromo-2-methoxy-benzenesulfonyl chloride (145 mg, 0.51 mmol), 3-methyl-isoxazol-5-ylamine (50 mg, 0.51 mmol), DMAP (75 mg, 0.61 mmol) in pyridine (2 mL) was stirred at 40° C. for 4 h. And then, water (10 mL) was added and the reaction mixture was extracted with DCM (10 mL×3). The extracts were dried over Na₂SO₄ and concentrated to dryness. The residue was purified by prep-HPLC to afford 10 mg (yield: 6%) of 5-bromo-2-methoxy-N-(3-methyl-isoxazol-5-yl)-benzenesulfonamide as yellow solid.

¹H NMR (DMSO-d6, 400 MHz): δ=12.13 (1H, s), 7.88 (1H, s), 7.85 (1H, d), 7.26 (1H, d), 5.65 (1H, s), 3.87 (3H, s), 2.11 (3H, s). MS: m/z 348.9 (M+H⁺).

Example V-6

2,5-Dimethoxy-N-(3-methyl-isoxazol-5-yl)-benzenesulfonamide

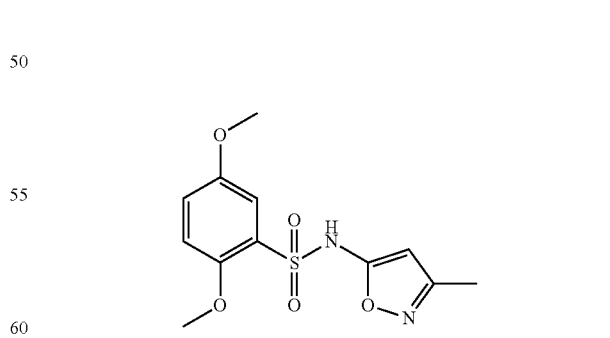

¹H NMR (DMSO-d6, 400 MHz): δ=11.99 (1H, brs), 7.32-7.17 (3H, m), 5.59 (1H, s), 3.80 (3H, s), 3.77 (3H, s), 2.08 (3H, s). MS: m/z 298.9 (M+H⁺).

Example V-7

5-Bromo-2-methoxy-N-(1H-pyrazol-3-yl)-benzenesulfonamide

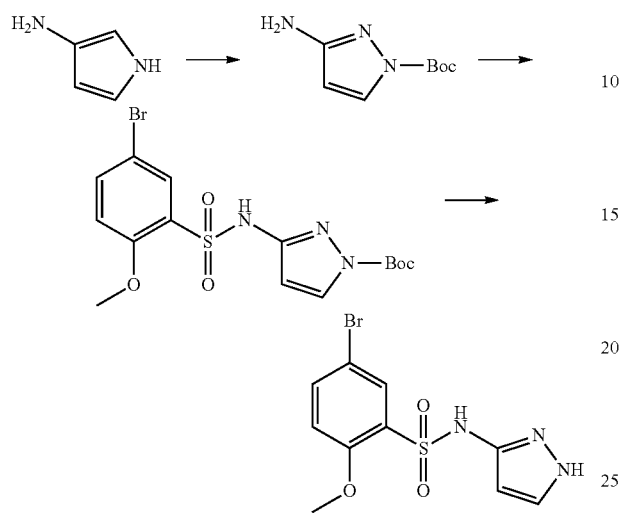

Step 1: To the mixture of 1H-pyrazol-3-ylamine (500 mg, 6.0 mmol), TEA (1.21 g, 12.0 mmol), DMAP (50 mg, 0.4 mmol) in dioxane (20 mL), was added (Boc)$_2$O (1.5 g, 6.9 mmol) dropwise at r.t. The mixture was stirred at r.t. for 4 h. The solution was concentrated in vacuum. The residue was diluted with EtOAc (20 mL), washed with water (20 mL×2), brine (20 mL) and dried over magnesium sulfate. The solution was filtered and concentrated in vacuum to afford 700 mg (yield: 64%) of crude 3-amino-pyrazole-1-carboxylic acid tert-butyl ester. MS: m/z 184.0 (M+H$^+$).

Step 2: This step is similar to Example V-1. MS: m/z 430.0 (M–H$^+$).

Step 3: The mixture of 3-(5-bromo-2-methoxy-benzenesulfonylamino)-pyrazole-1-carboxylic acid tert-butyl ester (200 mg, 0.46 mmol) in HCl (4.0 M in MeOH, 10 mL) was stirred at r.t. for 60 minutes. The solvent was evaporated and the residue was purified by prep-TLC (PE/EtOAc, 2/1) to afford 11 mg (yield: 7%) of 5-bromo-2-methoxy-N-(1H-pyrazol-3-yl)-benzenesulfonamide as white solid.

$^1$H NMR (DMSO-d6, 400 MHz): δ=12.34 (1H, s), 7.78-7.73 (2H, m), 7.49 (1H, t), 7.17 (1H, d), 5.85 (1H, s), 3.85 (3H, s). MS: m/z 331.8 (M+H$^+$).

Example V-8

2,5-Dimethoxy-N-(1H-pyrazol-3-yl)-benzenesulfonamide

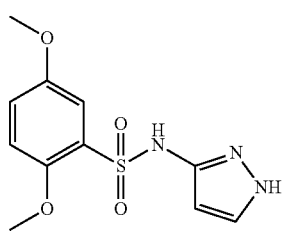 [SMILES: COc1ccc(OC)c(S(=O)(=O)Nc2cc[nH]n2)c1]

This compound was prepared as described in Example V-5.

$^1$H NMR (DMSO-d6, 400 MHz): δ=7.96 (1H, d), 7.29-7.25 (2H, m), 7.16 (1H, d), 5.81 (1H, d), 5.50 (2H, s), 3.77 (3H, s), 3.70 (3H, s). MS: m/z 284.0 (M+H$^+$).

Example V-9

5-Bromo-2-methoxy-N-(1-methyl-1H-pyrazol-3-yl)-benzenesulfonamide

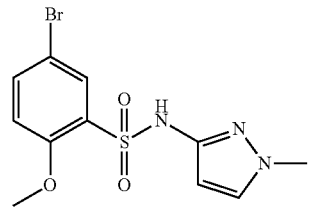 [SMILES: COc1ccc(Br)cc1S(=O)(=O)Nc1ccn(C)n1]

This compound was prepared as described in Example V-1.

$^1$H NMR (DMSO-d6, 400 MHz): δ=10.27 (1H, s), 7.76-7.73 (2H, m), 7.46 (1H, d), 7.18 (1H, d), 5.81 (1H, d), 3.87 (3H, s), 3.64 (3H, s). MS: m/z 348.0 (M+H$^+$).

Example V-10

2,5-Dimethoxy-N-(1-methyl-1H-pyrazol-3-yl)-benzenesulfonamide

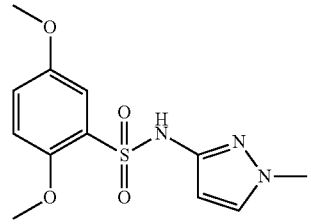 [SMILES: COc1ccc(OC)c(S(=O)(=O)Nc2ccn(C)n2)c1]

This compound was prepared as described in Example V-1.

$^1$H NMR (DMSO-d6, 400 MHz): δ=10.09 (1H, s), 7.43 (1H, d), 7.23 (1H, t), 7.14 (2H, d), 5.79 (1H, d), 3.81 (3H, s), 3.72 (3H, s), 3.63 (3H, s). MS: m/z 298.0 (M+H$^+$).

Example V-11

5-Bromo-2-methoxy-N-(2-methyl-2H-pyrazol-3-yl)-benzenesulfonamide

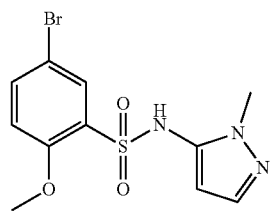 [SMILES: COc1ccc(Br)cc1S(=O)(=O)Nc1ccnn1C]

This compound was prepared as described in Example V-1.

$^1$H NMR (DMSO-d6, 400 MHz): δ=10.27 (1H, s), 7.84 (1H, dd), 7.65 (1H, d), 7.28 (1H, s), 7.26 (1H, t), 5.67 (1H, s), 3.94 (3H, s), 3.63 (3H, s). MS: m/z 346.0 (M+H$^+$).

Example V-12

2,5-Dimethoxy-N-(2-methyl-2H-pyrazol-3-yl)-benzenesulfonamide

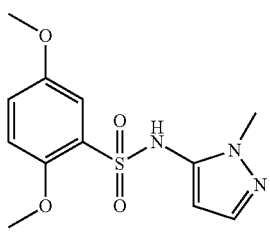 [SMILES: COc1ccc(OC)c(S(=O)(=O)Nc2ccnn2C)c1]

This compound was prepared as described in Example V-1.

$^1$H NMR (DMSO-d6, 400 MHz): δ=10.09 (1H, s), 7.25-7.21 (3H, m), 7.12 (1H, s), 5.66 (1H, d), 3.89 (3H, s), 3.72 (3H, s), 3.63 (3H, s). MS: m/z 298.1 (M+H$^+$).

Example V-13

5-Bromo-2-methoxy-N-(1-methyl-5-trifluoromethyl-1H-pyrazol-3-yl)-benzenesulfonamide

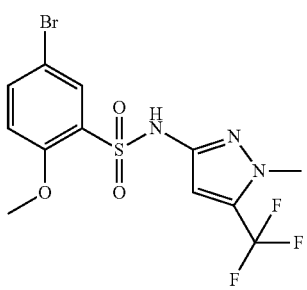 [SMILES: COc1ccc(Br)cc1S(=O)(=O)Nc1cc(C(F)(F)F)n(C)n1]

This compound was prepared as described in Example V-1.

$^1$H NMR (DMSO-d6, 400 MHz): δ=10.76 (1H, s), 7.78-7.82 (2H, m), 7.20 (1H, d), 6.45 (1H, s), 3.82 (3H, s), 3.79 (3H, s). MS: m/z 415.7 (M+H$^+$).

Example V-14

2,5-Dimethoxy-N-(1-methyl-5-trifluoromethyl-1H-pyrazol-3-yl)-benzenesulfonamide

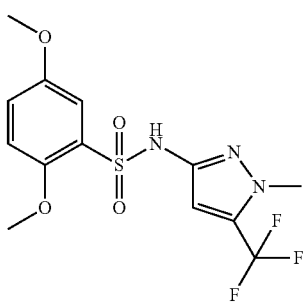 [SMILES: COc1ccc(OC)c(S(=O)(=O)Nc2cc(C(F)(F)F)n(C)n2)c1]

This compound was prepared as described in Example V-1.

$^1$H NMR (DMSO-d6, 400 MHz): δ=10.63 (1H, s), 7.27 (1H, d), 7.20-7.14 (2H, m), 6.41 (1H, s), 3.78 (3H, s), 3.76 (3H, s), 3.73 (3H, s). MS: m/z 366.0 (M+H$^+$).

Example V-15

5-Bromo-2-methoxy-N-thiazol-2-yl-benzenesulfonamide

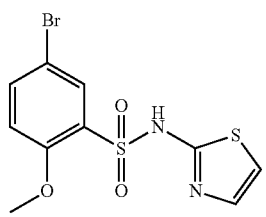 [SMILES: COc1ccc(Br)cc1S(=O)(=O)Nc1nccs1]

This compound was prepared as described in Example V-1.

$^1$H NMR (DMSO-d6, 400 MHz): δ=12.75 (1H, s), 7.86 (1H, d), 7.72 (1H, dd), 7.27 (1H, d), 7.14 (1H, d), 6.87 (1H, d), 3.70 (3H, s). MS: m/z 350.9 (M+H$^+$).

Example V-16

2,5-Dimethoxy-N-thiazol-2-yl-benzenesulfonamide

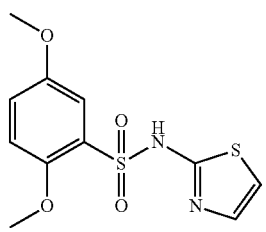 [SMILES: COc1ccc(OC)c(S(=O)(=O)Nc2nccs2)c1]

This compound was prepared as described in Example V-1.

$^1$H NMR (DMSO-d6, 400 MHz): δ=12.63 (1H, s), 7.33 (1H, d), 7.24 (1H, d), 7.13-7.11 (2H, m), 6.84 (1H, d), 3.75 (3H, s), 3.64 (3H, s). MS: m/z 301.0 (M+H$^+$).

Example V-17

5-Bromo-2-methoxy-N-(5-methyl-[1,3,4]thiadiazol-2-yl)-benzenesulfonamide

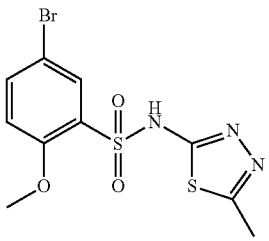 [SMILES: COc1ccc(Br)cc1S(=O)(=O)Nc1nnc(C)s1]

This compound was prepared as described in Example V-1.

$^1$H NMR (DMSO-d6, 400 MHz): δ=13.95 (1H, s), 7.87 (1H, d), 7.78 (1H, dd), 7.18 (1H, d), 3.74 (3H, s), 2.53 (3H, s). MS: m/z 365.9 (M+H$^+$).

Example V-18

2,5-Dimethoxy-N-(5-methyl-[1,3,4]thiadiazol-2-yl)-benzenesulfonamide

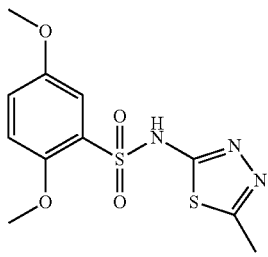

This compound was prepared as described in Example V-1.

$^1$H NMR (DMSO-d6, 400 MHz): δ=13.82 (1H, s), 7.32 (1H, d), 7.14-7.12 (2H, m), 3.75 (3H, s), 3.65 (3H, s), 2.51 (3H, s). MS: m/z 316.0 (M+H$^+$).

Example V-19

5-Bromo-2-methoxy-N-(5-trifluoromethyl-[1,3,4]thiadiazol-2-yl)-benzenesulfonamide

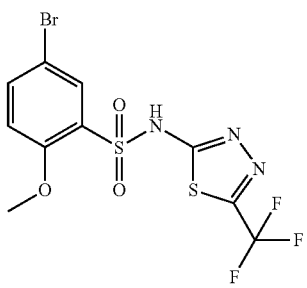 [SMILES: COc1ccc(Br)cc1S(=O)(=O)Nc1nnc(C(F)(F)F)s1]

This compound was prepared as described in Example V-1.

$^1$H NMR (DMSO-d6, 400 MHz): δ=10.57 (1H, s), 7.87 (1H, d), 7.75 (1H, s), 7.17 (1H, d), 3.69 (3H, s). MS: m/z 419.9 (M+H$^+$).

Example V-20

N-(5-Difluoromethyl-[1,3,4]thiadiazol-2-yl)-2,5-dimethoxy-benzenesulfonamide

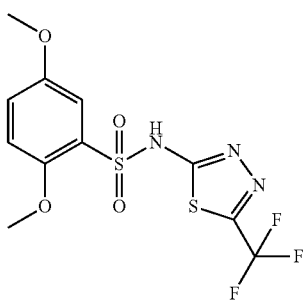 [SMILES: COc1ccc(OC)c(S(=O)(=O)Nc2nnc(C(F)(F)F)s2)c1]

This compound was prepared as described in Example V-1.

$^1$H NMR (CD$_3$OD, 400 MHz): δ=7.45 (1H, s), 7.00 (1H, t), 3.76 (3H, s), 3.63 (3H, s). MS: m/z 370.0 (M+H$^+$).

Example V-21

5-Bromo-2-methoxy-N-(5-methyl-[1,3,4]oxadiazol-2-yl)-benzenesulfonamide

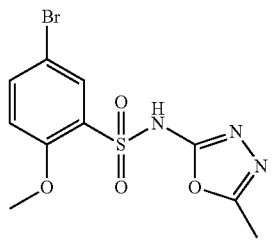 [SMILES: COc1ccc(Br)cc1S(=O)(=O)Nc1nnc(C)o1]

This compound was prepared as described in Example V-1.

$^1$H NMR (DMSO-d6, 400 MHz): δ=13.48 (1H, s), 7.90 (1H, d), 7.75 (1H, dd), 7.17 (1H, d), 3.76 (3H, s), 2.35 (3H, s). MS: m/z 349.9 (M+H$^+$).

Example V-22

2,5-Dimethoxy-N-(5-methyl-[1,3,4]oxadiazol-2-yl)-benzenesulfonamide

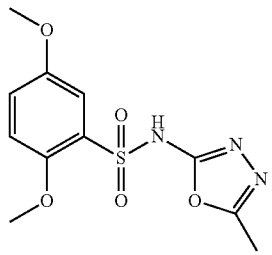 [SMILES: COc1ccc(OC)c(S(=O)(=O)Nc2nnc(C)o2)c1]

This compound was prepared as described in Example V-1.

$^1$H NMR (DMSO-d6, 400 MHz): δ=13.28 (1H, s), 7.37 (1H, d), 7.14-7.11 (2H, m), 3.77 (3H, s), 3.70 (3H, s), 2.36 (3H, s). MS: m/z 300.0 (M+H$^+$).

Example V-23

2,5-Dimethoxy-N-pyrazin-2-yl-benzenesulfonamide

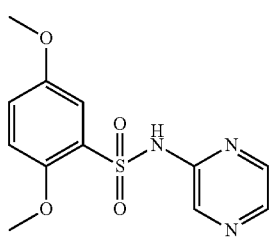 [SMILES: COc1ccc(OC)c(S(=O)(=O)Nc2cnccn2)c1]

This compound was prepared as described in Example V-1.

¹H NMR (DMSO-d6, 400 MHz): δ=11.30 (1H, s), 8.34 (1H, s), 8.21-8.17 (2H, m), 7.39 (1H, d), 7.19 (1H, dd), 7.11 (1H, d), 3.77 (3H, s), 3.68 (3H, s). MS: m/z 296.1 (M+H⁺).

Example V-24

5-Bromo-2-methoxy-N-pyridazin-3-yl-benzenesulfonamide

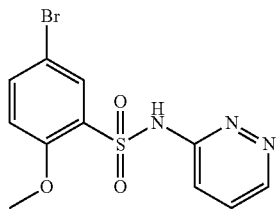 [SMILES: COc1ccc(Br)cc1S(=O)(=O)Nc1cccnn1]

This compound was prepared as described in Example V-1.

¹H NMR (DMSO-d6, 400 MHz): δ=14.41 (1H, d), 8.35 (1H, d), 8.68 (1H, d), 7.92 (1H, d), 7.77-7.71 (2H, m), 7.14 (1H, d), 3.66 (3H, s). MS: m/z 346.0 (M+H⁺).

Example V-25

2,5-Dimethoxy-N-pyridazin-3-yl-benzenesulfonamide

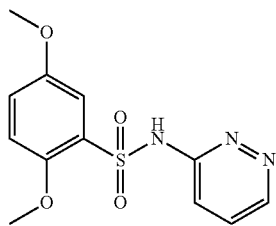 [SMILES: COc1ccc(OC)c(S(=O)(=O)Nc2cccnn2)c1]

This compound was prepared as described in Example V-1.

¹H NMR (DMSO-d6, 400 MHz): δ=11.00 (1H, s), 8.35 (1H, s), 8.15-8.12 (1H, m), 7.71 (1H, dd), 7.38 (1H, d), 7.13-7.08 (2H, m), 3.77 (3H, s), 3.60 (3H, s). MS: m/z 296.1 (M+H⁺).

Example V-26

5-Bromo-2-methoxy-N-pyridazin-4-yl-benzenesulfonamide

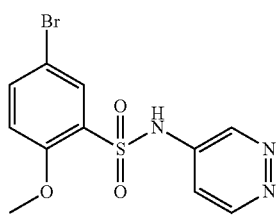 [SMILES: COc1ccc(Br)cc1S(=O)(=O)Nc1ccnnc1]

This compound was prepared as described in Example V-1.

¹H NMR (DMSO-d6, 400 MHz): δ=14.37 (1H, s), 8.53 (1H, t), 8.31 (1H, s), 7.89 (1H, d), 7.70 (1H, d), 7.38 (1H, dd), 7.12 (1H, d), 3.71 (3H, s). MS: m/z 345.9 (M+H⁺).

Example V-27

2,5-Dimethoxy-N-pyridazin-4-yl-benzenesulfonamide

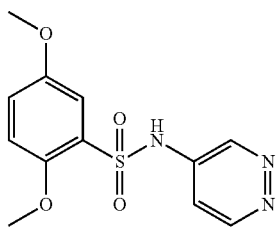 [SMILES: COc1ccc(OC)c(S(=O)(=O)Nc2ccnnc2)c1]

This compound was prepared as described in Example V-1.

¹H NMR (DMSO-d6, 400 MHz): δ=14.25 (1H, s), 8.49-8.45 (1H, m), 8.27 (1H, s), 7.38-7.34 (2H, m), 7.11-7.07 (2H, m), 3.76 (3H, s), 3.65 (3H, s). MS: m/z 296.1 (M+H⁺).

Example V-28

5-Bromo-2-methoxy-N-pyrimidin-2-yl-benzenesulfonamide

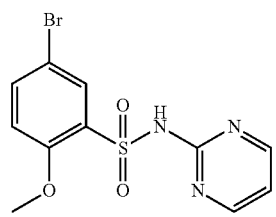 [SMILES: COc1ccc(Br)cc1S(=O)(=O)Nc1ncccn1]

This compound was prepared as described in Example V-1.

¹H NMR (DMSO-d6, 400 MHz): δ=14.36 (1H, s), 8.54 (1H, d), 8.33 (1H, s), 7.89 (1H, d), 7.70 (1H, d), 7.37 (1H, t), 7.12 (1H, d), 3.71 (3H, s). MS: m/z 343.9 (M+H⁺).

Example V-29

2,5-Dimethoxy-N-pyrimidin-2-yl-benzenesulfonamide

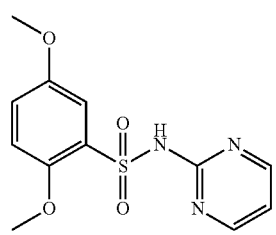 [SMILES: COc1ccc(OC)c(S(=O)(=O)Nc2ncccn2)c1]

This compound was prepared as described in Example V-1.

¹H NMR (DMSO-d6, 400 MHz): δ=11.69 (1H, s), 8.48-8.44 (2H, m), 7.43 (1H, d), 7.17 (1H, d), 7.11 (1H, d), 7.09 (1H, d), 7.02 (1H, d), 3.78 (3H, s), 3.76 (3H, s). MS: m/z 296.1 (M+H⁺).

Example VI

Example VI-1

5-Bromo-2-methoxy-pyridine-3-sulfonic acid quinolin-3-ylamide

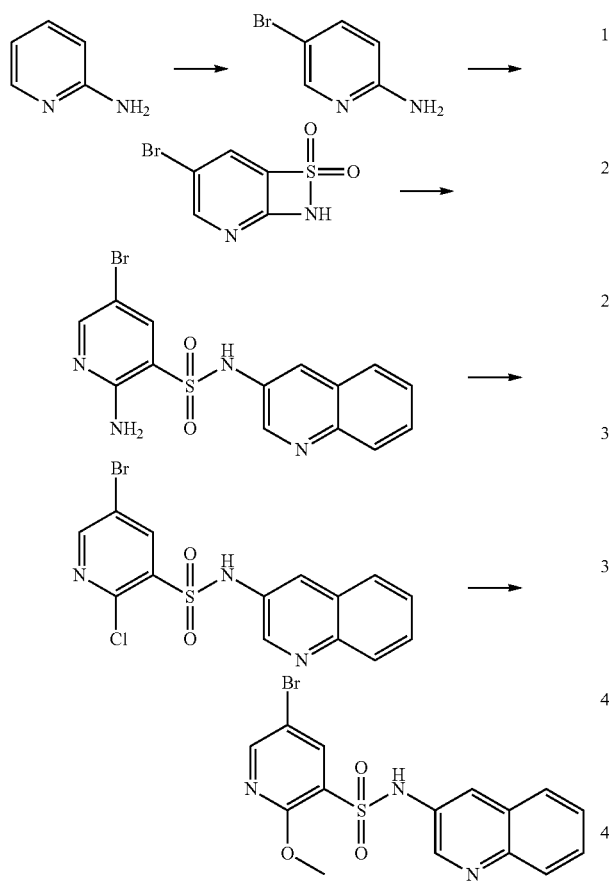

Step 1: To the mixture of pyridin-2-ylamine (10.0 g, 106 mmol) in acetone (200 mL), was added NBS (22.6 g, 127 mmol) portionwise at 0° C. The mixture was warmed to room temperature and stirred overnight. Solvent was evaporated in vacuum. The residue was purified by silica gel column (DCM/MeOH, 20/1) to afford 18 g (yield: 98%) of 5-bromo-pyridin-2-ylamine as yellow solid.

¹H NMR (DMSO-d6): δ=7.94 (1H, d), 7.61 (1H, dd), 6.43 (1H, d), 6.10 (2H, brs).

Step 2: The mixture of 5-bromo-pyridin-2-ylamine (8.0 g, 46.2 mmol) in ClSO₃H (20 mL) was stirred at 200° C. for 4 h. After cooled to room temperature, the mixture was poured into ice water and neutralized with NaHCO₃ solid. The aqueous phase was extracted with EtOAc (50 mL×3). The extracts were dried over Na₂SO₄ and concentrated in vacuum to give a residue, which was purified by silica gel column (DCM/MeOH, 20/1) to afford 2.5 g (yield: 23%) of 4-bromo-7-thia-2,8-diaza-bicyclo[4.2.0]octa-1,3,5-triene 7,7-dioxide.

¹H NMR (DMSO-d6): δ=9.11 (1H, brs), 8.47 (1H, d), 8.08 (1H, d).

Step 3: The mixture of 4-bromo-7-thia-2,8-diaza-bicyclo[4.2.0]octa-1,3,5-triene 7,7-dioxide (1.0 g, 4.3 mmol), quinolin-3-ylamine (735 mg, 5.1 mmol) in pyridine (20 mL) was stirred at room temperature overnight. Solvent was evaporated in vacuum. The residue was washed with DCM (5 mL×2). The resulting solid was collected by filtration to afford 800 mg (yield: 49%) of 2-amino-5-bromo-pyridine-3-sulfonic acid quinolin-3-ylamide as white solid.

¹H NMR (DMSO-d6): δ=11.07 (1H, brs), 8.63 (1H, d), 8.23 (1H, d), 7.98-7.93 (4H, m), 7.69-7.66 (1H, m), 7.60-7.58 (1H, m), 6.95 (2H, brs). MS: m/z 379.0 (M+H⁺).

Step 4: To the mixture of 2-amino-5-bromo-pyridine-3-sulfonic acid quinolin-3-ylamide (600 mg, 1.6 mmol) in concentrated HCl (40 mL) was added NaNO₂ (110 mg, 69 mmol) portionwise at 0° C. The mixture was slowly warmed up to room temperature. The suspension was filtered to afford 1.0 g (75% purity on LCMS) of 5-bromo-2-chloro-pyridine-3-sulfonic acid quinolin-3-ylamide as white solid. MS: m/z 397.9 (M+H⁺).

Step 5: The mixture of 5-bromo-2-chloro-pyridine-3-sulfonic acid quinolin-3-ylamide (300 mg crude), NaOMe (200 mg, 3.7 mmol) in MeOH (3 mL) was stirred at 100° C. in a sealed tube for 2 h. The solvent was evaporated in vacuum and the residue was purified by silica gel column to afford 40 mg (two step yield: 21%) of 5-bromo-2-methoxy-pyridine-3-sulfonic acid quinolin-3-ylamide as white solid.

¹H NMR (DMSO-d6): δ=11.01 (1H, brs), 8.69 (1H, d), 8.53 (1H, d), 8.33 (1H, d), 8.00 (1H, d), 7.93-7.89 (2H, m), 7.66-7.63 (1H, m), 7.56-7.53 (1H, m), 3.91 (3H, s). MS: m/z 393.6 (M+H⁺).

Example VI-2

2,5-Dimethoxy-N-methyl-N-(quinolin-3-yl)pyridine-3-sulfonamide

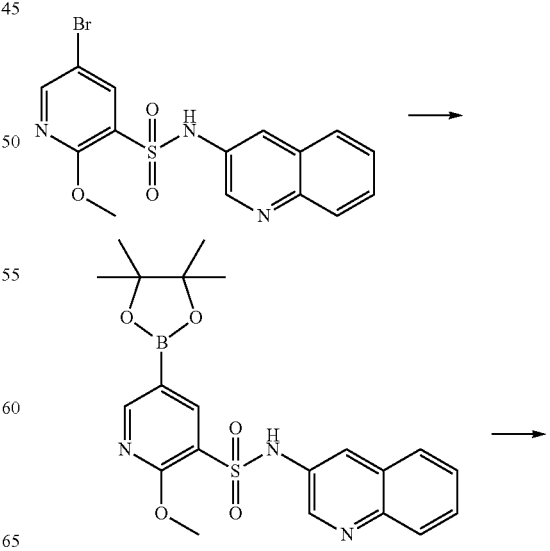

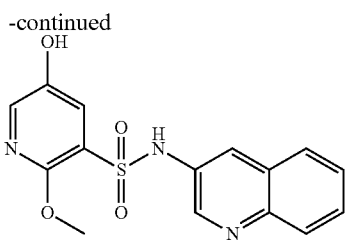

Step 1: To a solution of 5-bromo-2-methoxy-pyridine-3-sulfonic acid quinolin-3-ylamide (100 mg, 0.25 mmol) in DMF (5 mL) was added Pd(PPh$_3$)$_4$ (10 mg), K$_2$CO$_3$ (70 mg, 0.5 mmol) and bis(pinacolato)diboron (127 mg, 0.5 mmol), and the mixture was irradiated by microwave at 120° C. for 2 h. LCMS showed that the reaction was complete. The resultant was poured into water, and extracted with EtOAc (20 mL×3). The extracts were dried over Na$_2$SO$_4$ and concentrated in vacuum to give crude 2-methoxy-5-(4,4,5,5-tetramethyl-[1,3,2]dioxaborolan-2-yl)-pyridine-3-sulfonic acid quinolin-3-ylamide.

Step 2: To crude 2-methoxy-5-(4,4,5,5-tetramethyl-[1,3,2]dioxaborolan-2-yl)-pyridine-3-sulfonic acid quinolin-3-ylamide in DCM (5 mL) was added H$_2$O$_2$ (2 mL) and AcOH (0.5 mL). The mixture was stirred at r.t for 1 h. TLC showed that the reaction was complete. The resultant was concentrated in vacuum and purified directly by silica gel plates (PE/EtOAc, 1:1) to give 25 mg (two-step yield: 29%) of 5-hydroxy-2-methoxy-pyridine-3-sulfonic acid quinolin-3-ylamide as colorless solid.

$^1$H NMR (CD$_3$OD, 400 MHZ): δ=8.55 (1H, d), 7.92 (1H, d), 7.82 (1H, d), 7.72-7.68 (2H, m), 7.57-7.53 (2H, m), 7.47-7.43 (1H, m), 3.82 (3H, s). MS: m/z 332 (M+H$^+$).

Example VII

Example VII-1

5-Bromo-2-methoxy-N-methyl-N-(quinolin-3-yl)benzenesulfonamide

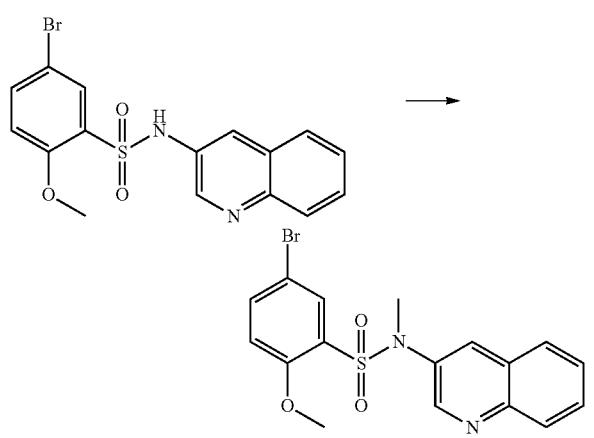

To a solution of 5-bromo-2-methoxy-N-(quinolin-3-yl)benzenesulfonamide (100 mg, 0.26 mmol) in THF (2 mL) was added K$_2$CO$_3$ (70 mg, 0.52 mmol) and methane iodide (74 mg, 0.52 mmol) at room temperature, then the mixture was stirred at room temperature overnight. The solvent was removed in vacuum. The residue was diluted with EtOAc (20 ml). The mixture was washed with water, brine and dried over Na$_2$SO$_4$. The solution was evaporated to dryness and purified by prep-HPLC (PE/EtOAc, 10/1) to afford 15 mg (yield: 14%) of 5-bromo-2-methoxy-N-methyl-N-(quinolin-3-yl)benzenesulfonamide as white solid.

$^1$H NMR (DMSO-d6, 400 MHz) δ: 8.82 (1H, d), 8.23 (1H, d), 8.01 (1H, d), 7.97 (1H, d), 7.83 (1H, dd), 7.82-7.73 (2H, m), 7.65 (1H, t), 7.21 (1H, d), 3.57 (3H, s), 3.38 (3H, s). MS: m/z 406.9 (M+H$^+$)

Example VII-2

5-Bromo-2-methoxy-N-ethyl-N-(quinolin-3-yl)benzenesulfonamide

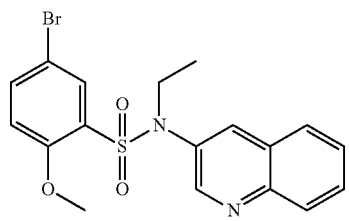 [SMILES: CCN(c1cnc2ccccc2c1)S(=O)(=O)c1cc(Br)ccc1OC]

To a solution of 5-bromo-2-methoxy-N-(quinolin-3-yl)benzenesulfonamide (100 mg, 0.26 mmol) in DMF (2 mL) was added K$_2$CO$_3$ (70 mg, 0.52 mmol) and ethyl bromide (40 mg, 0.31 mmol) at room temperature, then the mixture was stirred at 80° C. overnight. After cooled to room temperature, the solvent was removed in vacuum. The residue was diluted with EtOAc (20 ml). The mixture was washed with water, brine and dried over Na$_2$SO$_4$. The solution was evaporated to dryness and purified by silica gel column (PE/EtOAc, 20/1) to afford 15 mg (yield: 14%) of 5-bromo-2-methoxy-N-ethyl-N-(quinolin-3-yl)benzenesulfonamide as white solid.

$^1$H NMR (DMSO-d6, 400 MHz) δ: 8.68 (1H, d), 8.25 (1H, d), 8.01 (2H, t), 7.85-7.76 (2H, m), 7.67-7.61 (2H, m), 7.27 (1H, d), 3.87 (2H, q), 3.77 (3H, s), 1.06 (3H, t). MS: m/z 420.9 (M+H$^+$)

Example VII-3

5-Bromo-2-methoxy-N-propyl-N-(quinolin-3-yl)benzenesulfonamide

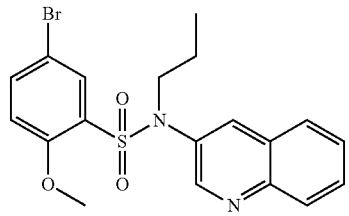 [SMILES: CCCN(c1cnc2ccccc2c1)S(=O)(=O)c1cc(Br)ccc1OC]

This compound was prepared as described in Example VII-2.

$^1$H NMR (DMSO-d6, 400 MHz) δ: 8.70 (1H, d), 8.27 (1H, d), 8.01 (2H, t), 7.84-7.75 (2H, m), 7.67-7.63 (2H, m), 7.26 (1H, d), 3.83-3.75 (5H, m), 1.44-1.35 (2H, m), 0.87 (3H, t). MS: m/z 434.9 (M+H$^+$)

Example VII-4

5-Bromo-N-isopropyl-2-methoxy-N-(quinolin-3-yl)benzenesulfonamide

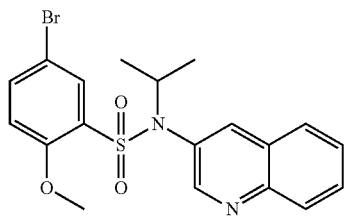 [SMILES: COc1ccc(Br)cc1S(=O)(=O)N(c1cnc2ccccc2c1)C(C)C]

This compound was prepared as described in Example VII-2.

$^1$H NMR (DMSO-d6, 400 MHz) δ: 8.43 (1H, d), 8.18 (1H, d), 8.06 (2H, t), 7.89-7.81 (2H, m), 7.67 (1H, t), 7.61 (1H, d), 7.34 (1H, d), 4.65-4.59 (1H, m), 3.99 (3H, s), 1.09 (6H, d). MS: m/z 435.0 (M+H$^+$)

Example VII-5

5-Bromo-N-butyl-2-methoxy-N-(quinolin-3-yl)benzenesulfonamide

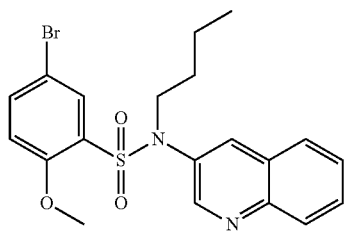 [SMILES: CCCCN(c1cnc2ccccc2c1)S(=O)(=O)c1cc(Br)ccc1OC]

This compound was prepared as described in Example VII-2.

$^1$H NMR (DMSO-d6, 400 MHz) δ: 8.70 (1H, d), 8.26 (1H, d), 8.01 (2H, t), 7.85-7.78 (2H, m), 7.67-7.63 (2H, m), 7.26 (1H, d), 3.83 (2H, t), 3.77 (3H, s), 1.37-1.28 (4H, m), 0.82 (3H, t). MS: m/z 449.0 (M+H$^+$)

Example VII-6

5-Bromo-N-benzyl-2-methoxy-N-(quinolin-3-yl)benzenesulfonamide

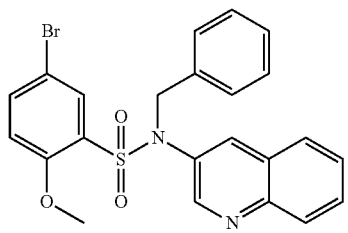 [SMILES: COc1ccc(Br)cc1S(=O)(=O)N(Cc1ccccc1)c1cnc2ccccc2c1]

This compound was prepared as described in Example VII-2.

$^1$H NMR (DMSO-d6, 400 MHz) δ: 8.55 (1H, d), 7.99 (1H, d), 7.92 (1H, s), 7.91 (1H, s), 7.71-7.60 (3H, m), 7.52 (1H, t), 7.30-7.18 (5H, m), 6.94 (1H, d), 5.05 (2H, s), 3.88 (3H, s). MS: m/z 483.0 (M+H$^+$)

Example VII-7

5-Bromo-2-methoxy-N-(2-methoxyethyl)-N-(quinolin-3-yl)benzenesulfonamide

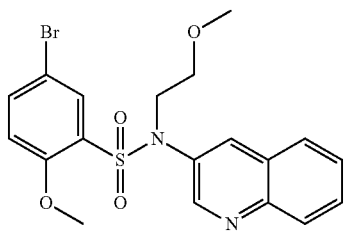 [SMILES: COCCN(c1cnc2ccccc2c1)S(=O)(=O)c1cc(Br)ccc1OC]

This compound was prepared as described in Example VII-2.

$^1$H NMR (DMSO-d6, 400 MHz) δ: 8.67 (1H, d), 8.22 (1H, d), 7.80 (2H, t), 7.84-7.75 (2H, m), 7.66-7.60 (2H, m), 7.28 (1H, d), 4.02 (2H, t), 3.84 (3H, s), 3.41 (2H, t), 3.13 (3H, s). MS: m/z 451.0 (M+H$^+$)

Example VII-8

5-Bromo-2-methoxy-N-(3-methoxypropyl)-N-(quinolin-3-yl)benzenesulfonamide

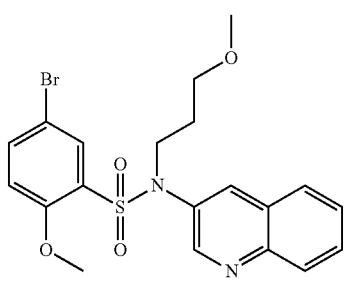 [SMILES: COCCCN(c1cnc2ccccc2c1)S(=O)(=O)c1cc(Br)ccc1OC]

This compound was prepared as described in Example VII-2.

$^1$H NMR (CDC$_3$, 400 MHz) δ: 8.66 (1H, d), 8.12 (1H, d), 8.09 (1H, d), 7.91 (1H, d), 7.81 (1H, d), 7.74 (1H, td), 7.61-7.55 (2H, m), 6.87 (1H, d), 3.96 (2H, t), 3.75 (3H, s), 3.44 (2H, t), 3.23 (3H, s), 1.85-1.77 (2H, t). MS: m/z 465.0 (M+H$^+$)

Example VII-9

5-Bromo-N-(2-(dimethylamino)ethyl)-2-methoxy-N-(quinolin-3-yl)benzenesulfonamide

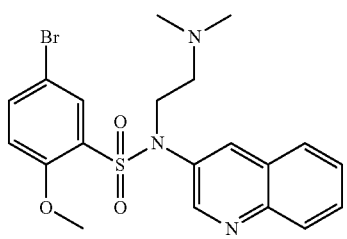 [SMILES: COc1ccc(Br)cc1S(=O)(=O)N(CCN(C)C)c1cnc2ccccc2c1]

This compound was prepared as described in Example VII-2.

¹H NMR (DMSO-d6, 400 MHz) δ: 8.63 (1H, d), 8.13 (1H, d), 7.92 (1H, d), 7.81 (1H, d), 7.73-7.67 (1H, m), 7.66-7.59 (2H, m), 7.58-7.54 (1H, m), 7.07 (1H, d), 3.93 (2H, t), 3.69 (3H, s), 2.41 (2H, t), 2.13 (6H, s). MS: m/z 464.0 (M+H⁺)

Example VII-10

N-allyl-5-bromo-2-methoxy-N-(quinolin-3-yl)benzenesulfonamide

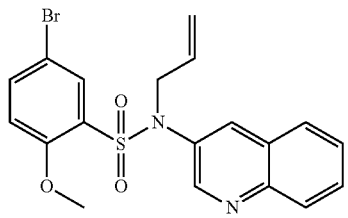 [SMILES: C=CCN(c1cnc2ccccc2c1)S(=O)(=O)c1cc(Br)ccc1OC]

This compound was prepared as described in Example VII-2.

¹H NMR (DMSO-d6, 400 MHz) δ: 8.68 (1H, d), 8.23 (1H, d), 7.99 (2H, t), 7.84 (1H, dd), 7.81-7.75 (1H, m), 7.68-7.60 (2H, m), 7.28 (1H, d), 5.83-5.74 (1H, m), 5.21-5.16 (1H, m), 5.07 (1H, d), 4.50 (2H, d), 3.81 (3H, s). MS: m/z 433.0 (M+H⁺)

Example VII-11

5-Bromo-2-methoxy-N-(prop-2-yn-1-yl)-N-(quinolin-3-yl)benzenesulfonamide

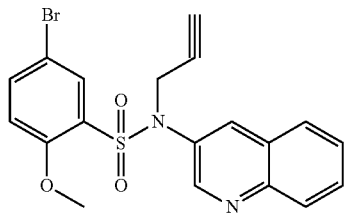 [SMILES: C#CCN(c1cnc2ccccc2c1)S(=O)(=O)c1cc(Br)ccc1OC]

This compound was prepared as described in Example VII-2.

¹H NMR (CDC₃, 400 MHz) δ: 8.71 (1H, d), 8.16 (1H, d), 8.08 (1H, d), 7.91 (1H, d), 7.82 (1H, d), 7.75 (1H, td), 7.65-7.57 (2H, m), 6.91 (1H, d), 4.71 (2H, d), 3.82 (3H, s), 2.24 (1H, t). MS: m/z 431.0 (M+H⁺)

Example VII-12

2,5-Dimethoxy-N-methyl-N-(quinolin-3-yl)benzenesulfonamide

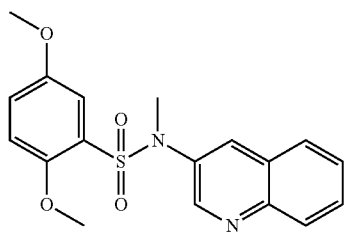 [SMILES: COc1ccc(OC)c(S(=O)(=O)N(C)c2cnc3ccccc3c2)c1]

This compound was prepared as described in Example VII-2.

¹H NMR (DMSO-d6, 400 MHz) δ: 8.79 (1H, d), 8.07-8.04 (2H, m), 7.78 (1H, d), 7.69 (1H, t), 7.55 (1H, t), 7.38 (1H, d), 7.04 (1H, dd), 6.89 (1H, d), 3.73 (3H, s), 3.63 (3H, s), 3.47 (3H, s). MS: m/z 359.1 (M+H⁺)

Example VII-13

2,5-Dimethoxy-N-ethyl-N-(quinolin-3-yl)benzenesulfonamide

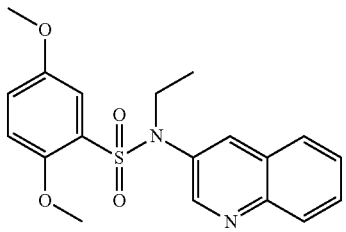 [SMILES: CCN(c1cnc2ccccc2c1)S(=O)(=O)c1cc(OC)ccc1OC]

This compound was prepared as described in Example VII-2.

¹H NMR (DMSO-d6, 400 MHz) δ: 8.67 (1H, d), 8.22 (1H, d), 8.00 (2H, t), 7.78 (1H, td), 7.66-7.61 (1H, m), 7.23-7.20 (2H, m), 7.10 (1H, t), 3.87 (2H, q), 3.70 (3H, s), 3.66 (3H, s), 1.06 (3H, t). MS: m/z 373.1 (M+H⁺).

Example VII-14

2,5-Dimethoxy-N-isopropyl-N-(quinolin-3-yl)benzenesulfonamide

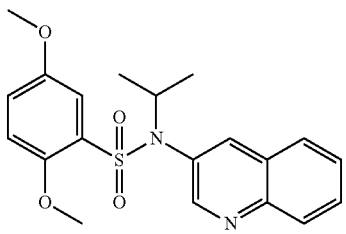 [SMILES: COc1ccc(OC)c(S(=O)(=O)N(c2cnc3ccccc3c2)C(C)C)c1]

This compound was prepared as described in Example VII-2.

¹H NMR (DMSO-d6, 400 MHz) δ: 8.42 (1H, d), 8.16 (1H, d), 8.05 (2H, t), 7.83 (1H, td), 7.68-7.63 (1H, m), 7.32-7.23 (2H, m), 7.08 (1H, d), 4.64-4.56 (1H, m), 3.92 (3H, s), 3.66 (3H, s), 1.09 (6H, d). MS: m/z 387.1 (M+H⁺).

Example VII-15

2,5-Dimethoxy-N-butyl-N-(quinolin-3-yl)benzenesulfonamide

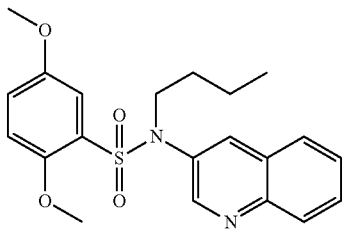 [SMILES: CCCCN(c1cnc2ccccc2c1)S(=O)(=O)c1cc(OC)ccc1OC]

This compound was prepared as described in Example VII-2.

¹H NMR (DMSO-d6, 400 MHz) δ: 8.69 (1H, d), 8.23 (1H, d), 8.02-7.97 (2H, m), 7.80-7.74 (1H, m), 7.63 (1H, t), 7.22-7.20 (2H, m), 7.08 (1H, s), 3.83 (2H, t), 3.72 (3H, s), 3.65 (3H, s), 1.40-1.26 (4 h, m), 0.81 (3H, t). MS: m/z 401.1 (M+H⁺)

Example VII-16

2,5-Dimethoxy-N-benzyl-N-(quinolin-3-yl)benzenesulfonamide

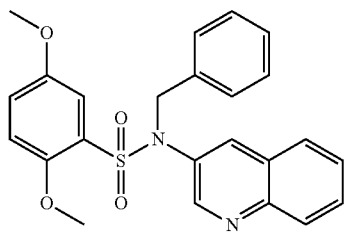 [SMILES: COc1ccc(OC)c(S(=O)(=O)N(Cc2ccccc2)c2cnc3ccccc3c2)c1]

This compound was prepared as described in Example VII-2.

¹H NMR (CDC₃, 400 MHz) δ: 8.57 (1H, d), 7.98 (1H, d), 7.90 (1H, d), 7.69-7.63 (2H, m), 7.52-7.47 (1H, m), 7.32-7.18 (6H, m), 7.06 (1H, dd), 7.00 (1H, d), 5.07 (2H, s), 3.88 (3H, s), 3.68 (3H, s). MS: m/z 435.1 (M+H⁺)

Example VII-17

2,5-Dimethoxy-N-(2-methoxyethyl)-N-(quinolin-3-yl)benzenesulfonamide

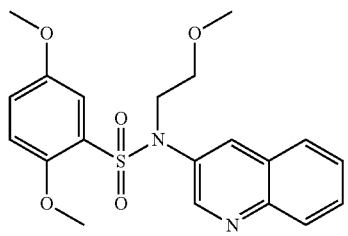 [SMILES: COCCN(c1cnc2ccccc2c1)S(=O)(=O)c1cc(OC)ccc1OC]

This compound was prepared as described in Example VII-2.

¹H NMR (CDC₃, 400 MHz) δ: 8.66 (1H, d), 8.11 (1H, d), 8.05 (1H, d), 7.78 (1H, d), 7.71 (1H, td), 7.58-7.52 (1H, m), 7.25 (1H, d), 7.02 (1H, dd), 6.95 (1H, d), 4.08 (2H, t), 3.84 (3H, s), 3.66 (3H, s), 3.56 (2H, t), 3.27 (3H, s). MS: m/z 403.1 (M+H⁺)

Example VII-18

2,5-Dimethoxy-N-(3-methoxypropyl)-N-(quinolin-3-yl)benzenesulfonamide

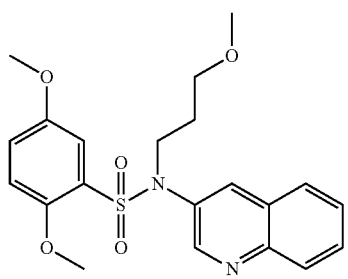 [SMILES: COCCCN(c1cnc2ccccc2c1)S(=O)(=O)c1cc(OC)ccc1OC]

This compound was prepared as described in Example VII-2.

¹H NMR (DMSO-d6, 400 MHz) δ: 8.71 (1H, d), 8.25 (1H, d), 8.01 (2H, t), 7.82-7.76 (1H, m), 7.64 (1H, t), 7.25-7.22 (2H, m), 7.11 (1H, s), 3.90 (2H, t), 3.73 (3H, s), 3.66 (3H, s), 3.35 (2H, t), 3.14 (3H, s), 1.68-1.61 (2H, m). MS: m/z 417.1 (M+H⁺)

Example VII-19

N-(2-(Dimethylamino)ethyl)-2,5-dimethoxy-N-(quinolin-3-yl)benzenesulfonamide

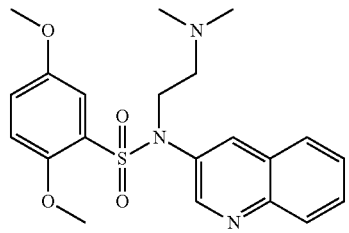 [SMILES: COc1ccc(OC)c(S(=O)(=O)N(CCN(C)C)c2cnc3ccccc3c2)c1]

This compound was prepared as described in Example VII-2.

¹H NMR (DMSO-d6, 400 MHz) δ: 8.71 (1H, d), 8.24 (1H, d), 7.99 (1H, d), 7.97 (1H, d), 7.77 (1H, t), 7.63 (1H, t), 7.25-7.20 (2H, m), 7.05 (1H, d), 4.16-4.00 (2H, m), 3.76 (3H, s), 3.63 (3H, s), 2.80-2.60 (2H, m), 2.36 (6H, s). MS: m/z 416.2 (M+H⁺)

Example VII-20

N-Allyl-2,5-dimethoxy-N-(quinolin-3-yl)benzenesulfonamide

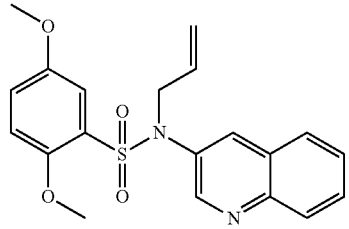 [SMILES: C=CCN(c1cnc2ccccc2c1)S(=O)(=O)c1cc(OC)ccc1OC]

This compound was prepared as described in Example VII-2.

¹H NMR (CDC₃, 400 MHz) δ: 8.61 (1H, d), 8.07-8.02 (2H, m), 7.78 (1H, d), 7.71 (1H, td), 7.55 (1H, t), 7.29 (1H, d), 7.04 (1H, dd), 6.96 (1H, d), 5.91-5.81 (1H, m), 5.15-5.06 (2H, m), 4.51 (2H, d), 3.82 (3H, s), 3.68 (3H, s). MS: m/z 385.1 (M+H⁺)

Example VII-21

2,5-Dimethoxy-N-(prop-2-yn-1-yl)-N-(quinolin-3-yl)benzenesulfonamide

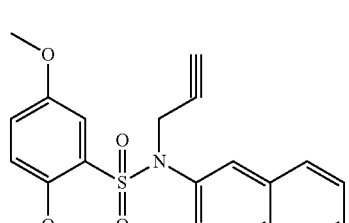

This compound was prepared as described in Example VII-2.

¹H NMR (CDC₃, 400 MHz) δ: 8.70 (1H, d), 8.15 (1H, d), 8.07 (1H, d), 7.80 (1H, d), 7.73 (1H, td), 7.57 (1H, t), 7.28 (1H, d), 7.07 (1H, dd), 6.97 (1H, d), 4.73 (2H, d), 3.84 (3H, s), 3.69 (3H, s), 2.22 (1H, t). MS: m/z 383.1 (M+H⁺)

Example VIII

Example VIII-1

5-Bromo-2-methoxy-N-(6-morpholinopyridin-3-yl)benzenesulfonamide

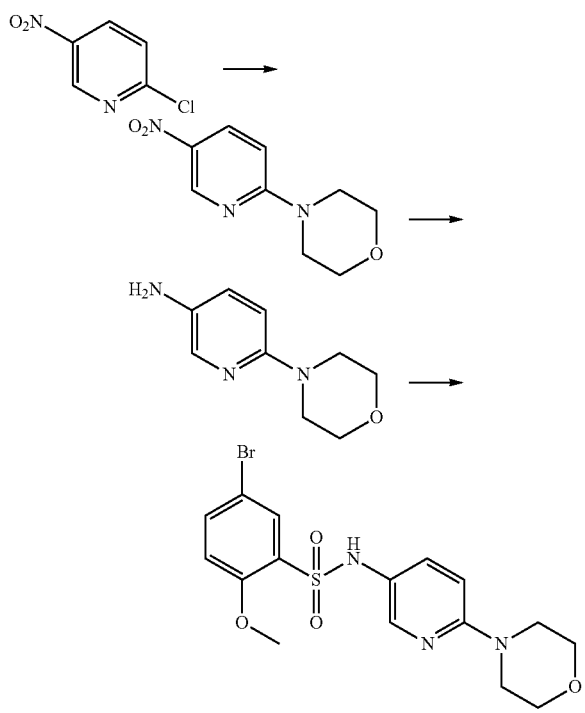

Step 1: To a solution of 2-chloro-5-nitropyridine (200 mg, 1.27 mmol) in DCM (10 mL) was added morpholine (115 mg, 1.27 mmol) and TEA (256 mg, 2.54 mmol), and the mixture was stirred at r.t overnight. TLC showed that the reaction was complete. The resultant was washed with water (100 mL) and brine (100 mL), concentrated in vacuum and purified by silica gel column (PE/EtOAc, 10/1) to give 210 mg (yield: 79%) of 4-(5-nitropyridin-2-yl)morpholine as a yellow solid. MS: m/z 210.1 (M+H⁺).

Step 2: To a solution of 4-(5-nitropyridin-2-yl)morpholine (210 mg, 1 mmol) in methanol (15 mL) was added Pd/C (20 mg), and the mixture was hydrogenated at r.t under atmosphere pressure for 3 h. TLC showed that the reaction was complete. The resultant was filtered to remove Pd/C, and the filtrate was purified by silica gel column (PE/EtOAc, 1/1) to give 150 mg (yield: 84%) of 6-morpholinopyridin-3-amine as a brown solid.

Step 3: To a solution of 6-morpholinopyridin-3-amine (80 mg, 0.45 mmol) in pyridine (5 mL) was added 5-bromo-2-methoxybenzene-1-sulfonyl chloride (126 mg, 0.45 mmol) and DMAP (10 mg), and the mixture was stirred at 60° C. overnight. LCMS showed that the reaction was complete. The resultant was concentrated in vacuum to remove pyridine and the residue was diluted with DCM (20 mL). The mixture was washed with 1N HCl (15 mL), dried over Na₂SO₄ and concentrated in vacuum. The crude product was purified by prep-TLC (DCM/MeOH, 15/1) to give 30 mg (yield: 16%) of 5-bromo-2-methoxy-N-(6-morpholinopyridin-3-yl)benzenesulfonamide as a white solid.

¹H NMR (DMSO-d6, 400 MHz): δ=9.72 (1H, brs), 7.80-7.76 (2H, m), 7.64 (1H, d), 7.23 (1H, d), 7.20 (1H, d), 6.72 (1H, d), 3.94 (3H, s), 3.64 (4H, t), 3.35-3.30 (4H, m). MS: m/z 428.0 (M+H⁺).

Example VIII-2

2,5-Dimethoxy-N-(6-morpholinopyridin-3-yl)benzenesulfonamide

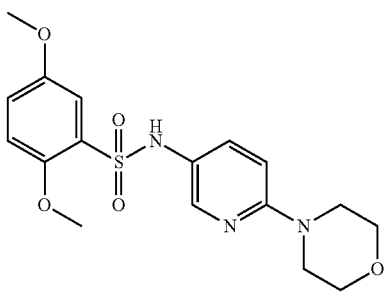 [SMILES: COc1ccc(OC)c(S(=O)(=O)Nc2ccc(N3CCOCC3)nc2)c1]

¹H NMR (DMSO-d6, 400 MHz): δ=9.55 (1H, brs), 7.79 (1H, d), 7.25 (1H, d), 7.17-7.12 (2H, m), 7.10 (1H, d), 6.70 (1H, d), 3.87 (3H, s), 3.68 (3H, s), 3.63 (4H, t), 3.33-3.29 (4H, m). MS: m/z 380.1 (M+H⁺).

Example VIII-3

5-Bromo-2-methoxy-N-(6-Amino-pyridin-3-yl)-benzenesulfonamide

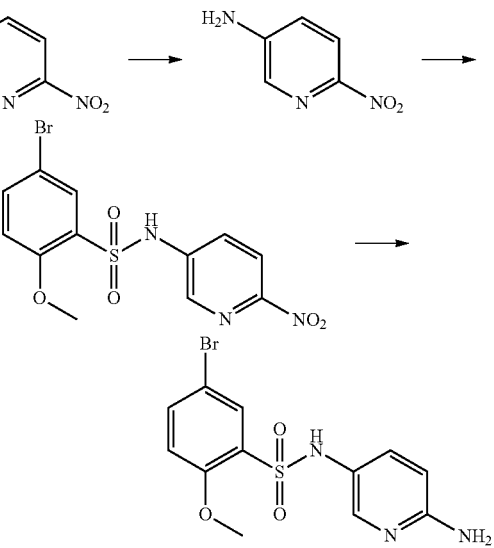

Step 1: To a solution of 5-chloro-2-nitropyridine (3 g, 19 mmol) in EtOH (30 mL) was added saturated NH₃·H₂O (20 mL), the mixture was stirred under 50 psi at 150° C. overnight. TLC showed that the reaction was complete. After the reaction mixture was cooled to r.t, the resulting solid was collected by filtration. The solid was washed with PE (100 mL) to give 0.7 g (yield: 26%) of 6-nitro-pyridin-3-ylamine as a yellow solid. MS: m/z 140.1 (M+H⁺).

Step 2: To a solution of 6-nitro-pyridin-3-ylamine (50 mg, 0.33 mmol) in DMF (3 mL) was added NaH (60% in mineral oil, 25 mg, 0.66 mmol), and the mixture was stirred at r.t for 30 min. Then 5-bromo-2-methoxy-benzenesulfonyl chloride (86 mg, 0.3 mmol) was added and the mixture was stirred at 50° C. overnight. TLC showed that the reaction was complete. The resultant was concentrated in vacuum to remove DMF. The residue was diluted with DCM (30 mL) and the mixture was washed with 1N HCl (30 mL×3). The organic layer dried over $Na_2SO_4$ and concentrated to dryness in vacuum. The residue was purified by silica gel column (PE/EtOAc, 1/1) to give 30 mg (yield: 26%) of 5-bromo-2-methoxy-N-(6-nitro-pyridin-3-yl)-benzenesulfonamide as a brown solid.

Step 3: To a solution of 5-bromo-2-methoxy-N-(6-nitro-pyridin-3-yl)-benzenesulfonamide (200 mg, 0.5 mmol) in methanol (20 mL) was added $SnCl_2.H_2O$ (450 mg, 2 mmol), and the mixture was stirred at reflux for 24 h. TLC showed that the reaction was complete. The resultant was concentrated in vacuum to remove MeOH. It was basified with saturated $NaHCO_3$ (10 mL). The suspension was filtered, and the filtrate was purified by pre-HPLC to give 56 mg (yield: 31%) of 5-bromo-2-methoxy-N-(6-Amino-pyridin-3-yl)-benzenesulfonamide as a brown solid.

¹H NMR (DMSO-d6): δ=9.46 (1H, brs), 7.74 (1H, dd), 7.60 (1H, d), 7.52 (1H, d), 7.20 (1H, d), 7.06 (1H, dd), 6.29 (1H, d), 5.85 (2H, brs), 3.93 (3H, s). MS: m/z 358.0 (M+H⁺).

Example VIII-4

2,5-Dimethoxy-N-(6-Amino-pyridin-3-yl)-benzenesulfonamide

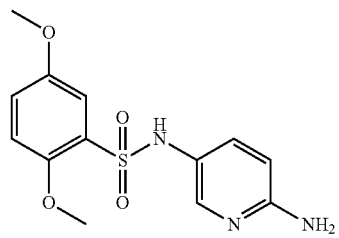 [SMILES: COc1ccc(OC)c(S(=O)(=O)Nc2ccc(N)nc2)c1]

This compound was prepared as described in Example VIII-3.

¹H NMR (CD₃OD-d6, 400 MHz): δ=7.58 (1H, dd), 7.48 (1H, d), 7.18 (1H, d), 7.09-7.04 (2H, m), 6.79 (1H, d), 3.81 (3H, s), 3.65 (3H, s). MS: m/z 310.1 (M+H⁺).

Example VIII-5

5-Bromo-2-methoxy-N-(6-methylamino-pyridin-3-yl)-benzenesulfonamide

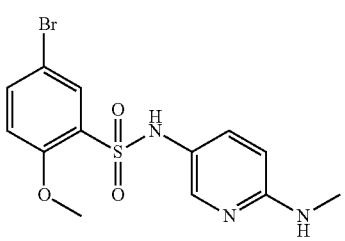 [SMILES: CNc1ccc(NS(=O)(=O)c2cc(Br)ccc2OC)cn1]

¹H NMR (DMSO-d6): δ=9.47 (1H, brs), 7.79-7.75 (1H, m), 7.62-7.59 (2H, m), 7.22 (1H, d), 7.09 (1H, dd), 6.48 (1H, d), 6.30 (1H, d), 3.96 (3H, s), 2.67 (3H, d). MS: m/z 372.0 (M+H⁺).

Example VIII-6

2,5-Dimethoxy-N-(6-methylamino-pyridin-3-yl)-benzenesulfonamide

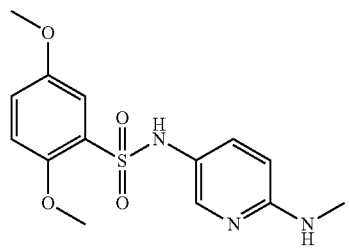 [SMILES: CNc1ccc(NS(=O)(=O)c2cc(OC)ccc2OC)cn1]

¹H NMR (DMSO-d6): δ=9.31 (1H, brs), 7.65 (1H, d), 7.21-7.17 (2H, m), 7.14-7.10 (2H, m), 6.46-6.44 (1H, d), 6.33-6.31 (1H, d), 3.93 (3H, s), 3.72 (3H, s), 2.69 (3H, d). MS: m/z 324.1 (M+H⁺)

Example VIII-7

5-Bromo-N-(6-(dimethylamino)pyridin-3-yl)-2-methoxybenzenesulfonamide

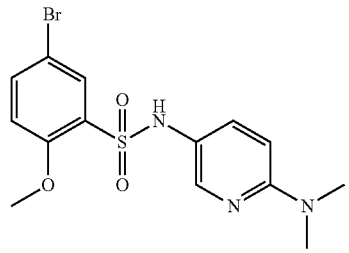 [SMILES: COc1ccc(Br)cc1S(=O)(=O)Nc1ccc(N(C)C)nc1]

¹H NMR (DMSO-d6, 400 MHz): δ=9.56 (1H, brs), 7.77 (1H, dd), 7.72 (1H, d), 7.61 (1H, s), 7.22-7.17 (2H, m), 6.50 (1H, d), 3.95 (3H, s), 2.93 (6H, s). MS: m/z 386.0 (M+H⁺)

Example VIII-8

N-(6-(Dimethylamino)pyridin-3-yl)-2,5-dimethoxy-benzenesulfonamide

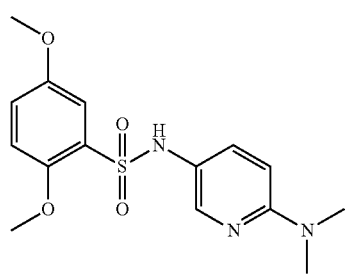 [SMILES: COc1ccc(OC)c(S(=O)(=O)Nc2ccc(N(C)C)nc2)c1]

¹H NMR (DMSO-d6, 400 MHz): δ=9.37 (1H, brs), 7.72 (1H, d), 7.21-7.14 (3H, m), 7.07 (1H, d), 6.49 (1H, d), 3.89 (3H, s), 3.68 (3H, s), 2.91 (6H, s). MS: m/z 338.1 (M+H⁺).

Example VIII-9

5-Bromo-N-(6-(diethylamino)pyridin-3-yl)-2-methoxybenzenesulfonamide

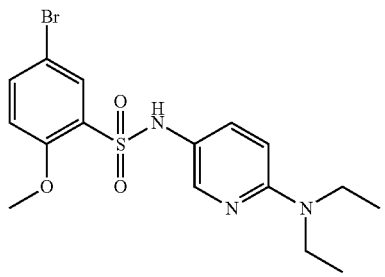 [SMILES: CCN(CC)c1ccc(NS(=O)(=O)c2cc(Br)ccc2OC)cn1]

¹H NMR (DMSO-d6, 400 MHz): δ=9.51 (1H, brs), 7.77 (1H, dd), 7.68 (1H, d), 7.63 (1H, d), 7.23 (1H, d), 7.15 (1H, dd), 6.46 (1H, d), 3.96 (3H, s), 3.38 (4H, q), 1.03 (6H, t). MS: m/z 414.1 (M+H⁺).

Example VIII-10

N-(6-(Diethylamino)pyridin-3-yl)-2,5-dimethoxybenzenesulfonamide

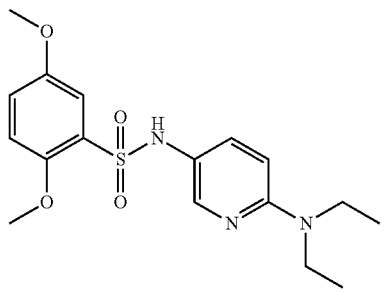 [SMILES: CCN(CC)c1ccc(NS(=O)(=O)c2cc(OC)ccc2OC)cn1]

¹H NMR (DMSO-d6, 400 MHz): δ=9.37 (1H, brs), 7.75 (1H, d), 7.23-7.18 (3H, m), 7.15-7.14 (1H, d), 6.51-6.48 (1H, d), 3.94 (3H, s), 3.75 (3H, s), 3.43 (4H, q), 1.08 (6H, t). MS: m/z 366.1 (M+H⁺).

Example VIII-11

5-Bromo-2-methoxy-N-(6-((2-methoxyethyl)amino)pyridin-3-yl)benzenesulfonamide

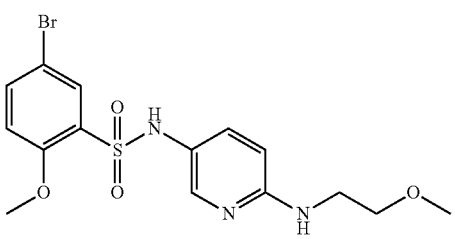 [SMILES: COCCNc1ccc(NS(=O)(=O)c2cc(Br)ccc2OC)cn1]

¹H NMR (DMSO-d6, 400 MHz): δ=9.48 (1H, brs), 7.76 (1H, dd), 7.63-7.57 (2H, m), 7.22 (1H, d), 7.06 (1H, dd), 6.58 (1H, t), 6.38 (1H, d), 3.95 (3H, s), 3.40-3.29 (4H, m), 3.23 (3H, s). MS: m/z 416.0 (M+H⁺).

Example VIII-12

2,5-Dimethoxy-N-(6-((2-methoxyethyl)amino)pyridin-3-yl)benzenesulfonamide

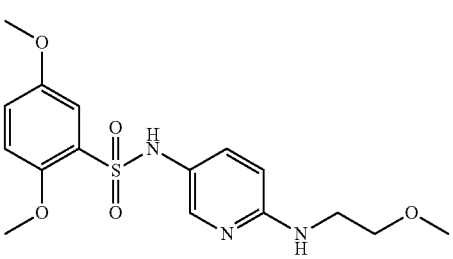 [SMILES: COCCNc1ccc(NS(=O)(=O)c2cc(OC)ccc2OC)cn1]

¹H NMR (DMSO-d6, 400 MHz): δ=9.29 (1H, brs), 7.59 (1H, d), 7.18-7.14 (2H, m), 7.08-7.06 (2H, m), 6.54 (1H, t), 6.37 (1H, d), 3.89 (3H, s), 3.69 (3H, s), 3.39-3.28 (4H, m), 3.23 (3H, s). MS: m/z 368.1 (M+H⁺).

Example VIII-13

5-Bromo-N-(6-((2-(dimethylamino)ethyl)amino)pyridin-3-yl)-2-methoxybenzenesulfonamide

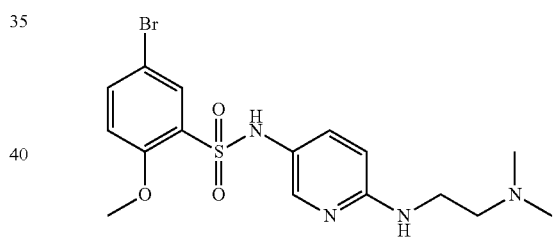

¹H NMR (DMSO-d6, 400 MHz): δ=9.74 (1H, brs), 9.70 (1H, brs), 7.77 (1H, dd), 7.68 (1H, d), 7.65 (1H, d), 7.25-7.21 (2H, m), 6.52 (1H, d), 3.94 (3H, s), 3.53 (2H, t), 3.20 (2H, t), 2.79 (6H, s). MS: m/z 429.1 (M+H⁺)

Example VIII-14

N-(6-((2-(Dimethylamino)ethyl)amino)pyridin-3-yl)-2,5-dimethoxybenzenesulfonamide

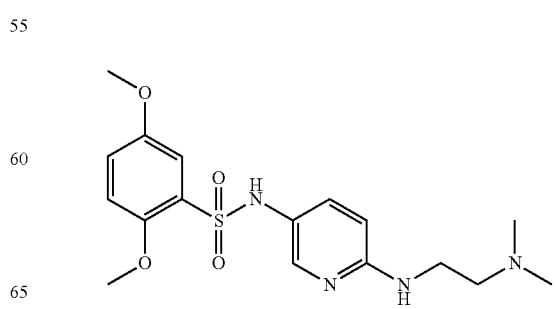

¹H NMR (CD₃OD, 400 MHZ): δ=6.83 (1H, s), 6.34-6.20 (4H, m), 5.53 (1H, d), 3.06 (3H, s), 2.81 (3H, s), 2.59 (2H, t), 2.08 (2H, t), 1.75 (6H, s). MS: m/z 381.2 (M+H⁺).

Example VIII-15

5-Bromo-2-methoxy-N-(6-(phenylamino)pyridin-3-yl)benzenesulfonamide

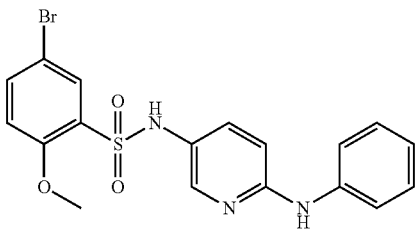 [SMILES: COc1ccc(Br)cc1S(=O)(=O)Nc1ccc(Nc2ccccc2)nc1]

¹H NMR (DMSO-d6, 400 MHz): δ=9.76 (1H, brs), 9.00 (1H, brs), 9.81-9.73 (2H, m), 7.67 (1H, d), 7.56 (2H, d), 7.29 (1H, dd), 7.25-7.19 (3H, m), 6.85 (1H, d), 6.72 (1H, d), 3.94 (3H, s). MS: m/z 434.0 (M+H⁺).

Example VIII-16

2,5-Dimethoxy-N-(6-morpholinopyridin-3-yl)benzenesulfonamide

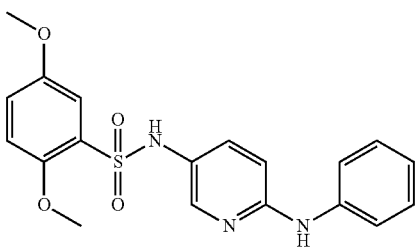 [SMILES: COc1ccc(OC)c(S(=O)(=O)Nc2ccc(Nc3ccccc3)nc2)c1]

¹H NMR (CDC₃, 400 MHz): δ=7.77 (1H, d), 7.40 (1H, dd), 7.33-7.23 (5H, m), 7.06-6.97 (3H, m), 6.84 (1H, s), 6.73 (1H, d), 6.46 (1H, brs), 4.03 (3H, s), 3.73 (3H, s). MS: m/z 386.1 (M+H⁺).

Example VIII-17

5-Bromo-2-methoxy-N-(3,4,5,6-tetrahydro-2H-[1,2']bipyridinyl-5'-yl)-benzenesulfonamide

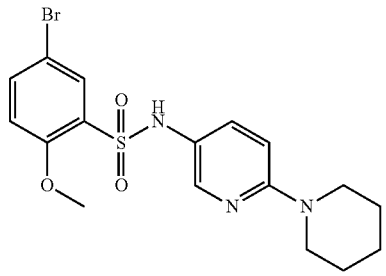 [SMILES: COc1ccc(Br)cc1S(=O)(=O)Nc1ccc(N2CCCCC2)nc1]

¹H NMR (DMSO-d6, 400 MHz): δ=9.60 (1H, brs), 7.78-7.71 (2H, m), 7.63 (1H, d), 7.22-7.16 (2H, m), 6.68 (1H, d), 3.93 (3H, s), 3.39 (4H, m), 1.56-1.46 (6H, m). MS: m/z 426.0 (M+H⁺).

Example VIII-18

2,5-Dimethoxy-N-(3,4,5,6-tetrahydro-2H-[1,2']bipyridinyl-5'-yl)-benzenesulfonamide

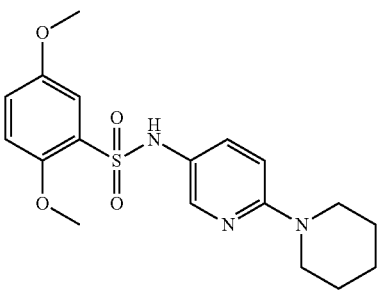 [SMILES: COc1ccc(OC)c(S(=O)(=O)Nc2ccc(N3CCCCC3)nc2)c1]

¹H NMR (DMSO-d6, 400 MHz): δ=9.44 (1H, brs), 7.73 (1H, d), 7.22-7.07 (4H, m), 6.67 (1H, d), 3.88 (3H, s), 3.74 (3H, s), 3.41-3.32 (4H, m), 1.55-1.45 (6H, m). MS: m/z 378.1 (M+H⁺).

Example VIII-19

5-Bromo-2-methoxy-N-[6-(4-methyl-piperazin-1-yl)-pyridin-3-yl]-benzenesulfonamide

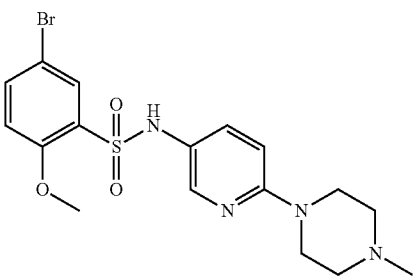 [SMILES: COc1ccc(Br)cc1S(=O)(=O)Nc1ccc(N2CCN(C)CC2)nc1]

¹H NMR (DMSO-d6, 400 MHz): δ=9.84 (1H, brs), 9.83 (1H, brs, TFA salt), 7.82 (1H, d), 7.78 (1H, dd), 7.66 (1H, d), 7.32 (1H, dd), 7.21 (1H, d), 6.84 (1H, d), 4.30-4.24 (2H, m), 3.93 (3H, s), 3.49-3.42 (2H, m), 3.06-2.95 (4H, m), 2.81 (3H, s). MS: m/z 441.1 (M+H⁺).

Example VIII-20

2,5-Dimethoxy-N-[6-(4-methyl-piperazin-1-yl)-pyridin-3-yl]-benzenesulfonamide

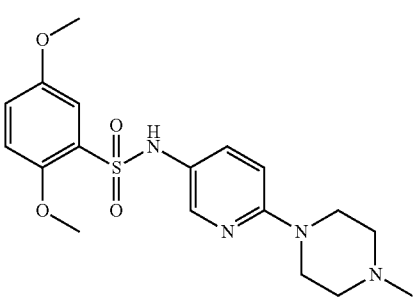 [SMILES: COc1ccc(OC)c(S(=O)(=O)Nc2ccc(N3CCN(C)CC3)nc2)c1]

¹H NMR (DMSO-d6, 400 MHz): δ=9.75 (1H, brs), 9.67 (1H, brs, TFA salt), 7.84 (1H, d), 7.33 (1H, dd), 7.16-7.11 (3H, m), 6.83 (1H, d), 4.25-4.20 (2H, m), 3.86 (3H, s), 3.69 (3H, s), 3.48-3.40 (2H, m), 3.09-2.95 (4H, m), 2.81 (3H, s). MS: m/z 393.2 (M+H⁺).

Example IX

Example IX-1

5-Bromo-N-(6-hydroxyquinolin-3-yl)-2-methoxy-benzenesulfonamide

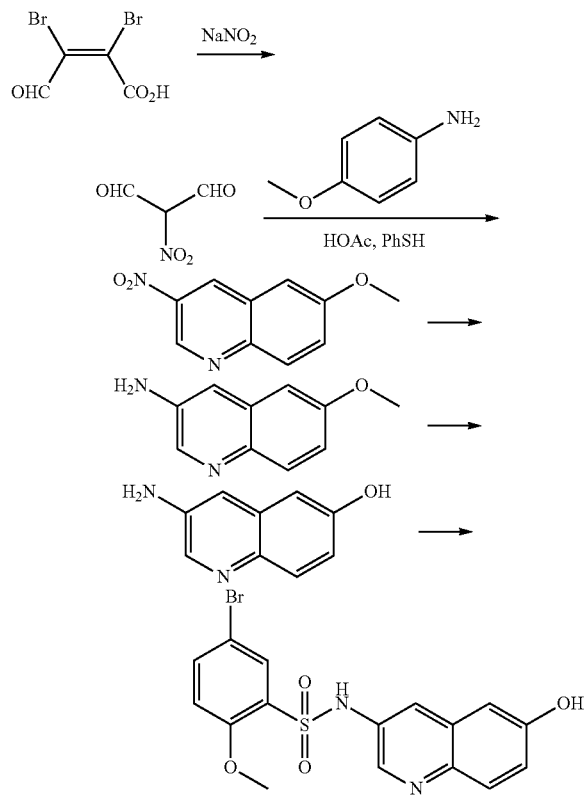

Step 1: In a 2 L three-necked round-bottomed flask, equipped with a thermometer, a dropping funnel, a mechanical stirrer and a gas vent, are placed sodium nitrite (258 g, 3.74 mol) and water (250 mL). The contents of the flask are heated and stirred to dissolve the solid. A solution of mucobromic acid (258 g, 1 mol) in warm 95% ethanol (250 mL) is placed in the dropping funnel and added dropwise with constant stirring over a period of 70-80 minutes. A mildly exothermic reaction occurs; the solution in the flask becomes deep red, and gas is evolved. During the addition, the temperature is kept at 54±1° C. by intermittent application of an ice bath to the flask. The mixture is stirred for an additional 10 minutes at 54±1° C. While being stirred continuously, it is then cooled to 0-5° by application of an ice bath. The fine, yellow precipitate is collected on a previously chilled Buchner funnel. The slightly moist cake of crude product is transferred to a 1 L flask and heated to boiling with a mixture of 95% ethanol (400 mL) and water (100 mL). The hot solution is filtered to remove a fine yellow solid, and the clear red filtrate is cooled to 0-5°. The recrystallized product is collected by filtration and dried in air at room temperature to afford 57 g (yield: 36%) of sodium nitromalonaldehyde monohydrate 2-nitromalonaldehyde as tan needles.

Step 2: To a mechanically stirred solution of p-anisidine (74.5 g, 0.6 mol) in 1.7 M aq.HCl (544 mL) was added a solution of 2-nitromalonaldehyde (monohydrate, 63.0 g, 0.4 mol) in water (520 mL). A yellow precipitate formed instantaneously and water was added to facilitate stirring. After 10 minutes, the precipitate was filtered, washed with water and air-dried. The filter cake (98.0 g) was dried to constant weight over $P_2O_5$ to give 68.0 g of enamine as a yellow amorphous solid. The enamine (68.0 g, 0.3 mol) was added to a vigorously stirred suspension of p-anisidine hydrochloride (97.6 g, 0.6 mol) in acetic acid (612 mL) and the mixture was heated to refluxed under $N_2$. After 20 minutes thiophenol (6.73 g, 0.06 mol) was added and the mixture heated at refluxed for 50 h. LC-MS showed the starting material was mostly consumed. The reaction mixture was concentrated in vacuum, and neutralized with sat. $NaHCO_3$ to pH=9. The aqueous phase was extracted with $CHCl_3$ (200 mL×3). The extracts were dried over $Na_2SO_4$ and concentrated to dryness in vacuum. The crude was purified by silica gel column (DCM/MeOH, 10/1) to give 30 g (yield: 25%) of 6-methoxy-3-nitroquinoline as brown solid.

Step 3: A vigorously suspension of 6-methoxy-3-nitroquinoline (21.2 g, 0.1 mol) in conc. HCl (320 mL) was heated to 50° C., the heating bath was removed, and $SnCl_2 \cdot H_2O$ (71.0 g, 0.3 mol) was added portion-wise over 3 minutes. The mixture was stirred vigorously for an additional 10 minutes and diluted with water to 1.0 L. The pH was brought to 9 by addition of 5 M NaOH. The aqueous layer was cooled and extracted with EtOAc (150 mL×3). The extracts were washed brine and dried over $Na_2SO_4$. The mixture was concentrated in vacuum and the crude was purified by silica gel column (DCM/MeOH, 10/1) to give 15 g (yield: 86%) of 6-methoxyquinolin-3-amine as brown solid. MS: m/z 175.1 (M+H$^+$).

Step 4: To a vigorously suspension of 6-methoxyquinolin-3-amine (1.0 g, 5.7 mol) in anhydrous $CH_2Cl_2$ (20 mL) at −60° C. was added $BBr_3$ (3.0 mL) portionwise over 20 minutes. The mixture was stirred vigorously for an additional 12 h and diluted with water to 100 mL. The aqueous layer was extracted with EtOAc (25 mL×3). The extracts were washed brine and dried over $Na_2SO_4$. The mixture was concentrated to dryness and the residue was purified by silica gel column (DCM/MeOH, 10/1) to give 500 mg (yield: 55%) of 3-aminoquinolin-6-ol as brown solid. MS: m/z 161.1 (M+H').

Step 5: A solution of 3-aminoquinolin-6-ol (150 mg, 0.9 mmol) and 5-bromo-2-methoxybenzene-1-sulfonyl chloride (143 mg, 0.5 mmol) in pyridine (5 mL) was heated to 40° C. for 12 h. The reaction mixture was concentrated in vacuum and the residue was purified by silica gel column (PE/EtOAc, 10/1) to give 50 mg (yield: 25%) of 5-bromo-N-(6-hydroxyquinolin-3-yl)-2-methoxybenzenesulfonamide as white solid.

$^1$H NMR (DMSO-d6, 400 MHz): δ=10.59 (1H, brs), 10.06 (1H, brs), 8.42 (1H, s), 7.85 (1H, s), 7.78-7.73 (3H, m), 7.20-7.17 (2H, m), 7.03 (1H, s), 3.85 (3H, s). MS: m/z 409.2 (M+H$^+$).

Example IX-2

5-Bromo-2-methoxy-N-(6-methoxyquinolin-3-yl)benzenesulfonamide

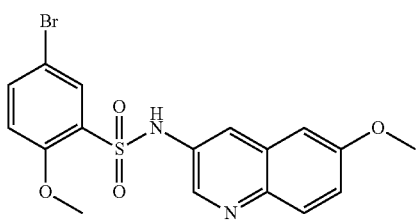 [SMILES: COc1ccc2ncc(NS(=O)(=O)c3cc(Br)ccc3OC)cc2c1]

This compound was prepared as described in step 5, Example IX-1.

$^1$H NMR (CDC$_3$, 400 MHz): δ=8.24 (1H, d), 7.91 (1H, d), 7.86 (1H, d), 7.80 (1H, d), 7.49 (1H, dd), 7.21-7.19 (1H, m), 6.95 (1H, d), 6.83 (1H, d), 3.98 (3H, s), 3.86 (3H, s). MS: m/z 423.0 (M+H$^+$).

Example IX-3

N-(6-Hydroxyquinolin-3-yl)-2,5-dimethoxybenzenesulfonamide

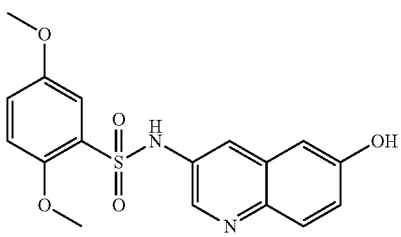 [SMILES: COc1ccc(OC)c(S(=O)(=O)Nc2cnc3ccc(O)cc3c2)c1]

This compound was prepared as described in step 5, Example IX-1.

$^1$H NMR (CDC$_3$, 400 MHz): δ=10.46 (1H, brs), 10.03 (1H, brs), 8.43 (1H, s), 7.73-7.70 (2H, m), 7.31 (1H, s), 7.18-7.11 (m, 3H), 6.99 (1H, s), 3.79 (3H, s), 3.71 (3H, s). MS: m/z 361.2 (M+H$^+$).

Example IX-4

3-(5-Bromo-2-methoxy-benzenesulfonylamino)-quinoline-6-carboxylic acid methyl ester

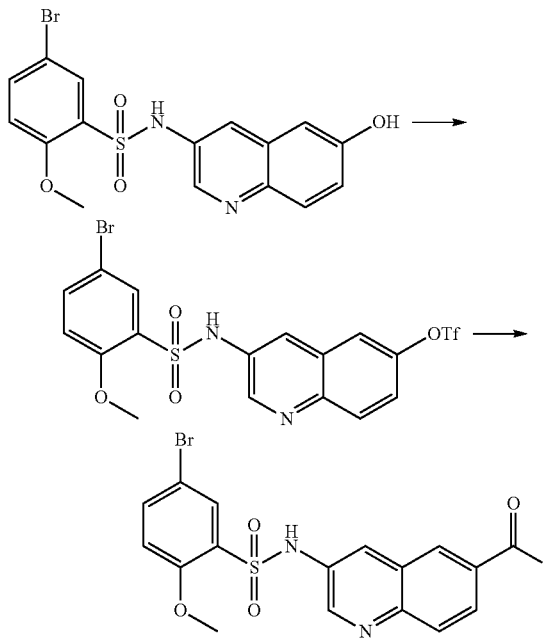

Step 1: All flasks used in the reaction were heated under vacuum for 30 minutes and purged with N$_2$ for 10 minutes. 1,1,1-trifluoro-N-phenyl-N-(trifluoromethylsulfonyl)methanesulfonamiden (214 mg, 0.6 mmol) was added into a solution of N-(6-hydroxyquinolin-3-yl)-2,5-dimethoxybenzenesulfonamide (122 mg, 0.3 mmol), DIPEA (0.12 mL, 0.7 mmol) in anhydrous THF (3 mL) at 0° C. and then the reaction was stirred at room temperature for 12 h. LC-MS showed the starting material was consumed completely. The mixture was concentrated in vacuum and the residue was purified by silica gel column (PE/EtOAc, 10/1) to give 100 mg of (yield: 66%) 3-(5-bromo-2-methoxyphenylsulfonamido)quinolin-6-yltrifluoromethanesulfonate as white solid. MS: m/z 541.1 (M+H$^+$).

Step 2: A solution of 3-(5-bromo-2-methoxyphenylsulfonamido)quinolin-6-yl trifluoromethanesulfonate (100 mg, 0.18 mmol), Pd(dppf)Cl$_2$ (20 mg, 0.02 mmol), NEt$_3$ (0.1 mL, 0.7 mmol) in MeOH (1 mL) and DMF (1 mL) was purged with CO for 3 times. The mixture was heated to 90° C. under 50 psi CO atmosphere for 17 h. The suspension was filtered, and the filtrate was concentrated in vacuum. The residue was purified silica gel column to give 60 mg (yield: 72%) of 3-(5-bromo-2-methoxy-benzenesulfonylamino)-quinoline-6-carboxylic acid methyl ester.

$^1$H NMR (CDC$_3$, 400 MHz): δ=8.65 (1H, s), 8.44 (1H, s), 8.08 (1H, d), 8.01 (1H, s), 7.90-7.88 (2H, m), 7.54 (1H, d), 6.97 (1H, d), 3.87 (3H, s), 3.78 (3H, s). MS: m/z 450.9 (M+H$^+$).

Example IX-5

3-(5-Bromo-2-methoxy-benzenesulfonylamino)-quinoline-6-carboxylic acid

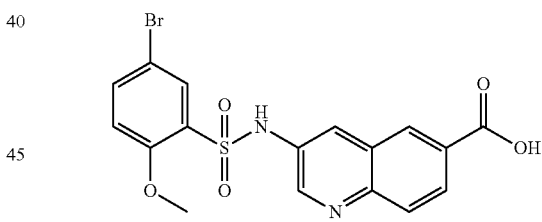

1.0 M LiOH (0.1 mL, 0.1 mmol) was added into a solution of 3-(5-bromo-2-methoxy-benzenesulfonylamino)-quinoline-6-carboxylic acid methyl ester (20 mg, 0.044 mmol) in THF (1 mL) and H$_2$O (1 mL) at 0° C. and the reaction was stirred at room temperature for 12 h. LC-MS showed the starting material was consumed completely. The mixture was concentrated in vacuum and the remaining solution was acidified to pH=3 with 2N HCl. The mixture was extracted with EtOAc (10 mL×3) and the extracts were dried over Na$_2$SO$_4$. The solvent was removed and the crude was purified by silica gel column (PE/EtOAc, 1/1) to give 10 mg (yield: 53%) of 3-(5-Bromo-2-methoxy-benzenesulfonylamino)-quinoline-6-carboxylic acid as white powder.

$^1$H NMR (CD$_3$OD, 400 MHz): δ=8.66 (1H, s), 8.44 (1H, s), 8.10 (1H, d), 8.02 (1H, s), 7.91-7.88 (2H, m), 7.55 (1H, d), 6.98 (1H, d), 3.79 (3H, s). MS: m/z 434.7 (M−H$^+$).

Example IX-6

3-(5-Bromo-2-methoxy-benzenesulfonylamino)-quinoline-6-carboxylic acid amide

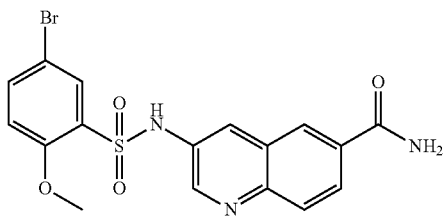 [SMILES: COc1ccc(Br)cc1S(=O)(=O)Nc1cnc2ccc(C(N)=O)cc2c1]

A suspension of 3-(5-bromo-2-methoxy-benzenesulfonylamino)-quinoline-6-carboxylic acid methyl ester (50 mg, 0.11 mmol) in NH$_3$.H$_2$O (2.5 mL) in a sealed tube was heated at 80° C. for 2 h. LC-MS showed the starting material was consumed completely. The solution was concentrated in vacuum, and the residue was purified by prep-HPLC to afford 9.8 mg (yield: 20%) of 3-(5-Bromo-2-methoxy-benzenesulfonylamino)-quinoline-6-carboxylic acid amide as orange solid.

$^1$H NMR (DMSO-d6, 400 MHz): δ=10.83 (1H, brs), 8.74 (1H, d), 8.41 (1H, d), 8.11 (1H, d), 8.03 (1H, d), 7.98-7.89 (2H, m), 7.88 (1H, d), 7.75-7.73 (1H, m), 7.52 (1H, brs), 7.15 (1H, d), 3.83 (3H, s). MS: m/z 436.0 (M+H$^+$).

Example IX-7

3-(5-Bromo-2-methoxy-benzenesulfonylamino)-quinoline-6-carboxylic acid methylamide

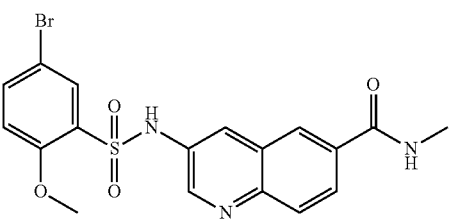 [SMILES: CNC(=O)c1ccc2ncc(NS(=O)(=O)c3cc(Br)ccc3OC)cc2c1]

A solution of 3-(5-bromo-2-methoxy-benzenesulfonylamino)-quinoline-6-carboxylic acid methyl ester (50 mg, 0.11 mmol) in MeNH$_2$/MeOH (2.5 mL) in sealed tube was heated at 80° C. for 2 h. LC-MS showed the starting material was consumed completely. The solution was concentrated in vacuum, and the residue was purified via prep-HPLC to afford 14.4 mg (yield: 29%) of 3-(5-bromo-2-methoxy-benzenesulfonylamino)-quinoline-6-carboxylic acid methylamide as white solid.

$^1$H NMR (DMSO-d6, 400 MHz): δ=10.81 (1H, brs), 8.76 (1H, d), 8.62 (1H, brs), 8.38 (1H, d), 8.04-8.02 (2H, m), 8.02 (1H, d), 7.89 (1H d), 7.77-7.74 (1H, m), 7.16 (1H, d), 3.93 (3H, s), 2.83 (3H, d). MS: m/z 450.0 (M+H$^+$).

Example IX-8

3-(2,5-Dimethoxy-benzenesulfonylamino)-quinoline-6-carboxylic acid methyl ester

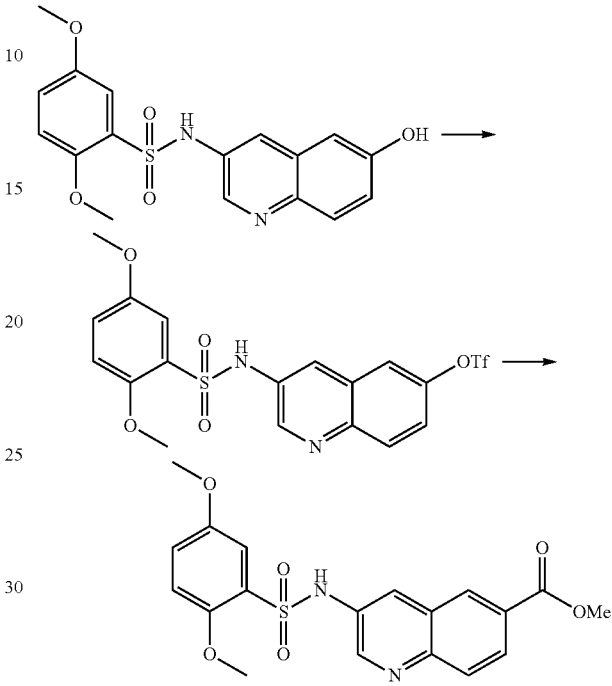

This compound was prepared as described in Example IX-4.

$^1$H NMR (CDC$_3$, 400 MHz): δ=8.73 (1H, s), 8.51 (1H, s), 8.22 (1H, d), 8.13 (1H, s), 8.06 (1H, d), 7.34 (1H, s), 7.36 (1H, s), 7.01-6.97 (2H, m), 4.03 (3H, s), 3.99 (3H, s), 3.72 (3H, s). MS: m/z 402.9 (M+H$^+$).

Example IX-9

3-(2,5-Dimethoxy-benzenesulfonylamino)-quinoline-6-carboxylic acid

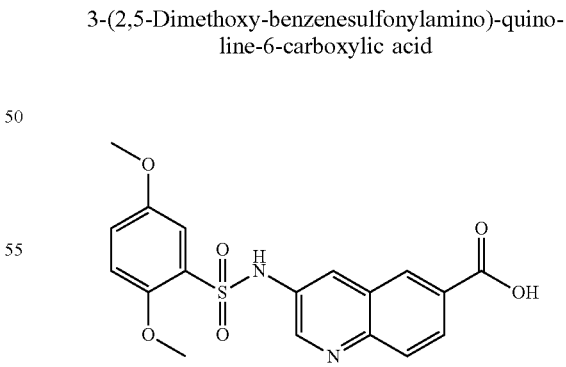

This compound was prepared as described in Example IX-5.

$^1$H NMR (CD$_3$OD, 400 MHz): δ=8.65 (1H, s), 8.39 (1H, s), 8.09 (1H, d), 7.99 (1H, d), 7.87 (1H, d), 7.32 (1H, d), 7.18-7.11 (2H, m), 3.76 (3H, s), 3.64 (3H, s). MS: m/z 386.8 (M−H$^+$).

Example IX-10

3-(2,5-Dimethoxy-benzenesulfonylamino)-quinoline-6-carboxylic acid amide

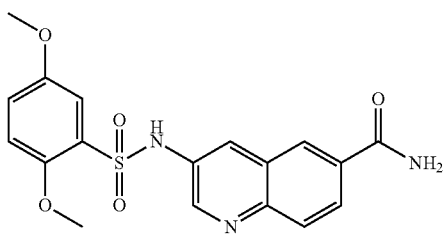 [SMILES: COc1ccc(OC)c(S(=O)(=O)Nc2cnc3ccc(C(N)=O)cc3c2)c1]

This compound was prepared as described in Example IX-6.

$^1$H NMR (DMSO-d6, 400 MHz): δ=10.67 (1H, brs), 8.77 (1H, d), 8.40 (1H, s), 8.12 (1H, s), 8.09-8.05 (1H, m), 8.03-7.93 (2H, m), 7.51 (1H, s), 7.34 (1H, d), 7.16-7.10 (2H, m), 3.79 (3H, s), 3.72 (3H, s). MS: m/z 388.1 (M+H$^+$).

Example IX-11

3-(2,5-Dimethoxy-benzenesulfonylamino)-quinoline-6-carboxylic acid methylamide

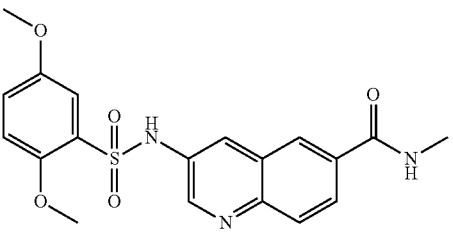 [SMILES: CNC(=O)c1ccc2ncc(NS(=O)(=O)c3cc(OC)ccc3OC)cc2c1]

This compound was prepared as described in Example IX-7.

$^1$H NMR (DMSO-d6, 400 MHz): δ=8.73 (1H, s), 8.58 (1H, s), 8.31 (1H, s), 7.99-7.92 (3H, m), 7.35-7.34 (1H, d), 7.12-7.08 (2H, m), 3.76 (3H, s), 3.47 (3H, s), 2.93 (3H, s). MS: m/z 401.9 (M+H$^+$).

Example IX-12

3-(2,5-Dimethoxy-benzenesulfonylamino)-quinoline-6-carboxylic acid propylamide

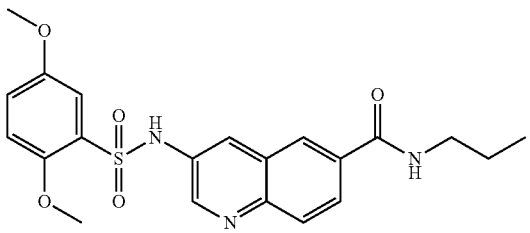 [SMILES: CCCNC(=O)c1ccc2ncc(NS(=O)(=O)c3cc(OC)ccc3OC)cc2c1]

This compound was prepared as described in Example IX-7.

$^1$H NMR (DMSO-d6, 400 MHz): δ=10.68 (1H, brs), 8.76 (1H, d), 8.61 (1H, t), 8.36 (1H, s), 8.03-8.00 (2H, m), 7.94 (1H, d), 7.34 (1H, d), 7.16-7.09 (2H, m), 4.02 (3H, s), 3.97 (3H, s), 3.28-3.23 (2H, m), 1.59-1.52 (2H, m), 0.91 (3H, t). MS: m/z 430.1 (M+H

Example IX-13

3-(2,5-Dimethoxy-benzenesulfonylamino)-quinoline-6-carboxylic acid cyclopropylamide

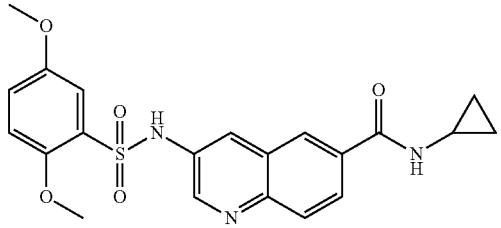 [SMILES: COc1ccc(OC)c(S(=O)(=O)Nc2cnc3ccc(C(=O)NC4CC4)cc3c2)c1]

To a solution of 3-(2,5-dimethoxy-benzenesulfonylamino)-quinoline-6-carboxylic acid (40 mg, 0.1 mmol), cyclopropylamide (30 mg, 0.5 mmol), NEt$_3$ (0.05 mL, 0.3 mmol) and catalytic amount of DMAP in DMF (1 mL) was added HATU (150 mg, 0.4 mmol) at 0° C. and then the reaction was stirred at room temperature for 12 h. LC-MS showed the starting material was consumed completely. The mixture was concentrated and the residue was purified by silica gel column (PE/EtOAc, 10/1) to give 10 mg (yield: 23%) of 3-(2,5-Dimethoxy-benzenesulfonylamino)-quinoline-6-carboxylic acid cyclopropylamide as white powder.

$^1$H NMR (CD$_3$OD, 400 MHz): δ=8.64 (1H, s), 8.16 (1H, s), 8.03 (1H, s), 7.96-7.84 (2H, m), 7.31 (1H, s), 7.00-6.94 (2H, m), 3.75 (3H, s), 3.63 (3H, s), 2.82-2.77 (1H, m), 0.76-0.71 (2H, m), 0.59-0.55 (2H, m). MS: m/z 428.1 (M+H$^+$).

Example IX-14

3-(2,5-Dimethoxy-benzenesulfonylamino)-quinoline-6-carboxylic acid cyclohexylamide

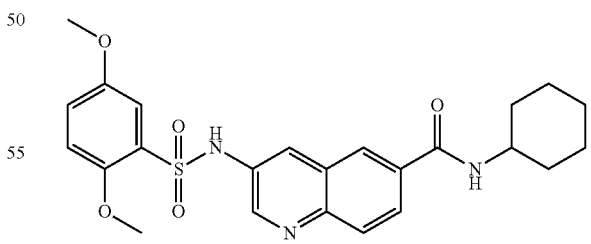

This compound was prepared as described in Example IX-13.

$^1$H NMR (CD$_3$OD, 400 MHz): δ=8.61 (1H, d), 8.14 (1H, d), 7.99 (1H, d), 7.92-7.84 (2H, m), 7.30 (1H, d), 6.99-6.94 (2H, m), 3.80-3.76 (1H, m), 3.76 (3H, s), 3.62 (3H, s), 1.89-1.87 (2H, m), 1.74-1.71 (2H, m), 1.34-1.26 (6H, m). MS: m/z 470.1 (M+H

Example IX-15

3-(2,5-Dimethoxy-benzenesulfonylamino)-quinoline-6-carboxylic acid cyclohexylamide

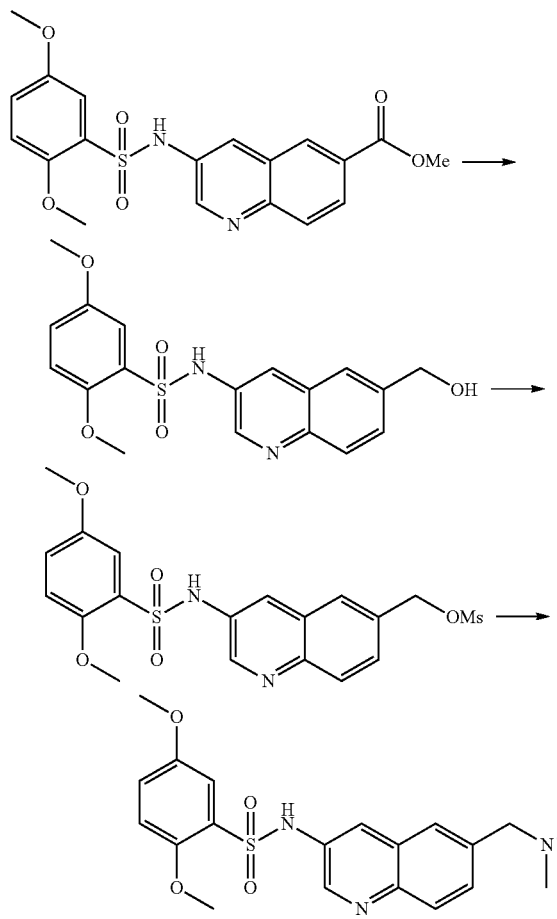

Step 1: To a solution of methyl 3-(2,5-dimethoxyphenylsulfonamido)quinoline-6-carboxylate (50 mg, 0.1 mmol) in anhydrous THF (2 mL) was added LiAlH$_4$ (20 mg, 0.5 mmol) at 0° C., and the reaction was stirred at room temperature for 12 h. The reaction was quenched with water (0.1 mL) and 15% NaOH (0.1 mL) at 0° C. The mixture was filtered through a pad of Na$_2$SO$_4$ and the filtrate was concentrated to dryness in vacuum. The residue was purified by silica gel column (PE/EtOAc, 10/1) to give 40 mg of N-(6-(hydroxymethyl)quinolin-3-yl)-2,5-dimethoxybenzenesulfonamide (yield: 85%) as light yellow sticky liquid. MS: m/z 375.1 (M+H$^+$).

Step 2: To a solution of N-(6-(hydroxymethyl)quinolin-3-yl)-2,5-dimethoxybenzenesulfonamide (40 mg, 0.1 mmol), NEt$_3$ (0.05 mL, 0.3 mmol) in THF (2 mL) at 0° C. was added methanesulfonyl chloride (50 mg, 0.4 mmol). The reaction was stirred at room temperature for 12 h. LC-MS showed the starting material was consumed completely. The mixture was concentrated in vacuum and the crude product was used directly for next step without further purification.

Step 3: The crude product was dissolved in dimethylamine in THF (2.0 M). The reaction was stirred at room temperature overnight. LC-MS showed the starting material was consumed completely. The mixture was concentrated in vacuum and the crude was purified by silica gel column (DCM/MeOH, 10:1) to give 5 mg of 3-(2,5-Dimethoxy-benzenesulfonylamino)-quinoline-6-carboxylic acid cyclohexylamide (two-step yield: 12%) as white solid.

$^1$H NMR (CD$_3$OD, 400 MHz): δ=8.61 (1H, s), 7.99 (1H, d), 7.93 (1H, d), 7.88 (1H, d), 7.60 (1H, dd), 7.31 (1H, d), 7.02-6.95 (2H, m), 4.35 (2H, s), 3.77 (3H, s), 3.64 (3H, s), 2.79 (6H, s). MS: m/z 402.0 (M+H$^+$).

Example IX-16

3-(2,5-Dimethoxy-benzenesulfonylamino)-quinoline-6-carboxylic acid cyclohexylamide

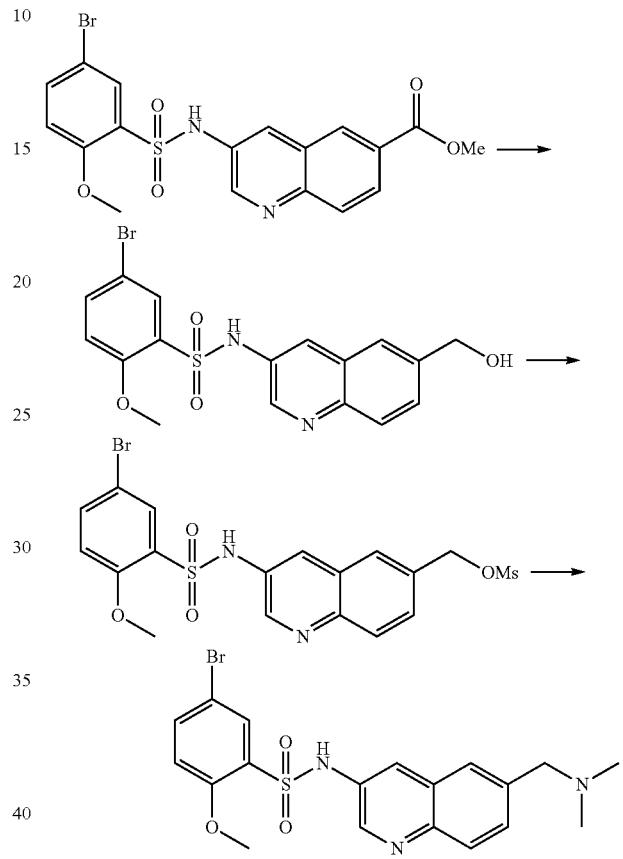

This compound was prepared as described in Example IX-15.

$^1$H NMR (CD$_3$OD, 400 MHZ): δ=8.61 (1H, d), 8.02 (1H, d), 7.96-7.91 (2H, m), 7.84 (1H, d), 7.63 (1H, d), 7.54 (1H, dd), 6.98 (1H, d), 4.38 (2H, s), 3.81 (3H, s), 2.79 (6H, s). MS: m/z 451.0 (M+H$^+$)

Example X

Example X-1

5-Bromo-N-quinolin-3-yl-2-trifluoromethoxy-benzenesulfonamide

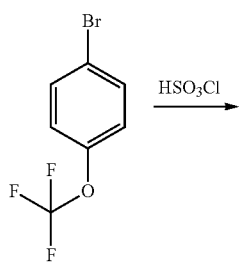

-continued

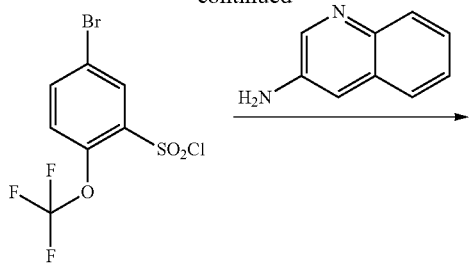

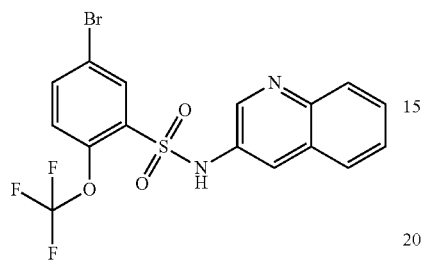

Step 1: A solution of 1-bromo-4-(trifluoromethoxy)benzene (1.0 g, 4.18 mmol) in ClSO₃H (10 mL) was stirred at room temperature overnight. TLC showed the starting material was consumed completely. The reaction mixture was poured into ice water (10 mL) and extracted with DCM (15×3). The combined organic layer was wash with brine (10 mL), dried over Na₂SO₄ and concentrated in vacuum to give 1 g (yield: 70%) of 5-bromo-2-(trifluoromethoxy)benzene-1-sulfonyl chloride as colorless oil.

Step 2: A mixture of 5-bromo-2-(trifluoromethoxy)benzene-1-sulfonyl chloride (150 mg, 0.44 mmol), quinolin-3-ylamine (64 mg, 0.44 mmol) and DMAP (5 mg) in pyridine (5 mL) was stirred at 70° C. overnight. TLC showed the starting material was consumed completely. The reaction mixture was diluted with EtOAc (20 mL), washed with water (20 mL), brine (10 mL) and dried over Na₂SO₄. The solution was concentrated in vacuum to give a residue, which was purified by prep-TLC (PE/EtOAc, 5/1) to give 33 mg (yield: 17%) of 5-bromo-N-quinolin-3-yl-2-trifluoromethoxy-benzenesulfonamide as off-white solid.

¹H NMR (CDC₃, 400 MHz): δ=8.59 (1H, s), 8.07 (1H, s), 8.06-8.02 (2H, m), 7.78 (1H, d), 7.71-7.65 (2H, m), 7.60-7.55 (1H, m), 7.56-7.26 (1H, m), 7.05 (1H, brs). MS: m/z 447.0 (M+H⁺).

Example X-2

5-Fluoro-N-quinolin-3-yl-2-trifluoromethoxy-benzenesulfonamide

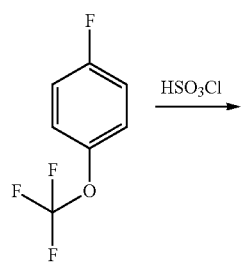

This compound was prepared as described in Example X-1.

¹H NMR (CDC₃, 400 MHz): δ=8.58 (1H, s), 8.04-8.01 (2H, m), 7.78 (1H, d), 7.72-7.63 (2H, m), 7.56 (1H, t), 7.43-7.38 (1H, m), 7.32-7.25 (1H, m), 7.06 (1H, brs). MS: m/z 387.1 (M+H⁺).

Example X-3

5-Chloro-N-quinolin-3-yl-2-trifluoromethoxy-benzenesulfonamide

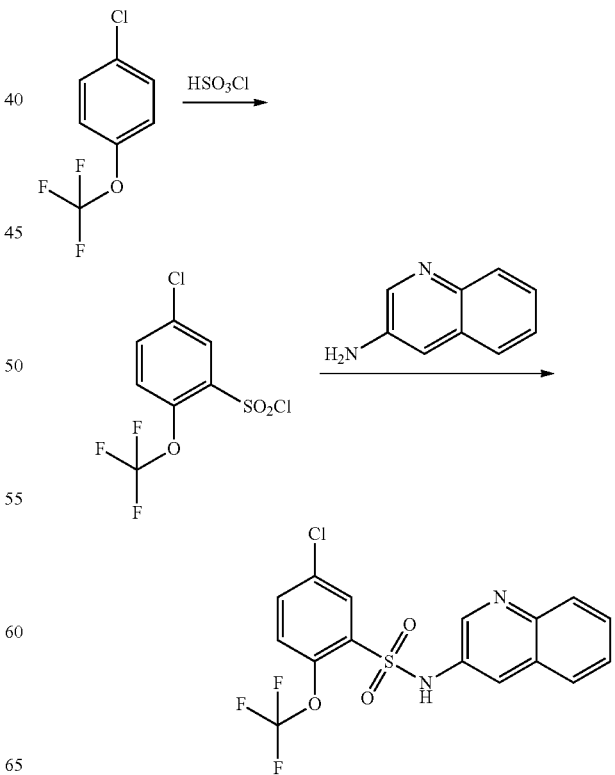

This compound was prepared as described in Example X-1.

$^1$H NMR (DMSO-d6, 400 MHz): δ=11.22 (1H, brs), 8.67 (1H, d), 8.04 (2H, dd), 7.94 (2H, d), 7.87-7.82 (1H, m), 7.68 (1H, t), 7.61-7.56 (2H, m). MS: m/z 403.0 (M+H$^+$).

Example X-4 and X-5

5-Methyl-N-quinolin-3-yl-2-trifluoromethoxy-benzenesulfonamide and 2-methyl-N-quinolin-3-yl-5-trifluoromethoxy-benzenesulfonamide

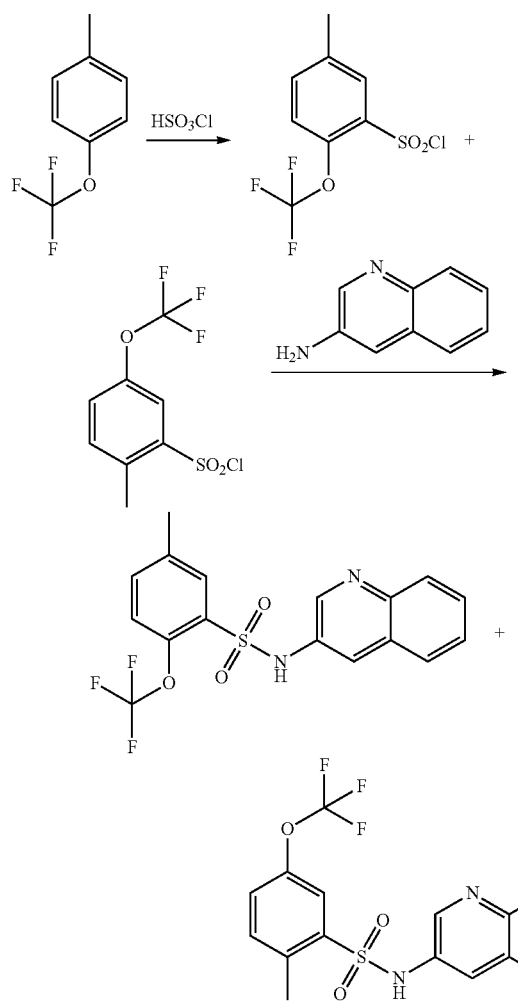

A mixture of 2-Methyl-5-trifluoromethoxy-benzenesulfonyl chloride and 5-Methyl-2-trifluoromethoxy-benzenesulfonyl chloride (ratio: 1/1) was obtained as described in Example X-1.

5-Methyl-N-quinolin-3-yl-2-trifluoromethoxy-benzenesulfonamide and 2-methyl-N-quinolin-3-yl-5-trifluoromethoxy-benzenesulfonamide were separated by prep-HPLC.

For 5-methyl-N-quinolin-3-yl-2-trifluoromethoxy-benzenesulfonamide:

$^1$H NMR (CDC$_3$, 400 MHz): δ=8.64 (1H, s), 8.04-8.00 (2H, m), 7.77-7.73 (2H, m), 7.65 (1H, t), 7.53 (1H, t), 7.34 (1H, dd), 7.29-7.24 (1H, m), 2.30 (3H, s). MS: m/z 383.0 (M+H$^+$).

For 2-methyl-N-quinolin-3-yl-5-trifluoromethoxy-benzenesulfonamide:

$^1$H NMR (CDC$_3$, 400 MHz): δ=8.63 (1H, d), 8.02 (1H, d), 7.96 (1H, d), 7.90 (1H, s), 7.70 (1H, d), 7.64 (1H, td), 7.54 (1H, t), 7.35-7.25 (2H, m), 2.66 (3H, s). MS: m/z 383.0 (M+H$^+$).

Example X-6

2-Methoxy-N-(quinolin-3-yl)-5-(trifluoromethoxy)benzenesulfonamide

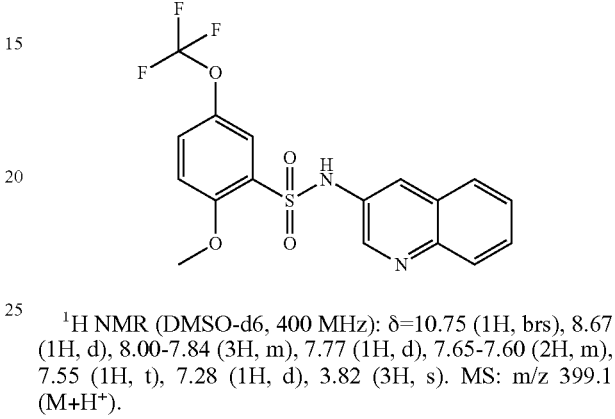

$^1$H NMR (DMSO-d6, 400 MHz): δ=10.75 (1H, brs), 8.67 (1H, d), 8.00-7.84 (3H, m), 7.77 (1H, d), 7.65-7.60 (2H, m), 7.55 (1H, t), 7.28 (1H, d), 3.82 (3H, s). MS: m/z 399.1 (M+H$^+$).

Example XI

Example XI-1

5-chloro-N-[5-(4-methoxy-phenyl)-pyridin-3-yl]-2-trifluoromethoxy-benzenesulfonamide

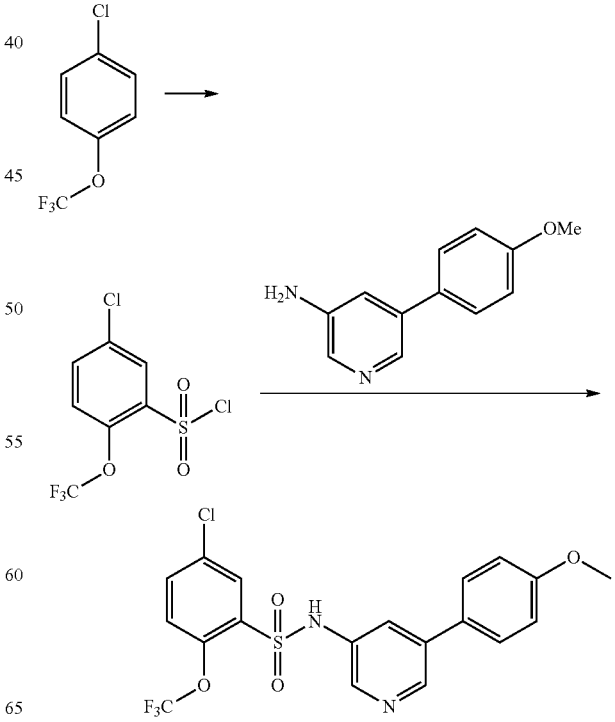

Step 1: A solution of 1-chloro-4-(trifluoromethoxy)benzene (5.0 g, 25.0 mmol) in ClSO₃H (35 mL) was stirred at room temperature overnight. TLC showed the starting material was consumed completely. The reaction mixture was poured into ice water (50 mL) and extracted with DCM (50×3). The combined organic layer was wash with brine (50 mL), dried over Na₂SO₄ and concentrated in vacuum to give 3.9 g (yield: 53%) of 5-chloro-2-(trifluoromethoxy)benzene-1-sulfonyl chloride as colorless oil.

Step 2: A mixture of 5-bromopyridin-3-amine (300 mg, 1.74 mmol), 4-methoxyphenylboronic acid (395 mg, 2.60 mmol), K₂CO₃ (240 mg, 5.10 mmol) and Pd(PPh₃)₄ (197 mg, 0.17 mmol) in DMF/H₂O (5 mL/1 mL) was purged with N₂ for 20 min. Then the mixture was stirred at 120° C. under microwave for 10 min. After cooled to room temperature, the solvent was removed in vacuum. The residue was diluted with EtOAc (30 mL). The mixture was washed with water, brine and dried over Na₂SO₄. The solution was evaporated to dryness and purified by silica gel column (DCM/MeOH, 1/0-40/1) to afford 264 mg (yield: 44%) of 5-(4-methoxyphenyl)pyridin-3-amine as white solid. MS: m/z 201.1 (M+H⁺).

Step 3: A mixture of 5-chloro-2-(trifluoromethoxy)benzene-1-sulfonyl chloride (150 mg, 0.5 mmol), 5-(4-methoxyphenyl)pyridin-3-amine (100 mg, 0.5 mmol) and DMAP (15 mg) in pyridine (5 mL) was stirred at 70° C. for 4 h. TLC showed the starting material was consumed completely. The reaction mixture was diluted with EtOAc (20 mL), washed with water (20 mL), brine (10 mL) and dried over Na₂SO₄. The solution was concentrated in vacuum to give a residue, which was purified by prep-HPLC to give 6.5 mg (yield: 3%) 5-chloro-N-[5-(4-methoxy-phenyl)-pyridin-3-yl]-2-trifluoromethoxy-benzenesulfonamide as white solid.

¹H NMR (CD₃OD, 400 MHz): δ=8.48 (1H, s), 8.20 (1H, s), 8.05 (1H, s), 7.77-7.75 (2H, m), 7.51-7.49 (3H, m), 7.04 (2H, d), 3.85 (3H, s). MS: m/z 458.9 (M+H⁺).

Example XI-2

2-Methoxy-N-(5-(4-methoxyphenyl)pyridin-3-yl)-5-(trifluoromethoxy)benzenesulfonamide

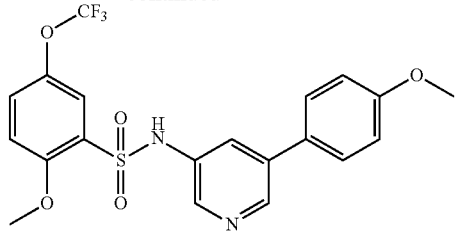

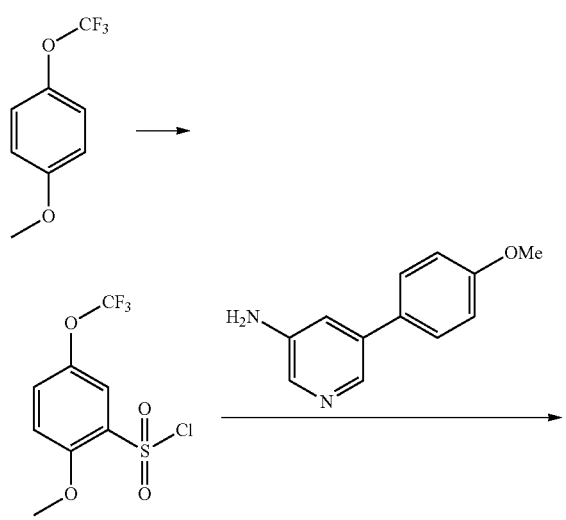

-continued

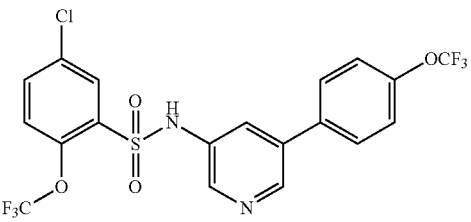 [SMILES: O=S(=O)(Nc1cncc(-c2ccc(OC(F)(F)F)cc2)c1)c1cc(Cl)ccc1OC(F)(F)F]

This compound was prepared as described in Example XI-1.

¹H NMR (DMSO-d6, 400 MHz): δ=11.62 (1H, brs), 8.49 (1H, s), 8.23 (1H, d), 7.34 (1H, d), 7.66-7.63 (2H, m), 7.49 (2H, d), 7.30 (1H, d), 7.04 (2H, d), 3.88 (3H, s), 3.80 (3H, s). MS: m/z 454.8 (M+H⁺).

Example XI-3

5-Chloro-2-(trifluoromethoxy)-N-(5-(4-(trifluoromethoxy)phenyl)pyridin-3-yl)benzenesulfonamide

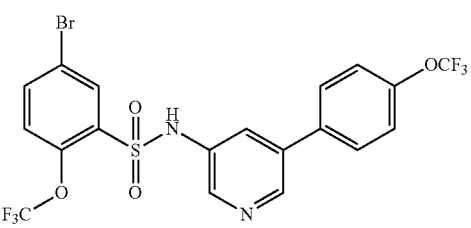

This compound was prepared as described in Example XI-1.

¹H NMR (DMSO-D6, 400 MHz): δ=11.19 (1H, brs), 8.65 (1H, d), 8.32 (1H, d), 8.05 (1H, d), 7.86 (1H, dd), 7.77-7.72 (3H, m), 7.62 (1H, d), 7.50 (2H, d). MS: m/z 512.7 (M+H⁺).

Example XI-4

5-Bromo-2-(trifluoromethoxy)-N-(5-(4-(trifluoromethoxy)phenyl)pyridin-3-yl)benzenesulfonamide This compound was prepared as described in Example XI-1.

¹H NMR (DMSO-d6, 400 MHz): δ=11.18 (1H, brs), 8.65 (1H, d), 8.31 (1H, d), 8.16 (1H, d), 8.00-7.97 (1H, m), 7.75-7.73 (3H, m), 7.54-7.49 (3H, m). MS: m/z 556.6 (M+H⁺).

Example XI-5

5-Chloro-N-(5-(3,4-dimethoxyphenyl)pyridin-3-yl)-2-(trifluoromethoxy)benzenesulfonamide

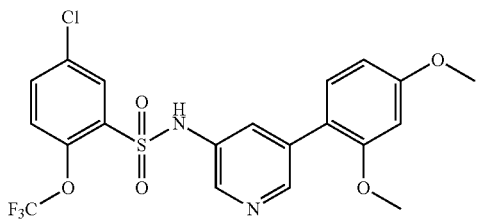

This compound was prepared as described in Example XI-1.

$^1$H NMR (CD$_3$OD, 400 MHz): δ=8.32 (1H, s), 8.18 (1H, d), 8.03 (1H, d), 7.74-7.72 (2H, m), 7.52 (1H, d), 7.20 (1H, d), 6.67-6.64 (2H, m), 3.84 (3H, s), 3.80 (3H, s). MS: m/z 488.9 (M+H$^+$).

Example XI-6

5-Bromo-N-(5-(3,4-dimethoxyphenyl)pyridin-3-yl)-2-(trifluoromethoxy)benzenesulfonamide

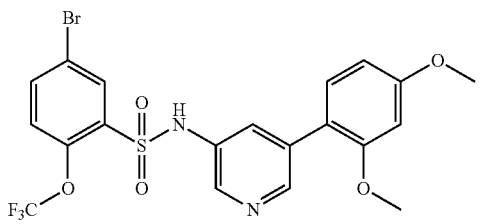 [SMILES: COc1ccc(-c2cncc(NS(=O)(=O)c3cc(Cl)ccc3OC(F)(F)F)c2)c(OC)c1]

This compound was prepared as described in Example XI-1.

$^1$H NMR (DMSO-d6, 400 MHz): δ=11.0 (1H, brs), 8.35 (1H, s), 8.21 (1H, d), 8.10-8.09 (1H, m), 8.00-8.79 (1H, m), 7.58-7.55 (2H, m), 7.20-7.19 (1H, d), 6.68-6.63 (2H, m), 3.77 (3H, s), 3.73 (3H, s). MS: m/z 532.9 (M+H$^+$).

Example XI-7

N-(5-(3,4-Dimethoxyphenyl)pyridin-3-yl)-2-methoxy-5-(trifluoromethoxy)benzenesulfonamide

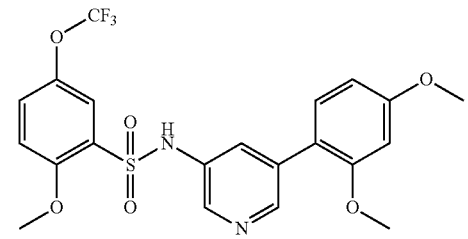 [SMILES: COc1ccc(-c2cncc(NS(=O)(=O)c3cc(OC(F)(F)F)ccc3OC)c2)c(OC)c1]

This compound was prepared as described in Example XI-1.

$^1$H NMR (CDC$_3$, 400 MHz): δ=8.41 (1H, d), 8.02 (1H, d), 7.73 (1H, d), 7.65-7.64 (1H, m), 7.30-7.29 (1H, m), 7.09-7.07 (1H, m), 6.98-6.96 (1H, d), 6.51-6.47 (2H, m), 3.98 (3H, s), 3.78 (3H, s), 3.70 (3H, s). MS: m/z 484.9 (M+H$^+$).

Example XI-8

5-Chloro-N-(5-(4-fluorophenyl)pyridin-3-yl)-2-(trifluoromethoxy)benzenesulfonamide

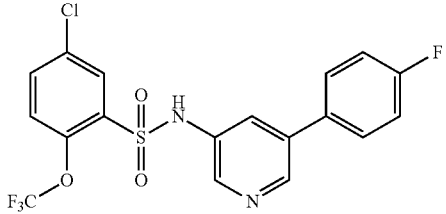

This compound was prepared as described in Example XI-1.

$^1$H NMR (DMSO-d6, 400 MHz): δ=11.11 (1H, brs), 8.61 (1H, d), 8.28 (1H, d), 8.05 (1H, d), 7.86 (1H, dd), 7.72 (1H, t), 7.68-7.58 (3H, m), 7.36-7.31 (2H, m). MS: m/z 446.9 (M+H$^+$).

Example XI-9

5-Bromo-N-(5-(4-fluorophenyl)pyridin-3-yl)-2-(trifluoromethoxy)benzenesulfonamide

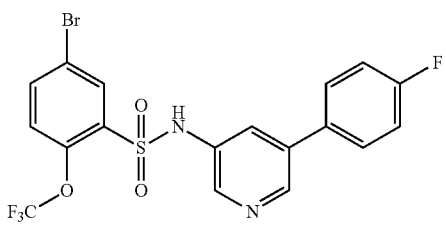 [SMILES: O=S(=O)(Nc1cncc(-c2ccc(F)cc2)c1)c1cc(Cl)ccc1OC(F)(F)F]

This compound was prepared as described in Example XI-1.

$^1$H NMR (DMSO-d6, 400 MHz): δ=11.06 (1H, s), 8.61 (1H, s), 8.27 (1H, s), 8.15 (1H, d), 8.00 (1H, d), 7.71-7.70 (1H, m), 7.66 (2H, dd), 7.54-7.51 (1H, m), 7.35 (2H, t). MS: m/z 490.8 (M+H$^+$).

Example XI-10

N-(5-(4-Fluorophenyl)pyridin-3-yl)-2-methoxy-5-(trifluoromethoxy)benzenesulfonamide

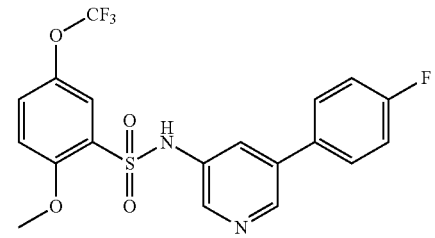 [SMILES: COc1ccc(OC(F)(F)F)cc1S(=O)(=O)Nc1cncc(-c2ccc(F)cc2)c1]

This compound was prepared as described in Example XI-1.

¹H NMR (DMSO-d6, 400 MHz): δ=10.72 (1H, brs), 8.53 (1H, d), 8.29 (1H, d), 7.69 (1H, s), 7.68-7.58 (4H, m), 7.35-7.30 (3H, m), 3.89 (3H, s). MS: m/z 442.8 (M+H⁺).

Example XI-11

5-Bromo-N-(5-(4-cyanophenyl)pyridin-3-yl)-2-(trifluoromethoxy)benzenesulfonamide

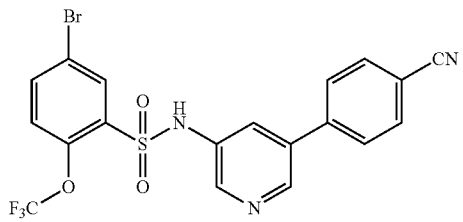 [SMILES: N#Cc1ccc(-c2cncc(NS(=O)(=O)c3cc(Br)ccc3OC(F)(F)F)c2)cc1]

This compound was prepared as described in Example XI-1.

¹H NMR (DMSO-d6, 400 MHz): δ=11.19 (1H, brs), 8.64 (1H, s), 8.32 (1H, d), 8.15 (1H, d), 7.98-7.94 (3H, m), 7.82-7.77 (3H, m), 7.51-7.49 (1H, m). MS: m/z 497.6 (M+H⁺).

Example XI-12

5-Chloro-N-(5-(furan-2-yl)pyridin-3-yl)-2-(trifluoromethoxy)benzenesulfonamide

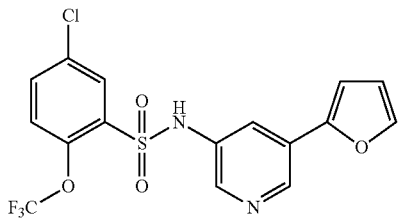 [SMILES: O=S(=O)(Nc1cncc(-c2ccco2)c1)c1cc(Cl)ccc1OC(F)(F)F]

This compound was prepared as described in Example XI-1.

¹H NMR (CD₃OD, 400 MHz): δ=8.53 (1H, s), 8.13 (1H, d), 8.03 (1H, d), 7.83 (1H, t), 7.67 (1H, dd), 7.63 (1H, d), 7.47 (1H, d), 6.89 (1H, d), 6.55 (1H, dd). MS: m/z 418.9 (M+H⁺).

Example XI-13

N-(5-(Furan-2-yl)pyridin-3-yl)-2-methoxy-5-(trifluoromethoxy)benzenesulfonamide

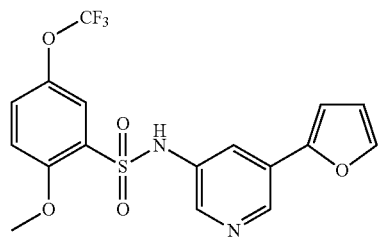 [SMILES: COc1ccc(OC(F)(F)F)cc1S(=O)(=O)Nc1cncc(-c2ccco2)c1]

This compound was prepared as described in Example XI-1.

¹H NMR (DMSO-d6, 400 MHz): δ=10.70 (1H, brs), 8.61 (1H, d), 8.20 (1H, d), 7.82 (1H, d), 7.75-7.70 (3H, m), 7.30 (1H, d), 7.04 (1H, d), 6.62 (1H, dd), 3.87 (3H, s). MS: m/z 414.8 (M+H⁺).

Example XI-14

5-Chloro-N-(5-(thiophen-2-yl)pyridin-3-yl)-2-(trifluoromethoxy)benzenesulfonamide

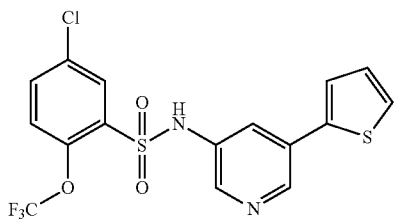

This compound was prepared as described in Example XI-1.

¹H NMR (CD₃OD, 400 MHz): δ=8.42 (1H, d), 8.08 (1H, d), 7.95 (1H, d), 7.68-7.67 (1H, m), 7.61 (1H, dd), 7.43-7.34 (3H, m), 7.07-7.05 (1H, m). MS: m/z 435.0 (M+H⁺).

Example XI-15

5-Bromo-N-(5-(thiophen-2-yl)pyridin-3-yl)-2-(trifluoromethoxy)benzenesulfonamide

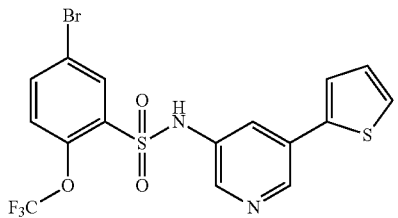 [SMILES: O=S(=O)(Nc1cncc(-c2cccs2)c1)c1cc(Br)ccc1OC(F)(F)F]

This compound was prepared as described in Example XI-1.

¹H NMR (DMSO-d6, 400 MHz): δ=10.70 (1H, brs), 8.23 (1H, s), 8.06 (1H, d), 7.97 (1H, s), 7.75 (1H, d), 7.56 (1H, d), 7.46 (1H, s), 7.41 (1H, d), 7.36 (1H, d), 7.13 (1H, dd). MS: m/z 478.9 (M+H⁺).

Example XI-16

2-Methoxy-N-(5-(thiophen-2-yl)pyridin-3-yl)-5-(trifluoromethoxy)benzenesulfonamide

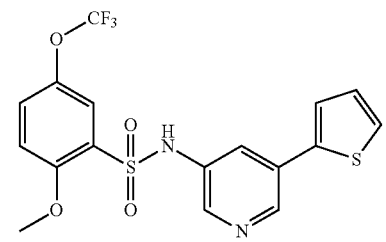 [SMILES: COc1ccc(OC(F)(F)F)cc1S(=O)(=O)Nc1cncc(-c2cccs2)c1]

This compound was prepared as described in Example XI-1.

$^1$H NMR (DMSO-d6, 400 MHz): δ=10.68 (1H, brs), 8.59 (1H, d), 8.24 (1H, d), 7.75 (1H, d), 7.68-7.65 (3H, m), 7.52 (1H, dd), 7.32 (1H, d), 7.17 (1H, dd), 3.89 (3H, s). MS: m/z 431.0 (M+H$^+$).

Example XI-17

N-([2,3'-Bipyridin]-5'-yl)-5-chloro-2-(trifluoromethoxy)benzenesulfonamide

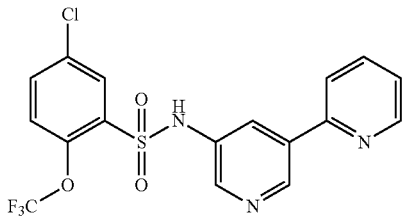 [SMILES: O=S(=O)(Nc1cncc(-c2ccccn2)c1)c1cc(Cl)ccc1OC(F)(F)F]

This compound was prepared as described in Example XI-1.

$^1$H NMR (DMSO-d6, 400 MHz): δ=11.11 (1H, brs), 8.98 (1H, d), 8.71 (1H, d), 8.37 (1H, d), 8.21 (1H, dd), 8.03-7.83 (4H, m), 7.43 (1H, d), 7.41 (1H, d). MS: m/z 430.0 (M+H$^+$).

Example XI-18

N-([2,3'-Bipyridin]-5'-yl)-5-bromo-2-(trifluoromethoxy)benzenesulfonamide

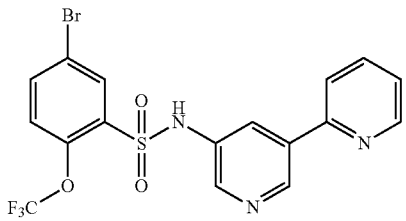

This compound was prepared as described in Example XI-1.

$^1$H NMR (DMSO-d6, 400 MHz): δ=11.12 (1H, brs), 8.95 (1H, s), 8.70 (1H, d), 8.35 (1H, d), 8.20 (1H, s), 8.13 (1H, d), 8.00-7.90 (3H, m), 7.50 (1H, d), 7.44-7.40 (1H, m). MS: m/z 474.0 (M+H$^+$).

Example XI-19

N-([2,3'-Bipyridin]-5'-yl)-2-methoxy-5-(trifluoromethoxy)benzenesulfonamide

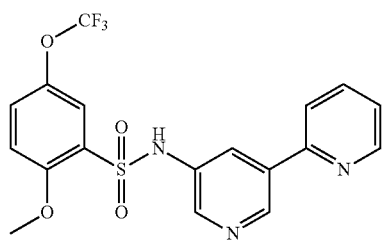 [SMILES: COc1ccc(OC(F)(F)F)cc1S(=O)(=O)Nc1cncc(-c2ccccn2)c1]

This compound was prepared as described in Example XI-1.

$^1$H NMR (DMSO-d6, 400 MHz): δ=10.71 (1H, brs), 8.89 (1H, d), 8.70-8.67 (1H, m), 8.36 (1H, d), 8.20 (1H, t), 7.94-7.90 (2H, m), 7.73 (1H, d), 7.63 (1H, dd), 7.44-7.40 (1H, m), 7.29 (1H, d), 3.87 (3H, s). MS: m/z 426.0 (M+H$^+$).

Example XI-20

5-Chloro-N-(5-(pyrazin-2-yl)pyridin-3-yl)-2-(trifluoromethoxy)benzenesulfonamide

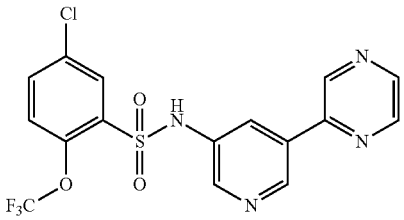

This compound was prepared as described in Example XI-1.

$^1$H NMR (DMSO-d6, 400 MHz): δ=11.20 (1H, brs), 9.26 (1H, s), 8.94 (1H, s), 8.75 (1H, s), 8.67 (1H, s), 8.38-8.35 (1H, m), 8.18 (1H, s), 8.01 (1H, s), 7.85-7.82 (1H, m), 7.58-7.55 (1H, m). MS: m/z 430.9 (M+H$^+$).

Example XI-21

5-Bromo-N-(5-(pyrazin-2-yl)pyridin-3-yl)-2-(trifluoromethoxy)benzenesulfonamide

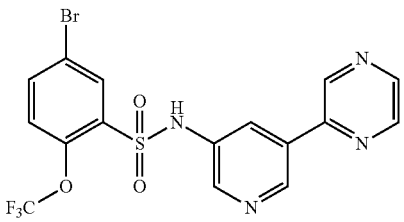 [SMILES: O=S(=O)(Nc1cncc(-c2cnccn2)c1)c1cc(Br)ccc1OC(F)(F)F]

This compound was prepared as described in Example XI-1.

$^1$H NMR (DMSO-d6, 400 MHz): δ=11.25 (1H, brs), 9.30 (1H, d), 9.07 (1H, s), 8.78 (1H, d), 8.70 (1H, d), 8.43 (1H, d), 8.24 (1H, s), 8.15 (1H, d), 8.00-7.96 (1H, m), 7.52 (1H, d). MS: m/z 474.7 (M+H$^+$).

Example XI-22

2-Methoxy-N-(5-(pyrazin-2-yl)pyridin-3-yl)-5-(trifluoromethoxy)benzenesulfonamide

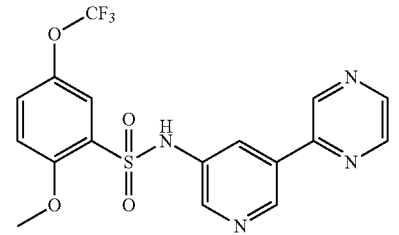 [SMILES: COc1ccc(OC(F)(F)F)cc1S(=O)(=O)Nc1cncc(-c2cnccn2)c1]

This compound was prepared as described in Example XI-1.

¹H NMR (DMSO-d6, 400 MHz): δ=10.55 (1H, brs), 9.25 (1H, d), 8.99 (1H, d), 8.75 (1H, dd), 8.68 (1H, d), 8.43 (1H, d), 8.22 (1H, t), 7.74 (1H, d), 7.64 (1H, dd), 7.30 (1H, d), 3.89 (3H, s). MS: m/z 426.8 (M+H⁺).

Example XI-23

5-chloro-N-(5-(pyrimidin-2-yl)pyridin-3-yl)-2-(trifluoromethoxy)benzenesulfonamide

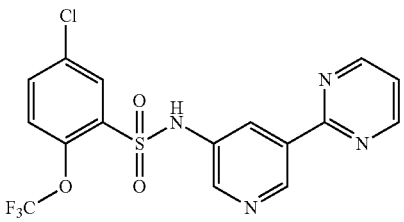 [SMILES: O=S(=O)(Nc1cncc(-c2ncccn2)c1)c1cc(Cl)ccc1OC(F)(F)F]

This compound was prepared as described in Example XI-1.

¹H NMR (CD₃OD, 400 MHz): δ=9.08 (1H, s), 8.79-8.75 (2H, m), 8.46 (1H, t), 8.28 (1H, d), 7.96 (1H, d), 7.57 (1H, dd), 7.34-7.30 (2H, m). MS: m/z 431.0 (M+H⁺).

Example XI-24

5-Bromo-N-(5-(pyrimidin-2-yl)pyridin-3-yl)-2-(trifluoromethoxy)benzenesulfonamide

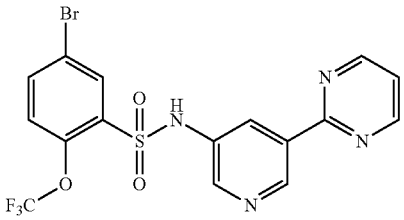

This compound was prepared as described in Example XI-1.

1H NMR (DMSO-d6, 400 MHz): δ=9.07 (1H, s), 8.94-8.90 (2H, m), 8.39-8.32 (2H, m), 8.11 (1H, d), 7.90-7.85 (1H, m), 7.52-7.42 (2H, m). MS: m/z 475.0 (M+H⁺).

Example XI-25

5-Chloro-N-(5-(thiazol-5-yl)pyridin-3-yl)-2-(trifluoromethoxy)benzenesulfonamide

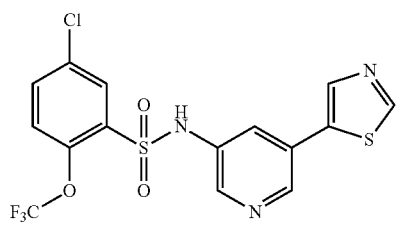 [SMILES: O=S(=O)(Nc1cncc(-c2cncs2)c1)c1cc(Cl)ccc1OC(F)(F)F]

This compound was prepared as described in Example XI-1.

¹H NMR (DMSO-D6, 400 MHz): δ=11.19 (1H, brs), 9.25 (1H, d), 9.16 (1H, d), 8.34 (1H, d), 8.28 (1H, d), 8.11 (1H, t), 8.01 (1H, d), 7.86-7.84 (1H, m), 7.61 (1H, d). MS: m/z 436.0 (M+H⁺).

Example XI-26

5-bromo-N-(5-(thiazol-5-yl)pyridin-3-yl)-2-(trifluoromethoxy)benzenesulfonamide

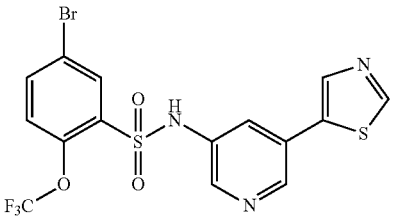

This compound was prepared as described in Example XI-1.

¹H NMR (DMSO-d6, 400 MHz): δ=10.54 (1H, brs), 9.24 (1H, d), 8.92 (1H, s), 8.36 (1H, s), 8.34 (1H, d), 8.14-8.10 (2H, m), 8.01 (1H, d), 7.52 (1H, d). MS: m/z 479.8 (M+H⁺).

Example XI-27

2-Methoxy-N-(5-(thiazol-5-yl)pyridin-3-yl)-5-(trifluoromethoxy)benzenesulfonamide

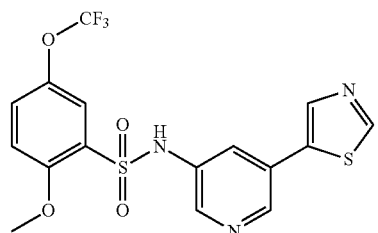

This compound was prepared as described in Example XI-1.

¹H NMR (DMSO-d6, 400 MHz): δ=11.20 (1H, s), 9.23 (1H, d), 8.84 (1H, s), 8.29-8.27 (2H, m), 8.15 (1H, s), 7.69 (1H, d), 7.63-7.62 (1H, m), 7.25 (1H, d), 3.87 (3H, s). MS: m/z 431.7 (M+H⁺).

Example XI-28

5-Chloro-N-(5-(thiazol-4-yl)pyridin-3-yl)-2-(trifluoromethoxy)benzenesulfonamide

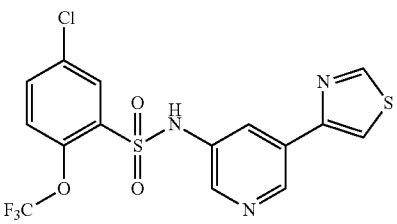 [SMILES: O=S(=O)(Nc1cncc(-c2cscn2)c1)c1cc(Cl)ccc1OC(F)(F)F]

This compound was prepared as described in Example XI-1.

¹H NMR (DMSO-D6, 400 MHz): δ=11.22 (1H, brs), 9.19 (1H, s), 8.68 (1H, s), 8.37 (1H, s), 8.25 (1H, s), 8.05 (1H, d), 7.86-7.84 (1H, m), 7.70 (1H, s), 7.62-7.60 (1H, m). MS: m/z 435.5 (M+H⁺).

Example XI-29

5-Bromo-N-(5-(thiazol-4-yl)pyridin-3-yl)-2-(trifluoromethoxy)benzenesulfonamide

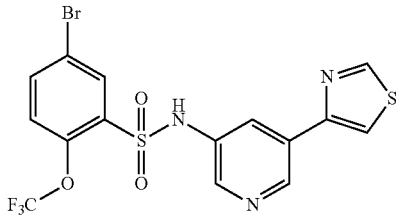

This compound was prepared as described in Example XI-1.

¹H NMR (DMSO-d6, 400 MHz): δ=11.22 (1H, brs), 9.19 (1H, s), 8.70 (1H, d), 8.38 (1H, d), 8.26 (1H, d), 8.16 (1H, d), 8.00 (1H, dd), 7.70 (1H, d), 7.53-7.50 (1H, m). MS: m/z 479.9 (M+H⁺).

Example XI-30

2-Methoxy-N-(5-(thiazol-4-yl)pyridin-3-yl)-5-(trifluoromethoxy)benzenesulfonamide

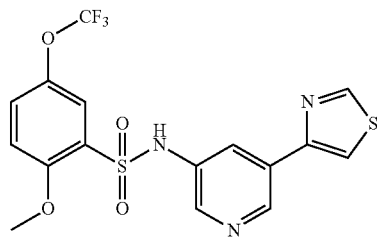 [SMILES: COc1ccc(OC(F)(F)F)cc1S(=O)(=O)Nc1cncc(-c2cscn2)c1]

This compound was prepared as described in Example XI-1.

¹H NMR (DMSO-d6, 400 MHz): δ=10.72 (1H, brs), 9.18 (1H, s), 8.63 (1H, s), 8.33 (1H, s), 8.31 (1H, s), 7.66 (1H, d), 7.65-7.63 (2H, m), 7.33 (1H, d), 3.87 (3H, s). MS: m/z 431.8 (M+H⁺).

Example XI-31

5-Bromo-N-(5-(1-methyl-1H-pyrazol-4-yl)pyridin-3-yl)-2-(trifluoromethoxy)benzenesulfonamide

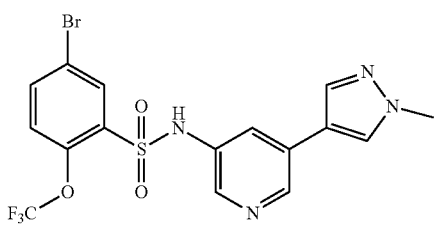 [SMILES: Cn1cc(-c2cncc(NS(=O)(=O)c3cc(Br)ccc3OC(F)(F)F)c2)cn1]

This compound was prepared as described in Example XI-1.

¹H NMR (DMSO-d6, 400 MHz): δ=10.89 (1H, brs), 8.56 (1H, d), 8.20 (1H, s), 8.14 (1H, d), 8.08 (1H, d), 7.98 (1H, d), 7.85 (1H, s), 7.61 (1H, t), 7.53-7.51 (1H, m), 3.86 (3H, s). MS: m/z 477.0 (M+H⁺).

Example XI-32

2-Methoxy-N-(5-(1-methyl-1H-pyrazol-4-yl)pyridin-3-yl)-5-(trifluoromethoxy)benzenesulfonamide

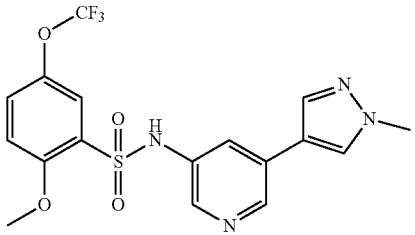 [SMILES: COc1ccc(OC(F)(F)F)cc1S(=O)(=O)Nc1cncc(-c2cnn(C)c2)c1]

This compound was prepared as described in Example XI-1.

¹H NMR (CDC₃, 400 MHz): δ=8.41 (1H, d), 7.92 (1H, d), 7.66-7.63 (3H, m), 7.57 (1H, s), 7.30 (1H, dd), 7.07 (1H, s), 6.97 (1H, d), 3.98 (3H, s), 3.89 (3H, s). MS: m/z 429.0 (M+H⁺).

Example XII

Example XII-1

Methyl 5-(5-chloro-2-(trifluoromethoxy)phenylsulfonamido)nicotinate

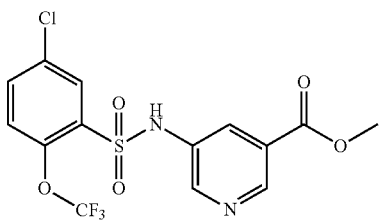 [SMILES: COC(=O)c1cncc(NS(=O)(=O)c2cc(Cl)ccc2OC(F)(F)F)c1]

¹H NMR (DMSO-d6, 400 MHz): δ=11.28 (1H, brs), 8.81 (1H, d), 8.57 (1H, dd), 8.02-7.98 (2H, m), 7.88 (1H, dd), 7.61 (1H, dd), 3.87 (3H, s). MS: m/z 411.0 (M+H⁺)

Example XII-2

5-(5-Bromo-2-(trifluoromethoxy)phenylsulfonamido)nicotinic acid

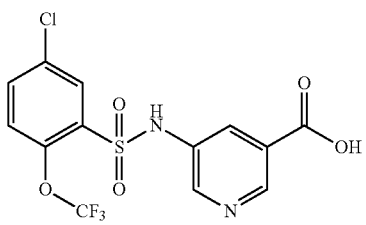 [SMILES: O=C(O)c1cncc(NS(=O)(=O)c2cc(Cl)ccc2OC(F)(F)F)c1]

¹H NMR (DMSO-d6, 400 MHz): δ=13.58 (1H, brs), 11.24 (1H, brs), 8.79 (1H, s), 8.52 (1H, d), 8.01-7.83 (3H, m), 7.61 (1H, d). MS: m/z 397.0 (M+H⁺).

Example XII-3

Cyclohexyl 5-(5-chloro-2-(trifluoromethoxy)phenyl-sulfonamido)nicotinate

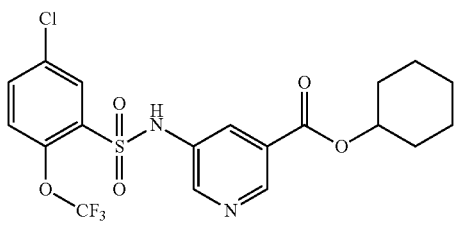 [SMILES: O=C(OC1CCCCC1)c1cncc(NS(=O)(=O)c2cc(Cl)ccc2OC(F)(F)F)c1]

¹H NMR (DMSO-d6, 400 MHz): δ=11.30 (1H, brs), 8.80 (1H, d), 8.55 (1H, d), 8.02-7.98 (2H, m), 7.90 (1H, dd), 7.62 (1H, dd), 4.96-4.94 (1H, m), 1.86-1.82 (2H, m), 1.69-1.67 (2H, m), 1.56-1.37 (6H, m). MS: m/z 479.1 (M+H⁺).

Example XII-4

Phenyl 5-(5-chloro-2-(trifluoromethoxy)phenylsul-fonamido)nicotinate

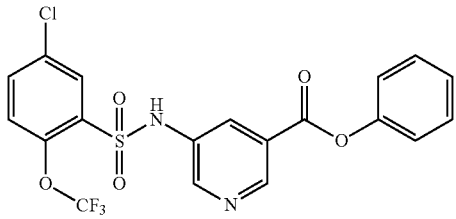 [SMILES: O=C(Oc1ccccc1)c1cncc(NS(=O)(=O)c2cc(Cl)ccc2OC(F)(F)F)c1]

¹H NMR (DMSO-d6, 400 MHz): δ=11.39 (1H, brs), 8.98 (1H, d), 8.63 (1H, d), 8.15-8.13 (1H, m), 8.04 (1H, d), 7.90 (1H, dd), 7.64 (1H, dd), 7.50-7.46 (2H, m), 7.35-7.28 (3H, m). MS: m/z 473.0 (M+H⁺).

Example XII-5

5-(5-Chloro-2-(trifluoromethoxy)phenylsulfona-mido)nicotinamide

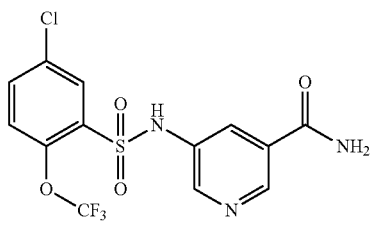 [SMILES: NC(=O)c1cncc(NS(=O)(=O)c2cc(Cl)ccc2OC(F)(F)F)c1]

¹H NMR (DMSO-d6, 400 MHz): δ=11.14 (1H, brs), 8.75 (1H, s), 8.43-8.41 (1H, m), 8.16 (1H, s), 7.98-7.81 (3H, m), 7.62-7.58 (2H, m). MS: m/z 396.0 (M+H⁺).

Example XII-6

5-(5-Chloro-2-(trifluoromethoxy)phenylsulfona-mido)-N-methylnicotinamide

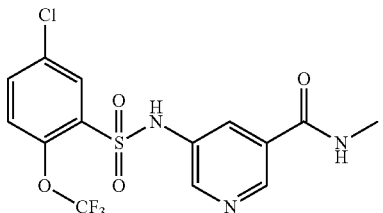

¹H NMR (DMSO-d6, 400 MHz): δ=11.14 (1H, brs), 8.73 (1H, d), 8.67-8.64 (1H, m), 8.43-8.42 (1H, m), 7.98 (1H, d), 7.89-7.82 (2H, m), 7.62 (1H, dd), 2.76 (3H, d). MS: m/z 410.0 (M+H⁺).

Example XII-7

5-(5-Chloro-2-(trifluoromethoxy)phenylsulfona-mido)-N-propylnicotinamide

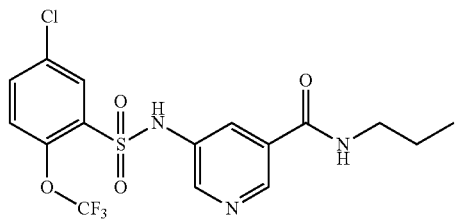 [SMILES: CCCNC(=O)c1cncc(NS(=O)(=O)c2cc(Cl)ccc2OC(F)(F)F)c1]

¹H NMR (DMSO-d6, 400 MHz): δ=11.14 (1H, brs), 8.73 (1H, s), 8.68-8.65 (1H, m), 8.42 (1H, d), 7.99 (1H, d), 7.88-7.85 (2H, m), 7.62 (1H, dd), 3.22-3.17 (2H, m), 1.54-1.48 (2H, m), 0.89-0.85 (3H, m). MS: m/z 438.0 (M+H⁺).

Example XII-8

5-(5-Chloro-2-(trifluoromethoxy)phenylsulfona-mido)-N-cyclohexylnicotinamide

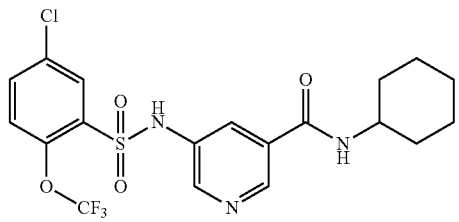 [SMILES: O=C(NC1CCCCC1)c1cncc(NS(=O)(=O)c2cc(Cl)ccc2OC(F)(F)F)c1]

¹H NMR (DMSO-d6, 400 MHz): δ=11.13 (1H, brs), 8.73 (1H, s), 8.44-8.41 (2H, m), 7.99 (1H, d), 7.89-7.86 (2H, m), 7.62 (1H, dd), 3.74-3.70 (1H, m), 1.79-1.71 (4H, m), 1.34-1.24 (6H, m). MS: m/z 478.1 (M+H⁺).

Example XII-9

Methyl 5-(5-bromo-2-(trifluoromethoxy)phenylsulfonamido)nicotinate

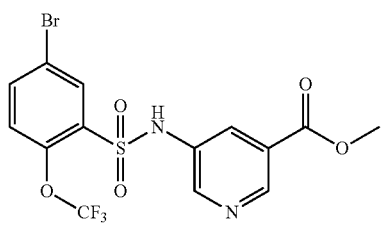

¹H NMR (DMSO-d6, 400 MHz): δ=11.28 (1H, brs), 8.80 (1H, d), 8.56-8.54 (1H, m), 8.13 (1H, d), 8.02-7.99 (2H, m), 7.55-7.52 (1H, m), 3.87 (3H, s). MS: m/z 454.9 (M+H⁺).

Example XII-10

5-(5-Bromo-2-(trifluoromethoxy)phenylsulfonamido)nicotinic acid

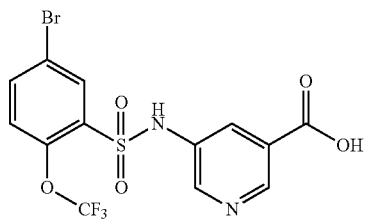

¹H NMR (DMSO-d6, 400 MHz): δ=13.57 (1H, brs), 11.25 (1H, brs), 8.77 (1H, d), 8.51 (1H, d), 8.10 (1H, d), 8.01-7.97 (2H, m), 7.54 (1H, dd). MS: m/z 441.0 (M+H⁺).

Example XII-11

Cyclohexyl 5-(5-bromo-2-(trifluoromethoxy)phenylsulfonamido)nicotinate

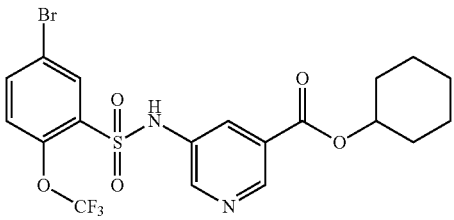 [SMILES: O=C(OC1CCCCC1)c1cncc(NS(=O)(=O)c2cc(Br)ccc2OC(F)(F)F)c1]

¹H NMR (DMSO-d6, 400 MHz): δ=11.28 (1H, brs), 8.80 (1H, d), 8.55 (1H, d), 8.13 (1H, d), 8.02-7.98 (2H, m), 7.55 (1H, dd), 4.97-4.94 (1H, m), 1.86-1.82 (2H, m), 1.69-1.67 (2H, m), 1.57-1.37 (6H, m). MS: m/z 523.0 (M+H⁺).

Example XII-12

Phenyl 5-(5-bromo-2-(trifluoromethoxy)phenylsulfonamido)nicotinate

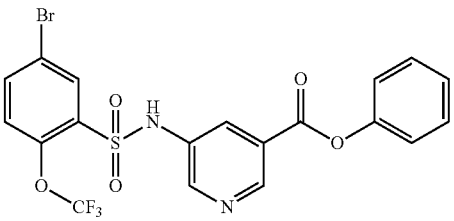 [SMILES: O=C(Oc1ccccc1)c1cncc(NS(=O)(=O)c2cc(Br)ccc2OC(F)(F)F)c1]

¹H NMR (DMSO-d6, 400 MHz): δ=11.38 (1H, brs), 8.98 (1H, d), 8.63 (1H, d), 8.17-8.13 (2H, m), 8.03 (1H, dd), 7.57 (1H, dd), 7.50-7.47 (2H, m), 7.35-7.29 (3H, m). MS: m/z 517.0 (M+H⁺).

Example XII-13

5-(5-Bromo-2-(trifluoromethoxy)phenylsulfonamido)nicotinamide

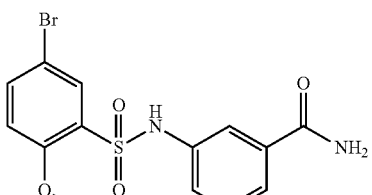

¹H NMR (DMSO-d6, 400 MHz): δ=11.11 (1H, brs), 8.77 (1H, s), 8.43 (1H, d), 8.17 (1H, s), 8.10 (1H, d), 8.00 (1H, dd), 7.92-7.91 (1H, m), 7.64 (1H, s), 7.54 (1H, dd). MS: m/z 440.0 (M+H⁺).

Example XII-14

5-(5-Bromo-2-(trifluoromethoxy)phenylsulfonamido)-N-methylnicotinamide

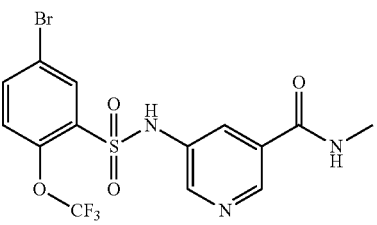 [SMILES: CNC(=O)c1cncc(NS(=O)(=O)c2cc(Br)ccc2OC(F)(F)F)c1]

¹H NMR (DMSO-d6, 400 MHz): δ=11.14 (1H, brs), 8.73 (1H, d), 8.66 (1H, d), 8.42 (1H, d), 8.10 (1H, d), 8.01-7.98 (1H, m), 7.89-7.88 (1H, m), 7.54 (1H, dd), 2.77 (3H, d). MS: m/z 454.0 (M+H⁺).

Example XII-15

Methyl 5-(2-methoxy-5-(trifluoromethoxy)phenyl-sulfonamido)nicotinate

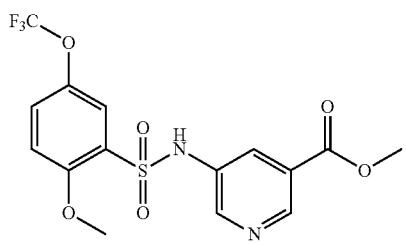 [SMILES: COC(=O)c1cncc(NS(=O)(=O)c2cc(OC(F)(F)F)ccc2OC)c1]

¹H NMR (DMSO-d6, 400 MHz): δ=10.89 (1H, brs), 8.73 (1H, d), 8.54 (1H, d), 7.99-7.98 (1H, m), 7.75-7.71 (2H, m), 7.30 (1H, d), 3.85 (3H, s), 3.83 (3H, s). MS: m/z 407.0 (M+H⁺).

Example XII-16

Propyl 5-(2-methoxy-5-(trifluoromethoxy)phenyl-sulfonamido)nicotinate

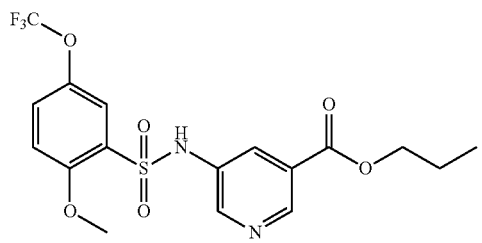

¹H NMR (DMSO-d6, 400 MHz): δ=10.89 (1H, brs), 8.73 (1H, d), 8.54 (1H, d), 8.00-7.99 (1H, m), 7.72-7.66 (2H, m), 7.32-7.29 (1H, d), 4.24-4.21 (2H, m), 3.84 (3H, s), 1.72-1.67 (2H, m), 0.95 (3H, t). MS: m/z 434.0 (M+H⁺).

Example XII-17

Cyclohexyl 5-(2-methoxy-5-(trifluoromethoxy)phenylsulfonamido)nicotinate

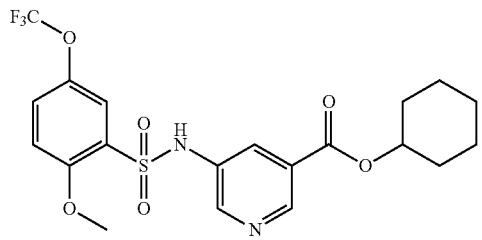 [SMILES: COc1ccc(OC(F)(F)F)cc1S(=O)(=O)Nc1cncc(C(=O)OC2CCCCC2)c1]

¹H NMR (DMSO-d6, 400 MHz): δ=11.86 (1H, brs), 8.72 (1H, s), 8.53 (1H, d), 7.99 (1H, d), 7.72-7.65 (2H, m), 7.31 (1H, d), 4.97-4.91 (1H, m), 3.86 (3H, s), 1.87-1.32 (10H, m). MS: m/z 475.1 (M+H⁺).

Example XII-18

Phenyl 5-(2-methoxy-5-(trifluoromethoxy)phenyl-sulfonamido)nicotinate

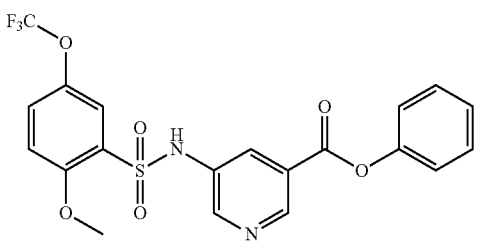 [SMILES: COc1ccc(OC(F)(F)F)cc1S(=O)(=O)Nc1cncc(C(=O)Oc2ccccc2)c1]

¹H NMR (DMSO-d6, 400 MHz): δ=11.97 (1H, brs), 8.91 (1H, d), 8.61 (1H, d), 8.13-8.12 (1H, m), 7.76 (1H, d), 7.70-7.67 (1H, m), 7.50-7.46 (2H, m), 7.35-7.27 (4H, m), 3.86 (3H, s). MS: m/z 469.0 (M+H⁺).

Example XII-19

5-(2-Methoxy-5-(trifluoromethoxy)phenylsulfonamido)nicotinamide

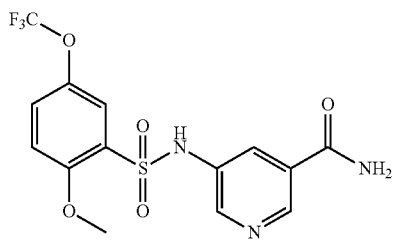 [SMILES: COc1ccc(OC(F)(F)F)cc1S(=O)(=O)Nc1cncc(C(N)=O)c1]

¹H NMR (DMSO-d6, 400 MHz): δ=10.74 (1H, brs), 8.66 (1H, s), 8.40 (1H, d), 8.11 (1H, s), 7.89 (1H, s), 7.70 (1H, d), 7.64 (1H, dd), 7.57 (1H, s), 7.28 (1H, d), 3.83 (3H, s). MS: m/z 392.0 (M+H⁺).

Example XII-20

5-(2-Methoxy-5-(trifluoromethoxy)phenylsulfonamido)-N-methylnicotinamide

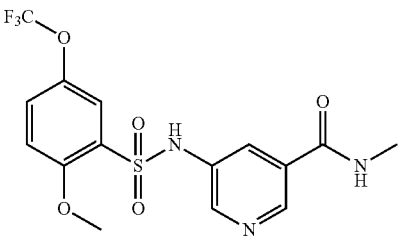 [SMILES: CNC(=O)c1cncc(NS(=O)(=O)c2cc(OC(F)(F)F)ccc2OC)c1]

¹H NMR (DMSO-d6, 400 MHz): δ=10.71 (1H, brs), 8.63 (1H, s), 8.60 (1H, brs), 8.40 (1H, d), 7.88 (1H, t), 7.70-7.63 (2H, m), 7.29 (1H, d), 3.83 (3H, s), 2.75 (3H, d). MS: m/z 406.0 (M+H⁺).

Example XII-21

5-(2-Methoxy-5-(trifluoromethoxy)phenylsulfonamido)-N-propylnicotinamide

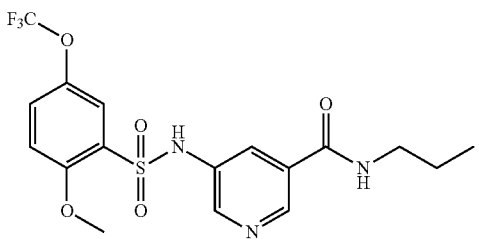 [SMILES: CCCNC(=O)c1cncc(NS(=O)(=O)c2cc(OC(F)(F)F)ccc2OC)c1]

$^1$H NMR (DMSO-d6, 400 MHz): δ=10.71 (1H, brs), 8.65 (1H, s), 8.64 (1H, brs), 8.40 (1H, d), 7.88 (1H, s), 7.70-7.64 (2H, m), 7.30 (1H, d), 3.84 (3H, s), 3.21-3.16 (2H, m), 1.51-1.47 (2H, m), 0.86 (3H, t). MS: m/z 434.0 (M+H$^+$).

Example XII-22

5-(2-Methoxy-5-(trifluoromethoxy)phenylsulfonamido)-N-cyclohexylnicotinamide

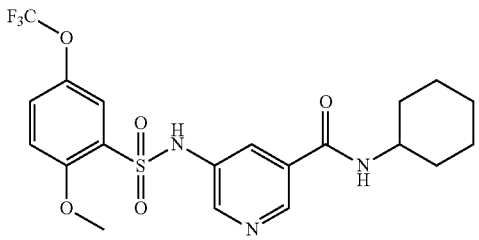 [SMILES: COc1ccc(OC(F)(F)F)cc1S(=O)(=O)Nc1cncc(C(=O)NC2CCCCC2)c1]

$^1$H NMR (DMSO-d6, 400 MHz): δ=10.69 (1H, brs), 8.64 (1H, d), 8.41-8.36 (2H, m), 7.86 (1H, s), 7.71-7.63 (2H, m), 7.30 (1H, d), 3.84 (3H, s), 3.70-3.68 (1H, m), 1.82-1.56 (5H, m), 1.30-1.00 (5H, m). MS: m/z 474.1 (M+H$^+$).

Example XII-23

5-[(5-Methoxy-2-trifluoromethoxy-benzenesulfonyl)-methyl-amino]-nicotinic acid methyl ester

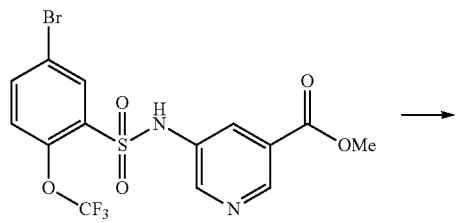

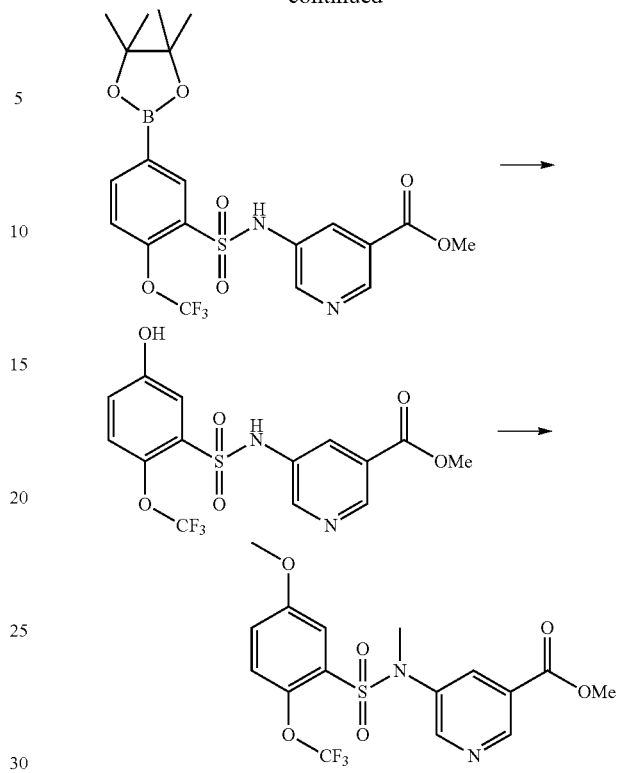

Step 1: 5-(5-Bromo-2-trifluoromethoxy-benzenesulfonylamino)-nicotinic acid methyl ester (200 mg, 0.44 mmol), bis(pinacolato)diboron (112 mg, 0.44 mmol), Pd(dppf)Cl$_2$ (25 mg, 2.2% mmol), AcOK (86 mg, 0.88 mmol) were stirred in 1,4-dioxane (5 mL) at 100° C. under N$_2$ for 4 hours. After cooled to room temperature, the mixture was partitioned between EtOAc (20 mL) and water (10 mL). The aqueous phase was extracted with EtOAc (10 mL×3) and the combined organic phase was dried over Na$_2$SO$_4$. The solution was concentrated in vacuum to give 150 mg of mixture of boronic acid and boronic ester.

Step 2: The above mixture was dissolved in THF (5 mL) followed by NaOH (18 mg, 0.44 mmol), H$_2$O$_2$ (0.5 mL). The mixture was stirred at 50° C. for 1 h. The solvent was concentrated in vacuum and the residue was dissolved in water (10 mL). The mixture was extracted with EtOAc (10 mL×3). The organic layer was washed with brine (10 mL) and dried over anhydrous Na$_2$SO$_4$. The solution was concentrated in vacuum. The residue was purified by prep-TLC (PE/EtOAc, 3/1) to afford 60 mg (two-step yield: 35%) of 5-(5-hydroxy-2-trifluoromethoxy-benzenesulfonylamino)-nicotinic acid methyl ester as white solid.

Step 3: To a solution of 5-(5-hydroxy-2-trifluoromethoxy-benzenesulfonylamino)-nicotinic acid methyl ester (60 mg, 0.15 mmol) in DMF (1 mL) was added K$_2$CO$_3$ (25 mg, 0.18 mmol) and methyl iodide (42 mg, 0.30 mmol) at room temperature, then the mixture was stirred at 80° C. overnight. After cooled to room temperature, the solvent was removed in vacuum. The residue was diluted with EtOAc (20 ml). The mixture was washed with water, brine and dried over Na$_2$SO$_4$. The solution was evaporated to dryness and purified by prep-HPLC to afford 18 mg (yield: 29%) of 5-[(5-methoxy-2-trifluoromethoxy-benzenesulfonyl)-methyl-amino]-nicotinic acid methyl ester as white solid.

$^1$H NMR (CD$_3$OD, 400 MHz): δ=8.88 (1H, d), 8.57 (1H, d), 8.09 (1H, t), 7.33 (1H, d), 7.26 (1H, d), 7.20-7.17 (1H, m), 3.85 (3H, s), 3.74 (3H, s), 3.25 (3H, s). MS: m/z 421.1 (M+H$^+$).

Example XIII

Example XIII-1

5-Fluoro-2-methoxy-N-pyridin-3-yl-benzenesulfonamide

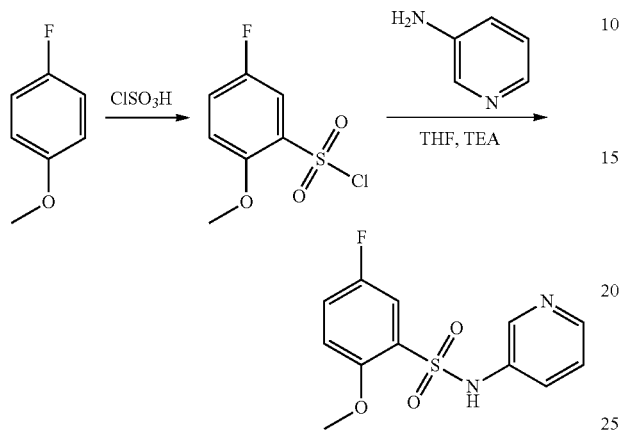

To a stirred ClSO₃H (50 mL) was added 1-fluoro-4-methoxy-benzene (10.0 g, 79.4 mmol) dropwise at 25° C. The mixture was stirred at this temperature for 3 hours. The mixture was poured into ice water (200 mL) and extracted with EtOAc (200 mL). The organic layer was washed with brine (100 mL), dried over Na₂SO₄ and evaporated in vacuum to give 12 g of crude product. The crude was purified by silica gel column chromatography (PE/EtOAc, 20/1) to give 10.0 g of 5-fluoro-2-methoxy-benzenesulfonyl chloride (yield: 56%) as yellow oil.

The mixture of 5-fluoro-2-methoxy-benzenesulfonyl chloride (3 g, 13.4 mmol), pyridine-3-ylamine (1.89 g, 13.3 mmol), TEA (2.7 g, 26.7 mmol) in anhydrous THF (30 mL) was stirred at room temperature overnight. To the mixture was added water (50 mL). The mixture was extracted with EtOAc (50 mL×3). The organic layer was dried over Na₂SO₄. The solution was concentrated to dryness and the residue solid was re-crystallized from DCM to give 2.3 g (yield: 52%) of 5-fluoro-2-methoxy-N-pyridin-3-yl-benzenesulfonamide as yellow solid.

$^1$H NMR (DMSO-d$_6$, 400 MHz): δ=10.45 (1H, brs), 8.31 (1H, d), 8.22 (1H, dd), 7.55 (1H, dd), 7.47-7.51 (2H, m), 7.19-7.29 (2H, m), 3.85 (3H, s). MS: m/z 283.0 (M+H$^+$).

Example XIII-2

5-Bromo-2-methoxy-N-pyridin-3-yl-benzenesulfonamide

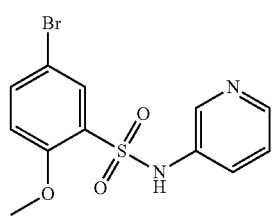 [SMILES: COc1ccc(Br)cc1S(=O)(=O)Nc1cccnc1]

To a stirred mixture of pyridine-3-ylamine (2.5 g, 8.8 mmol) and 5-bromo-2-methoxy-benzenesulfonyl chloride (15.8 g, 55.6 mmol) in pyridine (60 mL) was added DMAP (187 mg, 0.88 mmol). The mixture was stirred at 40° C. for 4 hours. The mixture was cooled, concentrated to dryness in vacuum. The residue was diluted with MeOH (100 mL) and stirred for 30 minutes. The suspended solid was filtered and washed with methanol (50 mL), evaporated in vacuum to give 12.1 g (yield: 70%) of 5-(5-bromo-2-methoxy-benzenesulfonylamino)-nicotinic acid methyl ester as white solid.

$^1$H NMR (DMSO-d$_6$, 400 MHz): δ=10.43 (1H, brs), 8.30 (1H, d), 8.23 (1H, dd), 7.78-7.74 (2H, m), 7.48-7.51 (1H, m), 7.28 (1H, dd), 7.17 (1H, d), 3.85 (3H, s). MS: m/z 342.8 (M+H$^+$).

Example XIII-3

5-Chloro-2-methoxy-N-pyridin-3-yl-benzenesulfonamide

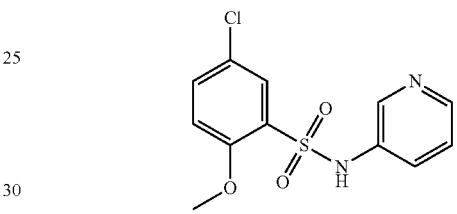

The procedure is similar to 5-bromo-2-methoxy-N-pyridin-3-yl-benzenesulfonamide in Example XIII-2.

$^1$H NMR (DMSO-d$_6$, 400 MHz): δ=10.44 (1H, brs), 8.30 (1H, d), 8.23 (1H, dd), 7.64-7.71 (2H, m), 7.48-7.51 (1H, m), 7.27 (1H, dd), 7.23 (1H, d), 3.86 (3H, s). MS: m/z 298.9 (M+H$^+$).

Example XIII-4

5-(5-Fluoro-2-trifluoromethoxy-benzenesulfonylamino)-nicotinamide

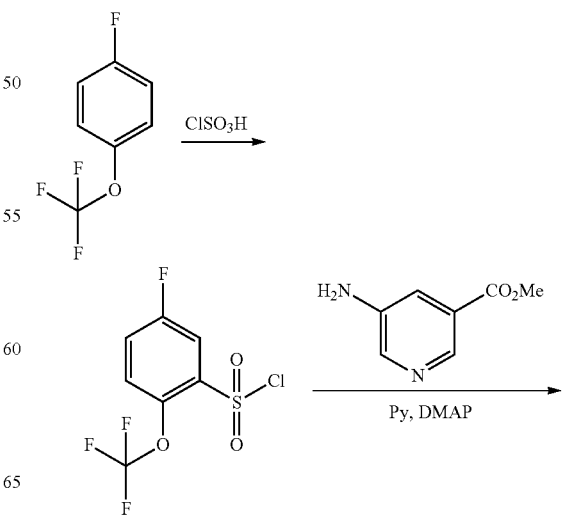

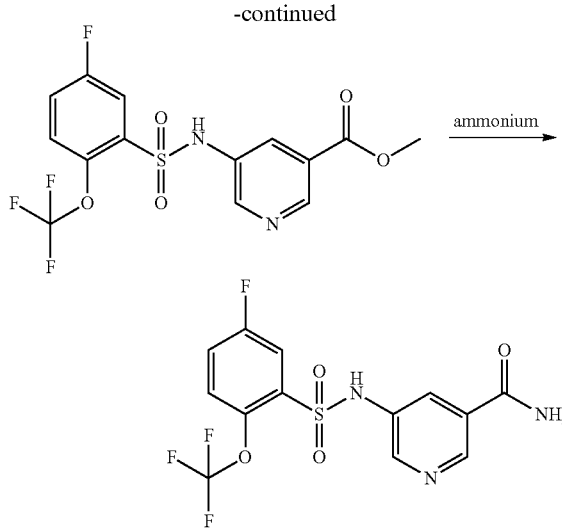

This compound was prepared as described in Example IV-16 and IV-17.

$^1$H NMR (DMSO-d$_6$, 400 MHz): δ=11.12 (1H, s), 8.76 (1H, d), 8.43 (1H, d), 8.16 (1H, s), 7.92 (1H, s), 7.83 (1H, dd), 7.68-7.63 (3H, m). MS: m/z 379.0 (M+H$^+$).

Example XIII-5

5-(5-Fluoro-2-methoxy-benzenesulfonylamino)-nicotinamide

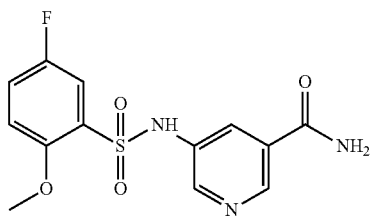 [SMILES: COc1ccc(F)cc1S(=O)(=O)Nc1cncc(C(N)=O)c1]

This compound was prepared as described in Example IV-16 and IV-17.

$^1$H NMR (DMSO-d$_6$, 400 MHz): δ=10.60 (1H, brs), 8.72 (1H, d), 8.44 (1H, d), 8.15 (1H, brs), 7.93 (1H, s), 7.64-7.61 (2H, m), 7.51-7.47 (1H, m), 7.27-7.24 (1H, m), 3.84 (3H, s). MS: m/z 326.0 (M+H$^+$).

Example XIII-6

5-Bromo-2-methoxy-N-[5-(2-methoxy-pyrimidin-5-yl)-pyridin-3-yl]-benzenesulfonamide

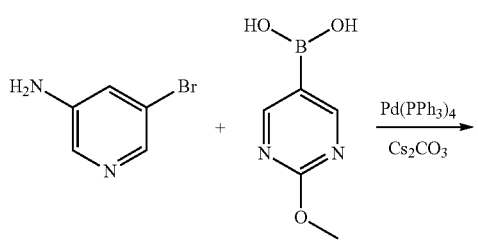

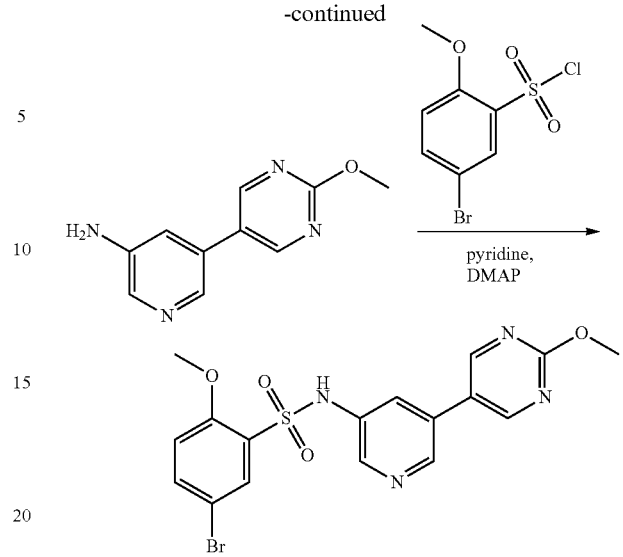

Step 1: The mixture of 5-bromo-pyriden-3-ylamine (2.6 g, 15 mmol), boronic acid (1.9 g, 12.5 mmol), Pd(PPh$_3$)$_4$ (1.45 g, 1.25 mmol), K$_2$CO$_3$ (5.18 g, 37.5 mmol) in DMF (50 mL) was stirred at 120° C. under N$_2$ overnight. The reaction mixture was concentrated in vacuum. The residue was purified by chromatography on silica gel eluting with EA, to give 1.2 g (yield: 47.5%) of 5-(2-methoxypyrimidin-5-yl)-3-pyridylamine as yellow solid.

$^1$H NMR (CDC$_3$, 400 MHz): δ=8.70 (2H, s), 8.17 (1H, d), 8.13 (1H, d), 7.07 (1H, dd), 4.07 (3H, s).

Step 2: To a stirred mixture of 5-(2-methoxypyrimidin-5-yl)-3-pyridylamine (0.876 g, 4.34 mmol) and 5-bromo-2-methoxy-benzenesulfonyl chloride (1.36 g, 4.77 mmol) in pyridine (10 mL) was added DMAP (26 mg, 0.22 mmol). The mixture was stirred at 55° C. for 17 hours. The mixture was cooled, concentrated to dryness. The residue was diluted with MeOH (100 mL) and stirred for 30 minutes. The suspended solid was filtered and washed with methanol (5 mL), evaporated in vacuum to dryness to give 0.96 g (yield: 49%) of 5-(5-bromo-2-methoxy-benzenesulfonylamino)-nicotinic acid methyl ester as yellow solid.

$^1$H NMR (DMSO-d$_6$, 400 MHz): δ 10.36 (s, 1H), 8.80 (2H, m), 8.58 (1H, s), 8.35 (1H, d), 7.88 (1H, d), 7.72-7.74 (2H, m), 7.17 (1H, d), 3.98 (3H, s), 3.83 (3H, s). MS: m/z 451 (M+H$^+$).

Example XIII-7

5-Fluoro-2-methoxy-N-[5-(2-methoxy-pyrimidin-5-yl)-pyridin-3-yl]-benzenesulfonamide

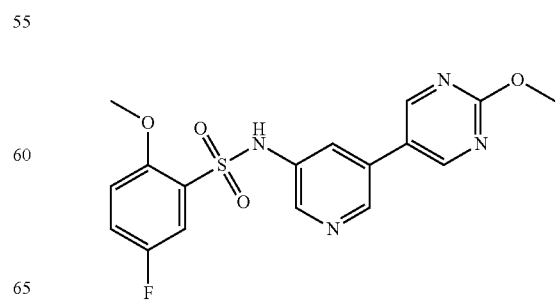

This compound was prepared as described in Example XIII-6.

¹H NMR (DMSO-d₆, 400 MHz): δ 10.61 (1H, s), 8.85 (2H, s), 8.59 (1H, d), 8.33 (1H, d), 7.75 (1H, dd), 7.66 (1H, dd), 7.49 (1H, td), 7.23 (1H, dd), 3.97 (3H, s), 3.85 (3H, s). MS: m/z 391 (M+H⁺).

Example XIII-8

5-Chloro-2-methoxy-N-[5-(2-methoxy-pyrimidin-5-yl)-pyridin-3-yl]-benzenesulfonamide

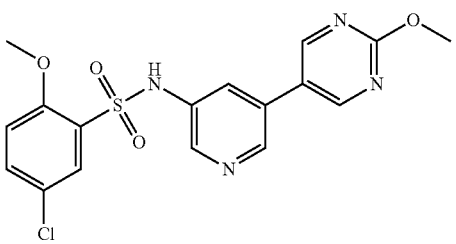 [SMILES: COc1ncc(-c2cncc(NS(=O)(=O)c3cc(F)ccc3OC)c2)cn1]

This compound was prepared as described in Example XIII-6.

¹H NMR (DMSO-d₆, 400 MHz): δ 10.6 (1H, brs), 8.85 (2H, m), 8.80 (1H, d), 8.33 (1H, d), 7.79 (1H, d), 7.74 (1H, d), 7.67 (1H, dd), 7.24 (1H, d), 3.97 (3H, s), 3.86 (3H, s). MS: m/z 407 (M+H⁺).

Example XIII-9

5-Chloro-2-methoxy-N-(6'-methoxy-[3,3']bipyridinyl-5-yl)-benzenesulfonamide

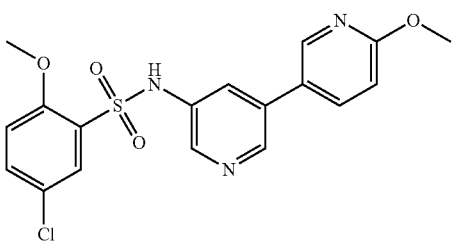 [SMILES: COc1ccc(-c2cncc(NS(=O)(=O)c3cc(Cl)ccc3OC)c2)cn1]

This compound was prepared as described in Example XIII-6.

¹H NMR (DMSO-d₆, 400 MHz): δ=10.58 (1H, s), 8.55 (1H, d), 8.40 (1H, d), 8.29 (1H, d), 7.93 (1H, dd), 7.78 (1H, d), 7.66 (1H, dd), 7.24 (1H, d), 6.95 (1H, d), 3.90 (3H, s), 3.86 (3H, s).

Example XIII-10

5-Fluoro-2-methoxy-N-(6'-methoxy-[3,3']bipyridinyl-5-yl)-benzenesulfonamide

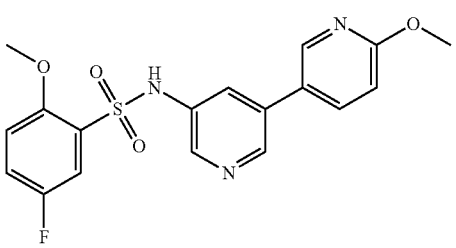 [SMILES: COc1ccc(-c2cncc(NS(=O)(=O)c3cc(F)ccc3OC)c2)cn1]

This compound was prepared as described in Example XIII-6.

¹H NMR (DMSO-d₆, 400 MHz): δ=10.56 (1H, s), 8.54 (1H, d), 8.39 (1H, d), 8.29 (1H, d), 7.93 (1H, dd), 7.62-7.68 (2H, m), 7.48-7.49 (1H, m), 7.23 (1H, dd), 6.95 (1H, d), 3.90 (3H, s), 3.85 (3H, s). MS: m/z 390.1 (M+H⁺).

Example XIII-11

5-Fluoro-2-methoxy-N-[5-(4-methoxy-phenyl)-pyridin-3-yl]-benzenesulfonamide

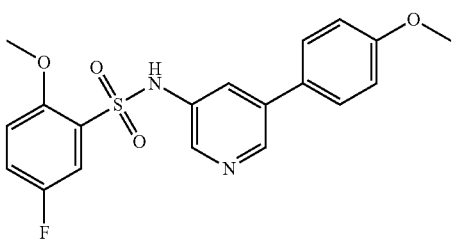 [SMILES: COc1ccc(-c2cncc(NS(=O)(=O)c3cc(F)ccc3OC)c2)cc1]

This compound was prepared as described in Example XIII-6.

¹H NMR (DMSO-d₆, 400 MHz): δ 10.51 (1H, s), 8.50 (1H, d), 8.24 (1H, d), 7.66 (1H, t), 7.61 (1H, dd), 7.51 (2H, d), 7.48 (1H, dd), 7.22 (1H, dd), 7.05 (2H, d), 3.85 (3H, s), 3.80 (3H, s). MS: m/z 389.1 (M+H⁺).

Example XIII-12

5-Chloro-2-methoxy-N-[5-(4-methoxy-phenyl)-pyridin-3-yl]-benzenesulfonamide

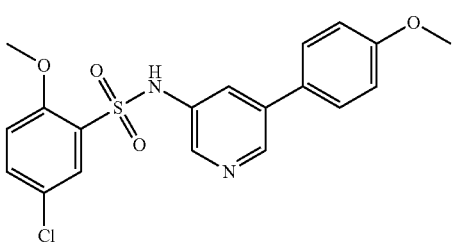

This compound was prepared as described in Example XIII-6.

¹H NMR (DMSO-d₆, 400 MHz): δ 10.52 (1H, s), 8.51 (1H, d), 8.24 (1H, d), 7.77 (1H, d), 7.70-7.62 (2H, m), 7.51 (2H, d), 7.24 (1H, d), 7.06 (2H, d), 3.86 (3H, s), 3.80 (3H, s). MS: m/z 405 (M+H⁺).

Example XIII-13

5-Fluoro-2-methoxy-N-[5-(4-cyano-phenyl)-pyridin-3-yl]-benzenesulfonamide

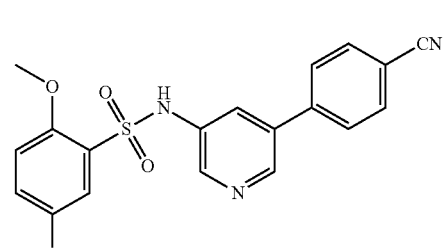

This compound was prepared as described in Example XIII-6.

$^1$H NMR (DMSO-d$_6$, 400 MHz): δ 10.62 (1H, s), 8.62 (1H, d), 8.36 (1H, d), 7.97 (2H, d), 7.88-7.71 (3H, m), 7.63 (1H, dd), 7.49 (1H, td), 7.23 (1H, dd), 3.83 (3H, s). MS: m/z 384 (M+H$^+$).

Example XIII-14

5-Chloro-2-methoxy-N-[5-(4-cyano-phenyl)-pyridin-3-yl]-benzenesulfonamide

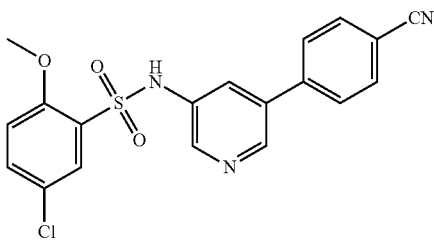 [SMILES: COc1ccc(Cl)cc1S(=O)(=O)Nc1cncc(-c2ccc(C#N)cc2)c1]

This compound was prepared as described in Example XIII-6.

$^1$H NMR (DMSO-d$_6$, 400 MHz): δ 10.64 (1H, s), 8.62 (1H, d), 8.35 (1H, d), 7.97 (2H, d), 7.82-7.75 (4H, m), 7.66 (1H, dd), 7.23 (1H, d), 3.84 (3H, s). MS: m/z 400.1 (M+H$^+$).

BIOLOGICAL EXAMPLES

Example I

Assays for Agents that Inhibit TNAP

Compound Screening Library

A compound library was supplied by the NIH Molecular Libraries Small Molecule Repository. Compounds were selected to represent diversified chemical space with clusters of closely related analogues to aid in the HTS-based structure-activity based relationship studies.

Expression and Preparation of Test Enzymes

Expression plasmids containing a secreted epitope-tagged TNAP were transfected into COS-1 cells for transient expression. The medium was replaced with Opti-MEM 24 h later and serum-free media containing secreted proteins was collected 60 hours after electroporation. The medium was dialyzed against TBS containing 1 mM MgCl$_2$ and 20 mM ZnC$_2$ (to remove phosphate) and filtered through a 0.22 μm cellulose acetate filter.

High Throughput Screening Assays i. TNAP Colorimetric Assay

A TNAP stock solution was diluted 120-fold and about 12 μl of diluted TNAP solution was dispensed into 96 well microtiter plates with half area bottom (Costar, Corning, N.Y.) by an auto dispenser (Matrix, Hudson, N.H.). A robotic liquid handler, Biomek™ FX (Beckman Coulter, Fullerton, Calif.) dispensed about 2.5 μl of each compound (dissolved in 10% DMSO) from the library plates. Plates were incubated at room temperature for at least one hour to allow TNAP to interact with each compound prior to addition of about 10.5 μl substrate solution (1.19 mM pNPP). After about 30 minutes of incubation, A$_{405\ nm}$ was measured with a microtiter plate reader, Analyst™ HT (Molecular Devices, Sunnyvale, Calif.). Both the enzyme (TNAP) and substrate (pNPP) solution were made in diethanolamine (DEA) buffers; the final reaction contains 1 M DEA-HCl buffer, pH about 9.8, containing about 1 mM MgCl$_2$ and about 20 μM ZnC$_2$. The concentration of TNAP and pNPP (final about 0.5 mM) were adjusted to obtain A$_{405\ nm}$~0.4, while maintaining good sensitivity to the known inhibitors levamisole and phosphate, used as positive controls. K$_m$ obtained with a 1/120 dilution of TNAP and a fixed incubation period of about 30 minutes, was 0.58+0.081 mM.

ii. TNAP Luminescence Assay

Compound aliquots (4 μL@ 100 μM in 10% DMSO) were added with about 8 μL of TNAP working solution, prepared by 800-fold dilution of TNAP in 2.5-fold assay buffer (250 mM DEA, pH 9.8, 2.5 mM MgCl$_2$, 0.05 mM ZnC$_2$). CDP-star substrate solution (about 8 μL of 125 μM in water) was added to each well. The final concentration of CDP-star was equal its K$_m$ value determined in the assay buffer. Plates (white 384-well small volume Greiner 784075) were incubated at room temperature for about 0.5 hour and luminescence signal was measured using an En Vision plate reader (PerkinElmer). Levamisole (1 mM final concentration) or 2% DMSO were utilized as positive and negative controls, respectively. Dose-response confirmation was performed under similar conditions using 10-point 2-fold serial dilution of compounds.

Enzyme Kinetic Experiments—Phosphatase Selectivity Assay

To determine the inhibition selectivity for inhibitor candidates, human TNAP, PLAP or IAP were added to microtiter plates followed by addition of the substrate pNPP (0.5 mM) and activity was measured in 1 M DEA-HCl buffer, pH 9.8 or in 1 M Tris-HCl buffer, pH 7.5, containing 1 mM MgCl$_2$ and 20 μM ZnC$_2$, in the presence of potential inhibitors (0-30 μM). TNAP, PLAP and IAP activities were adjusted to an approximate λA$_{405\ nm}$, equivalent to 1, measured after 30 min. Residual AP activity in the presence of inhibitors was expressed as percentage of the control activity. To investigate the mechanism of inhibition, double reciprocal plots of enzyme activity (expressed as mA$_{405\ nm}$ min-1) vs. substrate concentration were constructed, in the presence of various concentrations of added inhibitors (0-30 μM). The y-axis intercepts of the 1/v vs. 1/[S] plots, were then plotted vs. [I] to graphically extract K$_i$ values as the x-intercept in this plot. The numerical values from y- and x-intercepts were derived via linear regression analysis, using software Prism 3.02 (GraphPad Software, CA). These analyses were performed, using pNPP as a substrate in 1 M DEA-HCl buffer, pH 9.8, as well as in 1 M Tris-HCl buffer, pH 7.5, to determine K$_i$ at optimal and physiological pH respectively. Inhibitors were further tested and sorted based on their kinetic properties at pH 7.4 using PPi, the relevant natural substrate of TNAP. In this part of the study, pyrophosphate sodium salt (99% ACS reagent, Sigma-Aldrich, St Louis, Mo.) was used as a substrate. Amounts of released phosphate were measured using the Biomol Green Reagent (Biomol Research Laboratories, Inc., Plymouth Meeting, Pa.). Finally, to document the potency of selected inhibitors in physiological media, TNAP inhibition by compounds of Formula I-IV (0-30 μM) was studied at pH 7.4, during catalysis of 0.1 mM pNPP, in the presence of increasing concentrations of Na$_2$HPO$_4$ (0-10 mM) and pyrophosphate (0-40 mM).

Compound docking was performed using the Flexx program, part of the Sybyl package from Trios, Inc. Formal charges were used for protein and compound atoms. Heteroatoms (phosphate, zincs and magnesium) were considered as part of the pocket while docking.

TNAP Activity in Plasma

Compounds of Formula I-IV described herein were added to Grenier 1536-well clear plates. 1.5 µl of 4× buffer and substrate mixture was added by MultiDrop Combi to the plates. 4.5 µl of mouse or human plasma was then added to the wells with a Bravo liquid handler. The 4× buffer and substrate mix consisted of 400 mM Tris, 80 µm $ZnC_2$, 4 mM $MgCl_2$ and either 4 mM paranitrophenol phosphate (pNPP) or 8 mM phenolphthalein monophosphate (PPMP) as substrate. The compounds and substrate were incubated in the plates with human plasma for 6 to 30 hours at room temperature with the assay plate sealed. The duration of steady-state catalysis depended on the phosphatase activity of the plasma. For pNPP substrate, $OD_{380}$ measurements were taken and the plasma catalytic rate was calculated. For PPMP substrate, color developer consisting of sodium carbonate and sodium hydroxide was added to adjust pH such that phenolphthalein color deepened but remained stable prior to $OD_{555}$ measurements and plasma catalytic rate calculation. Using two substrates, compounds that optically interfere with the spectrophotometric assay were filtered out.

Table 1 below shows assay data for certain compounds of Formula I-IV described herein.

For the TNAP (PPi) data, "A" indicates an IC50 of less than 0.1 µM, "B" indicates an IC50 of greater than or equal to 0.1 µM and less than or equal to 1 µM, and "C" indicates and IC50 of greater than 1 µM.

For the human plasma TNAP data (pNPP), "A" indicates an IC50 of less than 5 µM, "B" indicates an IC50 of greater than or equal to 5 µM and less than or equal to 50 µM, and "C" indicates an IC50 of greater than 50 µM.

TABLE 1

Biological Activity of Compounds of Formula I-IV.

| EXAMPLE | TNAP (PPi) IC50 (µM) | TNAP human plasma (pNPP) IC50 (µM) |
| --- | --- | --- |
| Example I-1 | A | A |
| Example I-2 | B | A |
| Example I-3 | A | A |
| Example I-4 | B | A |
| Example I-5 | C | |
| Example I-6 | B | |
| Example I-7 | B | B |
| Example I-8 | B | |
| Example I-9 | B | |
| Example I-10 | C | |
| Example I-11 | C | |
| Example I-12 | C | |
| Example I-13 | C | |
| Example I-14 | B | B |
| Example I-15 | C | |
| Example I-16 | C | |
| Example I-17 | C | |
| Example I-18 | C | |
| Example I-19 | C | |
| Example I-20 | C | |
| Example I-21 | C | |
| Example I-22 | C | |
| Example I-23 | C | |
| Example II-1 | A | A |
| Example II-2 | A | B |
| Example II-3 | A | B |
| Example II-4 | C | C |
| Example II-5 | A | |
| Example II-6 | B | C |
| Example II-7 | B | |
| Example II-8 | C | |
| Example II-9 | B | |
| Example II-10 | A | |
| Example II-11 | C | |
| Example II-12 | C | |
| Example II-13 | A | B |
| Example II-14 | B | |
| Example II-15 | A | A |
| Example II-16 | B | |
| Example II-17 | B | |
| Example II-18 | C | |
| Example II-19 | C | |
| Example II-20 | B | |
| Example II-21 | B | |
| Example II-22 | C | |
| Example II-23 | B | |
| Example III-1 | A | B |
| Example III-2 | B | B |
| Example III-3 | A | B |
| Example III-4 | B | |
| Example III-5 | B | |
| Example III-6 | B | |
| Example III-7 | A | A |
| Example III-8 | A | A |
| Example III-9 | A | A |
| Example III-10 | B | C |
| Example III-11 | B | C |
| Example III-12 | B | C |
| Example III-13 | B | C |
| Example III-14 | B | C |
| Example III-15 | B | C |
| Example III-16 | A | C |
| Example III-17 | A | C |
| Example III-18 | A | C |
| Example III-19 | B | C |
| Example III-20 | B | C |
| Example III-21 | B | C |
| Example III-22 | B | C |
| Example III-23 | B | B |
| Example III-24 | B | C |
| Example III-25 | A | |
| Example III-26 | A | |
| Example III-27 | A | |
| Example III-28 | A | |
| Example III-29 | A | C |
| Example III-30 | A | B |
| Example III-31 | A | B |
| Example III-32 | A | |
| Example III-33 | A | B |
| Example III-34 | B | |
| Example III-35 | A | |
| Example III-36 | A | |
| Example III-37 | B | B |
| Example III-38 | B | C |
| Example III-39 | B | C |
| Example III-40 | A | |
| Example III-41 | A | |
| Example III-42 | A | |
| Example III-43 | B | |
| Example III-44 | B | |
| Example III-45 | B | |
| Example III-46 | A | |
| Example III-47 | A | |
| Example III-48 | A | |
| Example III-49 | B | |
| Example III-50 | B | |
| Example III-51 | B | |
| Example III-52 | B | |
| Example III-53 | B | |
| Example III-54 | B | |
| Example III-55 | A | |
| Example III-56 | A | |
| Example III-57 | A | |
| Example III-58 | A | |
| Example III-59 | A | |
| Example III-60 | A | |

TABLE 1-continued

Biological Activity of Compounds of Formula I-IV.

| EXAMPLE | TNAP (PPi) IC50 (µM) | TNAP human plasma (pNPP) IC50 (µM) |
|---|---|---|
| Example III-61 | B | B |
| Example III-62 | A | |
| Example III-63 | A | |
| Example III-64 | A | A |
| Example III-65 | A | |
| Example III-66 | A | |
| Example III-67 | A | |
| Example III-68 | A | |
| Example III-69 | A | |
| Example III-70 | A | B |
| Example III-71 | A | B |
| Example III-72 | A | B |
| Example III-73 | A | |
| Example III-74 | A | |
| Example III-75 | A | |
| Example III-76 | A | B |
| Example III-77 | A | C |
| Example III-78 | A | C |
| Example III-79 | A | |
| Example III-80 | A | |
| Example III-81 | A | |
| Example III-82 | A | |
| Example III-83 | A | |
| Example III-84 | A | |
| Example III-85 | A | |
| Example III-86 | A | |
| Example III-87 | A | |
| Example III-88 | A | A |
| Example III-89 | A | A |
| Example III-90 | A | A |
| Example III-91 | B | |
| Example III-92 | A | B |
| Example III-93 | A | B |
| Example III-94 | A | |
| Example III-95 | A | |
| Example III-96 | A | |
| Example IV-1 | A | A |
| Example IV-2 | A | A |
| Example IV-3 | A | B |
| Example IV-4 | A | B |
| Example IV-5 | A | |
| Example IV-6 | A | |
| Example IV-7 | A | A |
| Example IV-8 | A | B |
| Example IV-9 | A | |
| Example IV-10 | A | |
| Example IV-11 | A | A |
| Example IV-12 | A | |
| Example IV-13 | A | |
| Example IV-14 | A | |
| Example IV-15 | A | |
| Example IV-16 | B | A |
| Example IV-17 | A | A |
| Example IV-18 | B | A |
| Example IV-19 | B | B |
| Example IV-20 | A | B |
| Example IV-21 | B | A |
| Example IV-22 | B | |
| Example IV-23 | B | C |
| Example IV-24 | C | B |
| Example IV-25 | B | B |
| Example IV-26 | A | A |
| Example IV-27 | B | |
| Example IV-28 | B | |
| Example IV-29 | A | |
| Example IV-30 | A | |
| Example IV-31 | B | |
| Example IV-32 | B | |
| Example IV-33 | B | |
| Example IV-34 | B | |
| Example IV-35 | B | |
| Example IV-36 | B | |
| Example IV-37 | B | |
| Example IV-38 | B | |
| Example IV-39 | A | |
| Example IV-40 | B | |
| Example IV-41 | B | |
| Example IV-42 | B | |
| Example IV-43 | B | B |
| Example IV-44 | A | |
| Example V-1 | C | |
| Example V-2 | C | |
| Example V-3 | C | C |
| Example V-4 | C | |
| Example V-5 | B | |
| Example V-6 | B | |
| Example V-7 | C | C |
| Example V-8 | C | C |
| Example V-9 | C | |
| Example V-10 | C | |
| Example V-11 | C | |
| Example V-12 | C | |
| Example V-13 | C | |
| Example V-14 | C | |
| Example V-15 | C | |
| Example V-16 | C | |
| Example V-17 | C | |
| Example V-18 | C | |
| Example V-19 | B | C |
| Example V-20 | C | C |
| Example V-21 | C | |
| Example V-22 | C | |
| Example V-23 | C | C |
| Example V-24 | B | |
| Example V-25 | C | |
| Example V-26 | C | |
| Example V-27 | C | |
| Example V-28 | C | |
| Example V-29 | C | |
| Example VI-1 | A | B |
| Example VI-2 | A | B |
| Example VII-1 | C | |
| Example VII-2 | C | |
| Example VII-3 | C | |
| Example VII-4 | C | |
| Example VII-5 | C | |
| Example VII-6 | C | |
| Example VII-7 | C | |
| Example VII-8 | C | |
| Example VII-9 | C | |
| Example VII-10 | C | |
| Example VII-11 | C | |
| Example VII-12 | C | |
| Example VII-13 | C | |
| Example VII-14 | C | |
| Example VII-15 | C | |
| Example VII-16 | C | |
| Example VII-17 | C | |
| Example VII-18 | C | |
| Example VII-19 | C | |
| Example VII-20 | C | |
| Example VII-21 | C | |
| Example VIII-1 | C | |
| Example VIII-2 | C | |
| Example VIII-3 | C | C |
| Example VIII-4 | C | B |
| Example VIII-5 | B | |
| Example VIII-6 | C | |
| Example VIII-7 | C | |
| Example VIII-8 | C | |
| Example VIII-9 | B | |
| Example VIII-10 | C | |
| Example VIII-11 | C | |
| Example VIII-12 | C | |
| Example VIII-13 | C | |
| Example VIII-14 | C | |

TABLE 1-continued

Biological Activity of Compounds of Formula I-IV.

| EXAMPLE | TNAP (PPi) IC50 (µM) | TNAP human plasma (pNPP) IC50 (µM) |
|---|---|---|
| Example VIII-15 | C | C |
| Example VIII-16 | C | C |
| Example VIII-17 | C | |
| Example VIII-18 | C | |
| Example VIII-19 | C | |
| Example VIII-20 | C | |
| Example IX-1 | A | |
| Example IX-2 | A | |
| Example IX-3 | A | |
| Example IX-4 | A | C |
| Example IX-5 | B | B |
| Example IX-6 | A | B |
| Example IX-7 | A | A |
| Example IX-8 | B | C |
| Example IX-9 | C | C |
| Example IX-10 | B | B |
| Example IX-11 | B | B |
| Example IX-12 | A | B |
| Example IX-13 | B | B |
| Example IX-14 | A | A |
| Example IX-15 | B | A |
| Example IX-16 | A | A |
| Example X-1 | A | |
| Example X-2 | B | |
| Example X-3 | A | C |
| Example X-4 | A | |
| Example X-5 | C | |
| Example X-6 | A | B |
| Example XI-1 | A | C |
| Example XI-2 | A | C |
| Example XI-3 | B | C |
| Example XI-4 | B | C |
| Example XI-5 | B | C |
| Example XI-6 | A | C |
| Example XI-7 | A | C |
| Example XI-8 | A | C |
| Example XI-9 | B | C |
| Example XI-10 | B | C |
| Example XI-11 | B | C |
| Example XI-12 | A | B |
| Example XI-13 | A | B |
| Example XI-14 | B | C |
| Example XI-15 | B | C |
| Example XI-16 | A | C |
| Example XI-17 | B | C |
| Example XI-18 | B | C |
| Example XI-19 | B | C |
| Example XI-20 | B | C |
| Example XI-21 | B | C |
| Example XI-22 | B | C |
| Example XI-23 | C | C |
| Example XI-24 | B | C |
| Example XI-25 | B | C |
| Example XI-26 | A | C |
| Example XI-27 | B | C |
| Example XI-28 | A | B |
| Example XI-29 | A | B |
| Example XI-30 | A | B |
| Example XI-31 | A | B |
| Example XI-32 | A | B |
| Example XII-1 | B | B |
| Example XII-2 | B | B |
| Example XII-3 | A | C |
| Example XII-4 | A | B |
| Example XII-5 | B | B |
| Example XII-6 | B | B |
| Example XII-7 | C | C |
| Example XII-8 | B | C |
| Example XII-9 | B | B |
| Example XII-10 | A | B |
| Example XII-11 | A | C |
| Example XII-12 | A | B |
| Example XII-13 | A | A |

TABLE 1-continued

Biological Activity of Compounds of Formula I-IV.

| EXAMPLE | TNAP (PPi) IC50 (µM) | TNAP human plasma (pNPP) IC50 (µM) |
|---|---|---|
| Example XII-14 | B | B |
| Example XII-15 | B | B |
| Example XII-16 | A | C |
| Example XII-17 | A | C |
| Example XII-18 | A | B |
| Example XII-19 | B | A |
| Example XII-20 | B | B |
| Example XII-21 | C | B |
| Example XII-22 | B | C |
| Example XII-23 | C | C |
| Example XIII-1 | | A |
| Example XIII-2 | | A |
| Example XIII-3 | | A |
| Example XIII-4 | | A |
| Example XIII-5 | | A |
| Example XIII-6 | | A |
| Example XIII-7 | | A |
| Example XIII-8 | | A |
| Example XIII-9 | | B |
| Example XIII-10 | | B |
| Example XIII-11 | | B |
| Example XIII-12 | | B |
| Example XIII-13 | | B |
| Example XIII-14 | | B |

| | | |
|---|---|---|
| 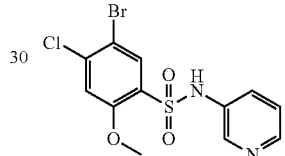 | A | A |
| 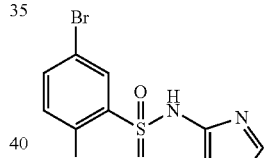 | C | |
| 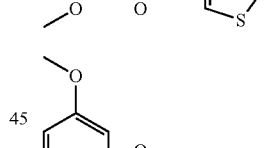 | | C |

A < 0.1 µM     A < 5 µM
0.1 µM ≤ B ≤ 1 µM   5 µM ≤ B ≤ 50 µM
C > 1 µM     C > 50 µM

Example 2

Mouse Model of Medial Vascular Calcification

A conditional knock-in model of GACI was generated via a Cre-mediated expression of a TNAP knock-in transgene (FIG. 1) to assess whether overexpression of TNAP in vascular smooth muscle cells (VSMC) is sufficient to cause medial vascular calcification (MVC). A vector containing the human TNAP coding sequence under the control of the ubiquitous CAG (CMV immediate early enhancer/chicken β-actin promoter fusion) promoter was produced. This construct also included a loxP-flanked "stop cassette" between the promoter and transgene to prevent overexpression in the absence of Cre recombinase. This transgenic construct was introduced into the hypoxanthine phosphoribosyltransferase (Hprt) locus on the X chromosome. Hprt encodes a constitutively expressed housekeeping enzyme involved in nucleotide metabolism and is located in a genomic region with an open chromatin structure that allows permanent access to transcription factors, allowing it to be constitutively active. Targeted insertion at this locus also overcomes any position effects that may occur with random integration methods. This mouse line, named $Hprt^{ALPL}$, was used to examine the effects of TNAP overexpression in VSMCs. $Hprt^{ALPL/ALPL}$ female mice were bred with male mice expressing Cre-recombinase under the control of the VSMC-specific transgelin promoter (Tagln-Cre) (Boucher P et al., Science 300: 329-322 (2003)). By breeding Tagln-Cre homozygous males with $Hprt^{ALPL/ALPL}$ homozygous females, all male offspring are [$Hprt^{ALPL/Y}$; Tagln-Cre$^{+/-}$] and all females are heterozygous for both transgenes.

Figure 2:
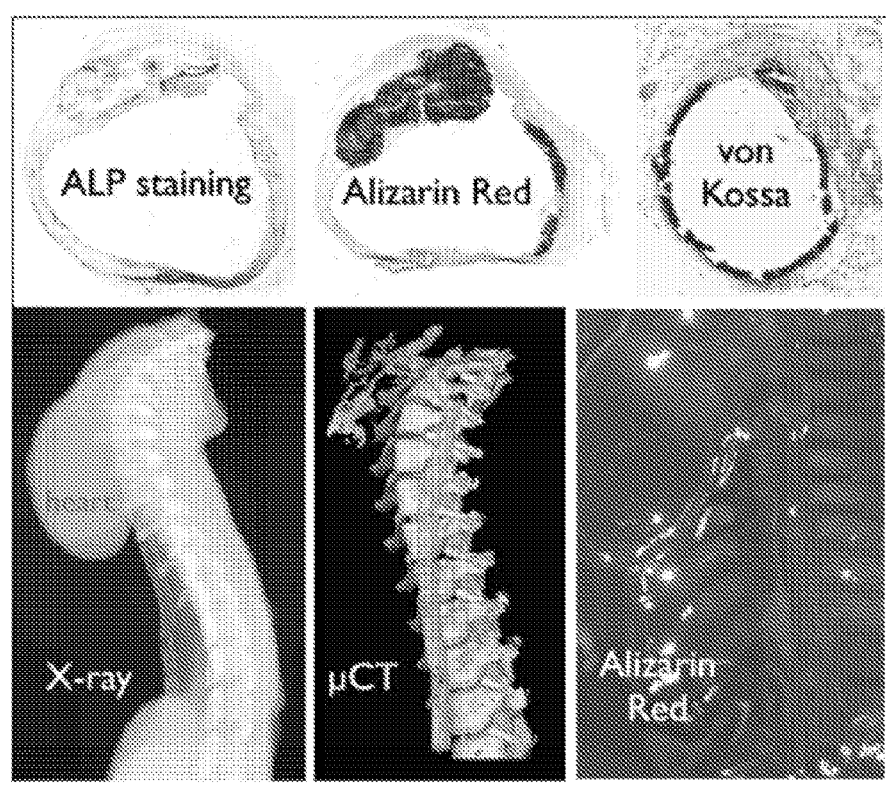
FIG. 2 illustrates the characterization of the phenotype of [Hprt$^{ALPL/Y}$; Tagln-Cre$^{+/-}$] mice. Top panels show histochemical staining for alkaline phosphatase activity (ALP), calcium deposition (Alizarin Red) and phosphate deposition (von Kossa). The lower panels show imaging of aortic calcification by X-ray and micro-computed tomography (gCT) and by whole-mount Alizarin Red staining
Figure 3:
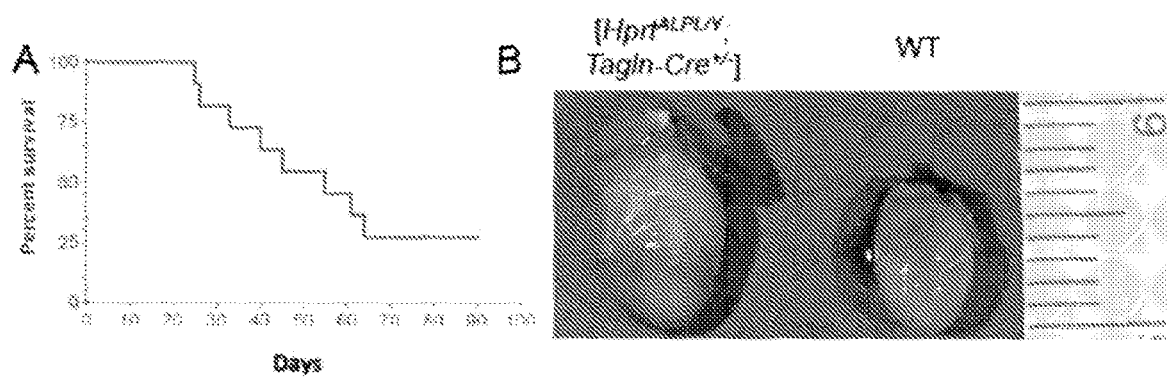
FIG. 3 illustrates the survival curve and heart size in male [Hprt$^{ALPL/Y}$; Tagln-Cre$^{+/-}$] mice. A) Survival curve is based on 17 male mice. B) Heart size at autopsy at 37 days of age.

Characterization of 30-day-old male [$Hprt^{ALPL/Y}$; Tagln-Cre$^{+/-}$] mice shows that overexpression of TNAP in vascular smooth muscle cells (VSMCs) leads to severe calcification, as shown by Alizarin Red and von Kossa staining, as well as X-ray and µCT analysis of the aorta (FIG. 2). Calcification becomes visible by X-ray by 14 days of age and progressively worsens with age until death before 3 months of age (FIG. 3A). The male [$Hprt^{ALPL/Y}$; Tagln-Cre$^{+/-}$] mice also showed 15-fold higher serum alkaline phosphatase activity than WT mice. Necropsy revealed greatly enlarged hearts in the [$Hprt^{ALPL/Y}$; Tagln-Cre$^{+/-}$] mice, indicating cardiac insufficiency as the likely cause of death in these animals (FIG. 3B).

Heterozygous female mice developed MVC more slowly and lived longer. No premature death or cardiac hypertrophy was observed in heterozygous female mice, up to 180 days of age. Alkaline phosphatase activity was found to be increased 4 fold in the heterozygous females as compared to wild-type mice. The data suggests that upregulation of TNAP expression in the vasculature is sufficient to cause MVC.

Example 3

Ex Vivo Study of Mineralization of Aortic Explants

Ex Vivo Studies—

Aortas are carefully cleaned, and cut into two segments for culture. Because of some heterogeneity within aortas, we routinely use eight aortic sections (four mice) per experimental variable. The smooth muscle cells remain viable in culture for at least two weeks with only minor histological changes. Aortic explants are cultured in Dulbecco's Modified Eagle Medium containing 60,000 cpm/mL of 45Ca and 2.9 mM NaH2PO4, to induce mineralization within nine to twelve days. After this culture period, aortic rings are dehydrated and treated with HCl to liberate calcium, which is then measured by liquid scintillation counting. In addition, we will culture VSMCs isolated from the aortas of each mouse model and measure PPi output and changes in gene expression that might be influenced by changes in either local or systemic ePPi concentrations, as per published methods (50).

Example 4

In Vivo [$Hprt_{ALPL}$; Tagln-Cre] Mouse Model

[$Hprt_{ALPL/Y}$; Tagln-Cre$_{+/-}$] male or [$Hprt_{ALPL/WT}$; Tagln-Cre$_{+/-}$] female mice and WT littermate controls are injected with a compound of Formula I-IV and its effectiveness in preventing MVC is assessed, while also any secondary effects of the treatment on skeletal mineralization or other organs is assessed. Evaluation of in vivo efficacy is accomplished by assessing the drug metabolism and pharmacokinetic (DMPK) properties of the TNAP inhibitor of Formula I-IV and assessing PK/PD relationships.

[$HPrt_{ALPL/Y}$; Tagln-Cre$_{+/-}$] male mice are dosed as a model of GACI. The treatment is initiated at 7 days-of-age and treatment continued for 7 weeks until 60 days of age. Residual plasma TNAP activity is used as a surrogate biomarker for treatment efficacy (see FIG. 9, Preliminary Results). Improved survival and changes in the degree of MVC and bone mineralization status is assessed by X-ray, CT, histomorphometry and dynamic histomorphometry and detailed histopathological examination of vascular and skeletal tissues is performed. Furthermore, a detailed histopathological examination of soft tissues is performed, with particular focus on liver and kidney, two organs that express TNAP in humans under physiological conditions. Renal function is studied by measuring serum potassium, sodium, blood urea nitrogen, and creatinine Hepatic function is examined by measuring albumin, liver transaminases, bilirubin, and gamma glutamyl transpeptidase levels. Serum phosphate, calcium and PTH levels are assessed to ensure that the compound of Formula I-IV does not change phosphate or calcium homeostasis. Serial echocardiography, measured by the Vevo 770 Micro-ultrasound System, PWV and blood pressure are used to monitor changes in cardiovascular function during treatment. Changes in concentrations of PPi in plasma and urine are monitored, as well as other biochemical parameters.

[$Hprt_{ALPL/WT}$; Tagln-Cre$_{+/-}$] female mice are used as a model of adult MVC. Here, dosing is initiated at 30 days, in some instances at 14 days-of-age (depending on when MVC becomes apparent) and the female mice are treated for four to eight weeks.

Example 5

Effect of Test Compound in Mouse Model of Medial Vascular Calcification

[$Hprt^{ALPL/Y}$; Tagln-Cre$^{+/-}$] male or [$Hprt^{ALPL/WT}$; Tagln-Cre$^{+/-}$] female mice and wild-type littermate controls are injected with a Test Compound of Formula I-IV in order to assess the effectiveness of a Test Compound in preventing medial vascular calcification. Characterization of levels of medial vascular calcification is performed as described above, with Alizarin Red and von Kossa staining, as well as X-ray and µCT analysis of the aorta. Secondary effects on skeletal or other organ mineralization due to the Test Compound are assessed.

Example 6

Pharmacokinetic Data of a Compound of Formula I-IV in Mice

The bioavailability and plasma pharmacokinetic properties in mice of a compound of Formula I-IV is measured following intravenous, intraperitoneal, subcutaneous, intramuscular and oral administration. Three wild-type mice per time point per route of administration are dosed at various levels. At least one group is dosed intravenously and at least one group is dosed by an extravascular route in order to assess oral bioavailability. Blood is sampled from each group at frequent intervals (e.g. 0.25, 0.5, 1, 2, 4, 6, 8, 12, 24, and 48 hours) and plasma levels of the test compound are assayed using liquid chromatography coupled with tandem mass spectrometry (LC-MS/MS). The plasma-concentration time data are analyzed to obtain the pharmacokinetic profile, including the area under the curve (AUC). Comparison of the AUCs after extravascular and intravenous dosing can be used to construct a time versus concentration graph from which we can determine half-life of the compound, clearance, volume of distribution, total exposure, and maximal concentrations.

Example 7

Vascular Calcification Clinical Trial

Human Clinical Trial of the Safety and/or Efficacy of a TNAP inhibitor (e.g., a compound of Formula I-IV, or a pharmaceutically acceptable salt thereof) therapy.

Objective:

To determine the safety, pharmacokinetics, and efficacy of administered TNAP inhibitor (e.g., a compound of Formula I-IV, or a pharmaceutically acceptable salt thereof).

Study Design:

This will be a Phase I, single-center, open-label, non-randomized dose escalation study followed by a Phase II study in vascular calcification patients (for example uremic patients). The diagnosis of vascular calcification is confirmed by a coronary artery calcium score of greater than 50. Patients must not have received other investigational agents within 3 months of study initiation. Fertile patients must agree to use adequate contraception throughout the study and for 18 months after cessation of treatment with a TNAP inhibitor (e.g., a compound of Formula I-IV). Patients must not be undertaking renal replacement therapy. Patients must also not have had a recent fracture (within the last 3 months). In addition, patients must not have an abnormal rhythm of the heart. Patients must also not currently be taking osteoporosis medication. In addition, patients must not have hypocalcaemia or pre-existing dental diseases. All subjects are evaluated for safety and all blood collections for pharmacokinetic analysis are collected as scheduled. All studies are performed with institutional ethics committee approval and patient consent.

Phase I:

Patients receive (e.g., intravenous, oral, ip, or the like) TNAP inhibitor (e.g., a compound of Formula I-IV, or a pharmaceutically acceptable salt thereof) daily for 4 weeks. Cohorts of 3-6 patients receive escalating doses of TNAP inhibitor (e.g., a compound of Formula I-IV, or a pharmaceutically acceptable salt thereof). Escalation will not be performed until all patients in the previous dose cohort have been treated for 4 weeks and until results obtained 4 weeks after treatment initiation do not reveal toxicity. Doses of TNAP inhibitor (e.g., a compound of Formula I-IV, or a pharmaceutically acceptable salt thereof) may be held or modified for toxicity based on assessments as outlined below. Dose escalation is considered complete, if 2 patients experience a Grade 3 Adverse Event (AE) or if 1 patient experiences Grade 4 AE at a particular cohort.

Phase II:

Patients receive TNAP inhibitor (e.g., a compound of Formula I-IV, or a pharmaceutically acceptable salt thereof) as in phase I at a suitable dose below the dose used in the final cohort. Treatment continues throughout a 24-month study period during which clinical (which includes safety and tolerability) assessments are performed.

Blood Sampling:

Serial blood is drawn by direct vein puncture before and after administration TNAP inhibitor (e.g., a compound of Formula I-IV, or a pharmaceutically acceptable salt thereof). Venous blood samples (5 mL) for determination of serum concentrations are obtained in-hospital during a 24-hour period. Each serum sample is divided into two aliquots. All serum samples are stored at −20° C. Serum samples are shipped on dry ice.

Pharmacokinetics:

Patients undergo plasma/serum sample collection for pharmacokinetic evaluation in-hospital during a 24-hour period. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response:

The primary outcome measure is safety and tolerability, based on conventional laboratory and clinical assessments. The secondary outcome measure is the assessment of changes arterial stiffness measured by pulse wave velocity, changes in vascular calcification on CT scans of superficial femoral artery and aorta, and changes in serum calcium and phosphate levels. Cardiovascular events, including myocardial ischemia, myocardial infarction, cardiac failure, stroke, and/or peripheral vascular disease are also assessed.

Example 8

Ankylosing Spondylitis Clinical Trial

Human Clinical Trial of the Safety and/or Efficacy of a TNAP inhibitor (e.g., a compound of Formula I-IV, or a pharmaceutically acceptable salt thereof) therapy.

Objective:

To determine the safety, pharmacokinetics, and efficacy of administered TNAP inhibitor (e.g., a compound of Formula I-IV, or a pharmaceutically acceptable salt thereof).

Study Design:

This will be a Phase I, single-center, open-label, non-randomized dose escalation study followed by a Phase II study in ankylosing spondylitis patients. Patients must have a diagnosis of AS according to the modified New York Criteria for ankylosing spondylitis, have had active AS based on the opinion of a physician for at least there months, and have active AS with a BASDAI>=4 at the time of the screening visit. Patients must not have received other investigational agents within 3 months of study initiation. Fertile patients must agree to use adequate contraception throughout the study and for 18 months after cessation of treatment with a TNAP inhibitor (e.g., a compound of Formula I-IV). Patients must not have a history of or current inflammatory joint disease of origin other than AS, e.g., rheumatoid arthritis, systemic lupus erythematosus, etc. In addition, patients must not have hypocalcaemia or pre-existing dental diseases. All subjects are evaluated for safety and all blood collections for pharmacokinetic analysis are collected as scheduled. All studies are performed with institutional ethics committee approval and patient consent.

Phase I:

Patients receive (e.g., intravenous, oral, ip, or the like) TNAP inhibitor (e.g., a compound of Formula I-IV, or a pharmaceutically acceptable salt thereof) daily for 4 weeks. Cohorts of 3-6 patients receive escalating doses of TNAP inhibitor (e.g., a compound of Formula I-IV, or a pharmaceutically acceptable salt thereof). Escalation will not be performed until all patients in the previous dose cohort have been treated for 4 weeks and until results obtained 4 weeks after treatment initiation do not reveal toxicity. Doses of TNAP inhibitor (e.g., a compound of Formula I-IV, or a pharmaceutically acceptable salt thereof) may be held or modified for toxicity based on assessments as outlined below. Dose escalation is considered complete, if 2 patients experience a Grade 3 Adverse Event (AE) or if 1 patient experiences Grade 4 AE at a particular cohort.

Phase II:

Patients receive TNAP inhibitor (e.g., a compound of Formula I-IV, or a pharmaceutically acceptable salt thereof) as in phase I at a suitable dose below the dose used in the final cohort. Treatment continues throughout a 24-month study period during which clinical (which includes safety and tolerability) assessments are performed.

Blood Sampling:

Serial blood is drawn by direct vein puncture before and after administration TNAP inhibitor (e.g., a compound of Formula I-IV, or a pharmaceutically acceptable salt thereof). Venous blood samples (5 mL) for determination of serum concentrations are obtained in-hospital during a 24-hour period. Each serum sample is divided into two aliquots. All serum samples are stored at −20° C. Serum samples are shipped on dry ice.

Pharmacokinetics:

Patients undergo plasma/serum sample collection for pharmacokinetic evaluation in-hospital during a 24-hour period. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response:

The primary outcome measure is safety and tolerability, based on conventional laboratory and clinical assessments. The secondary outcome measure is the assessment of change of the Ankylosing Spondylitis Disease Activity Score (AS-DAS) and the Bath Ankylosing Spondylitis Disease Activity Index (BASDAI).

Example 9

Pseudoxanthoma Elasticum Clinical Trial

Human Clinical Trial of the Safety and/or Efficacy of a TNAP inhibitor (e.g., a compound of Formula I-IV, or a pharmaceutically acceptable salt thereof) therapy.

Objective:

To determine the safety, pharmacokinetics, and efficacy of administered TNAP inhibitor (e.g., a compound of Formula I-IV, or a pharmaceutically acceptable salt thereof).

Study Design:

This will be a Phase I, single-center, open-label, non-randomized dose escalation study followed by a Phase II study in pseudoxanthoma elasticum patients. The diagnosis of pseudoxanthoma elasticum must be confirmed by biopsy (documenting some calcification of elastic fibers) and the patient must have a clinical disease severity grade of at least "1" (poorly defined, barely visible macules) at screening. Patients must not have received other investigational agents within 3 months of study initiation. Fertile patients must agree to use adequate contraception throughout the study and for 18 months after cessation of treatment with a TNAP inhibitor (e.g., a compound of Formula I-IV). Patients must not be undertaking renal replacement therapy. Patients must also not have had a recent fracture (within the last 3 months). In addition, patients must not have an abnormal rhythm of the heart. Patients must also not currently be taking osteoporosis medication. In addition, patients must not have hypocalcaemia or pre-existing dental diseases. All subjects are evaluated for safety and all blood collections for pharmacokinetic analysis are collected as scheduled. All studies are performed with institutional ethics committee approval and patient consent.

Phase I:

Patients receive (e.g., intravenous, oral, ip, or the like) TNAP inhibitor (e.g., a compound of Formula I-IV, or a pharmaceutically acceptable salt thereof) daily for 4 weeks. Cohorts of 3-6 patients receive escalating doses of TNAP inhibitor (e.g., a compound of Formula I-IV, or a pharmaceutically acceptable salt thereof). Escalation will not be performed until all patients in the previous dose cohort have been treated for 4 weeks and until results obtained 4 weeks after treatment initiation do not reveal toxicity. Doses of TNAP inhibitor (e.g., a compound of Formula I-IV, or a pharmaceutically acceptable salt thereof) may be held or modified for toxicity based on assessments as outlined below. Dose escalation is considered complete, if 2 patients experience a Grade 3 Adverse Event (AE) or if 1 patient experiences Grade 4 AE at a particular cohort.

Phase II:

Patients receive TNAP inhibitor (e.g., a compound of Formula I-IV, or a pharmaceutically acceptable salt thereof) as in phase I at a suitable dose below the dose used in the final cohort. Treatment continues throughout a 24-month study period during which clinical (which includes safety and tolerability) assessments are performed.

Blood Sampling:

Serial blood is drawn by direct vein puncture before and after administration TNAP inhibitor (e.g., a compound of Formula I-IV, or a pharmaceutically acceptable salt thereof). Venous blood samples (5 mL) for determination of serum concentrations are obtained in-hospital during a 24-hour period. Each serum sample is divided into two aliquots. All serum samples are stored at −20° C. Serum samples are shipped on dry ice.

Pharmacokinetics:

Patients undergo plasma/serum sample collection for pharmacokinetic evaluation in-hospital during a 24-hour period. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response:

The primary outcome measure is safety and tolerability, based on conventional laboratory and clinical assessments. The secondary outcome measure is a change in elastic fiber calcification. A blinded dermatopathologist will grade skin biopsies on the density of von Kossa staining Other secondary outcome measures include changes in skin lesions, and changes in disease progression, based on ophthalmologic examinations.

Example 10

Calciphylaxis Clinical Trial

Human Clinical Trial of the Safety and/or Efficacy of a TNAP inhibitor (e.g., a compound of Formula I-IV, or a pharmaceutically acceptable salt thereof) therapy.

Objective:

To determine the safety, pharmacokinetics, and efficacy of administered TNAP inhibitor (e.g., a compound of Formula I-IV, or a pharmaceutically acceptable salt thereof).

Study Design:

This will be a Phase I, single-center, open-label, non-randomized dose escalation study followed by a Phase II study in calciphylaxis patients. The diagnosis of pseudoxanthoma elasticum must be confirmed by a skin biopsy or initial dermatology visit within the previous 5 years, and a serum phosphorus level greater than 4.5 mg/dL. Patients must not have received other investigational agents within 3 months of study initiation. Fertile patients must agree to use adequate contraception throughout the study and for 18 months after cessation of treatment with a TNAP inhibitor (e.g., a compound of Formula I-IV). Patients must not be undertaking renal replacement therapy. Patients must also not have had a recent fracture (within the last 3 months). In addition, patients must not have an abnormal rhythm of the heart. Patients must also not currently be taking osteoporosis medication. In addition, patients must not have hypocalcaemia or pre-existing dental diseases. All subjects are evaluated for safety and all blood collections for pharmacokinetic analysis are collected as scheduled. All studies are performed with institutional ethics committee approval and patient consent.

Phase I:

Patients receive (e.g., intravenous, oral, ip, or the like) TNAP inhibitor (e.g., a compound of Formula I-IV, or a pharmaceutically acceptable salt thereof) daily for 4 weeks. Cohorts of 3-6 patients receive escalating doses of TNAP inhibitor (e.g., a compound of Formula I-IV, or a pharmaceutically acceptable salt thereof). Escalation will not be performed until all patients in the previous dose cohort have been treated for 4 weeks and until results obtained 4 weeks after treatment initiation do not reveal toxicity. Doses of TNAP inhibitor (e.g., a compound of Formula I-IV, or a pharmaceutically acceptable salt thereof) may be held or modified for toxicity based on assessments as outlined below. Dose escalation is considered complete, if 2 patients experience a Grade 3 Adverse Event (AE) or if 1 patient experiences Grade 4 AE at a particular cohort.

Phase II:

Patients receive TNAP inhibitor (e.g., a compound of Formula I-IV, or a pharmaceutically acceptable salt thereof) as in phase I at a suitable dose below the dose used in the final cohort. Treatment continues throughout a 24-month study period during which clinical (which includes safety and tolerability) assessments are performed.

Blood Sampling:

Serial blood is drawn by direct vein puncture before and after administration TNAP inhibitor (e.g., a compound of Formula I-IV, or a pharmaceutically acceptable salt thereof). Venous blood samples (5 mL) for determination of serum concentrations are obtained in-hospital during a 24-hour period. Each serum sample is divided into two aliquots. All serum samples are stored at −20° C. Serum samples are shipped on dry ice.

Pharmacokinetics:

Patients undergo plasma/serum sample collection for pharmacokinetic evaluation in-hospital during a 24-hour period. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response:

The primary outcome measure is safety and tolerability, based on conventional laboratory and clinical assessments. The secondary outcome measure is a change in elastic fiber calcification. A blinded dermatopathologist will grade skin biopsies on the density of von Kossa staining Other secondary outcome measures include changes in skin lesions, and changes in disease progression, based on ophthalmologic examinations.

Example 11

Parenteral Composition of a Compound of Formula I-IV

To prepare a parenteral pharmaceutical composition suitable for administration by injection, 100 mg of a compound of Formula I-IV, or a water soluble pharmaceutically acceptable salt thereof, is dissolved in DMSO and then mixed with 10 ml of 0.9% sterile saline solution. The mixture is incorporated into a dosage unit suitable for administration by injection.

Example 12

Oral Composition of a Compound of Formula I-IV

To prepare a pharmaceutical composition for oral delivery, 400 mg of a compound of Formula I-IV and the following ingredients are mixed intimately and pressed into single scored tablets.

| Tablet Formulation | |
|---|---|
| Ingredient | Quantity per tablet mg |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

| Capsule Formulation | |
|---|---|
| Ingredient | Quantity per capsule mg |
| compound | 200 |
| lactose spray dried | 148 |
| magnesium stearate | 2 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A compound of Formula I, or a pharmaceutically acceptable salt, polymorph, solvate, tautomer, or N-oxide thereof:

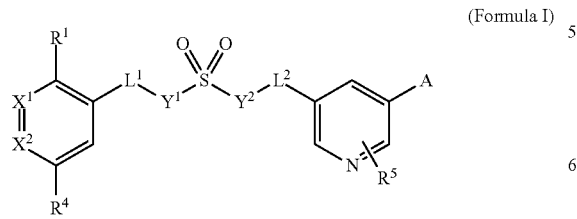

(Formula I)

wherein:
$Y^1$ is a bond, and $Y^2$ is —N($R^6$)—;
$L^1$ and $L^2$ are each a bond;
$X^1$ is =N— or =C($R^2$)—;
$X^2$ is =N— or =C($R^3$)—;
$R^1$ and $R^4$ are independently selected from the group consisting of —F, —Cl, —Br, —CN, —C(O)—N($R^7$)—$R^8$, —C(O)—O—$R^9$, —OMe, —OCF$_3$, optionally substituted phenyl, and optionally substituted 5- or 6-membered heteroaryl;
$R^2$, $R^3$, and $R^5$ are hydrogen;
$R^6$ is hydrogen;
$R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;
$R^9$ is selected from the group consisting of hydrogen, optionally substituted alkyl, haloalkyl, optionally substituted cycloalkyl, optionally substituted heterocycloalkyl, and optionally substituted phenyl; and
A is —C(O)—N($R^7$)—$R^8$, or —C(O)—O—$R^9$,
or A is an optionally substituted phenyl or optionally substituted 5- or 6-membered heteroaryl, wherein A is selected from:

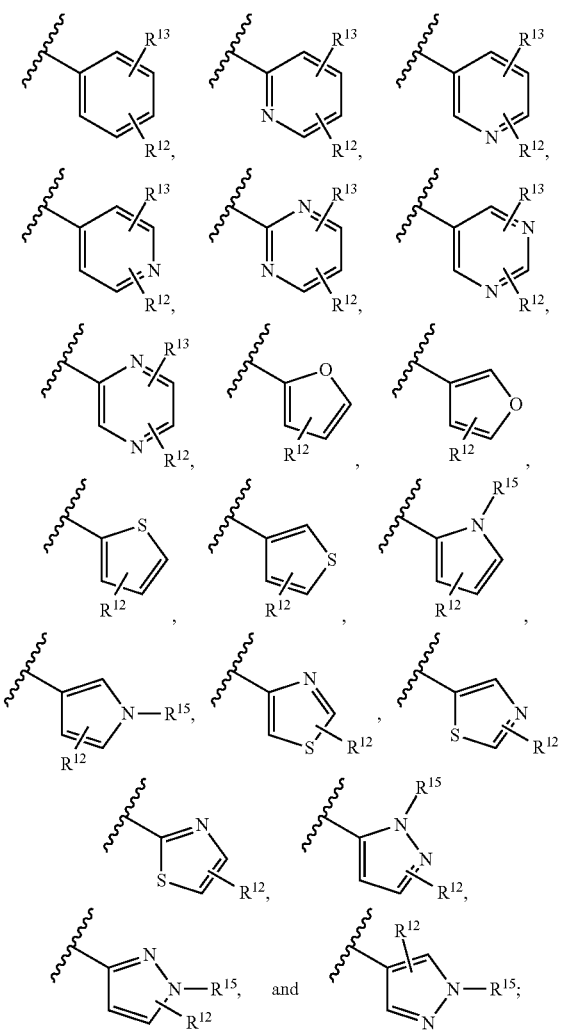

$R^{12}$ and $R^{13}$ are independently selected from the group consisting of hydrogen, halogen, —CN, —OH, —C(O)—O—$R^{19}$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^{19}$ is selected from the group consisting of hydrogen, optionally substituted alkyl, haloalkyl, optionally substituted cycloalkyl, optionally substituted heterocycloalkyl, and optionally substituted phenyl; and $R^{15}$ is hydrogen or optionally substituted alkyl.

2. The compound of claim 1, or a pharmaceutically acceptable salt thereof, wherein:

$Y^1$ is a bond and $Y^2$ is —N($R^6$)—;

$X^2$ is =C($R^3$)—;

$L^1$ is a bond;

$L^2$ is a bond; and $R^6$ is hydrogen as shown in Formula Ie:

(Formula Ie)

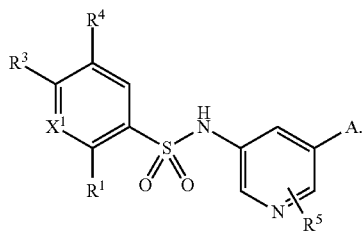

3. The compound of claim 1, or a pharmaceutically acceptable salt thereof, wherein $X^1$ is =C($R^2$)—.

4. The compound of claim 1, or a pharmaceutically acceptable salt thereof, wherein $R^4$ is optionally substituted phenyl, optionally substituted 5- or 6-membered heteroaryl, —C(O)—N($R^7$)—$R^8$, or —C(O)—O—$R^9$.

5. The compound of claim 1, or a pharmaceutically acceptable salt thereof, wherein $R^1$ and $R^4$ are independently selected from the group consisting of F, —Cl, —Br, —CN, —OMe, and —OCF$_3$.

6. The compound of claim 1, or a pharmaceutically acceptable salt thereof, wherein A is optionally substituted phenyl or optionally substituted 5- or 6-membered heteroaryl, wherein A is selected from:

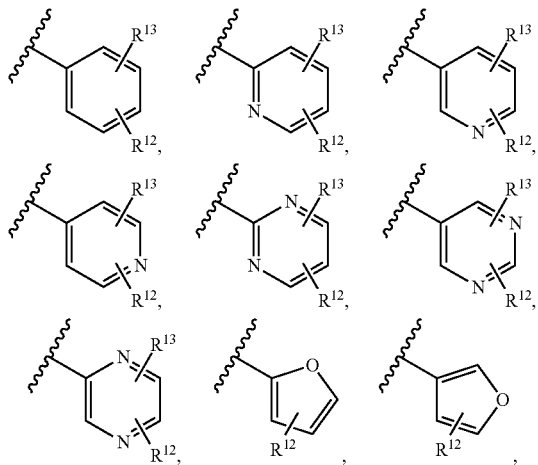

-continued

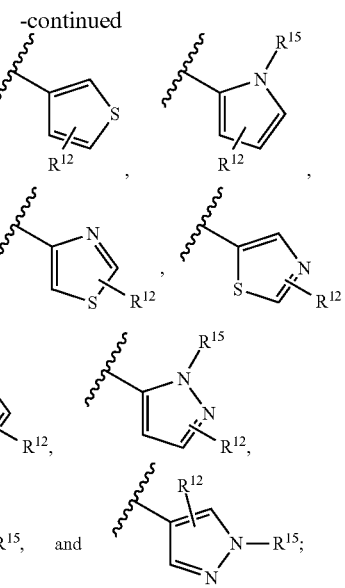

$R^{12}$ and $R^{13}$ are independently selected from the group consisting of hydrogen, halogen, —CN, —OH, —C(O)—O—$R^{19}$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^{19}$ is selected from the group consisting of hydrogen, optionally substituted alkyl, haloalkyl, optionally substituted cycloalkyl, optionally substituted heterocycloalkyl, and optionally substituted phenyl; and $R^{15}$ is hydrogen or optionally substituted alkyl.

7. The compound of claim 1, or a pharmaceutically acceptable salt thereof, wherein:

A is

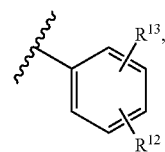

wherein $R^{12}$ and $R^{13}$ are independently selected from the group consisting of hydrogen, —F, —CN, —OH, —OMe, and —C(O)—O-Me; or A is —C(O)—O—$R^9$; or A is —C(O)—N($R^7$)—$R^8$.

8. The compound of claim 7, or a pharmaceutically acceptable salt thereof, wherein A is —C(O)—O—$R^9$, wherein $R^9$ is selected from hydrogen, optionally substituted alkyl, optionally substituted cycloalkyl, and optionally substituted phenyl.

9. The compound of claim 7, or a pharmaceutically acceptable salt thereof, wherein A is —C(O)—N($R^7$)—$R^8$, wherein $R^7$ and $R^8$ together with the nitrogen atom to which they are attached form an optionally substituted heterocycloamino.

10. The compound of claim 9, or a pharmaceutically acceptable salt thereof, wherein the optionally substituted heterocycloamino is an optionally substituted pyrrolidine, an optionally substituted piperidine, an optionally substituted morpholine, or an optionally substituted piperazine.

11. The compound of claim 7, or a pharmaceutically acceptable salt thereof, wherein A is —C(O)—N(R⁷)—R⁸, wherein R⁷ is hydrogen and R⁸ is optionally substituted alkyl, optionally substituted cycloalkyl, or optionally substituted phenyl.

12. The compound of claim 7, or a pharmaceutically acceptable salt thereof, wherein A is —C(O)—N(R⁷)—R⁸, wherein R⁷ and R⁸ are hydrogen.

13. A pharmaceutical composition comprising a compound of claim 1, or a pharmaceutically acceptable salt thereof, and a pharmaceutically acceptable excipient.

14. A compound that has one of the following structures:

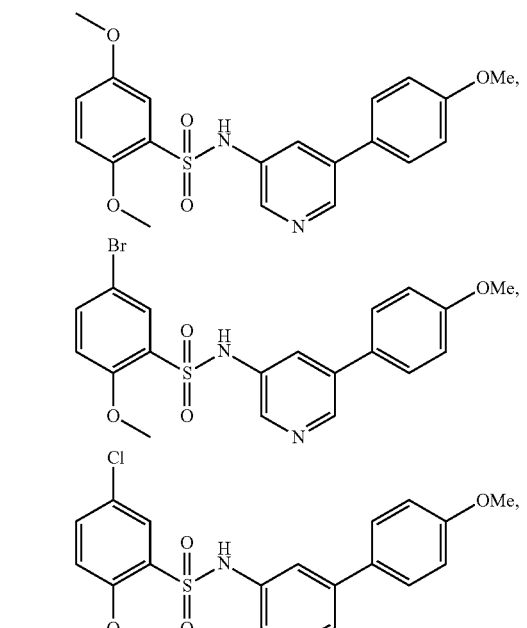

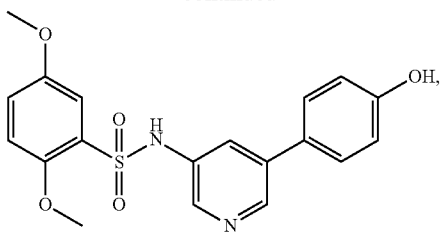

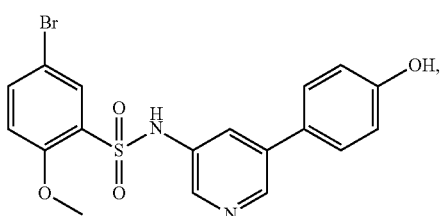

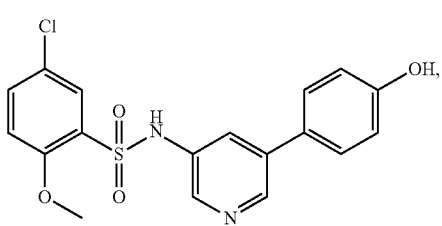

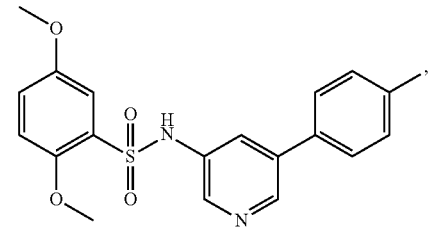

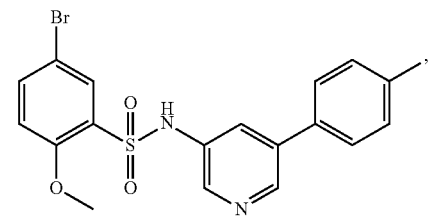

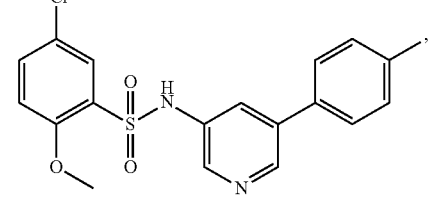

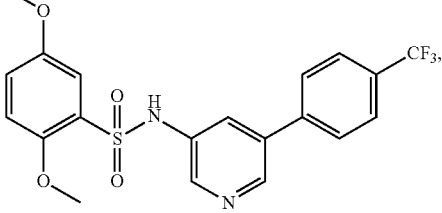

211
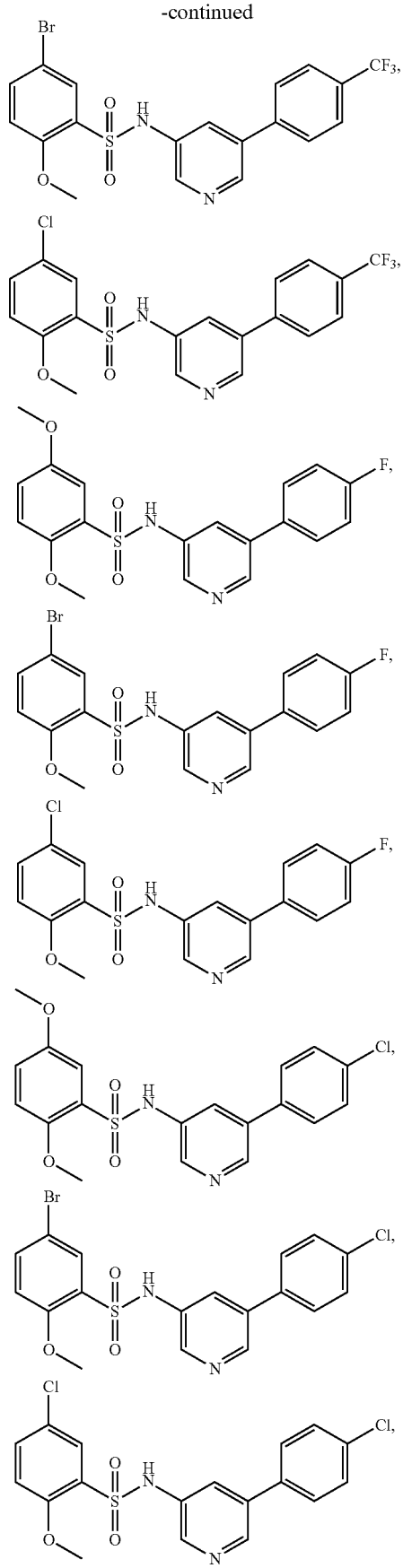
212
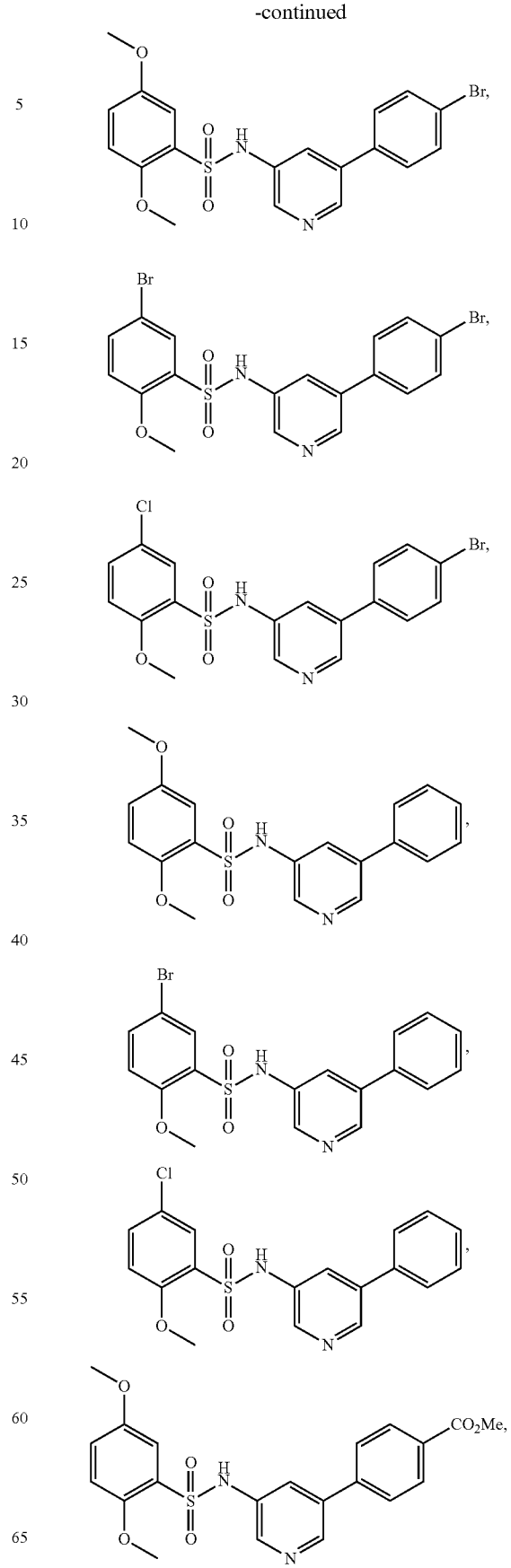

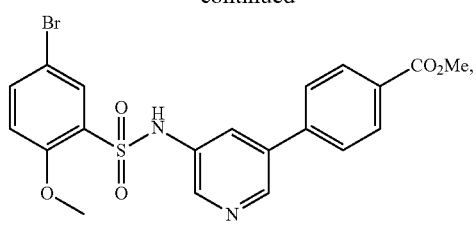
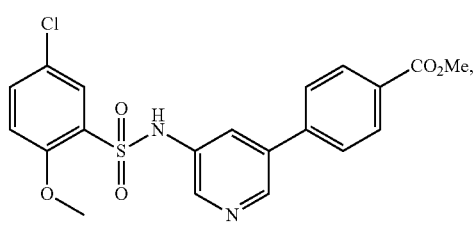
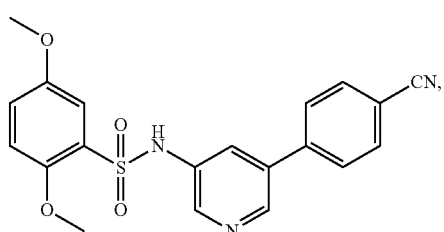
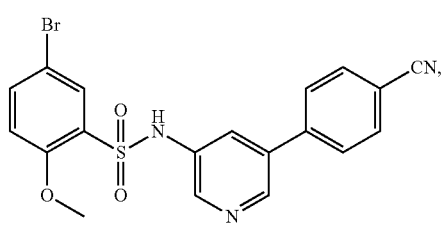
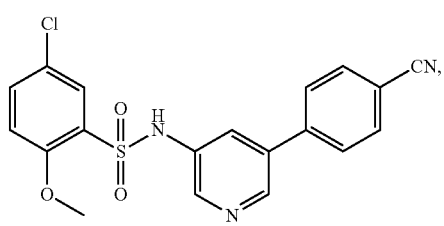
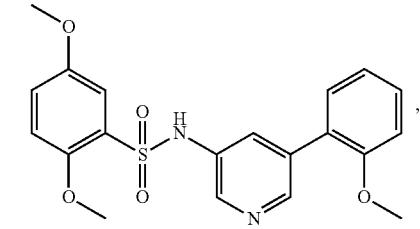
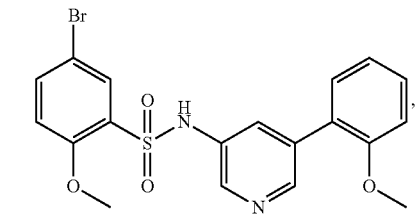
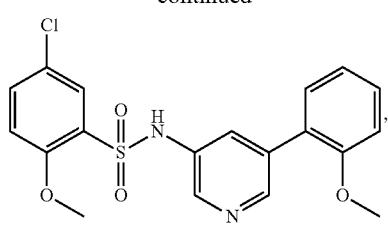
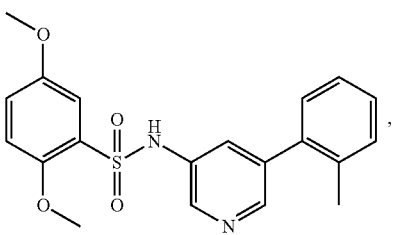
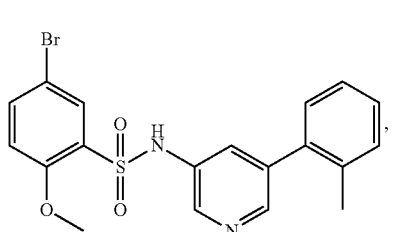
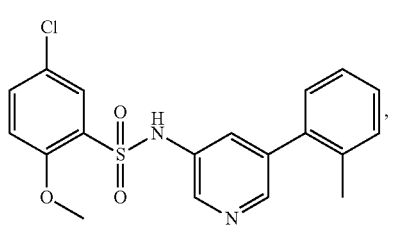
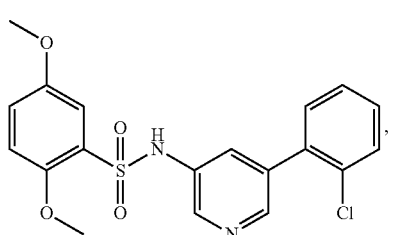
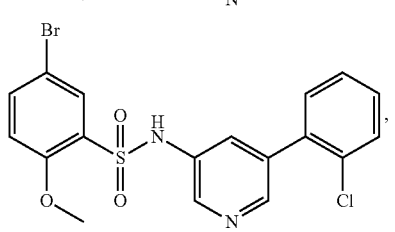
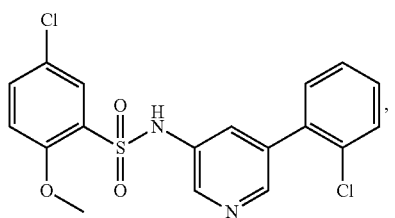

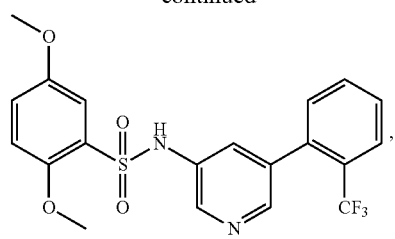
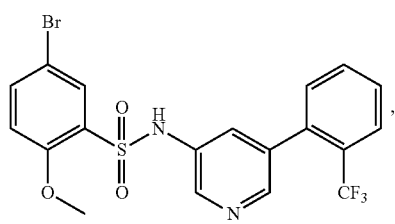
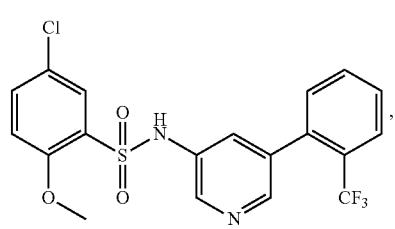
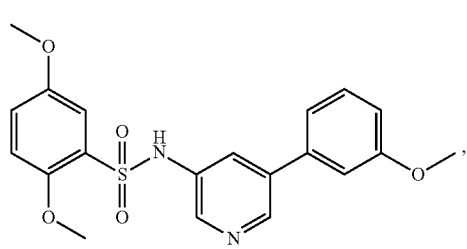
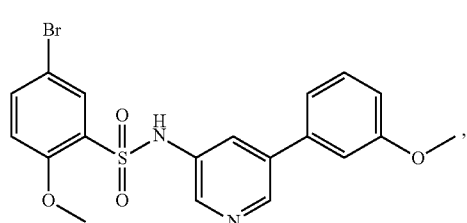
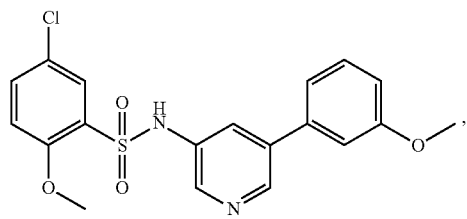
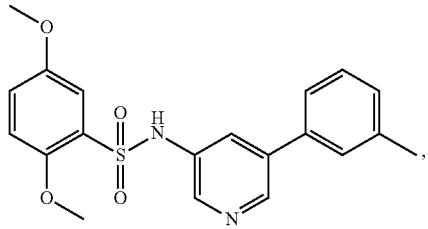
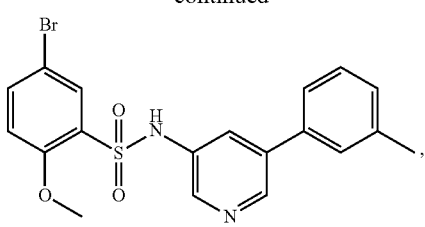
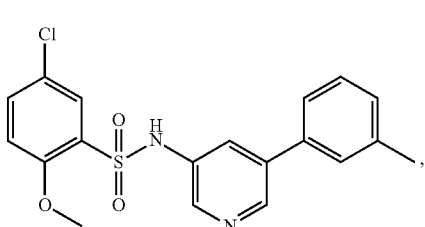
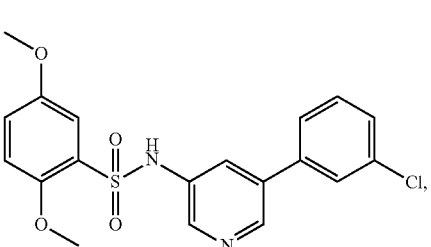
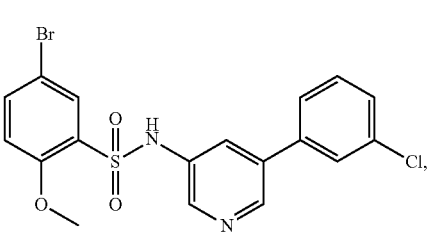
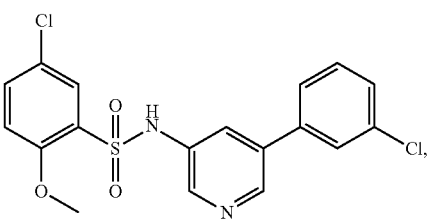
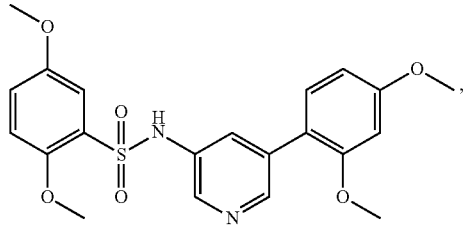
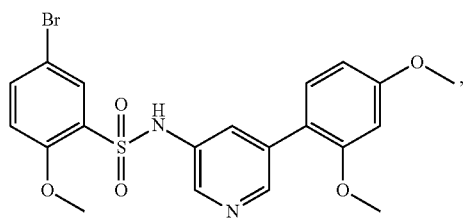

217
-continued
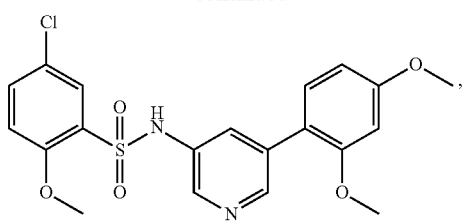
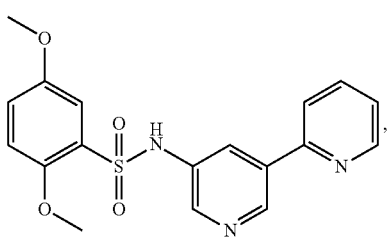
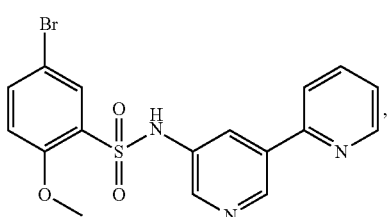
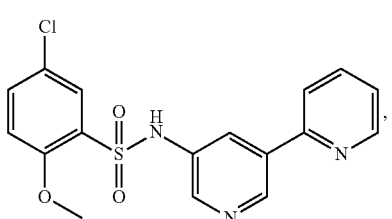
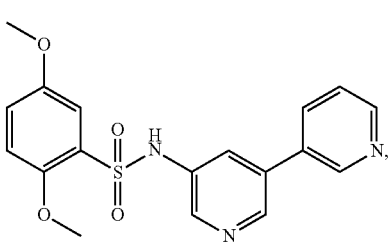
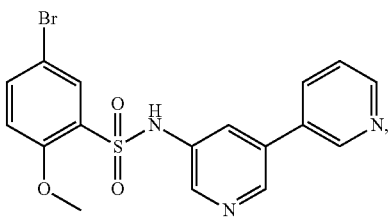
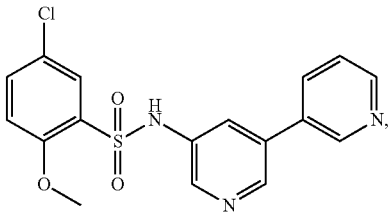
218
-continued
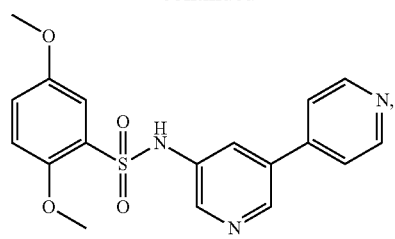
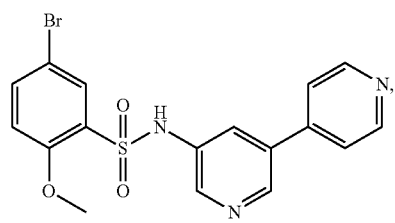
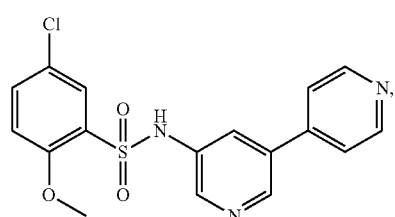
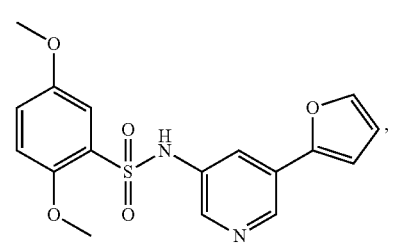
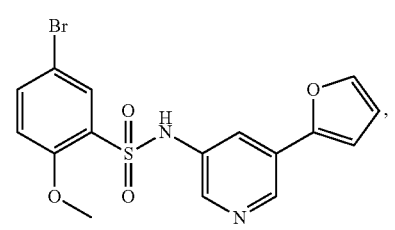
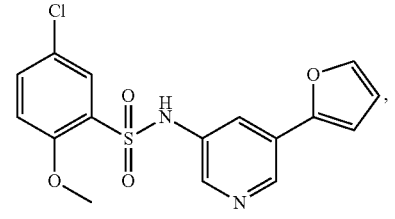
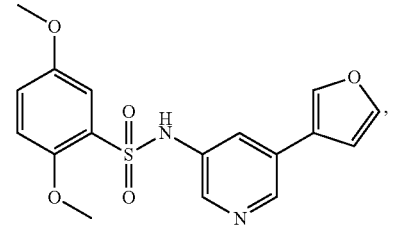

219
-continued
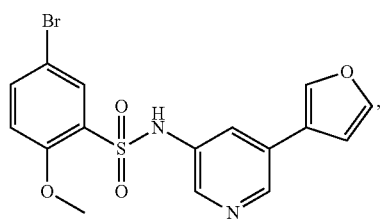
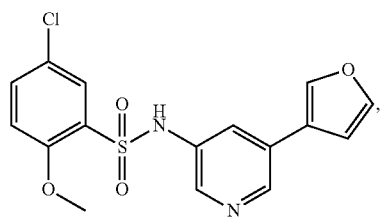
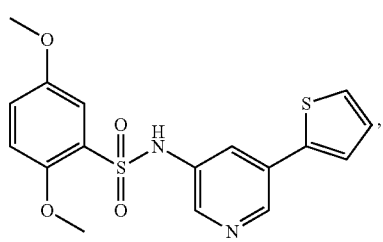
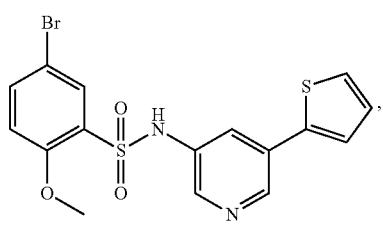
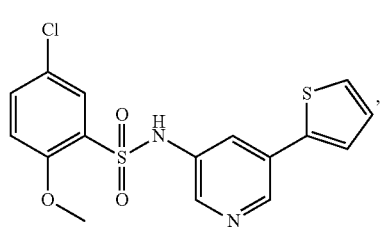
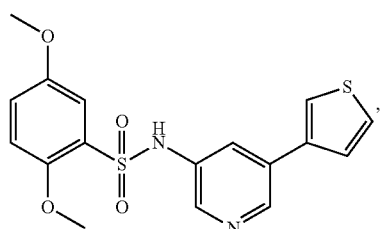
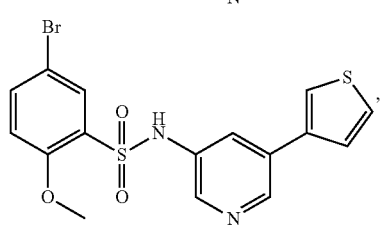
220
-continued
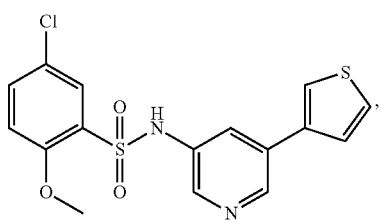
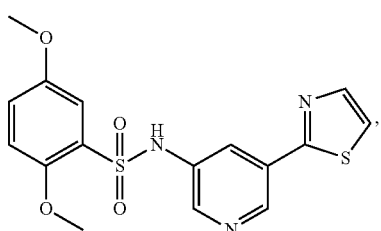
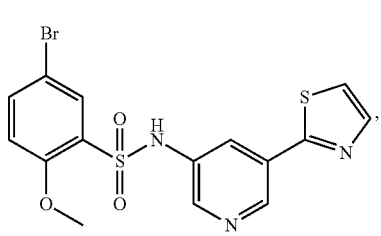
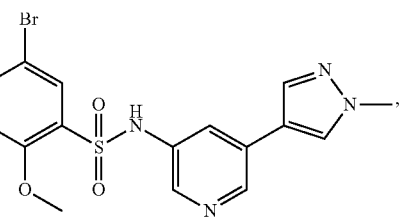
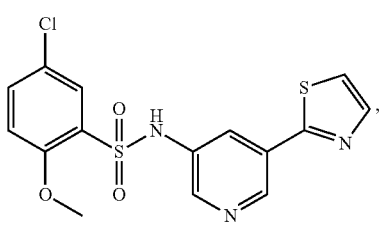
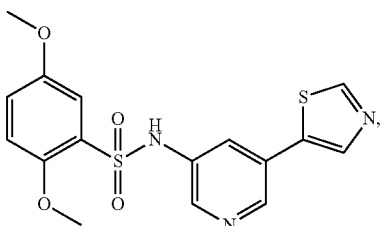
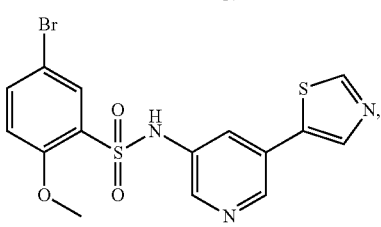

-continued
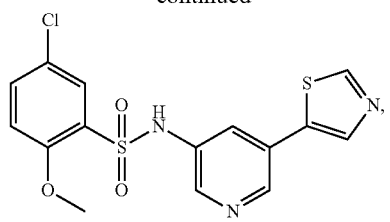
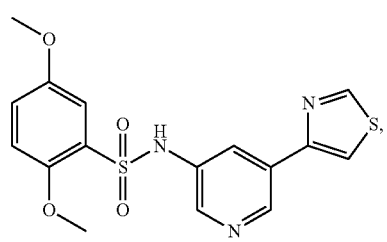
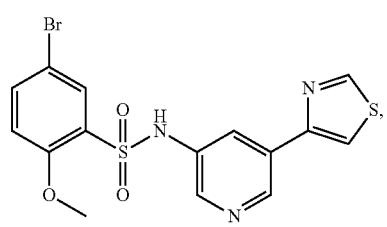
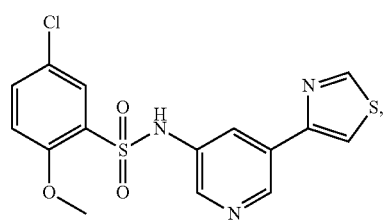
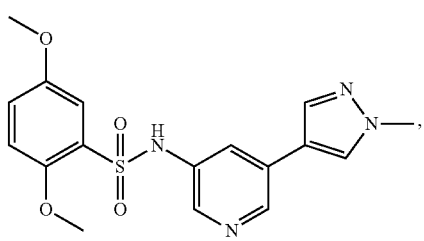
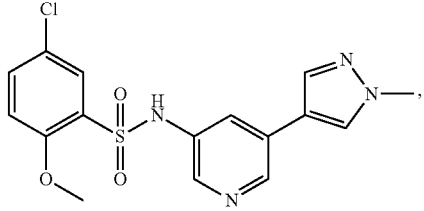
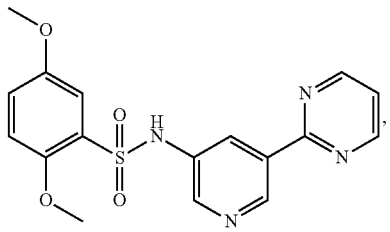
-continued
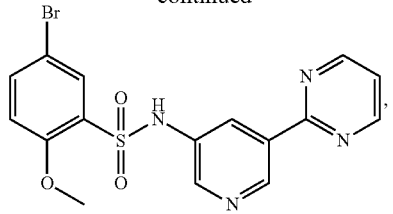
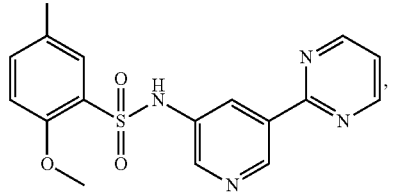
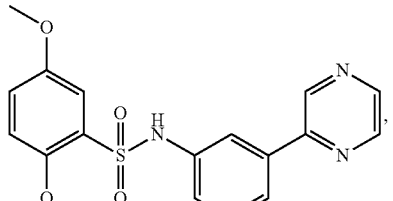
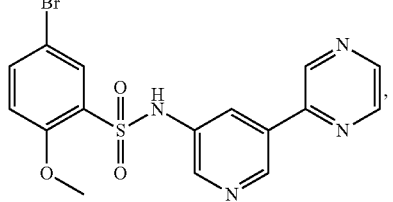
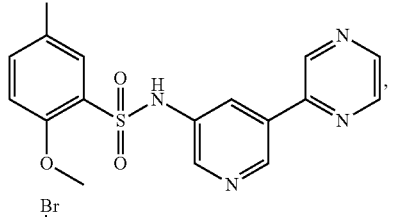
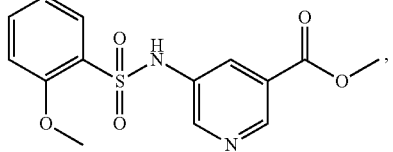
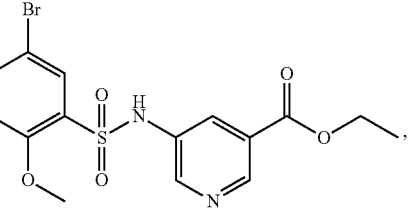
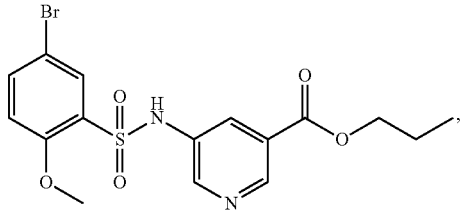

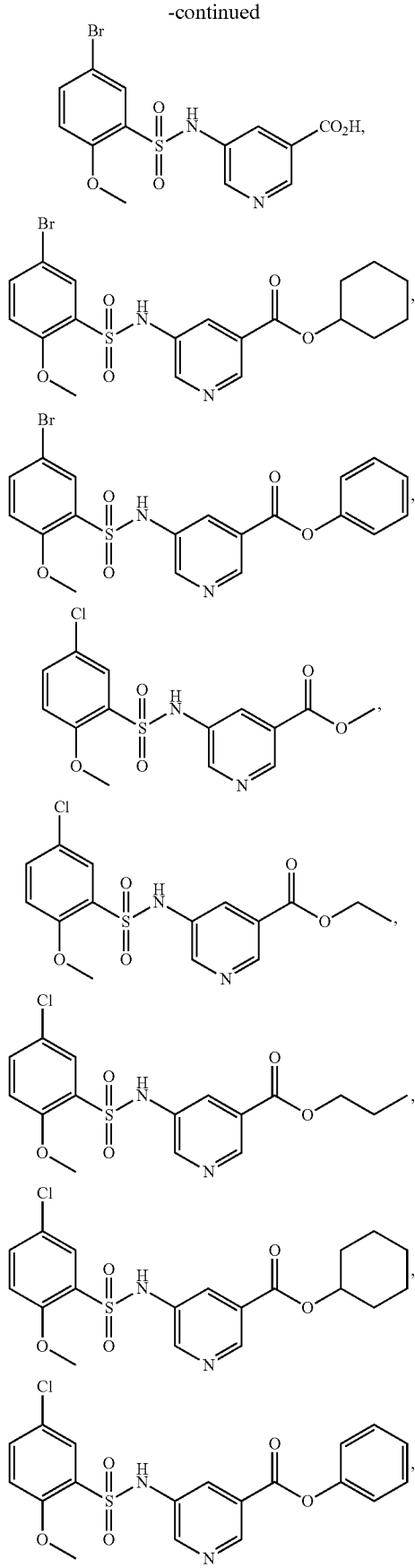
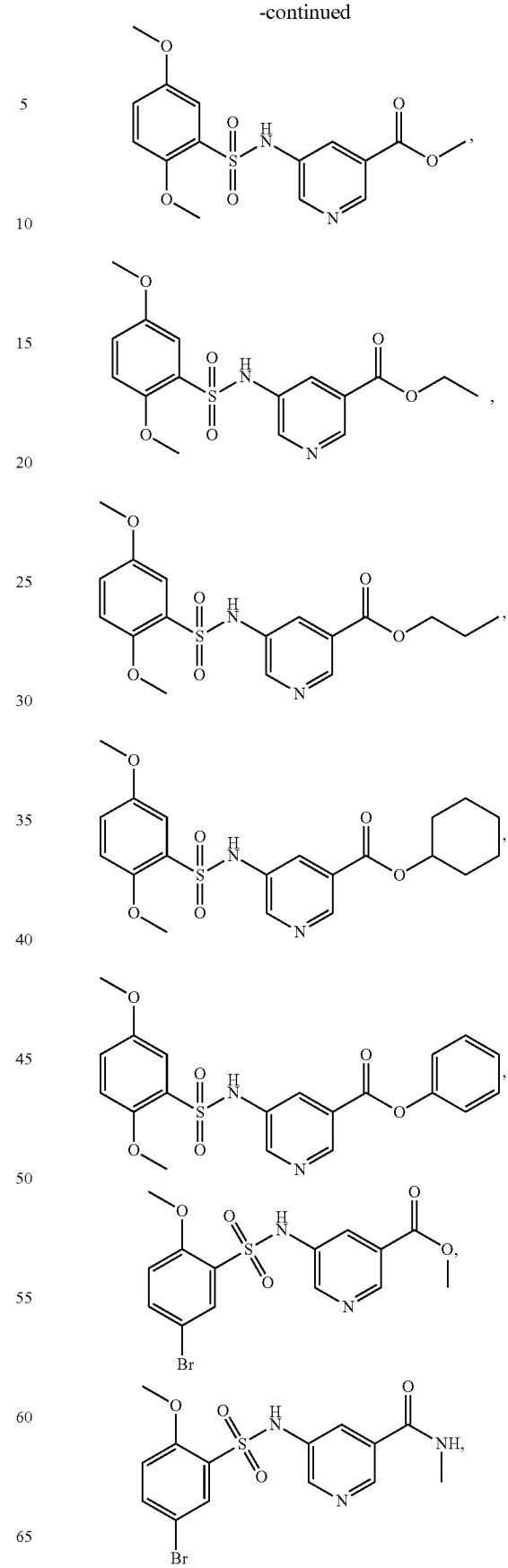

225
-continued
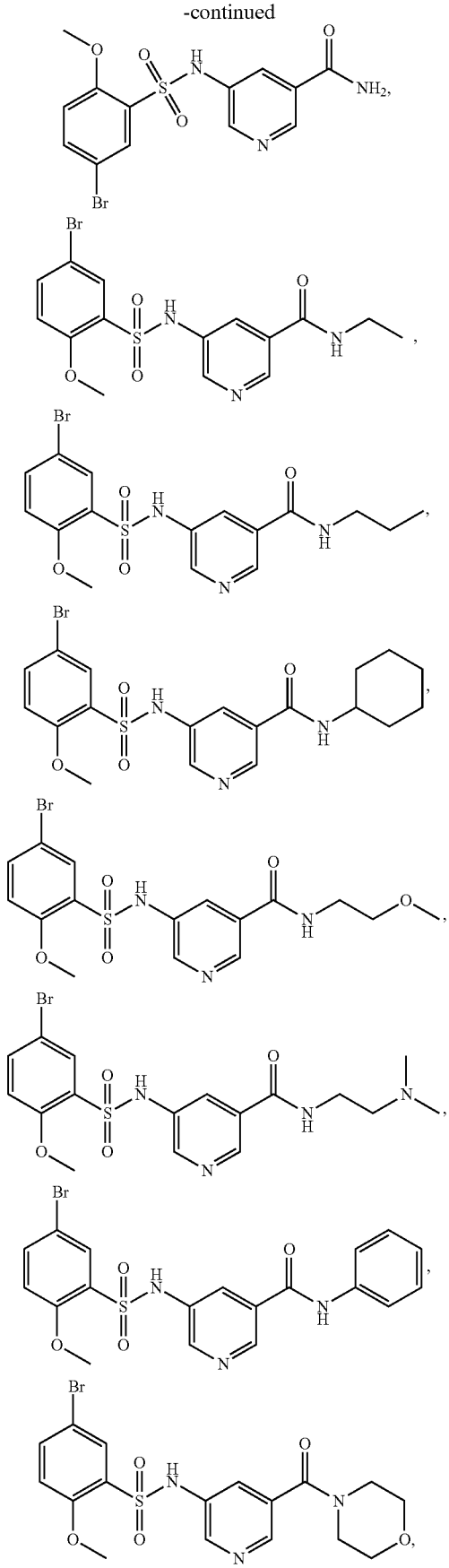
226
-continued
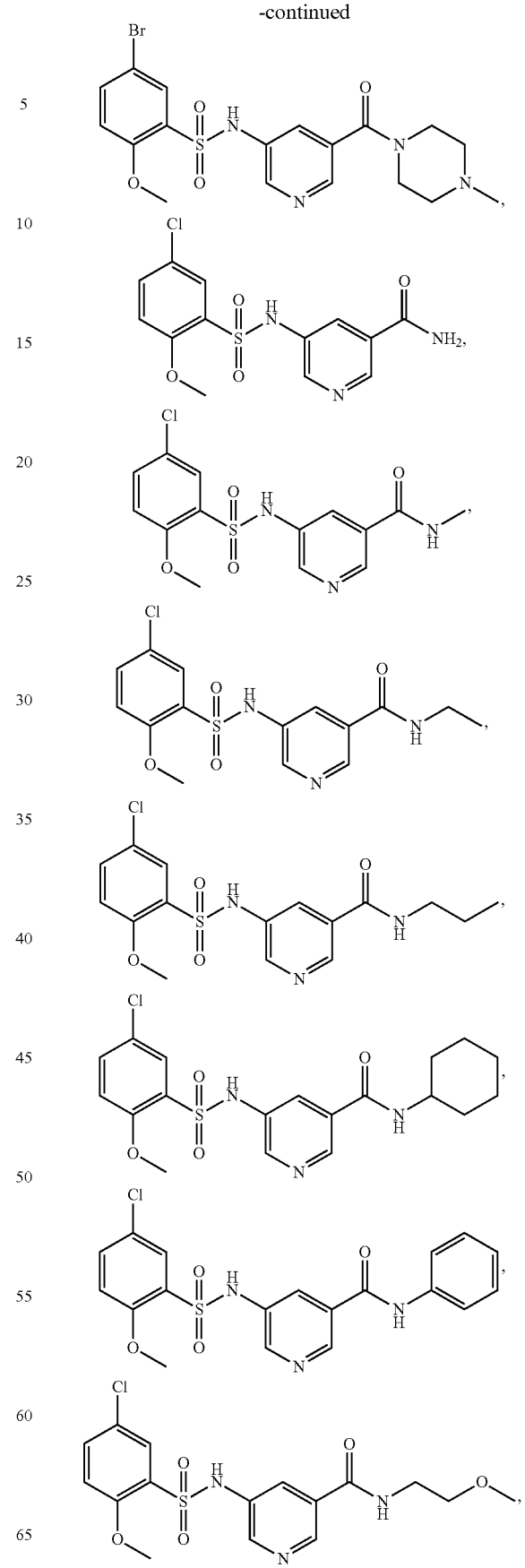

227
-continued
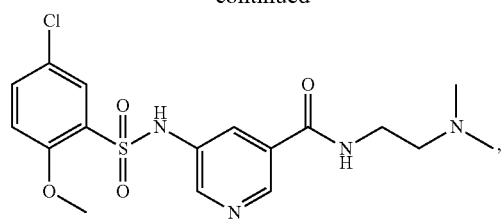
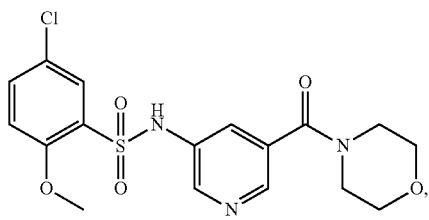
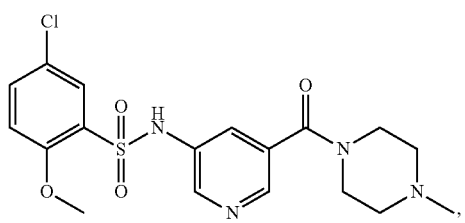
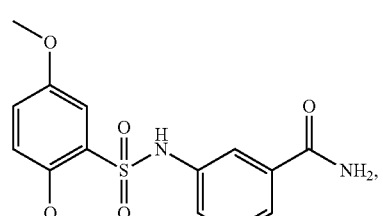
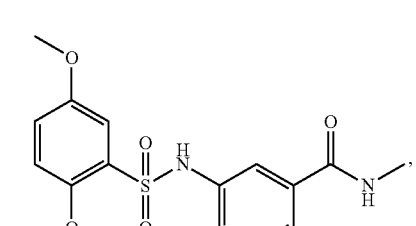
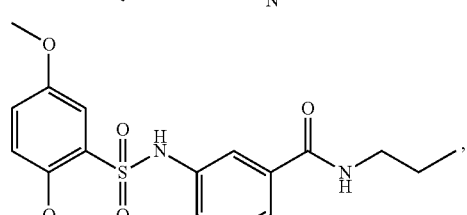
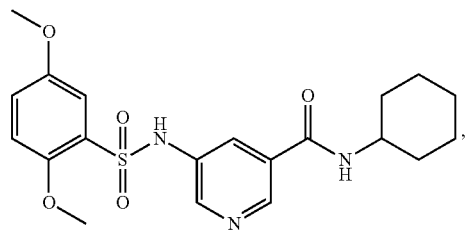
228
-continued
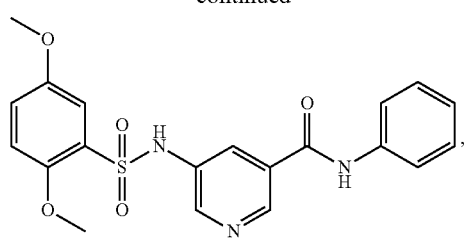
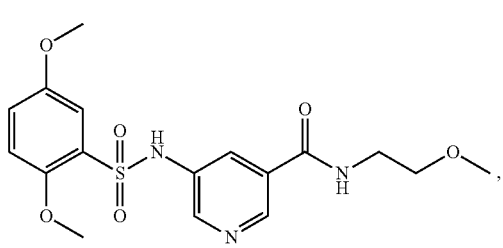
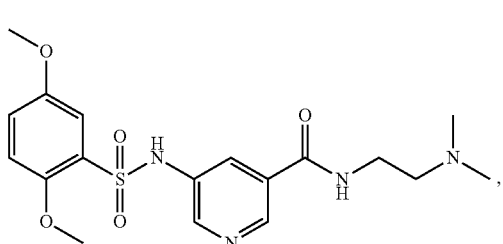
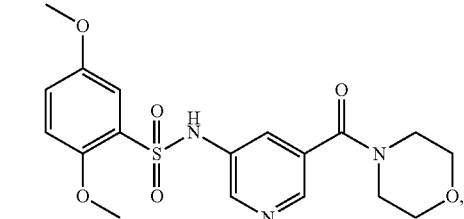
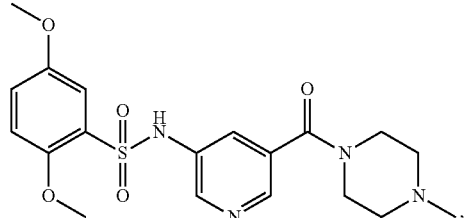
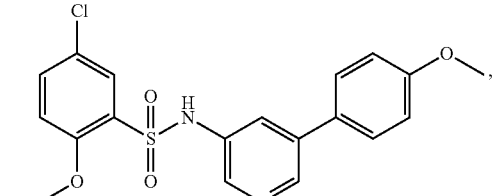
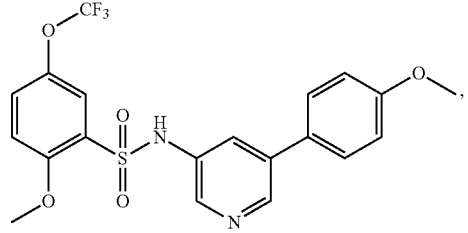

-continued
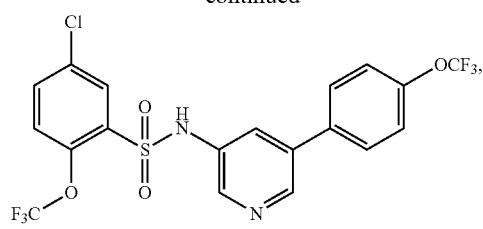
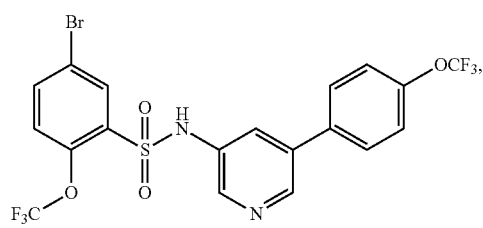
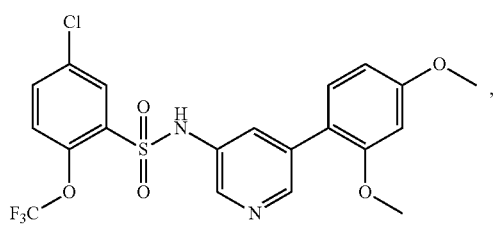
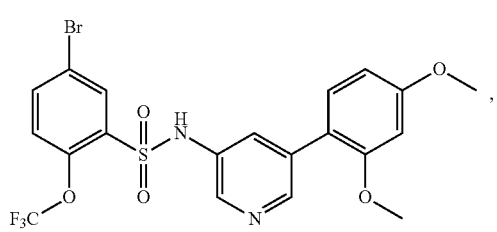
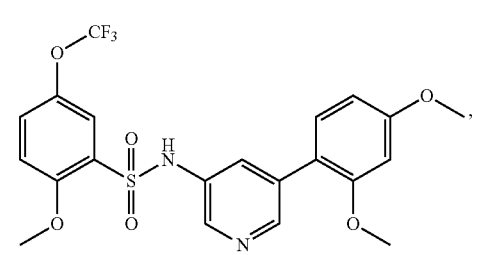
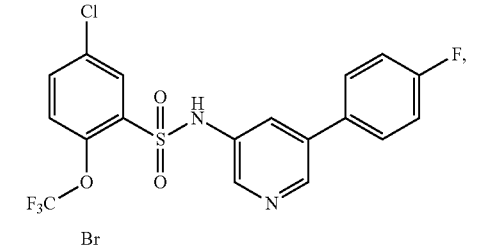
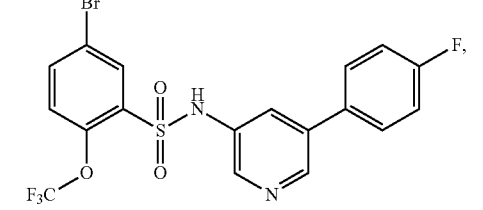
-continued
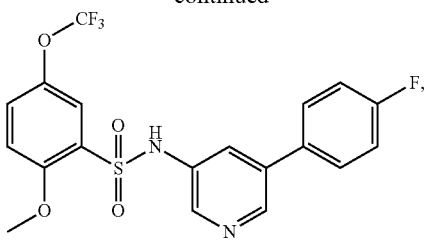
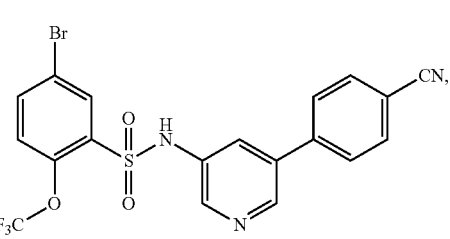
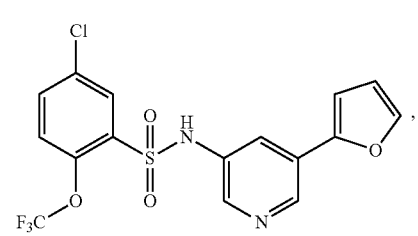
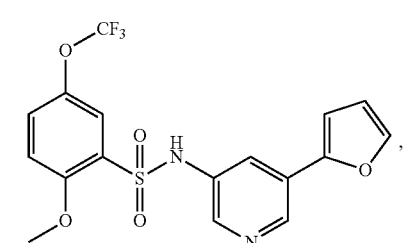
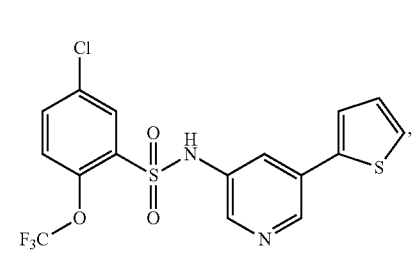
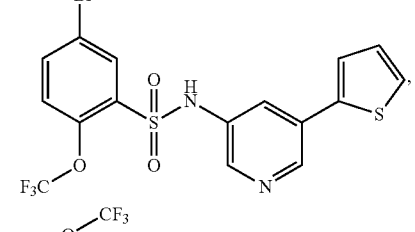
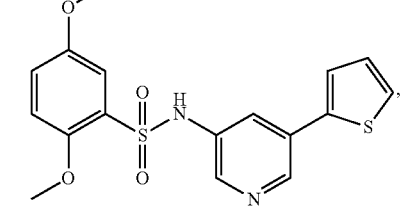

231
-continued
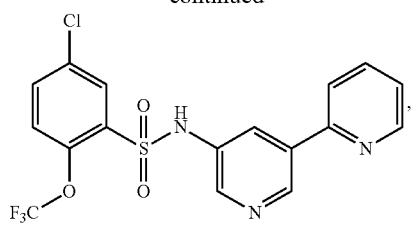
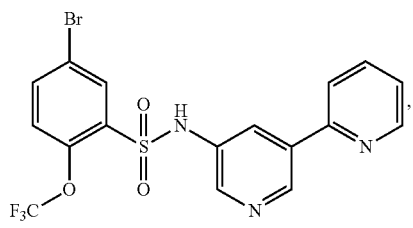
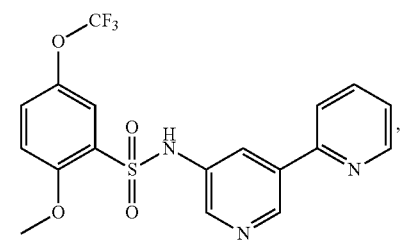
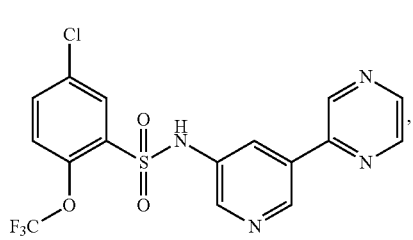
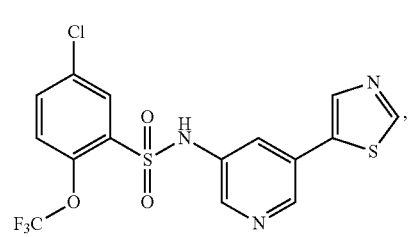
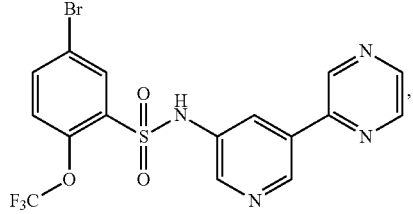
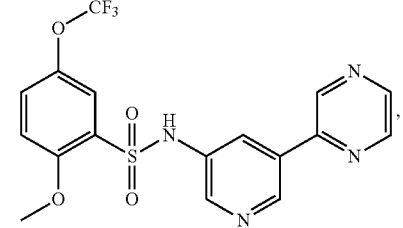
232
-continued
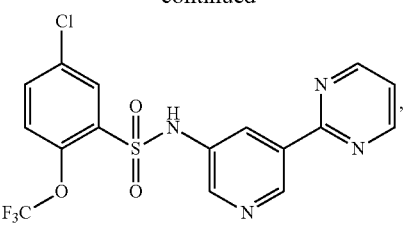
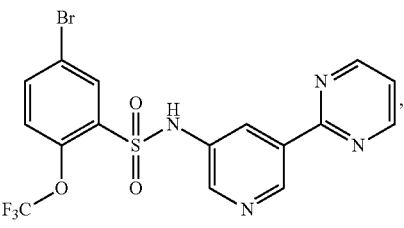
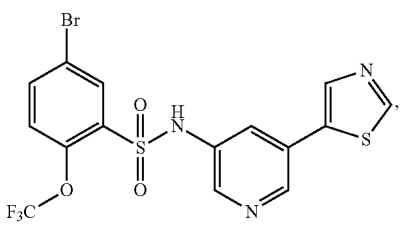
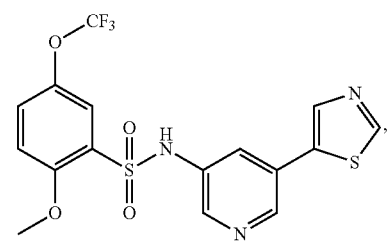
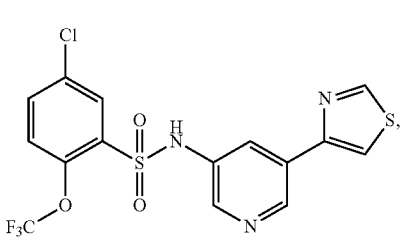
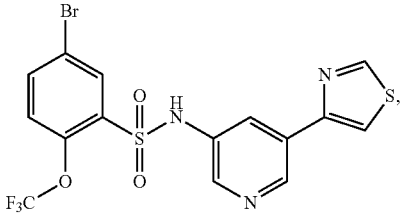
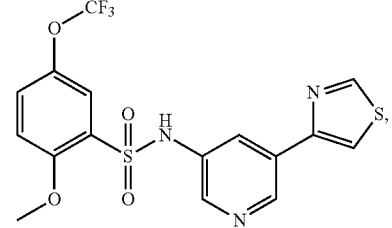

-continued
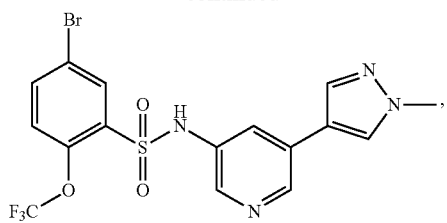
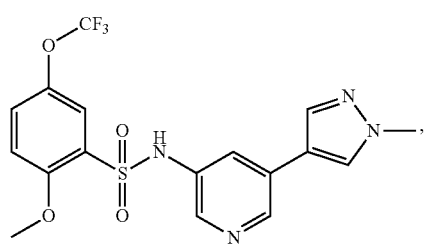
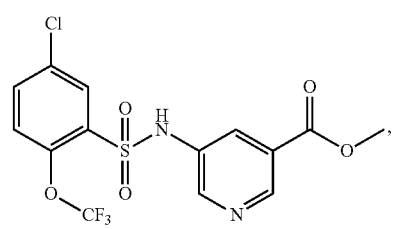
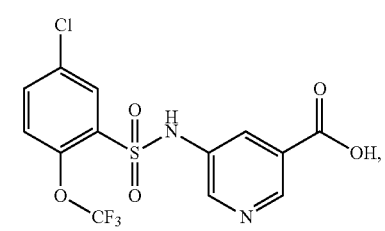
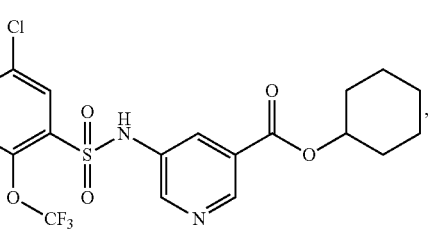
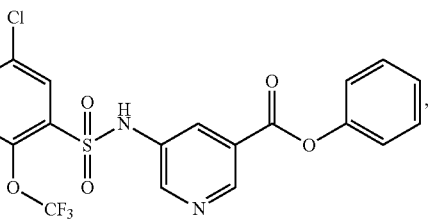
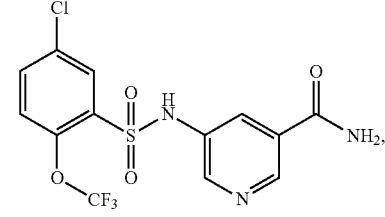
-continued
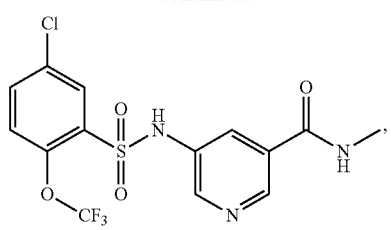
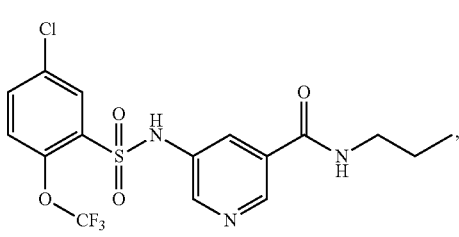
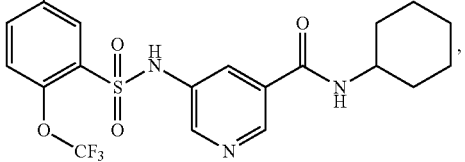
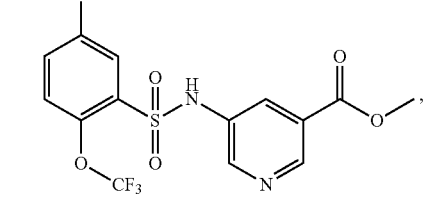
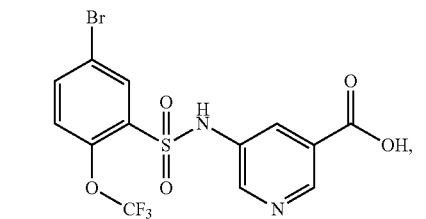
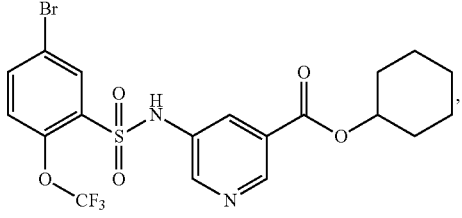
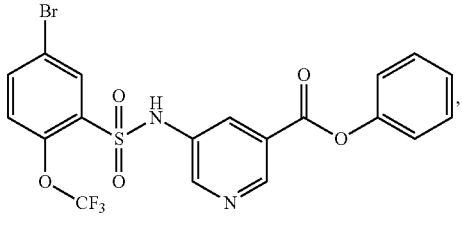

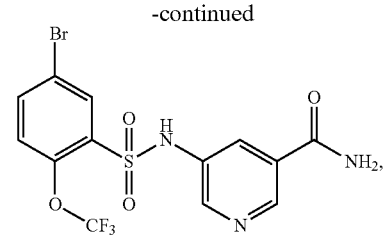
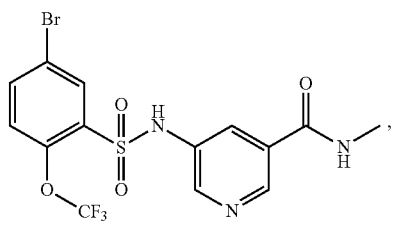
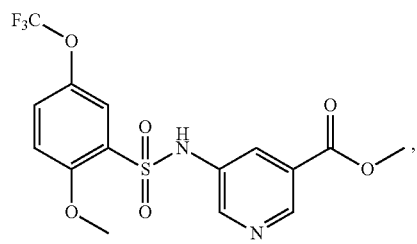
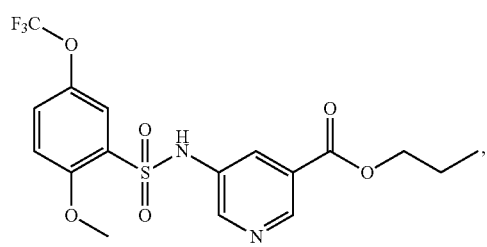
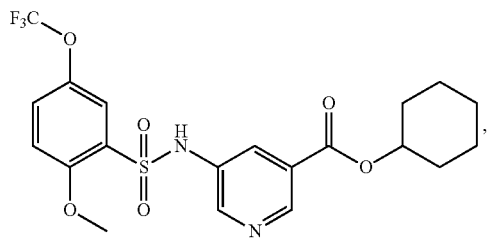
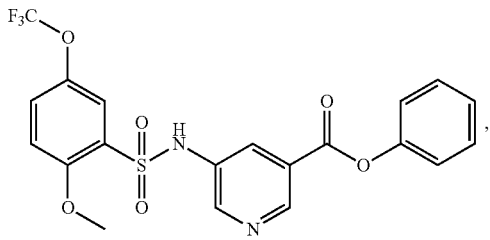
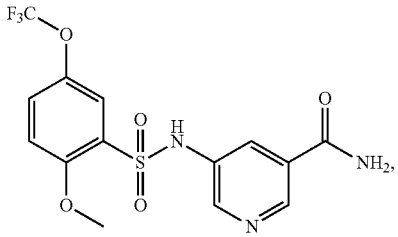
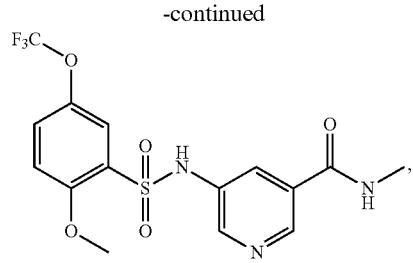
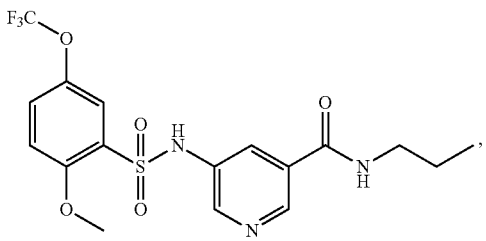
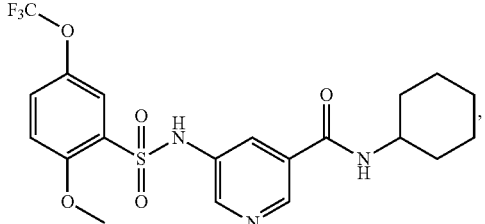
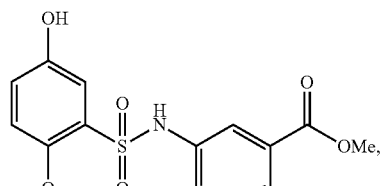
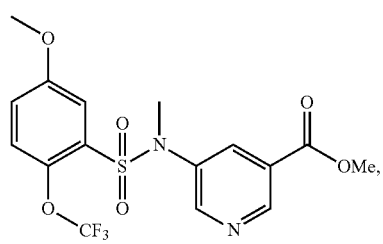
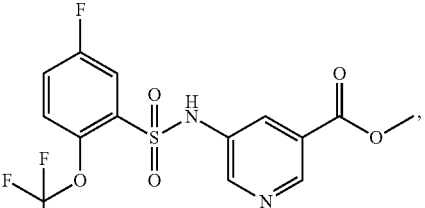
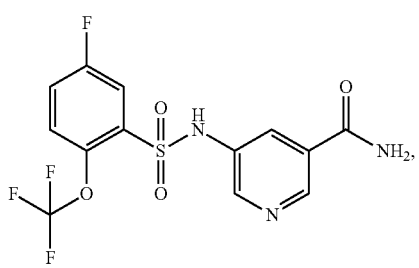

-continued
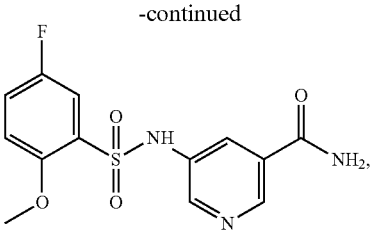
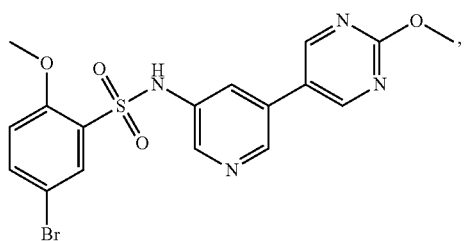
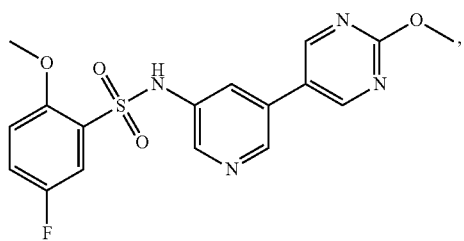
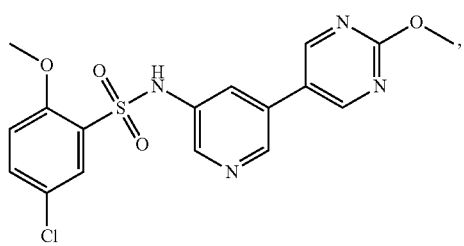
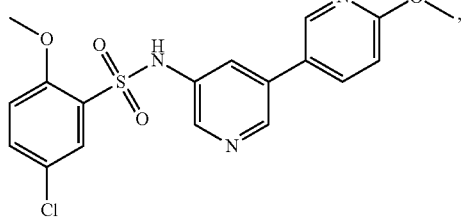
-continued
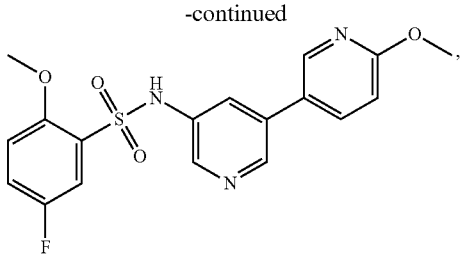
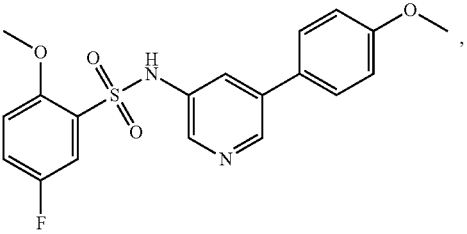
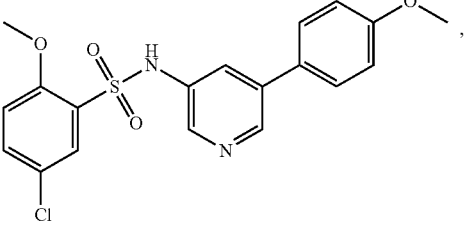
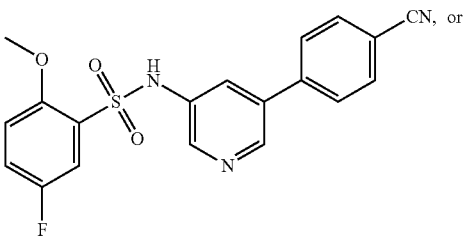
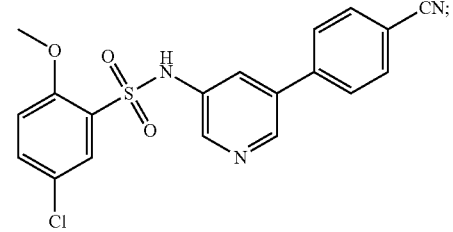
or a pharmaceutically acceptable salt thereof.
* * * * *